United States Patent
Jantos et al.

(10) Patent No.: US 9,273,036 B2
(45) Date of Patent: *Mar. 1, 2016

(54) OXINDOLE DERIVATIVES CARRYING AN OXETANE SUBSTITUENT AND USE THEREOF FOR TREATING VASOPRESSINE-RELATED DISEASES

(71) Applicant: AbbVie Deutschland GmbH & Co. KG, Wiesbaden (DE)

(72) Inventors: Katja Jantos, Wiesbaden (DE); Wilfred Braje, Wiesbaden (DE); Herve Geneste, Wiesbaden (DE); Andreas Kling, Wiesbaden (DE); Liliane Unger, Wiesbaden (CH); Berthold Behl, Wiesbaden (DE); Marcel van Gaalen, Wiesbaden (DE); Wilfried Hornberger, Wiesbaden (DE); Loic Laplanche, Wiesbaden (DE); Silke Weber, Wiesbaden (DE)

(73) Assignee: AbbVie Deutschland GmbH & Co. KG, Wiesbaden (DE)

(*) Notice: Subject to any disclaimer, the term of this patent is extended or adjusted under 35 U.S.C. 154(b) by 0 days.

This patent is subject to a terminal disclaimer.

(21) Appl. No.: 14/214,154

(22) Filed: Mar. 14, 2014

(65) Prior Publication Data

US 2014/0343074 A1 Nov. 20, 2014

Related U.S. Application Data

(60) Provisional application No. 61/781,468, filed on Mar. 14, 2013.

(51) Int. Cl.
| | | |
|---|---|---|
| *A61K 31/496* | (2006.01) | |
| *A61K 31/454* | (2006.01) | |
| *C07D 405/14* | (2006.01) | |
| *C07D 487/08* | (2006.01) | |

(52) U.S. Cl.
CPC ............ *C07D 405/14* (2013.01); *C07D 487/08* (2013.01)

(58) Field of Classification Search
None
See application file for complete search history.

(56) References Cited

U.S. PATENT DOCUMENTS

| 7,902,379 B2 | 3/2011 | Lubisch et al. |
|---|---|---|
| 2008/0318923 A1 | 12/2008 | Sekiguchi et al. |
| 2011/0065720 A1 | 3/2011 | Netz et al. |
| 2011/0077253 A1 | 3/2011 | Oost et al. |
| 2011/0092513 A1 | 4/2011 | Braje et al. |
| 2011/0092516 A1 | 4/2011 | Braje et al. |
| 2011/0105454 A1 | 5/2011 | Braje et al. |
| 2011/0257194 A1 | 10/2011 | Lubisch et al. |

FOREIGN PATENT DOCUMENTS

| WO | 2005030755 | 4/2005 |
|---|---|---|
| WO | 2008080970 | 7/2008 |
| WO | 2008080971 | 7/2008 |
| WO | 2008080972 | 7/2008 |
| WO | 2008080973 | 7/2008 |
| WO | 2010142739 | 12/2010 |

OTHER PUBLICATIONS

Scheurer, M.A., et al., The Journal of Thoracic and Cardiovascular Surgery, Feb. 2005, pp. 464-466.*
Decaux, G. et al., "Non-peptide arginine-vasopressin antagonists: the vaptans," Lancet (2008) 371:1624-1632.
Diaz, G.J. et al., "The [3H]dofetilde binding assay is a predictive screening tool for hERG blockade and proarrhythmia: comparison of intact cell and membrane preparations and effects of altering [K+]o," J. Pharm. Toxic Meth. (2004) 50:187-199.
Lemmens-Gruber, R. et al., "Vasopressin antagonists," Cell Mol. Life Sci. (2006) 63:1766-1779.
Ryckmans, T., "Modulation of the vasopressin system for the treatment of CNS diseases," Curr. Opin. Drug Disc. & Dev. (2010) 13:538-547.
Thibonnier, M., "Development and therapeutic indications of orally-active non-peptide vasopressin receptor antagonists," Exp. Opin. Invest. Drugs (1998) 7(5):729-740.
Griebel G., et al., "Anxiolytic- and Antidepressant-Like Effects of the Non-Peptide Vasopressin V1b Receptor Antagonist, SSR149415, Suggest an Innovative Approach for the Treatment of Stress-Related Disorders," Proceedings of the National Academy of Sciences, 2002, vol. 99 (9), pp. 6370-6375.
Griebel G., et al., "The Vasopressin V1b Receptor as a Therapeutic Target in Stress-Related Disorders," Current Drug Targets. CNS and Neurological Disorders, 2003, vol. 2 (3), pp. 191-200.

(Continued)

*Primary Examiner* — Emily Bernhardt
(74) *Attorney, Agent, or Firm* — Lisa V. Mueller; Michael Best & Friedrich LLP

(57) ABSTRACT

The present invention relates to novel substituted oxindole derivatives of formula (I), pharmaceutical compositions comprising them, and their use for the treatment of vasopressin-related disorders

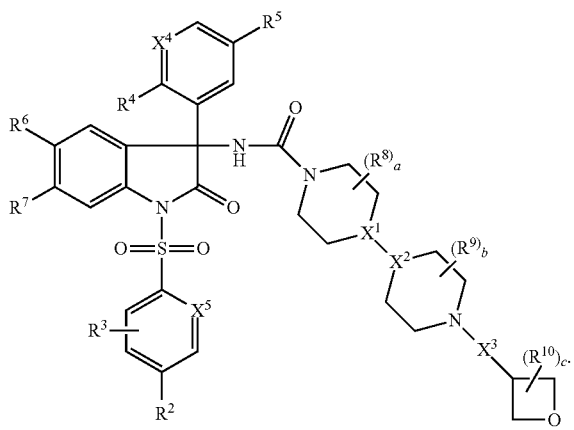

27 Claims, No Drawings

(56) References Cited

OTHER PUBLICATIONS

Hays R.M., et al., "Vasopressin Antagonists—Progress and Promise," The New England Journal of Medicine, 2006, vol. 355 (20), pp. 2146-2148.

International Search Report for Application No. PCT/EP2014/054973, mailed on Apr. 15, 2014, 4 pages.

Jupp B., et al., "New Horizons for therapeutics in Drug and Alcohol Abuse," Pharmacology & Therapeutics, 2010, vol. 125 (1), pp. 138-168.

Ring R.N., et al., "The Central Vasopressinergic System: Examining the Opportunities for Psychiatric Drug Development," Current Pharmaceutical Design, 2005, vol. 11 (2), pp. 205-225.

Zhou Y., et al., "Alcohol: a Stimulant Activating Brain Stress Responsive Systems With Persistent Neuroadaptation," Neuropharmacology, 2014, vol. 87, pp. 51-58.

* cited by examiner

OXINDOLE DERIVATIVES CARRYING AN OXETANE SUBSTITUENT AND USE THEREOF FOR TREATING VASOPRESSINE-RELATED DISEASES

CROSS-REFERENCE TO RELATED APPLICATIONS

This claims priority to U.S. patent application Ser. No. 61/781,468, filed on Mar. 14, 2013, the entire contents of which are fully incorporated herein by reference.

The present invention relates to novel substituted oxindole derivatives, pharmaceutical compositions comprising them, and their use for the treatment of vasopressin-related disorders.

Vasopressin is an endogenous hormone which exerts various effects on organs and tissues. It is suspected that the vasopressin system is involved in various pathological states such as, for example, heart failure and high blood pressure. At present, three receptors (V1a, V1b or V3 and V2) via which vasopressin mediates its numerous effects are known. Antagonists of these receptors are therefore being investigated as possible new therapeutic approaches for the treatment of diseases (M. Thibonnier, Exp. Opin. Invest. Drugs 1998, 7(5), 729-740; T. Ryckmans, Current Opinion in Drug Discovery & Development 13 (2010), 538-547; G. Decaux et al., Lancet 371 (2008), 1624-1632; R. Lemmens-Gruber, M. Kamyar, Cell. Mol. Life. Sci. 63 (2006), 1766-1779).

1-Phenylsulfonyl-1,3-dihydro-2H-indol-2-ones have previously been described as ligands of vasopressin receptors, for example in WO 2005/030755, WO 2006/005609, WO 2006/080574, WO 2008/080970, WO 2008/080971, WO 2008/080972, WO 2008/080973, WO 2009/071687, WO 2009/071689, WO 2009/071690, WO2009/071691, WO 2009/083559, WO 2010/009775 or WO 2010/142739.

Besides the binding affinity for the vasopressin V1b receptor, further properties may be advantageous for the treatment and/or prophylaxis of vasopressin-related disorders, such as, for example:

1.) a selectivity for the vasopressin V1b receptor compared with the vasopressin V1a receptor, i.e. the quotient of the binding affinity for the V1a receptor (Ki(V1a) (determined in the unit "nanomolar (nM)") and the binding affinity for the V1b receptor (Ki(V1b)) (determined in the unit "nanomolar (nM)"). A larger quotient Ki(V1a)/Ki(V1b) means a greater V1b selectivity;
2.) a selectivity for the vasopressin V1b receptor compared with the vasopressin V2 receptor, i.e. the quotient of the binding affinity for the V2 receptor (Ki(V2) (determined in the unit "nanomolar (nM)") and the binding affinity for the V1b receptor (Ki(V1b)) (determined in the unit "nanomolar (nM)"). A larger quotient Ki(V2)/Ki(V1b) means a greater V1b selectivity;
3.) a selectivity for the vasopressin V1b receptor compared with the oxytocin OT receptor, i.e. the quotient of the binding affinity for the OT receptor (Ki(OT) (determined in the unit "nanomolar (nM)") and the binding affinity for the V1b receptor (Ki(V1b)) (determined in the unit "nanomolar (nM)"). A larger quotient Ki(OT)/Ki(V1b) means a greater V1b selectivity.
4.) the metabolic stability, for example determined from the half-lives, measured in vitro, in liver microsomes from various species (e.g. rat or human);
5.) no or only low inhibition of cytochrome P450 (CYP) enzymes: cytochrome P450 (CYP) is the name for a superfamily of heme proteins having enzymatic activity (oxidase). They are also particularly important for the degradation (metabolism) of foreign substances such as drugs or xenobiotics in mammalian organisms. The principal representatives of the types and subtypes of CYP in the human body are: CYP 1A2, CYP 2C9, CYP 2D6 and CYP 3A4. If CYP 3A4 inhibitors (e.g. grapefruit juice, cimetidine, erythromycin) are used at the same time as medicinal substances which are degraded by this enzyme system and thus compete for the same binding site on the enzyme, the degradation thereof may be slowed down and thus effects and side effects of the administered medicinal substance may be undesirably enhanced;
6.) a suitable solubility in water (in mg/ml);
7.) suitable pharmacokinetics (time course of the concentration of the compound of the invention in plasma or in tissue, for example brain). The pharmacokinetics can be described by the following parameters: half-life (in h), volume of distribution (in $l \cdot kg^{-1}$), plasma clearance (in $l \cdot h^{-1} \cdot kg^{-1}$), AUC (area under the curve, area under the concentration-time curve, in $ng \cdot h \cdot l^{-1}$), oral bioavailability (the dose-normalized ratio of AUC after oral administration and AUC after intravenous administration), the so-called brain-plasma ratio (the ratio of AUC in brain tissue and AUC in plasma);
8.) no or only low blockade of the hERG channel: compounds which block the hERG channel may cause a prolongation of the QT interval and thus lead to serious disturbances of cardiac rhythm (for example so-called "torsade de pointes"). The potential of compounds to block the hERG channel can be determined by means of the displacement assay with radiolabelled dofetilide which is described in the literature (G. J. Diaz et al., Journal of Pharmacological and Toxicological Methods, 50 (2004), 187-199). A smaller IC50 in this dofetilide assay means a greater probability of potent hERG blockade. In addition, the blockade of the hERG channel can be measured by electrophysiological experiments on cells which have been transfected with the hERG channel, by so-called whole-cell patch clamping (G. J. Diaz et al., Journal of Pharmacological and Toxicological Methods, 50 (2004), 187-199).

It was therefore an object of the present invention to provide compounds for the treatment or prophylaxis of various vasopressin-related diseases. The compounds were intended to have a high activity and selectivity, especially a high affinity and selectivity vis-à-vis the vasopressin V1b receptor. In addition, the substance of the invention was intended to have one or more of the aforementioned advantages 1.) to 8.).

The object is achieved by compounds of the formula I

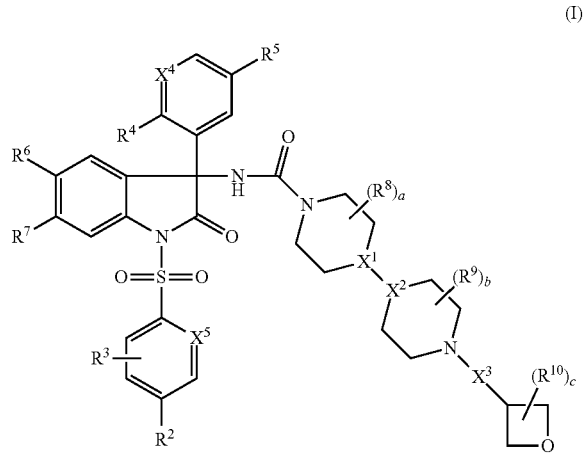

(I)

wherein
$X^1$ and $X^2$ are N or CH, with the proviso that $X^1$ and $X^2$ are not simultaneously N;
$X^3$ is a bond, $C_1$-$C_4$-alkylene, $C_1$-$C_4$-haloalkylene or CO;

$X^4$ is N or CH;

$X^5$ is C—$R^1$ or N;

$R^1$, $R^2$ and $R^3$, independently of each other, are selected from hydrogen, halogen, cyano, $C_1$-$C_3$-alkyl, fluorinated $C_1$-$C_3$-alkyl, $C_1$-$C_3$-hydroxyalkyl, $C_1$-$C_3$-alkoxy and fluorinated $C_1$-$C_3$-alkoxy;

$R^4$ is selected from $C_1$-$C_3$-alkoxy;

$R^5$ is selected from hydrogen and $C_1$-$C_3$-alkoxy;

$R^6$ is selected from cyano and halogen;

$R^7$ is selected from hydrogen, halogen and cyano;

$R^8$ and $R^9$, independently of each other and independently of each occurrence, are selected from halogen, $C_1$-$C_4$-alkyl, $C_1$-$C_4$-haloalkyl, $C_1$-$C_4$-alkoxy and $C_1$-$C_4$-haloalkoxy, with the proviso that $R^8$ and $R^9$ are not halogen, $C_1$-$C_4$-alkoxy or $C_1$-$C_4$-haloalkoxy if they are bound to a carbon atom in α-position to a nitrogen ring atom; or two non-geminal radicals $R^8$ form together a group —$(CH_2)_n$—, where n is 1, 2, 3 or 4, where 1 or 2 hydrogen atoms in this group may be replaced a methyl group; or two non-geminal radicals $R^9$ form together a group —$(CH_2)_n$—, where n is 1, 2, 3 or 4, where 1 or 2 hydrogen atoms in this group may be replaced a methyl group;

each $R^{10}$ is independently selected from halogen, $C_1$-$C_4$-alkyl and $C_1$-$C_4$-haloalkyl;

a is 0, 1, 2, 3 or 4;

b is 0, 1, 2, 3 or 4; and c is 0, 1, 2, 3 or 4;

and N-oxides, stereoisomers and the pharmaceutically acceptable salts thereof, and the compound of the formula I, wherein at least one of the atoms has been replaced by its stable, non-radioactive isotope.

Accordingly, the present invention relates to compounds of the formula I (also "compounds I" hereinafter) and the N-oxides, stereoisomers and the pharmaceutically acceptable salts of the compounds I of the compounds I.

In another aspect, the invention relates to a pharmaceutical composition comprising a therapeutically effective amount of at least one compound of formula I or an N-oxide, a stereoisomer or a pharmaceutically acceptable salt thereof, or comprising at least one compound as defined above or below wherein at least one of the atoms has been replaced by its stable, non-radioactive isotope, preferably wherein at least one hydrogen atom has been replaced by a deuterium atom, in combination with at least one pharmaceutically acceptable carrier and/or auxiliary substance.

In yet another aspect, the invention relates to a compound of formula I or an N-oxide, a stereoisomer or a pharmaceutically acceptable salt thereof for use as a medicament.

In yet another aspect, the invention relates to a compound of formula I or an N-oxide, a stereoisomer or a pharmaceutically acceptable salt thereof for the treatment and/or prophylaxis of vasopressin-related diseases, especially of disorders which respond to the modulation of the vasopressin receptor, in particular of the V1b receptor.

In yet another aspect, the invention relates to the use of a compound of formula I or of an N-oxide, a stereoisomer or a pharmaceutically acceptable salt thereof for the manufacture of a medicament for the treatment and/or prophylaxis of vasopressin-related diseases; especially of disorders which respond to the modulation of the vasopressin receptor, in particular of the V1b receptor.

The pharmaceutically acceptable salts of compounds of the formula I, which are also referred to as physiologically tolerated salts, are ordinarily obtainable by reacting the free base of the compounds I of the invention (i.e. of the compounds I according to structural formula I) with suitable acids. Examples of suitable acids are listed in "Fortschritte der Arzneimittelforschung", 1966, Birkhäuser Verlag, vol. 10, pp. 224-285. These include for example hydrochloric acid, citric acid, tartaric acid, lactic acid, phosphoric acid, methanesulfonic acid, acetic acid, trifluoroacetic acid, formic acid, maleic acid and fumaric acid.

Halogen in the terms of the present invention is fluorine, chlorine, bromine or iodine, preferably fluorine, chlorine or bromine and especially fluorine or chlorine.

$C_1$-$C_3$-Alkyl is a linear or branched alkyl radical having 1 to 3 carbon atoms, such as methyl, ethyl, n-propyl or isopropyl. $C_1$-$C_4$-Alkyl is a linear or branched alkyl radical having 1 to 4 carbon atoms, such as methyl, ethyl, n-propyl, isopropyl, n-butyl, sec-butyl, isobutyl or tert-butyl.

$C_1$-$C_4$-Haloalkyl is $C_1$-$C_4$-alkyl as defined above wherein at least one, e.g. 1, 2, 3, 4 or all of the hydrogen atoms are replaced by a halogen atom. Preferably, $C_1$-$C_4$-haloalkyl is fluorinated $C_1$-$C_4$-alkyl. This is a straight-chain or branched alkyl group having from 1 to 4, in particular 1 to 3 carbon atoms (=fluorinated $C_1$-$C_3$-alkyl), more preferably 1 or 2 carbon atoms (=fluorinated $C_1$-$C_2$-alkyl), wherein at least one, e.g. 1, 2, 3, 4 or all of the hydrogen atoms are replaced by fluorine atoms, such as in fluoromethyl, difluoromethyl, trifluoromethyl, 1-fluoroethyl, (R)-1-fluoroethyl, (S)-1-fluoroethyl, 2-fluoroethyl, 1,1-difluoroethyl, 2,2-difluoroethyl, 2,2,2-trifluoroethyl, 1-fluoropropyl, (R)-1-fluoropropyl, (S)-1-fluoropropyl, 2-fluoropropyl, 3-fluoropropyl, 1,1-difluoropropyl, 2,2-difluoropropyl, 3,3-difluoropropyl, 3,3,3-trifluoropropyl, 2-fluoropropyl, 2-fluoro-1-methylethyl, (R)-2-fluoro-1-methylethyl, (S)-2-fluoro-1-methylethyl, 2,2-difluoro-1-methylethyl, (R)-2,2-difluoro-1-methylethyl, (S)-2,2-difluoro-1-methylethyl, 1,2-difluoro-1-methylethyl, (R)-1,2-difluoro-1-methylethyl, (S)-1,2-difluoro-1-methylethyl, 2,2,2-trifluoro-1-methylethyl, (R)-2,2,2-trifluoro-1-methylethyl, (S)-2,2,2-trifluoro-1-methylethyl, 2-fluoro-1-(fluoromethyl)ethyl, 1-(difluoromethyl)-2,2-difluoroethyl, 1-fluorobutyl, (R)-1-fluorobutyl, (S)-1-fluorobutyl, 2-fluorobutyl, 3-fluorobutyl, 4-fluorobutyl, 1,1-difluorobutyl, 2,2-difluorobutyl, 3,3-difluorobutyl, 4,4-difluorobutyl, 4,4,4-trifluorobutyl, etc.

$C_1$-$C_4$-Hydroxyalkyl is $C_1$-$C_4$-alkyl as defined above wherein one of the hydrogen atoms is replaced by a hydroxyl group. Examples are hydroxymethyl, 1- and 2-hydroxyethyl, 1-, 2- and 3-hydroxy-n-propyl, 1-(hydroxymethyl)-ethyl and the like.

$C_1$-$C_3$-Alkoxy is a linear or branched alkyl radical linked via an oxygen atom and having 1 to 3 carbon atoms. Examples are methoxy, ethoxy, n-propoxy and isopropoxy. $C_1$-$C_4$-Alkoxy is a linear or branched alkyl radical linked via an oxygen atom and having 1 to 4 carbon atoms. Examples are methoxy, ethoxy, n-propoxy, isopropoxy, n-butoxy, sec-butoxy, isobutoxy and tert-butoxy.

$C_1$-$C_4$-Haloalkoxy is $C_1$-$C_4$-alkoxy as defined above wherein at least one, e.g. 1, 2, 3, 4 or all of the hydrogen atoms are replaced by a halogen atom. Preferably, $C_1$-$C_4$-haloalkoxy is fluorinated $C_1$-$C_4$-alkoxy. This is a straight-chain or branched alkoxy group having from 1 to 4, in particular 1 to 3 carbon atoms (=fluorinated $C_1$-$C_3$-alkoxy), more preferably 1 or 2 carbon atoms (=fluorinated $C_1$-$C_2$-alkoxy), wherein at least one, e.g. 1, 2, 3, 4 or all of the hydrogen atoms are replaced by fluorine atoms, such as in fluoromethoxy, difluoromethoxy, trifluoromethoxy, 1-fluoroethoxy, (R)-1-fluoroethoxy, (S)-1-fluoroethoxy, 2-fluoroethoxy, 1,1-difluoroethoxy, 2,2-difluoroethoxy, 2,2,2-trifluoroethoxy, 1-fluoropropoxy, (R)-1-fluoropropoxy, (S)-1-fluoropropoxy, 2-fluoropropoxy, 3-fluoropropoxy, 1,1-difluoropropoxy, 2,2-difluoropropoxy, 3,3-difluoropropoxy, 3,3,3-trifluoropropoxy, 2-fluoro-1-methylethoxy, (R)-2-fluoro-1-methylethoxy, (S)-2-fluoro-1-methylethoxy, 2,2-difluoro-1-methylethoxy, (R)-2,2-difluoro-1-methylethoxy, (S)-2,2-difluoro-1-methylethoxy, 1,2-difluoro-1-methylethoxy, (R)-1,2-difluoro-1-methylethoxy, (S)-1,2-difluoro-1-methylethoxy, 2,2,2-trifluoro-1-methylethoxy, (R)-2,2,2-trifluoro-1-methylethoxy, (S)-2,2,2-trifluoro-1-methylethoxy, 2-fluoro-1-(fluoromethyl)ethoxy, 1-(difluoromethyl)-2,2-difluoroethoxy, (R)-1-fluorobutoxy, (S)-1-fluorobutoxy, 2-fluorobutoxy, 3-fluorobutoxy, 4-fluorobutoxy, 1,1-difluorobutoxy, 2,2-difluorobutoxy, 3,3-difluorobutoxy, 4,4-difluorobutoxy, 4,4,4-trifluorobutoxy, etc $C_1$-$C_4$-Alkylene is a divalent bridging group, such as $CH_2$, $CH_2CH_2$, $CH(CH_3)$, $(CH_2)_3$, $CH(CH_3)CH_2$, $CH_2CH(CH_3)$, $C(CH_3)_2$, $(CH_2)_4$, $CH(CH_3)CH_2CH_2$, $C(CH_3)_2CH_2$, $CH_2CH(CH_3)CH_2$, $CH_2C(CH_3)_2$, $CH_2CH_2CH(CH_3)$, $CH_2C(CH_3)_2$ and the like.

$C_1$-$C_4$-Haloalkylene is a divalent $C_1$-$C_4$-alkylene bridging group as defined above, wherein at least one, e.g. 1, 2, 3, 4 or all of the hydrogen atoms are replaced by a halogen atom. Preferably, $C_1$-$C_4$-haloalkylene is fluorinated $C_1$-$C_4$-alkylene. Examples are CHF, $CF_2$, $CHFCH_2$, $CF_2CH_2$, $CH_2CHF$, $CH_2CF_2$, $CF_2CF_2$, $CF(CH_3)$, $CH(CF_3)$, $CF(CF_3)$, $CHFCH_2CH_2$, $CH_2CHFCH_2$, $CH_2CF_2CH_2$, $CH_2CH(CF_3)CH_2$ and the like.

The compounds of the invention of the formula I and their N-oxides, stereoisomers and pharmacologically acceptable salts may also be present in the form of solvates or hydrates. Solvates mean in the context of the present invention crystalline forms of the compounds I or of their pharmaceutically acceptable salts which comprise solvent molecules incorporated in the crystal lattice. The solvent molecules are preferably incorporated in stoichiometric ratios. Hydrates are a specific form of solvates; the solvent in this case being water.

The statements made hereinafter concerning suitable and preferred features of the invention, especially concerning the radicals $R^1$, $R^2$, $R^3$, $R^4$, $R^5$, $R^6$, $R^7$, $R^8$, $R^9$, $R^{10}$, $X^1$, $X^2$, $X^3$, $X^4$, $X^5$, a, b, c, and n in the compound I, but also concerning the features of the process of the invention and of the use according to the invention apply both taken on their own as well as preferably in any possible combination with one another.

The compounds I are preferably provided in the form of the free base (i.e. according to structural formula I) or in the form of their acid addition salts.

In a preferred embodiment, $R^1$, $R^2$ and $R^3$, independently of each other, are selected from hydrogen, fluorine, cyano, methyl, fluoromethyl, difluoromethyl, trifluoromethyl, methoxy, fluoromethoxy, difluoromethoxy and trifluoromethoxy. More preferably, $R^1$, $R^2$ and $R^3$, independently of each other, are selected from hydrogen, fluorine, cyano, methyl and methoxy.

Preferably, $R^1$ is selected from hydrogen, fluorine, methyl, fluoromethyl, difluoromethyl, trifluoromethyl, methoxy, fluoromethoxy, difluoromethoxy and trifluoromethoxy. More preferably, $R^1$ is selected from hydrogen, fluorine, methyl and methoxy.

Preferably, $R^2$ is selected from hydrogen, fluorine, cyano, methyl, fluoromethyl, difluoromethyl, trifluoromethyl, methoxy, fluoromethoxy, difluoromethoxy and trifluoromethoxy. More preferably, $R^2$ is selected from hydrogen, fluorine, cyano, methoxy, fluoromethoxy, difluoromethoxy and trifluoromethoxy. In particular, $R^2$ is selected from hydrogen, cyano and methoxy.

Preferably, $R^3$ is selected from hydrogen, fluorine, methyl, fluoromethyl, difluoromethyl and trifluoromethyl. More preferably, $R^3$ is selected from hydrogen, fluorine and methyl.

$R^3$ is preferably bound in 3- or 5 position, relative to the 2- and 4-positions of $R^1$ and $R^2$.

Preferably, $R^4$ is selected from methoxy and ethoxy.

Preferably, $R^5$ is hydrogen or methoxy, and in particular hydrogen.

Preferably, $R^6$ is selected from cyano, fluorine and chlorine.

Preferably, $R^7$ is selected from hydrogen and fluorine.

Preferably, each $R^8$ is independently selected from halogen and $C_1$-$C_4$-alkyl, preferably from F, Cl and $CH_3$, with the proviso that $R^8$ is not halogen if it is bound to a carbon atom in α-position to a nitrogen ring atom, or two non-geminal radicals $R^8$ form together a group —$CH_2$— or —$CH_2CH_2$—, preferably —$CH_2$—. More preferably, two non-geminal radicals $R^8$ form together a group —$CH_2$—. The two non-geminal radicals $R^8$ forming together a group —$CH_2$— are preferably bound in 2- and 5-positions, relative to the 4-position of $X^1$.

Preferably, each $R^9$ is independently selected from halogen and $C_1$-$C_4$-alkyl, preferably from F, Cl and $CH_3$, with the proviso that $R^8$ is not halogen if it is bound to a carbon atom in α-position to a nitrogen ring atom, or two non-geminal radicals $R^9$ form together a group —$CH_2$— or —$CH_2CH_2$—, preferably —$CH_2$—. More preferably, two non-geminal radicals $R^9$ form together a group —$CH_2$—. The two non-geminal radicals $R^9$ forming together a group —$CH_2$— are preferably bound in 2- and 5-positions, relative to the 1-position of $X^2$.

Preferably, each $R^{10}$ is independently selected from halogen and $C_1$-$C_4$-alkyl, preferably from F, Cl and $CH_3$.

In one embodiment, $X^1$ is N and $X^2$ is CH.
In another embodiment, $X^1$ is CH and $X^2$ is N.
In another embodiment, $X^1$ is CH and $X^2$ is CH.
Preferably, $X^3$ is a bond or $CH_2$. Specifically, $X^3$ is a bond.
$X^4$ is N or CH. Specifically, $X^4$ is N.
$X^5$ is C—$R^1$ or N. Specifically, $X^5$ is C—$R^1$.
Preferably, a is 0, 1 or 2, in particular 0.
Preferably, b is 0, 1 or 2, in particular 0 or 2.
Preferably, c is 0, 1 or 2, more preferably 0 or 1, in particular 0.

The invention preferably relates to compounds of the formula I in which
$R^1$, $R^2$ and $R^3$, independently of each other, are selected from hydrogen, fluorine, cyano, methyl and methoxy;
$R^4$ is selected from methoxy and ethoxy;
$R^5$ is hydrogen or methoxy;
$R^6$ is selected from cyano, fluorine and chlorine;
$R^7$ is hydrogen or fluorine;
each $R^8$ is independently selected from halogen and $C_1$-$C_4$-alkyl or two non-geminal radicals $R^8$ form together a group —$CH_2$— or —$CH_2CH_2$—;
each $R^9$ is independently selected from halogen and $C_1$-$C_4$-alkyl or two non-geminal radicals $R^9$ form together a group —$CH_2$— or —$CH_2CH_2$—;
each $R^{10}$ is independently selected from halogen and $C_1$-$C_4$-alkyl;
$X^1$ is N or CH;
$X^2$ is N or CH;
where $X^2$ and $X^3$ are not simultaneously N;
$X^3$ is a bond or $CH_2$;
$X^4$ is N or CH;
$X^5$ is C—$R^1$ or N;
a is 0, 1 or 2;
b is 0, 1 or 2;
c is 0, 1 or 2;
and the pharmaceutically acceptable salts thereof.

The invention more preferably relates to compounds of the formula I in which
$R^1$ is selected from hydrogen, fluorine, methyl and methoxy;
$R^2$ is selected from hydrogen, cyano and methoxy;
$R^3$ is selected from hydrogen, fluorine and methyl;
$R^4$ is selected from methoxy and ethoxy;
$R^5$ is hydrogen;
$R^6$ is selected from cyano, fluorine and chlorine;
$R^7$ is hydrogen or fluorine;
each $R^8$ is independently selected from F, Cl and methyl or two non-geminal radicals $R^8$ form together a group —$CH_2$—;
each $R^9$ is independently selected from F, Cl and methyl or two non-geminal radicals $R^9$ form together a group —$CH_2$—;
each $R^{10}$ is independently selected from F, Cl and methyl;
$X^1$ is N or CH;
$X^2$ is N or CH;
where $X^2$ and $X^3$ are not simultaneously N;
$X^3$ is a bond or $CH_2$;
$X^4$ is N or CH;
$X^5$ is C—$R^1$ or N;
a is 0, 1 or 2, preferably 0;
b is 0, 1 or 2, preferably 0 or 2;
c is 0, 1 or 2, preferably 0;
and the pharmaceutically acceptable salts thereof.

The invention particularly relates to compounds of the formula I in which
$R^1$ is selected from hydrogen, fluorine, methyl and methoxy;
$R^2$ is selected from hydrogen, cyano and methoxy;
$R^3$ is selected from hydrogen, fluorine and methyl;
$R^4$ is selected from methoxy and ethoxy;
$R^5$ is hydrogen;
$R^6$ is selected from cyano, fluorine and chlorine;
$R^7$ is hydrogen or fluorine;
two non-geminal radicals $R^9$ form together a group —$CH_2$—;
$X^1$ is N or CH;
$X^2$ is N or CH;
where $X^2$ and $X^3$ are not simultaneously N;
$X^3$ is a bond or $CH_2$;
$X^4$ is N;
$X^5$ is C—$R^1$;
a is 0;
b is 0 or 2;
c is 0;
and the pharmaceutically acceptable salts thereof.

The invention particularly relates to compounds of the formula I in which
$R^1$ is selected from hydrogen, fluorine, methyl and methoxy;
$R^2$ is selected from hydrogen, cyano and methoxy;
$R^3$ is selected from hydrogen, fluorine and methyl;
$R^4$ is selected from methoxy and ethoxy;
$R^5$ is hydrogen;
$R^6$ is selected from cyano, fluorine and chlorine;
$R^7$ is hydrogen or fluorine;
two non-geminal radicals $R^9$ form together a group —$CH_2$—;
$X^1$ is N or CH;
$X^2$ is N or CH;
where $X^2$ and $X^3$ are not simultaneously N;
$X^3$ is a bond or $CH_2$;
$X^4$ is CH;
$X^5$ is C—$R^1$;
a is 0;
b is 0 or 2;
c is 0;
and the pharmaceutically acceptable salts thereof.

The invention particularly relates to compounds of the formula I in which
$R^1$ is selected from hydrogen, fluorine, methyl and methoxy;
$R^2$ is selected from hydrogen, cyano and methoxy;
$R^3$ is selected from hydrogen, fluorine and methyl;
$R^4$ is selected from methoxy and ethoxy;
$R^5$ is hydrogen;
$R^6$ is selected from cyano, fluorine and chlorine;
$R^7$ is hydrogen or fluorine;
two non-geminal radicals $R^9$ form together a group —$CH_2$—;
$X^1$ is N or CH;
$X^2$ is N or CH;
where $X^2$ and $X^3$ are not simultaneously N;
$X^3$ is a bond or $CH_2$;
$X^4$ is N;
$X^5$ is N;
a is 0;
b is 0 or 2;
c is 0;
and the pharmaceutically acceptable salts thereof.

The invention particularly relates to compounds of the formula I in which
$R^1$ is selected from hydrogen, fluorine, methyl and methoxy;
$R^2$ is selected from hydrogen, cyano and methoxy;
$R^3$ is selected from hydrogen, fluorine and methyl;
$R^4$ is selected from methoxy and ethoxy;
$R^5$ is hydrogen;
$R^6$ is selected from cyano, fluorine and chlorine;
$R^7$ is hydrogen or fluorine;
two non-geminal radicals $R^9$ form together a group —$CH_2$—;
$X^1$ is N or CH;
$X^2$ is N or CH;
where $X^2$ and $X^3$ are not simultaneously N;
$X^3$ is a bond or $CH_2$;
$X^4$ is CH;
$X^5$ is N;
a is 0;
b is 0 or 2;
c is 0;
and the pharmaceutically acceptable salts thereof.

Examples of preferred embodiment of the present invention are compounds of the formulae I.1 to I.72 and the N-oxides, stereoisomers and the pharmaceutically acceptable salts thereof, in which the radicals $R^1$, $R^2$, $R^3$, $R^6$ and $R^7$ have one of the above general or preferred meanings, $R^{8a}$, $R^{8b}$, $R^{8c}$ and $R^{8d}$ are hydrogen or have one of the general or preferred meanings given above for $R^8$, $R^{9a}$, $R^{9b}$, $R^{9c}$ and $R^{9d}$ are hydrogen or have one of the general or preferred meanings given above for $R^9$, and $R^{10a}$, $R^{10b}$, $R^{10c}$ and $R^{10d}$ are hydrogen or have one of the general or preferred meanings given above for $R^{10}$. In particular, preferred compounds are the individual compounds compiled in the tables 1 to 2160 below. Moreover, the meanings mentioned below for the individual variables in the tables are per se, independently of the combination in which they are mentioned, a particularly preferred embodiment of the substituents in question.

I.1
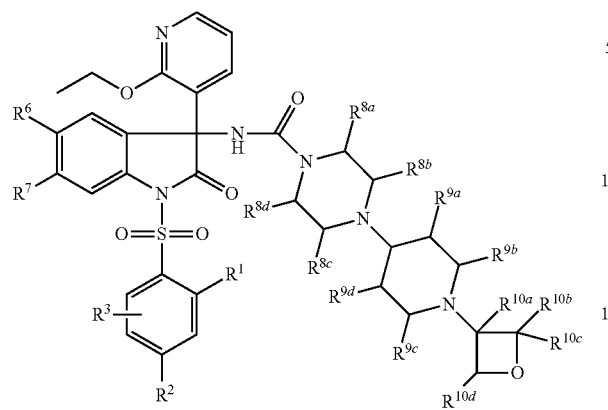
I.2
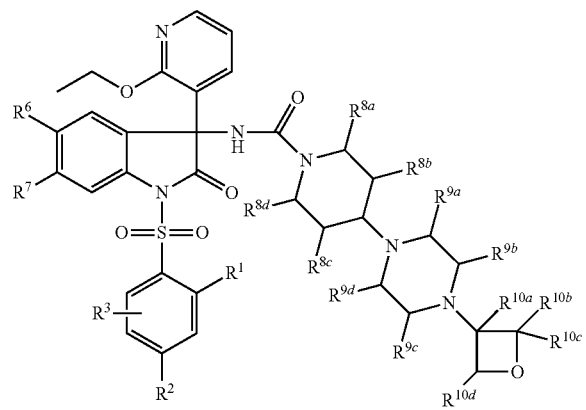
I.3
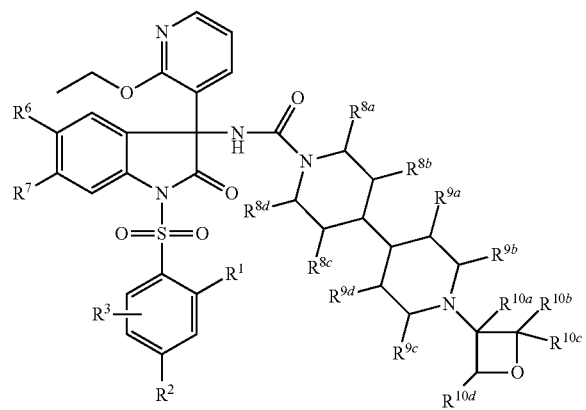
-continued
I.4
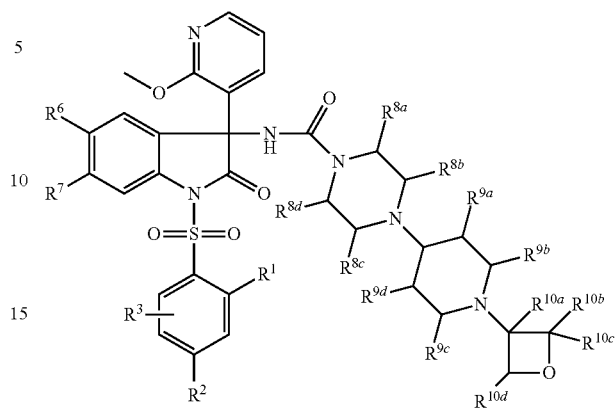
I.5
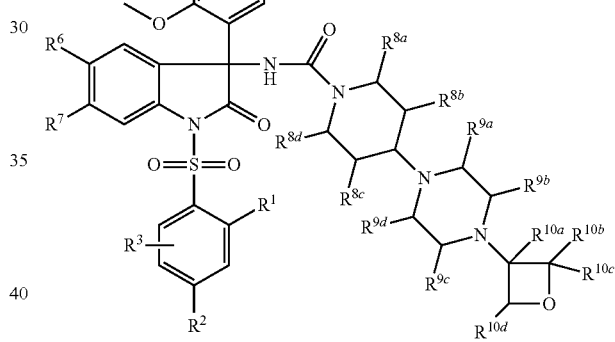
I.6
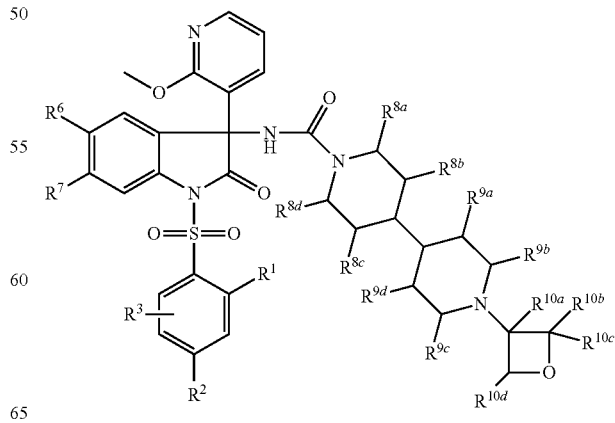

I.7
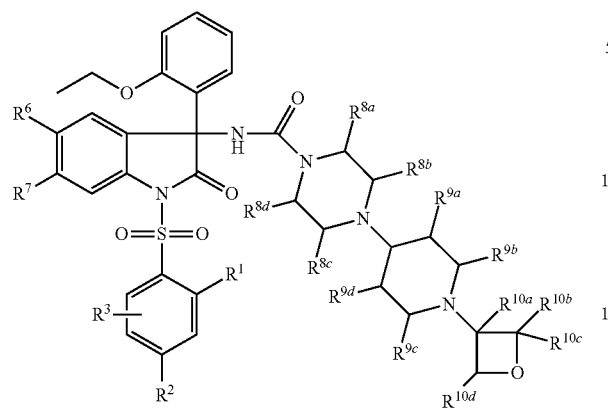
I.10
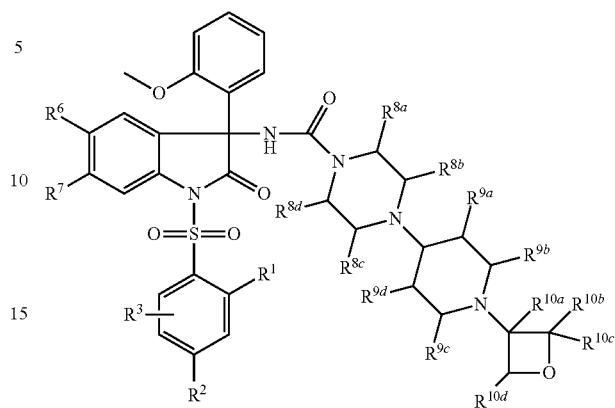
I.8
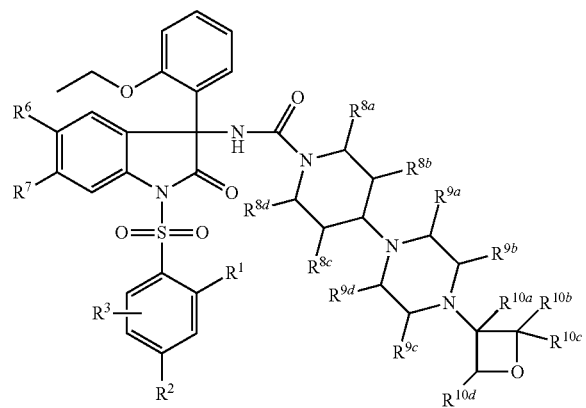
I.11
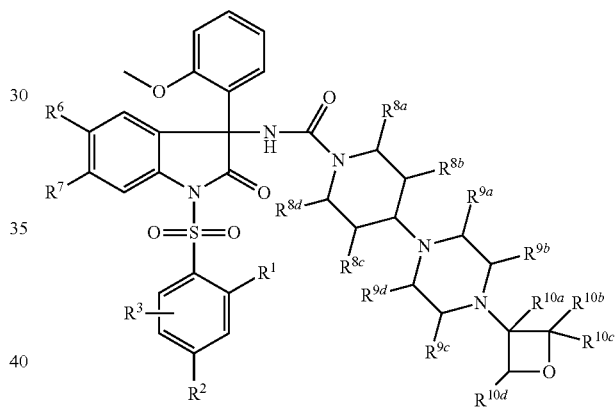
I.9
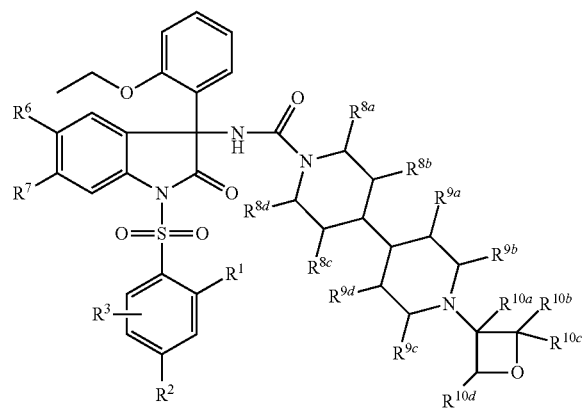
I.12
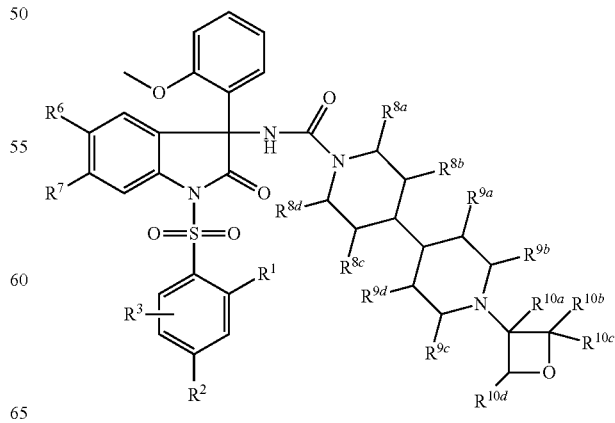

I.13
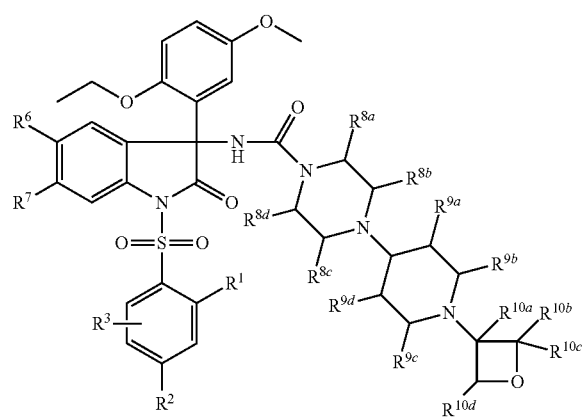
I.16
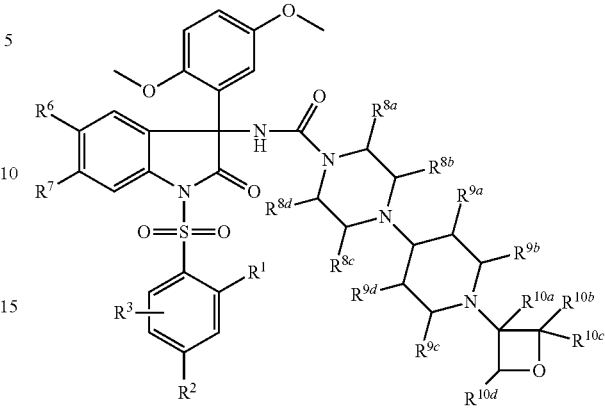
I.14
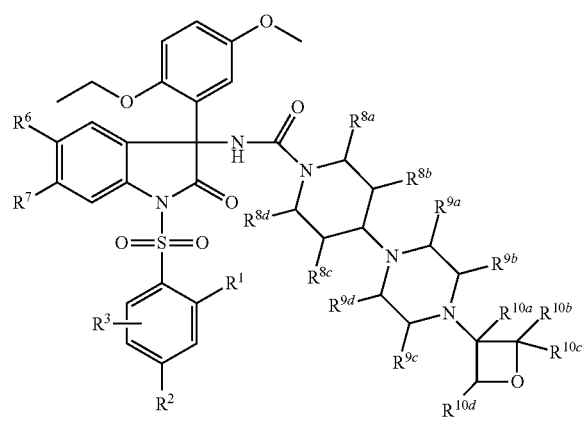
I.17
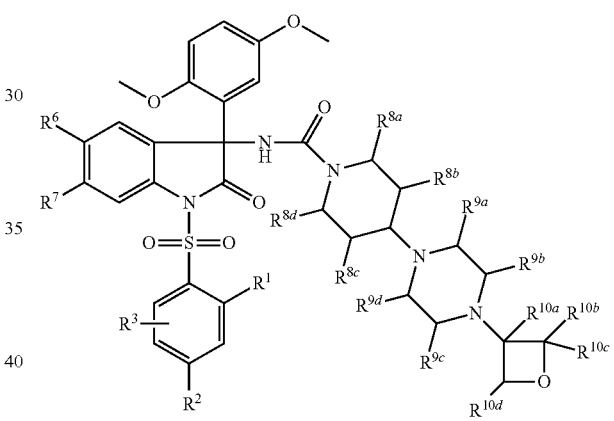
I.15
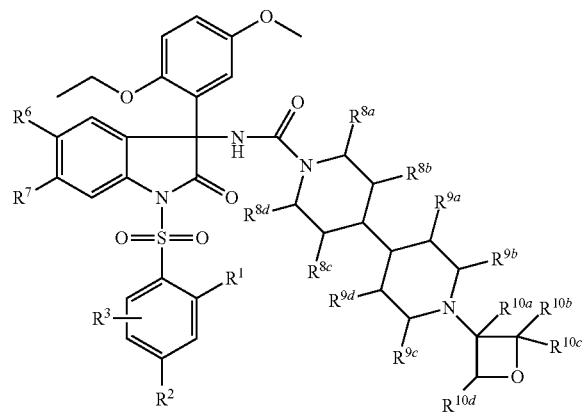
I.18
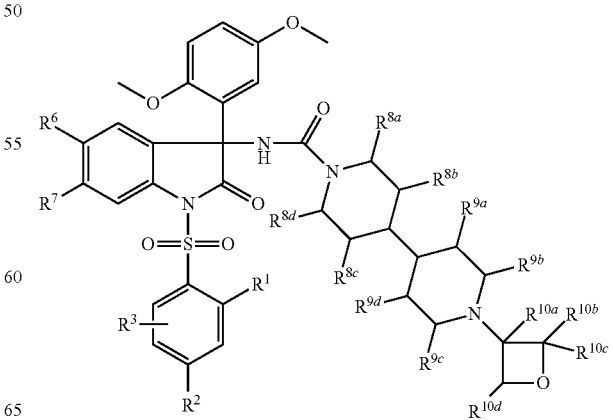

I.19
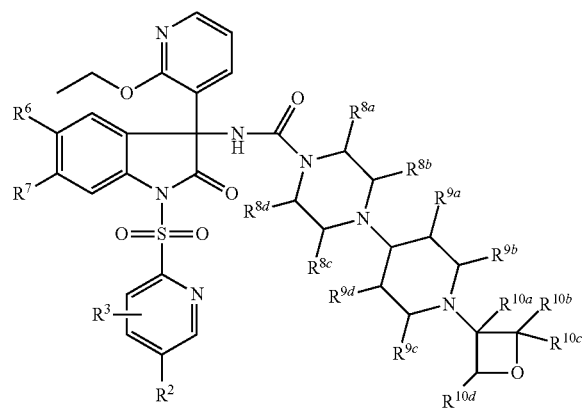
I.22
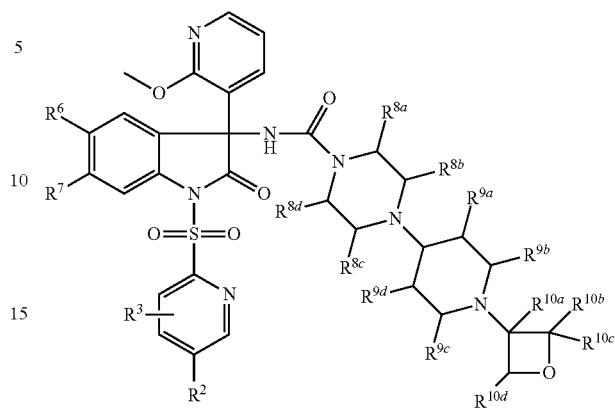
I.20
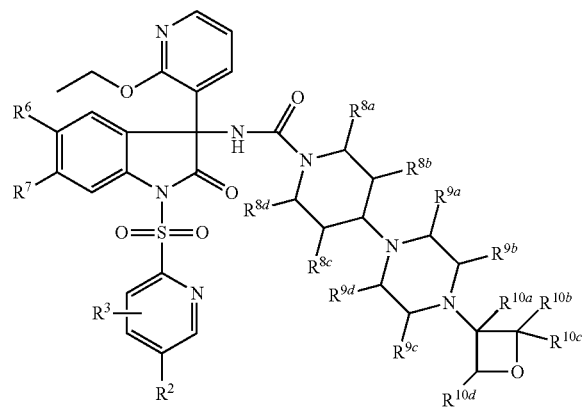
I.23
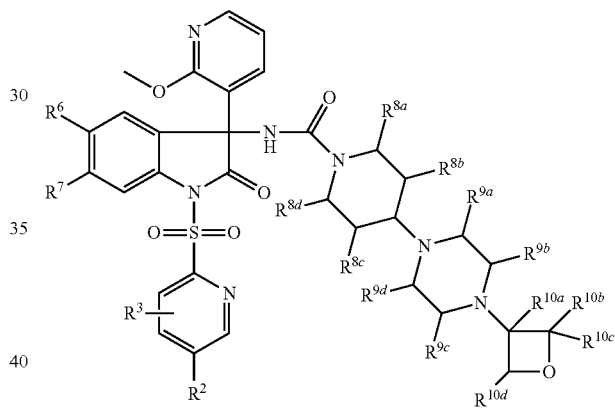
I.21
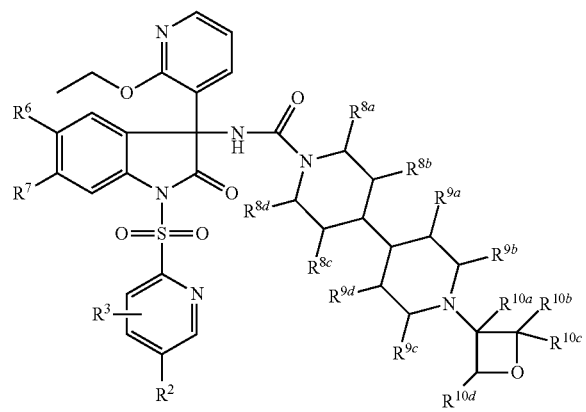
I.24
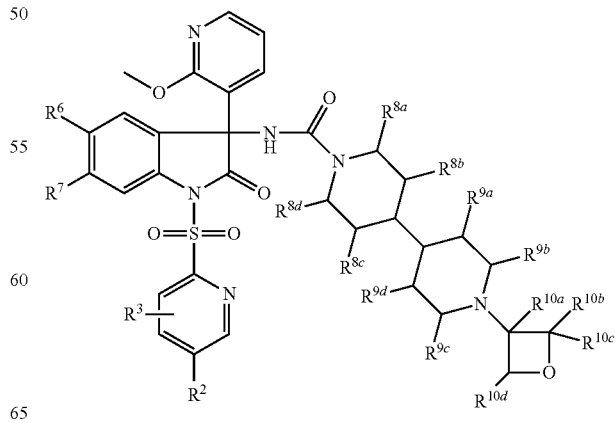

I.25
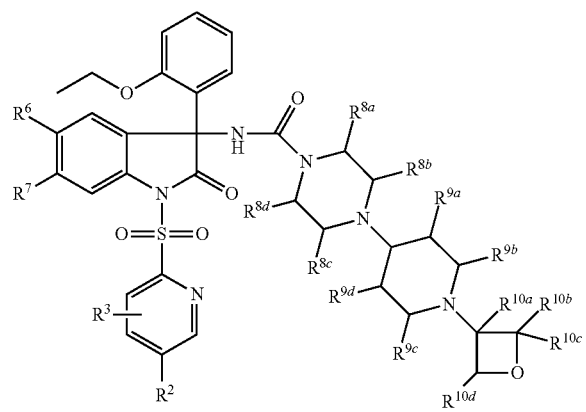
I.26
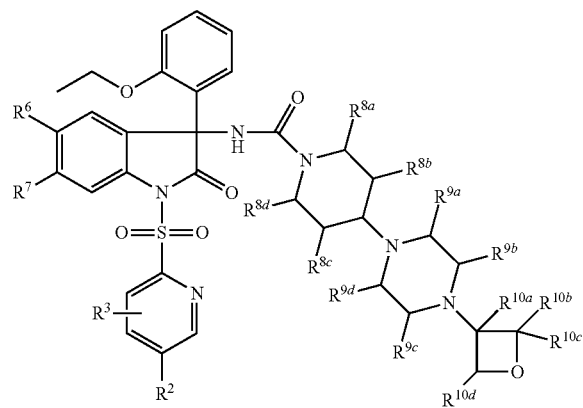
I.27
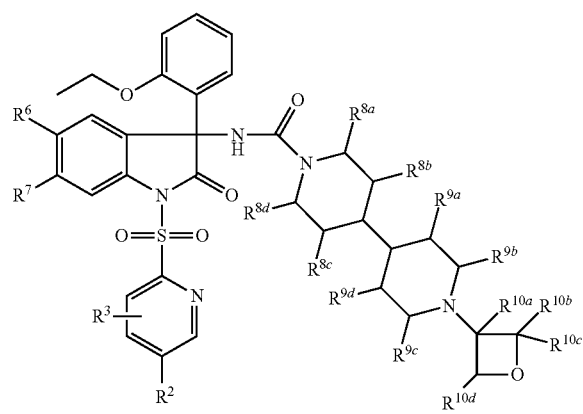
I.28
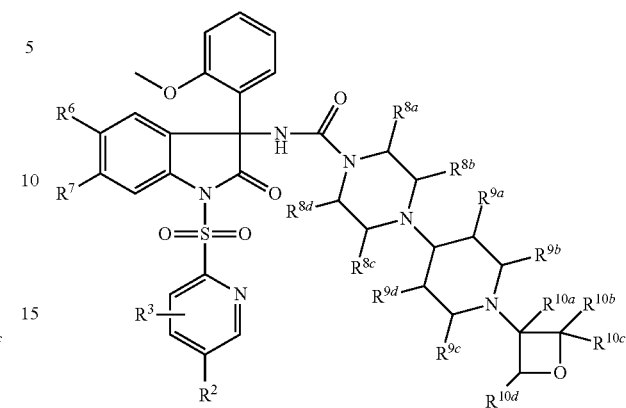
I.29
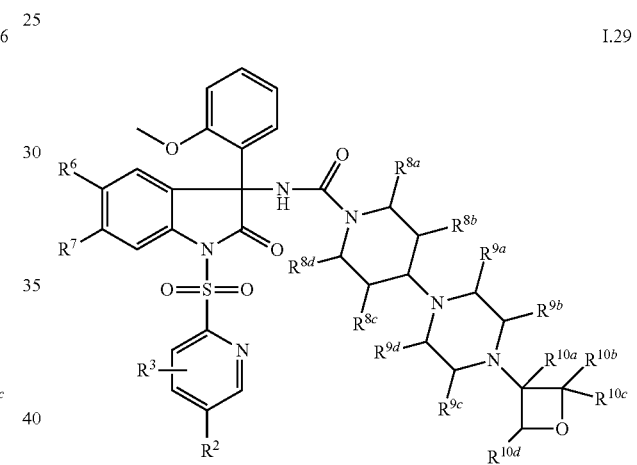
I.30
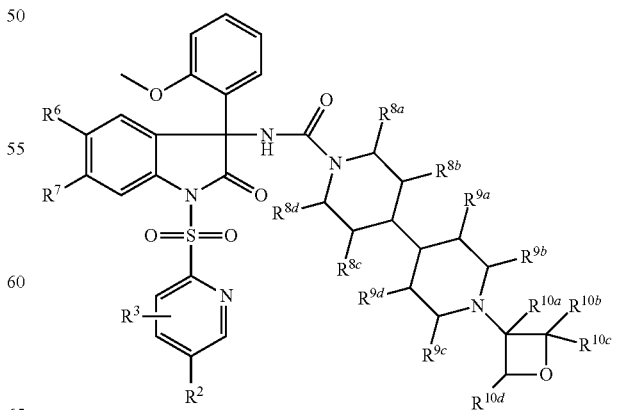

-continued
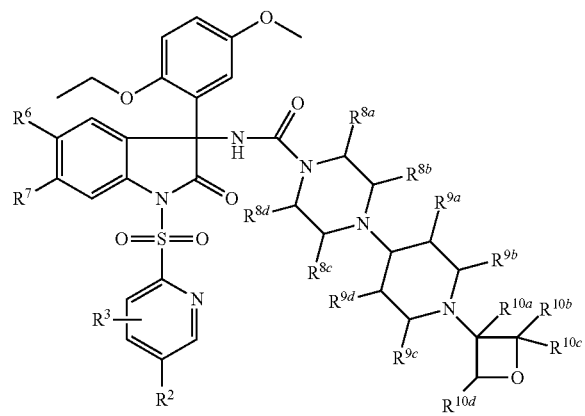
I.31
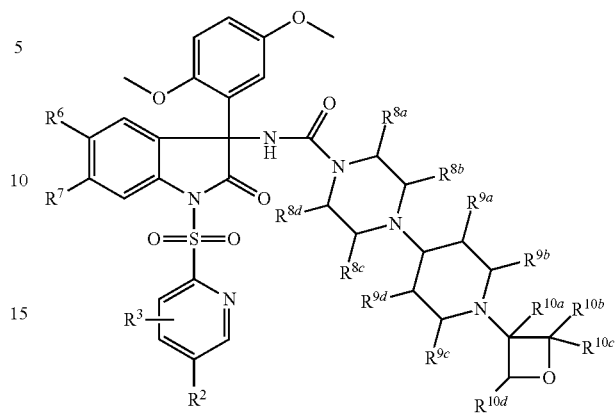
I.34
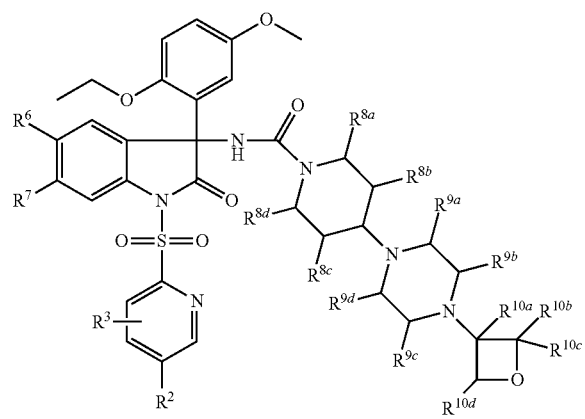
I.32
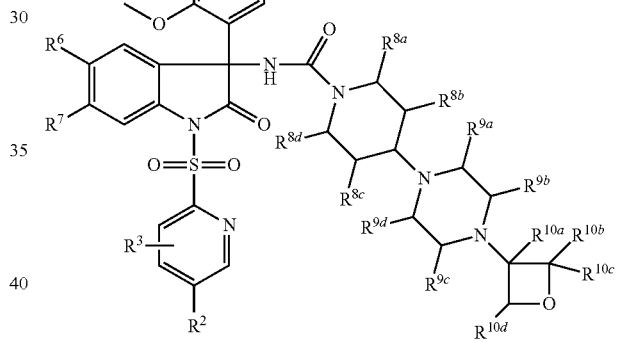
I.35
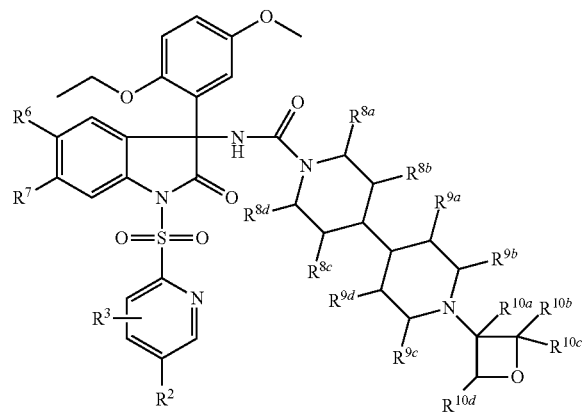
I.33
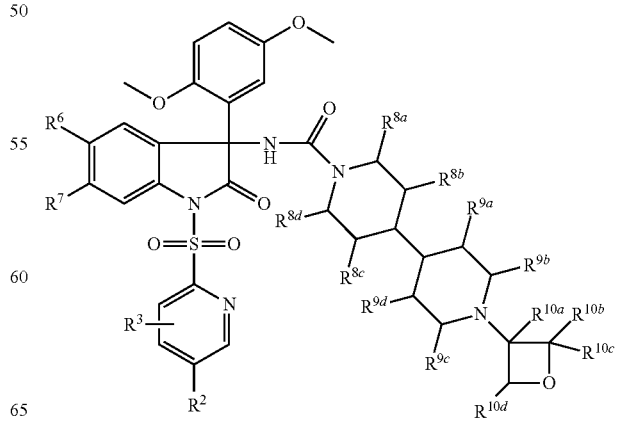
I.36

I.37
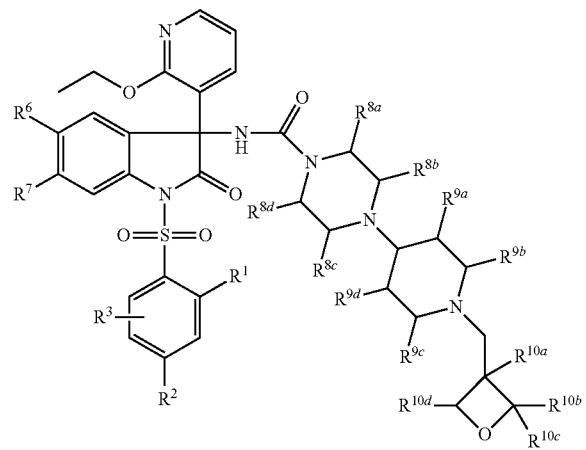
I.40
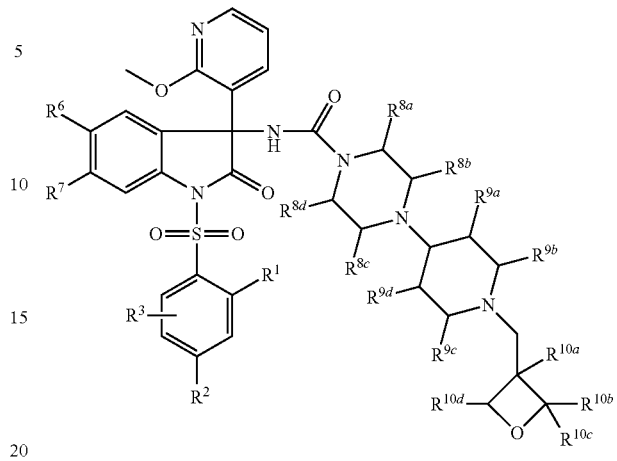
I.38
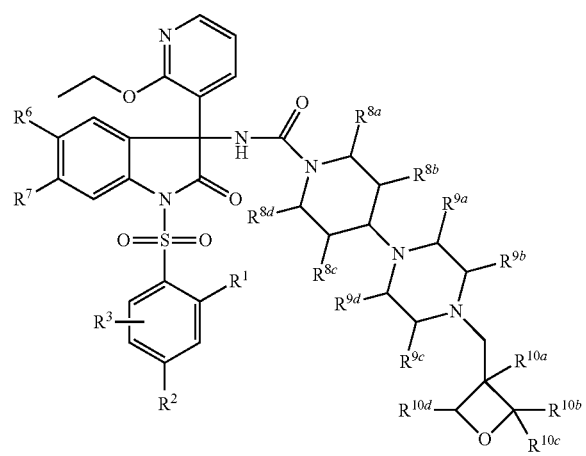
I.41
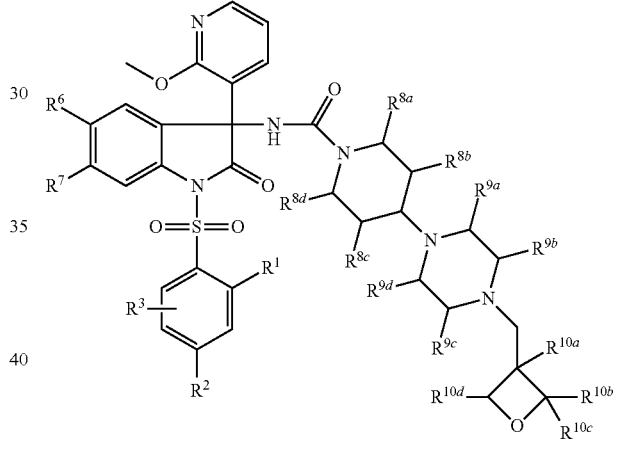
I.39
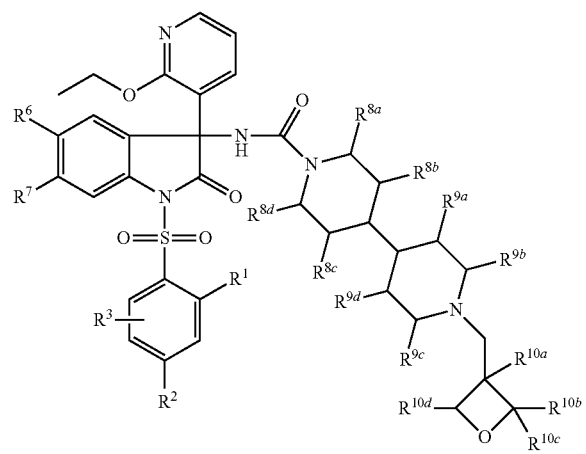
I.42
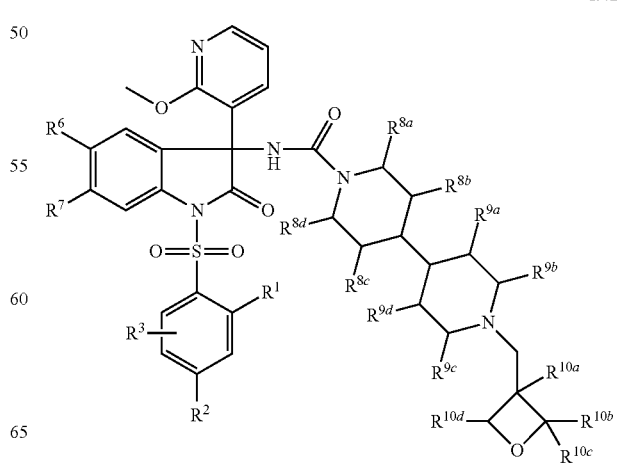

I.43
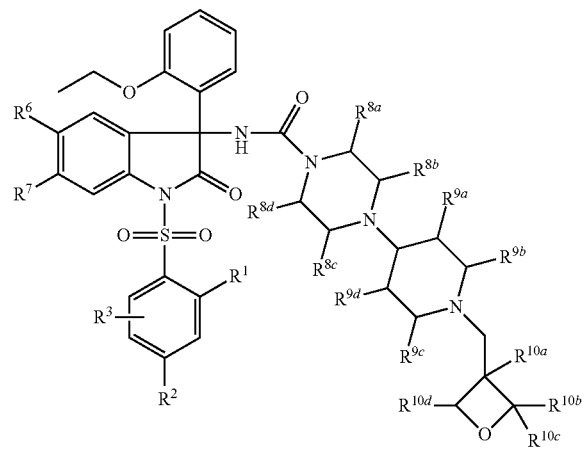
I.44
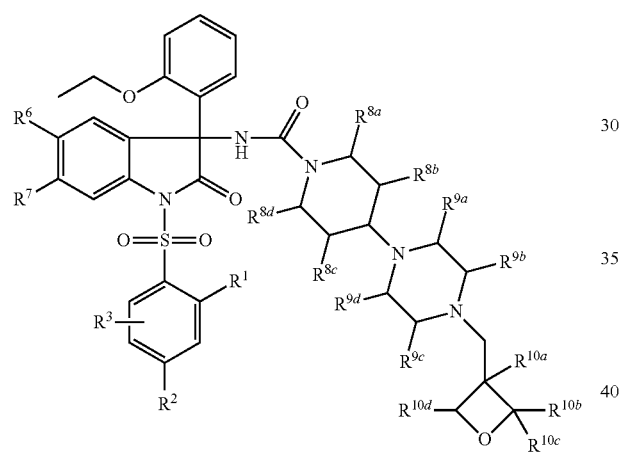
I.45
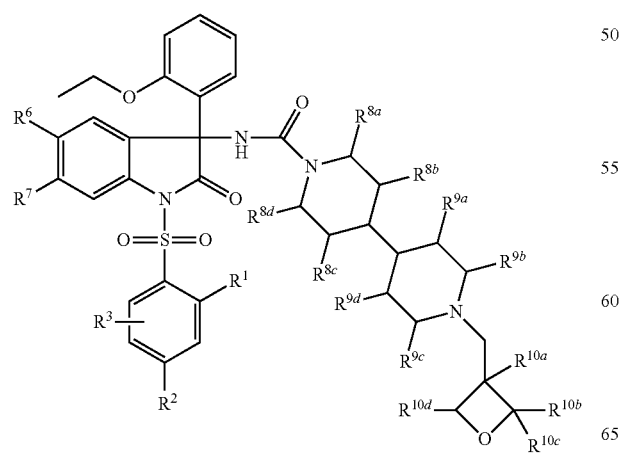
I.46
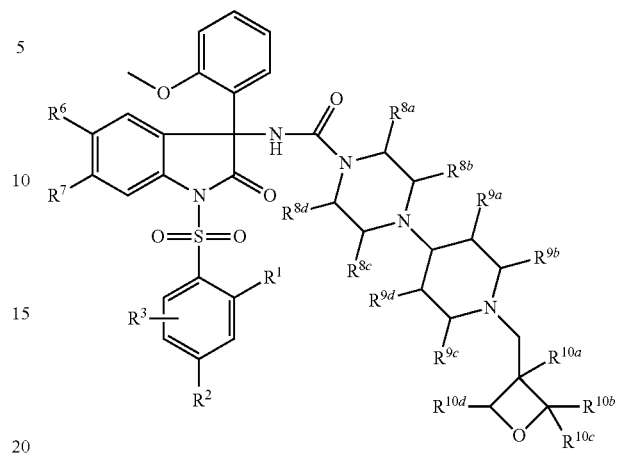
I.47
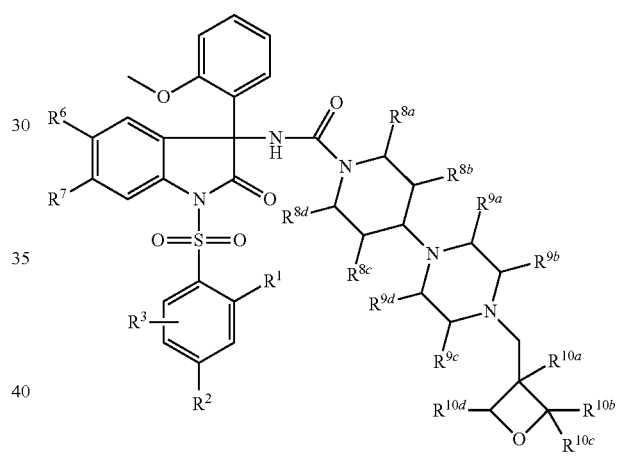
I.48
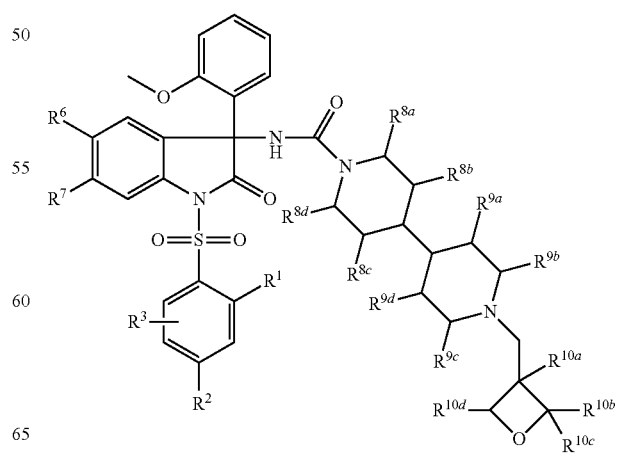

-continued
I.49
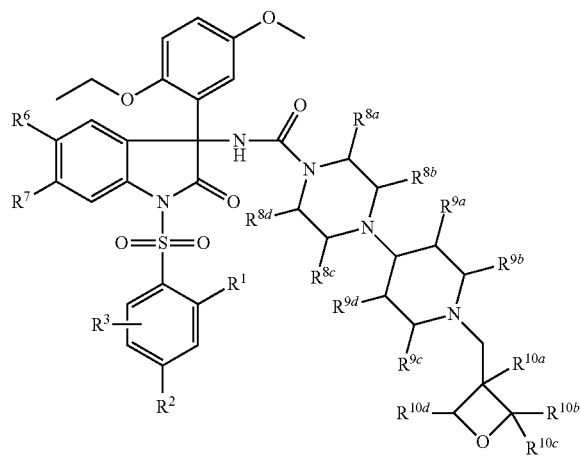
I.50
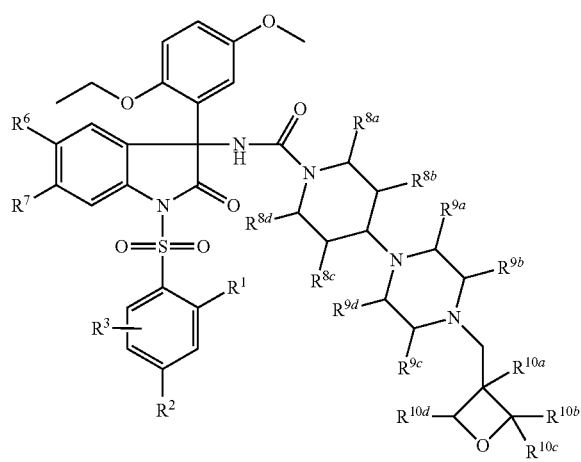
I.51
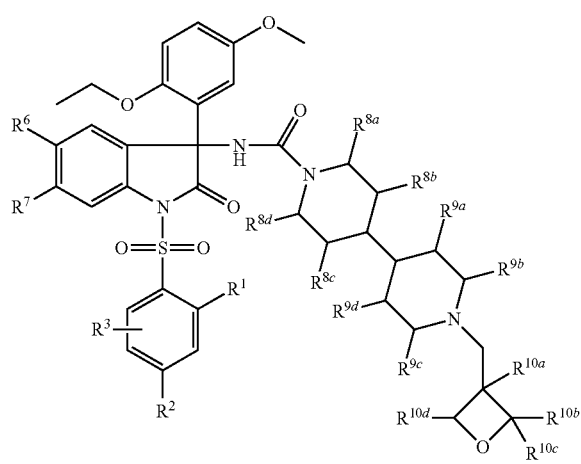
-continued
I.52
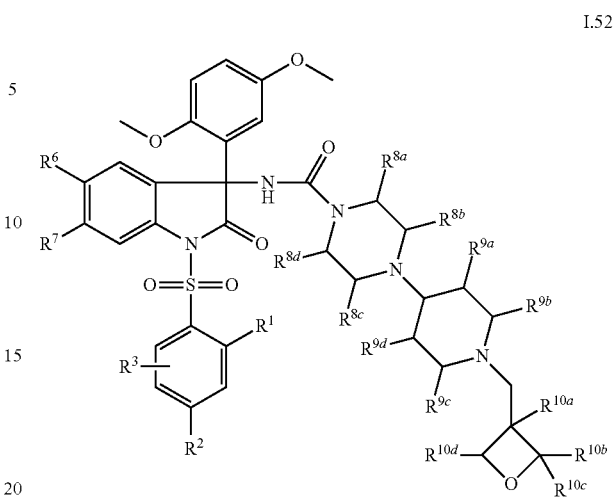
I.53
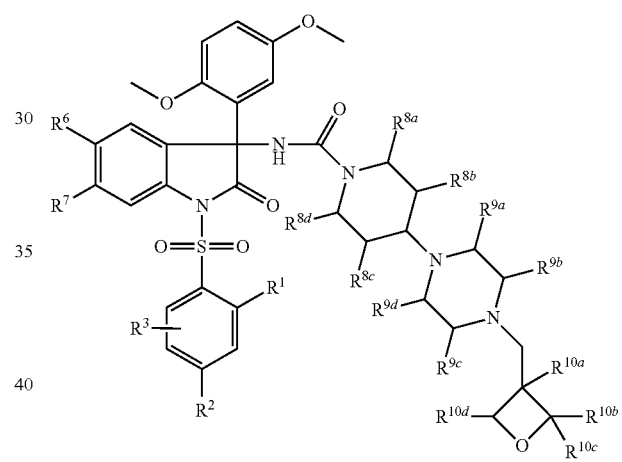
I.54
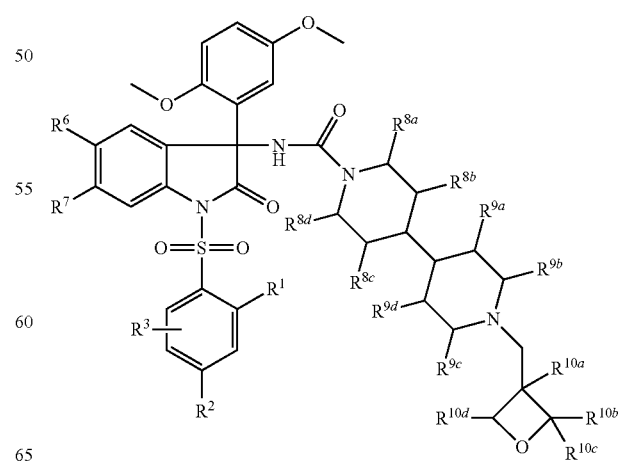

I.55
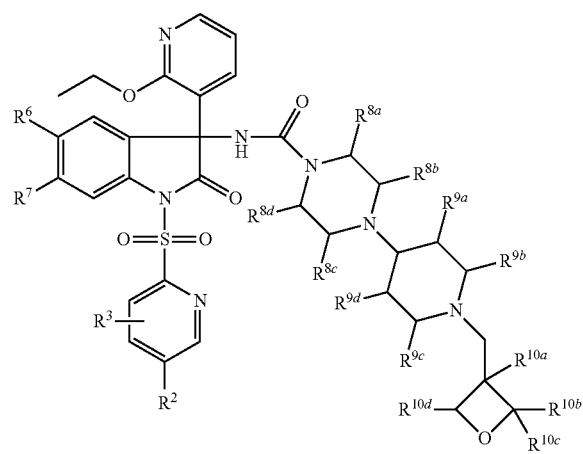
I.56
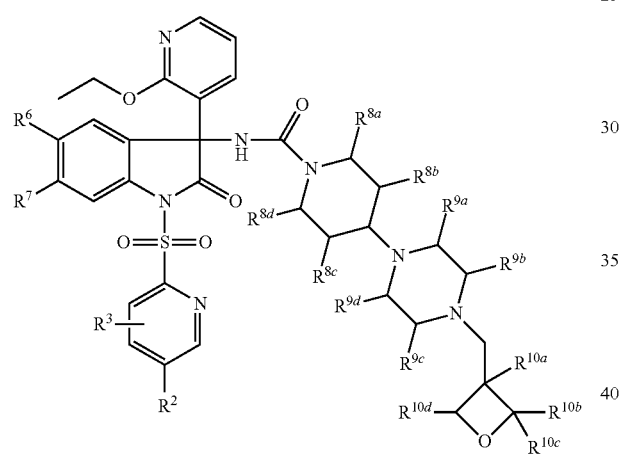
I.57
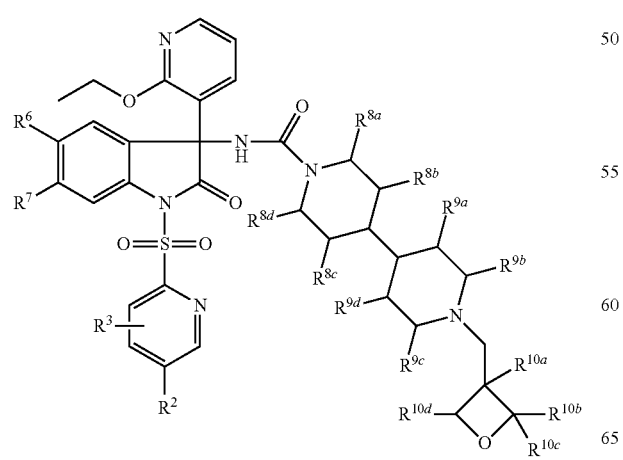
I.58
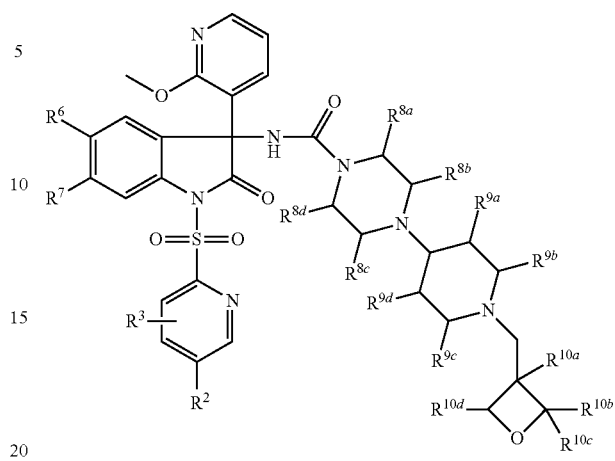
I.59
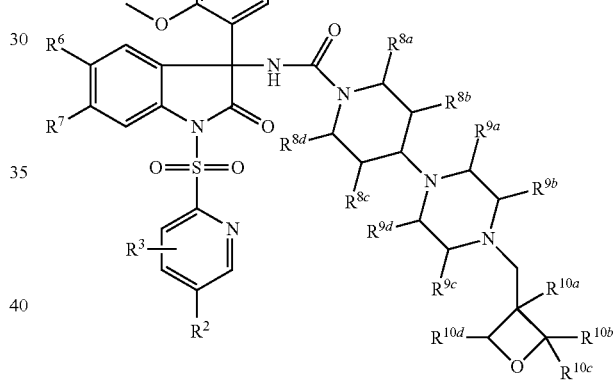
I.60
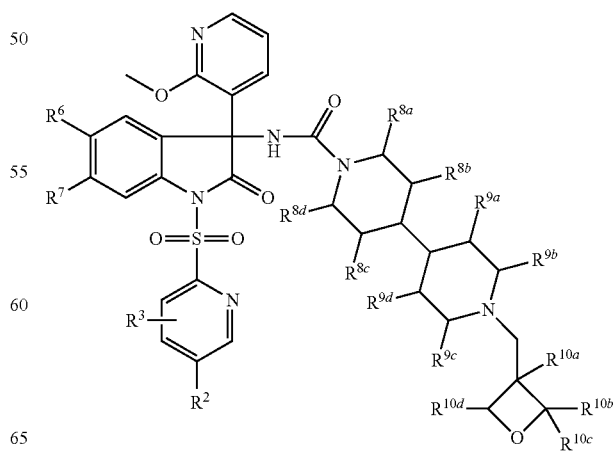

-continued
I.61
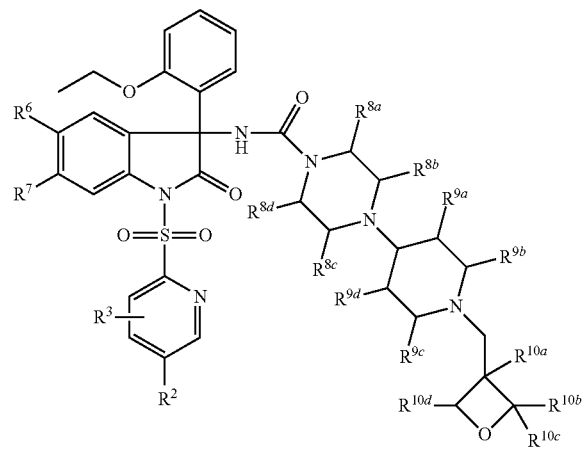
I.62
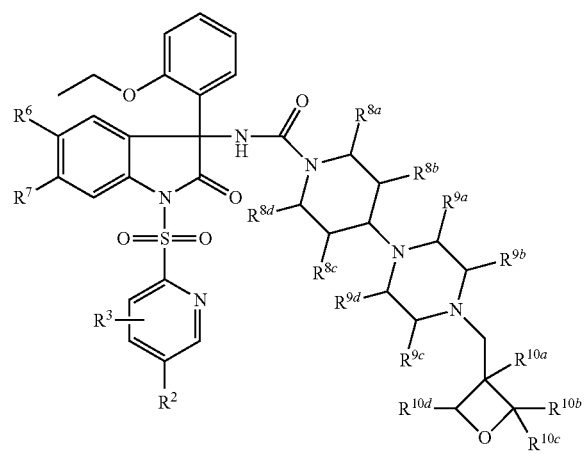
I.63
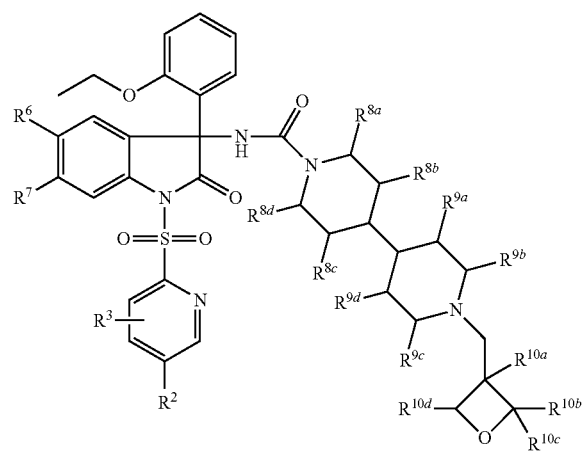
-continued
I.64
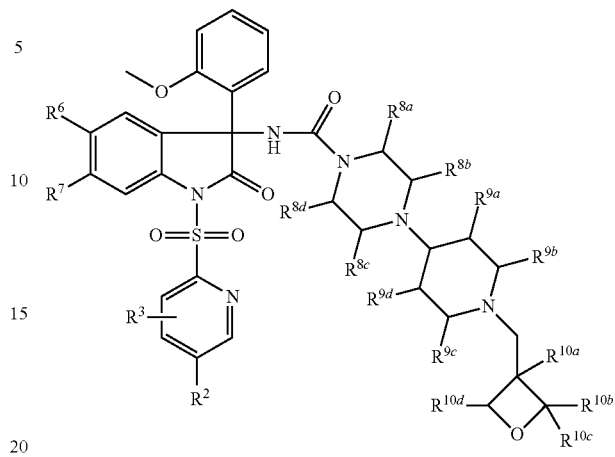
I.65
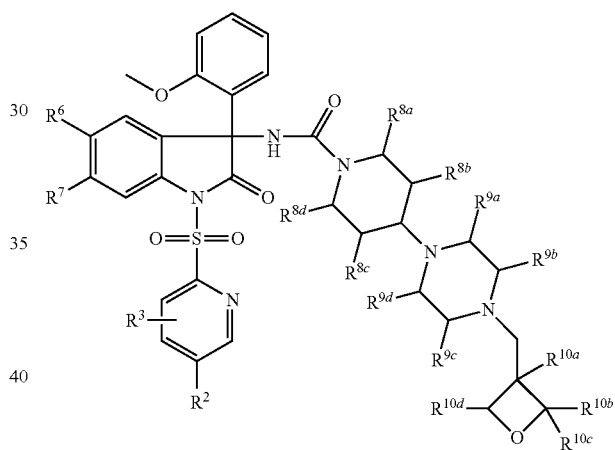
I.66
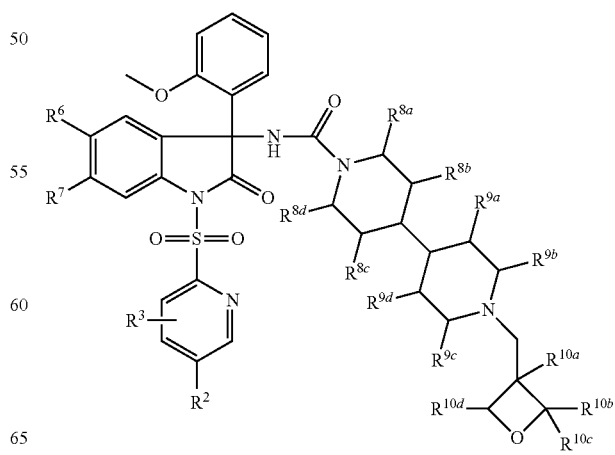

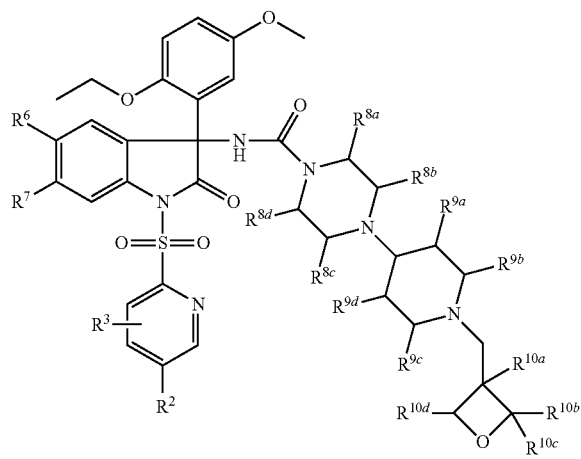
I.67
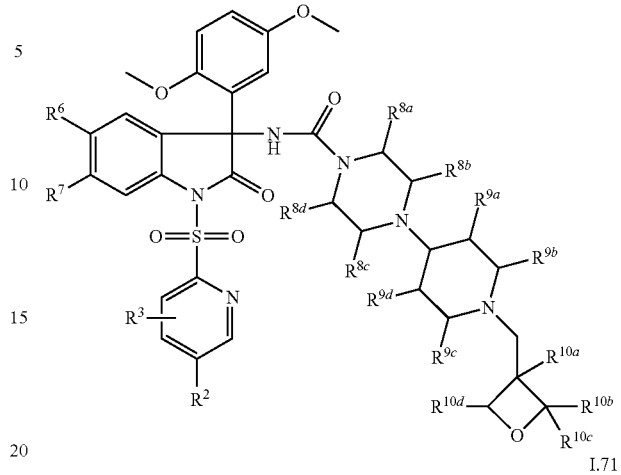
I.70
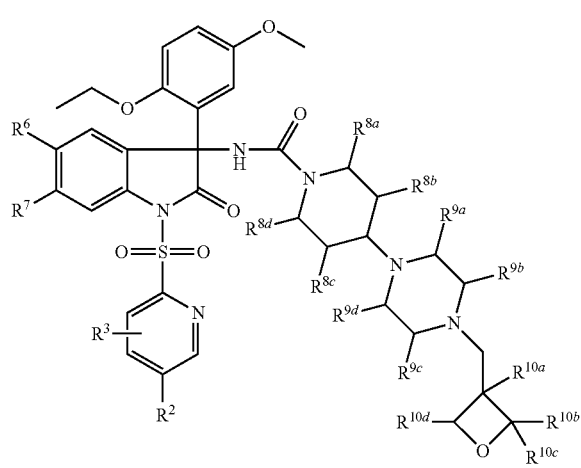
I.68
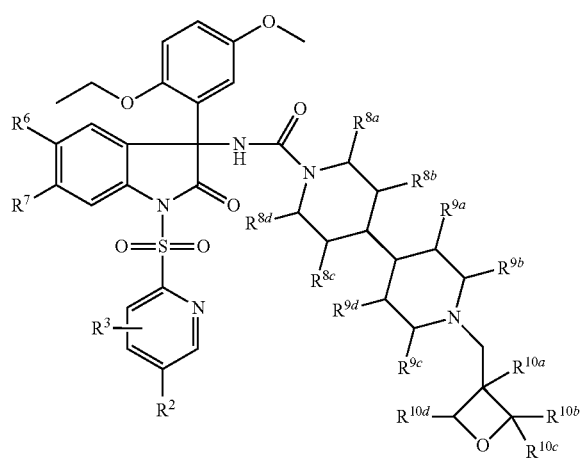
I.69
I.71
I.72
Table 1
Compounds of the formula I.1 in which $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A
Table 2
Compounds of the formula I.1 in which $R^{8a}$ is methyl, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 3

Compounds of the formula I.1 in which $R^{8b}$ is methyl, $R^{8a}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 4

Compounds of the formula I.1 in which $R^{8a}$ and $R^{8b}$ are methyl, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 5

Compounds of the formula I.1 in which $R^{8a}$ and $R^{8c}$ are methyl, $R^{8b}$, $R^{8d}$, $R^{9a}$, $R^{9b}$, $R^{9c}$, $R^{9d}$, $R^{10a}$, $R^{10c}$ and $R^{10d}$ are hydrogen, and $R^1$, $R^2$, $R^3$, $R^6$ and $R^7$ for a compound corresponds in each case to one row of Table A Table 6

Compounds of the formula I.1 in which $R^{8a}$ and $R^{8d}$ are methyl, $R^{8b}$, $R^{8c}$, $R^{9a}$, $R^{9b}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 7

Compounds of the formula I.1 in which $R^{8a}$ and $R^{8c}$ form together a group —$CH_2$—, $R^{8b}$, $R^{8d}$, $R^{9a}$, $R^{9b}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 8

Compounds of the formula I.1 in which $R^{9a}$ is methyl, $R^{8a}$, $R^{8b}$, $R^{8c}$, $R^{8d}$, $R^{9b}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 9

Compounds of the formula I.1 in which $R^{9b}$ is methyl, $R^{8a}$, $R^{8b}$, $R^{8c}$, $R^{8d}$, $R^{9a}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 10

Compounds of the formula I.1 in which $R^{9a}$ and $R^{9b}$ are methyl, $R^{8a}$, $R^{8b}$, $R^{8c}$, $R^{8d}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 11

Compounds of the formula I.1 in which $R^{9a}$ and $R^{9c}$ are methyl, $R^{8a}$, $R^{8b}$, $R^{8c}$, $R^{8d}$, $R^{9b}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 12

Compounds of the formula I.1 in which $R^{9a}$ and $R^{9d}$ are methyl, $R^{8a}$, $R^{8b}$, $R^{8c}$, $R^{8d}$, $R^{9b}$, $R^{9c}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 13

Compounds of the formula I.1 in which $R^{9a}$ is fluorine, $R^{8a}$, $R^{8b}$, $R^{8c}$, $R^{8d}$, $R^{9b}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 14

Compounds of the formula I.1 in which $R^{9a}$ and $R^{9d}$ are fluorine, $R^{8a}$, $R^{8b}$, $R^{8c}$, $R^{8d}$, $R^{9b}$, $R^{9c}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 15

Compounds of the formula I.1 in which $R^{9a}$ is chlorine, $R^{8a}$, $R^{8b}$, $R^{8c}$, $R^{8d}$, $R^{9b}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 16

Compounds of the formula I.1 in which $R^{9a}$ and $R^{9d}$ are chlorine, $R^{8a}$, $R^{8b}$, $R^{8c}$, $R^{8d}$, $R^{9b}$, $R^{9c}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 17

Compounds of the formula I.1 in which $R^{9a}$ and $R^{9c}$ form together a group —$CH_2$—, $R^{8a}$, $R^{8b}$, $R^{8c}$, $R^{8d}$, $R^{9b}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 18

Compounds of the formula I.1 in which $R^{8a}$ and $R^{9a}$ are methyl $R^{8b}$, $R^{8c}$, $R^{8d}$, $R^{9b}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 19

Compounds of the formula I.1 in which $R^{8b}$ and $R^{9b}$ are methyl $R^{8a}$, $R^{8c}$, $R^{8d}$, $R^{9a}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 20

Compounds of the formula I.1 in which $R^{10a}$ is methyl, $R^{8a}$, $R^{8b}$, $R^{8c}$, $R^{8d}$, $R^{9a}$, $R^{9b}$, $R^{9c}$, $R^{9d}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 21

Compounds of the formula I.1 in which $R^{10b}$ is methyl, $R^{8a}$, $R^{8b}$, $R^{8c}$, $R^{8d}$, $R^{9a}$, $R^{9b}$, $R^{9c}$, $R^{9d}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 22

Compounds of the formula I.1 in which $R^{10a}$ and $R^{10b}$ are methyl, $R^{8a}$, $R^{8b}$, $R^{8c}$, $R^{8d}$, $R^{9a}$, $R^{9b}$, $R^{9c}$, $R^{9d}$, $R^{10c}$ and $R^{10d}$ are hydrogen, and $R^1$, $R^2$, $R^3$, $R^6$ and $R^7$ for a compound corresponds in each case to one row of Table A Table 23

Compounds of the formula I.1 in which $R^{10b}$ and $R^{10c}$ are methyl, $R^{8a}$, $R^{8b}$, $R^{8c}$, $R^{8d}$, $R^{9a}$, $R^{9b}$, $R^{9c}$, $R^{9d}$, $R^{10a}$ and $R^{10d}$ are hydrogen, and $R^1$, $R^2$, $R^3$, $R^6$ and $R^7$ for a compound corresponds in each case to one row of Table A Table 24

Compounds of the formula I.1 in which $R^{10a}$, $R^{10b}$ and $R^{10c}$ are methyl, $R^{8a}$, $R^{8b}$, $R^{8c}$, $R^{8d}$, $R^{9a}$, $R^{9b}$, $R^{9c}$, $R^{9d}$ and $R^{10d}$ are hydrogen, and $R^1$, $R^2$, $R^3$, $R^6$ and $R^7$ for a compound corresponds in each case to one row of Table A Table 25

Compounds of the formula I.1 in which $R^{10a}$, $R^{10b}$ and $R^{10d}$ are methyl, $R^{8a}$, $R^{8b}$, $R^{8c}$, $R^{8d}$, $R^{9a}$, $R^{9b}$, $R^{9c}$, $R^{9d}$ and $R^{10c}$ are hydrogen, and $R^1$, $R^2$, $R^3$, $R^6$ and $R^7$ for a compound corresponds in each case to one row of Table A Table 26

Compounds of the formula I.1 in which $R^{8a}$, $R^{9a}$ and $R^{10a}$ are methyl $R^{8b}$, $R^{8c}$, $R^{8d}$, $R^{9b}$, $R^{9c}$, $R^{9d}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 27

Compounds of the formula I.1 in which $R^{10a}$ is fluorine, $R^{8a}$, $R^{8b}$, $R^{8c}$, $R^{8d}$, $R^{9a}$, $R^{9b}$, $R^{9c}$, $R^{9d}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 28

Compounds of the formula I.1 in which $R^{10b}$ is fluorine, $R^{8a}$, $R^{8b}$, $R^{8c}$, $R^{8d}$, $R^{9a}$, $R^{9b}$, $R^{9c}$, $R^{9d}$, $R^{10a}$, $R^{10c}$ and $R^{10d}$ are hydrogen, and $R^1$, $R^2$, $R^3$, $R^6$ and $R^7$ for a compound corresponds in each case to one row of Table A Table 29

Compounds of the formula I.1 in which $R^{10a}$ is chlorine, $R^{8a}$, $R^{8b}$, $R^{8c}$, $R^{8d}$, $R^{9a}$, $R^{9b}$, $R^{9c}$, $R^{9d}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 30

Compounds of the formula I.1 in which $R^{10b}$ is chlorine, $R^{8a}$, $R^{8b}$, $R^{8c}$, $R^{8d}$, $R^{9a}$, $R^{9b}$, $R^{9c}$, $R^{9d}$, $R^{10a}$, $R^{10c}$ and $R^{10d}$ are hydrogen, and $R^1$, $R^2$, $R^3$, $R^6$ and $R^7$ for a compound corresponds in each case to one row of Table A Table 31

Compounds of the formula I.2 in which $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 32

Compounds of the formula I.2 in which $R^{8a}$ is methyl, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 33

Compounds of the formula I.2 in which $R^{8b}$ is methyl, $R^{8a}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 34

Compounds of the formula I.2 in which $R^{8a}$ and $R^{8b}$ are methyl, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 35

Compounds of the formula I.2 in which $R^{8a}$ and $R^{8c}$ are methyl, $R^{8b}$, $R^{8d}$, $R^{9a}$, $R^{9b}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 36

Compounds of the formula I.2 in which $R^{8a}$ and $R^{8d}$ are methyl, $R^{8b}$, $R^{8c}$, $R^{9a}$, $R^{9b}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 37

Compounds of the formula I.2 in which $R^{8b}$ is fluorine, $R^{8a}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 38

Compounds of the formula I.2 in which $R^{8b}$ and $R^{8c}$ are fluorine, $R^{8a}$, $R^{8d}$, $R^{9a}$, $R^{9b}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 39

Compounds of the formula I.2 in which $R^{8b}$ is chlorine, $R^{8a}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 40

Compounds of the formula I.2 in which $R^{8b}$ and $R^{8c}$ are chlorine, $R^{8a}$, $R^{8d}$, $R^{9a}$, $R^{9b}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 41

Compounds of the formula I.2 in which $R^{8a}$ and $R^{8c}$ form together a group —$CH_2$—, $R^{8b}$, $R^{8d}$, $R^{9a}$, $R^{9b}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 42

Compounds of the formula I.2 in which $R^{9a}$ is methyl, $R^{8a}$, $R^{8b}$, $R^{8c}$, $R^{8d}$, $R^{9b}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 43

Compounds of the formula I.2 in which $R^{9b}$ is methyl, $R^{8a}$, $R^{8b}$, $R^{8c}$, $R^{8d}$, $R^{9a}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 44

Compounds of the formula I.2 in which $R^{9a}$ and $R^{9b}$ are methyl, $R^{8a}$, $R^{8b}$, $R^{8c}$, $R^{8d}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 45

Compounds of the formula I.2 in which $R^{9a}$ and $R^{9c}$ are methyl, $R^{8a}$, $R^{8b}$, $R^{8c}$, $R^{8d}$, $R^{9b}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 46

Compounds of the formula I.2 in which $R^{9a}$ and $R^{9d}$ are methyl, $R^{8a}$, $R^{8b}$, $R^{8c}$, $R^{8d}$, $R^{9b}$, $R^{9c}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 47

Compounds of the formula I.2 in which $R^{9a}$ and $R^{9c}$ form together a group —$CH_2$—, $R^{8a}$, $R^{8b}$, $R^{8c}$, $R^{8d}$, $R^{9b}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 48

Compounds of the formula I.2 in which $R^{8a}$ and $R^{9a}$ are methyl $R^{8b}$, $R^{8c}$, $R^{8d}$, $R^{9b}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 49

Compounds of the formula I.2 in which $R^{8b}$ and $R^{9b}$ are methyl $R^{8a}$, $R^{8c}$, $R^{8d}$, $R^{9a}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 50

Compounds of the formula I.2 in which $R^{10a}$ is methyl, $R^{8a}$, $R^{8b}$, $R^{8c}$, $R^{8d}$, $R^{9a}$, $R^{9b}$, $R^{9c}$, $R^{9d}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 51

Compounds of the formula I.2 in which $R^{10b}$ is methyl, $R^{8a}$, $R^{8b}$, $R^{8c}$, $R^{8d}$, $R^{9a}$, $R^{9b}$, $R^{9c}$, $R^{9d}$, $R^{10a}$, $R^{10c}$ and $R^{10d}$ are hydrogen, and $R^1$, $R^2$, $R^3$, $R^6$ and $R^7$ for a compound corresponds in each case to one row of Table A Table 52

Compounds of the formula I.2 in which $R^{10a}$ and $R^{10b}$ are methyl, $R^{8a}$, $R^{8b}$, $R^{8c}$, $R^{8d}$, $R^{9a}$, $R^{9b}$, $R^{9c}$, $R^{9d}$, $R^{10c}$ and $R^{10d}$ are hydrogen, and $R^1$, $R^2$, $R^3$, $R^6$ and $R^7$ for a compound corresponds in each case to one row of Table A Table 53

Compounds of the formula I.2 in which $R^{10b}$ and $R^{10c}$ are methyl, $R^{8a}$, $R^{8b}$, $R^{8c}$, $R^{8d}$, $R^{9a}$, $R^{9b}$, $R^{9c}$, $R^{9d}$, $R^{10a}$ and $R^{10d}$ are hydrogen, and $R^1$, $R^2$, $R^3$, $R^6$ and $R^7$ for a compound corresponds in each case to one row of Table A Table 54

Compounds of the formula I.2 in which $R^{10a}$, $R^{10b}$ and $R^{10c}$ are methyl, $R^{8a}$, $R^{8b}$, $R^{8c}$, $R^{8d}$, $R^{9a}$, $R^{9b}$, $R^{9c}$, $R^{9d}$ and $R^{10d}$ are hydrogen, and $R^1$, $R^2$, $R^3$, $R^6$ and $R^7$ for a compound corresponds in each case to one row of Table A Table 55
Compounds of the formula I.2 in which $R^{10a}$, $R^{10b}$ and $R^{10d}$ are methyl, $R^{8a}$, $R^{8b}$, $R^{8c}$, $R^{8d}$, $R^{9a}$, $R^{9b}$, $R^{9c}$, $R^{9d}$ and $R^{10c}$ are hydrogen, and $R^1$, $R^2$, $R^3$, $R^6$ and $R^7$ for a compound corresponds in each case to one row of Table A Table 56
Compounds of the formula I.2 in which $R^{8a}$, $R^{9a}$ and $R^{10a}$ are methyl $R^{8b}$, $R^{8c}$, $R^{8d}$, $R^{9b}$, $R^{9c}$, $R^{9d}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 57
Compounds of the formula I.2 in which $R^{10a}$ is fluorine, $R^{8a}$, $R^{8b}$, $R^{8c}$, $R^{8d}$, $R^{9a}$, $R^{9b}$, $R^{9c}$, $R^{9d}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 58
Compounds of the formula I.2 in which $R^{10b}$ is fluorine, $R^{8a}$, $R^{8b}$, $R^{8c}$, $R^{8d}$, $R^{9a}$, $R^{9b}$, $R^{9c}$, $R^{9d}$, $R^{10a}$, $R^{10c}$ and $R^{10d}$ are hydrogen, and $R^1$, $R^2$, $R^3$, $R^6$ and $R^7$ for a compound corresponds in each case to one row of Table A Table 59
Compounds of the formula I.2 in which $R^{10a}$ is chlorine, $R^{8a}$, $R^{8b}$, $R^{8c}$, $R^{8d}$, $R^{9a}$, $R^{9b}$, $R^{9c}$, $R^{9d}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 60
Compounds of the formula I.2 in which $R^{10b}$ is chlorine, $R^{8a}$, $R^{8b}$, $R^{8c}$, $R^{8d}$, $R^{9a}$, $R^{9b}$, $R^{9c}$, $R^{9d}$, $R^{10a}$, $R^{10c}$ and $R^{10d}$ are hydrogen, and $R^1$, $R^2$, $R^3$, $R^6$ and $R^7$ for a compound corresponds in each case to one row of Table A Table 61
Compounds of the formula I.3 in which $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 62
Compounds of the formula I.3 in which $R^{8a}$ is methyl, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 63
Compounds of the formula I.3 in which $R^{8b}$ is methyl, $R^{8a}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 64
Compounds of the formula I.3 in which $R^{8a}$ and $R^{8b}$ are methyl, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 65
Compounds of the formula I.3 in which $R^{8a}$ and $R^{8c}$ are methyl, $R^{8b}$, $R^{8d}$, $R^{9a}$, $R^{9b}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 66
Compounds of the formula I.3 in which $R^{8a}$ and $R^{8d}$ are methyl, $R^{8b}$, $R^{8c}$, $R^{9a}$, $R^{9b}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 67
Compounds of the formula I.2 in which $R^{8b}$ is fluorine, $R^{8a}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 68
Compounds of the formula I.2 in which $R^{8b}$ and $R^{8c}$ are fluorine, $R^{8a}$, $R^{8d}$, $R^{9a}$, $R^{9b}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 69
Compounds of the formula I.2 in which $R^{8b}$ is chlorine, $R^{8a}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 70
Compounds of the formula I.2 in which $R^{8b}$ and $R^{8c}$ are chlorine, $R^{8a}$, $R^{8d}$, $R^{9a}$, $R^{9b}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 71
Compounds of the formula I.3 in which $R^{8a}$ and $R^{8c}$ form together a group —CH$_2$—, $R^{8b}$, $R^{8d}$, $R^{9a}$, $R^{9b}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 72
Compounds of the formula I.3 in which $R^{9a}$ is methyl, $R^{8a}$, $R^{8b}$, $R^{8c}$, $R^{8d}$, $R^{9b}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 73
Compounds of the formula I.3 in which $R^{9b}$ is methyl, $R^{8a}$, $R^{8b}$, $R^{8c}$, $R^{8d}$, $R^{9a}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 74
Compounds of the formula I.3 in which $R^{9a}$ and $R^{9b}$ are methyl, $R^{8a}$, $R^{8b}$, $R^{8c}$, $R^{8d}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 75
Compounds of the formula I.3 in which $R^{9a}$ and $R^{9c}$ are methyl, $R^{8a}$, $R^{8b}$, $R^{8c}$, $R^{8d}$, $R^{9b}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 76
Compounds of the formula I.3 in which $R^{9a}$ and $R^{9d}$ are methyl, $R^{8a}$, $R^{8b}$, $R^{8c}$, $R^{8d}$, $R^{9b}$, $R^{9c}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 77
Compounds of the formula I.3 in which $R^{9a}$ is fluorine, $R^{8a}$, $R^{8b}$, $R^{8c}$, $R^{8d}$, $R^{9b}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 78
Compounds of the formula I.3 in which $R^{9a}$ and $R^{9d}$ are fluorine, $R^{8a}$, $R^{8b}$, $R^{8c}$, $R^{8d}$, $R^{9b}$, $R^{9c}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 79
Compounds of the formula I.3 in which $R^{9a}$ is chlorine, $R^{8a}$, $R^{8b}$, $R^{8c}$, $R^{8d}$, $R^{9b}$, $R^{9c}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 80
Compounds of the formula I.3 in which $R^{9a}$ and $R^{9d}$ are chlorine, $R^{8a}$, $R^{8b}$, $R^{8c}$, $R^{8d}$, $R^{9b}$, $R^{9c}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 81
Compounds of the formula I.3 in which $R^{9a}$ and $R^{9c}$ form together a group —$CH_2$—, $R^{8a}$, $R^{8b}$, $R^{8c}$, $R^{8d}$, $R^{9b}$, $R^{9d}$, $R^{10a}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 82
Compounds of the formula I.3 in which $R^{10a}$ is methyl, $R^{8a}$, $R^{8b}$, $R^{8c}$, $R^{8d}$, $R^{9a}$, $R^{9b}$, $R^{9c}$, $R^{9d}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 83
Compounds of the formula I.3 in which $R^{10b}$ is methyl, $R^{8a}$, $R^{8b}$, $R^{8c}$, $R^{8d}$, $R^{9a}$, $R^{9b}$, $R^{9c}$, $R^{9d}$, $R^{10a}$, $R^{10c}$ and $R^{10d}$ are hydrogen, and $R^1$, $R^2$, $R^3$, $R^6$ and $R^7$ for a compound corresponds in each case to one row of Table A Table 84
Compounds of the formula I.3 in which $R^{10a}$ and $R^{10b}$ are methyl, $R^{8a}$, $R^{8b}$, $R^{8c}$, $R^{8d}$, $R^{9a}$, $R^{9b}$, $R^{9c}$, $R^{9d}$, $R^{10c}$ and $R^{10d}$ are hydrogen, and $R^1$, $R^2$, $R^3$, $R^6$ and $R^7$ for a compound corresponds in each case to one row of Table A Table 85
Compounds of the formula I.3 in which $R^{10b}$ and $R^{10c}$ are methyl, $R^{8a}$, $R^{8b}$, $R^{8c}$, $R^{8d}$, $R^{9a}$, $R^{9b}$, $R^{9c}$, $R^{9d}$, $R^{10a}$ and $R^{10d}$ are hydrogen, and $R^1$, $R^2$, $R^3$, $R^6$ and $R^7$ for a compound corresponds in each case to one row of Table A Table 86
Compounds of the formula I.3 in which $R^{10a}$, $R^{10b}$ and $R^{10c}$ are methyl, $R^{8a}$, $R^{8b}$, $R^{8c}$, $R^{8d}$, $R^{9a}$, $R^{9b}$, $R^{9c}$, $R^{9d}$ and $R^{10d}$ are hydrogen, and $R^1$, $R^2$, $R^3$, $R^6$ and $R^7$ for a compound corresponds in each case to one row of Table A Table 87
Compounds of the formula I.3 in which $R^{10a}$ is fluorine, $R^{8a}$, $R^{8b}$, $R^{8c}$, $R^{8d}$, $R^{9a}$, $R^{9b}$, $R^{9c}$, $R^{9d}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 88
Compounds of the formula I.3 in which $R^{10b}$ is fluorine, $R^{8a}$, $R^{8b}$, $R^{8c}$, $R^{8d}$, $R^{9a}$, $R^{9b}$, $R^{9c}$, $R^{9d}$, $R^{10a}$, $R^{10c}$ and $R^{10d}$ are hydrogen, and $R^1$, $R^2$, $R^3$, $R^6$ and $R^7$ for a compound, corresponds in each case to one row of Table A Table 89
Compounds of the formula I.3 in which $R^{10a}$ is chlorine, $R^{8a}$, $R^{8b}$, $R^{8c}$, $R^{8d}$, $R^{9a}$, $R^{9b}$, $R^{9c}$, $R^{9d}$, $R^{10b}$, $R^{10c}$ and $R^{10d}$ are hydrogen, and $R^1$, $R^2$, $R^3$, $R^6$ and $R^7$ for a compound corresponds in each case to one row of Table A Table 90
Compounds of the formula I.3 in which $R^{10b}$ is chlorine, $R^{8a}$, $R^{8b}$, $R^{8c}$, $R^{8d}$, $R^{9a}$, $R^{9b}$, $R^{9c}$, $R^{9d}$, $R^{10a}$, $R^{10c}$ and $R^{10d}$ are hydrogen, and $R^1$, $R^2$, $R^3$, $R^6$ and $R^7$ for a compound corresponds in each case to one row of Table A Tables 91 to 120
Compounds of the formula I.4 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 1 to 30, and $R^1$, $R^2$, $R^3$, $R^6$ and $R^7$ for a compound corresponds in each case to one row of Table A Tables 121 to 150
Compounds of the formula I.5 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 31 to 60, and $R^1$, $R^2$, $R^3$, $R^6$ and $R^7$ for a compound corresponds in each case to one row of Table A Tables 151 to 180
Compounds of the formula I.6 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 61 to 90, and $R^1$, $R^2$, $R^3$, $R^6$ and $R^7$ for a compound corresponds in each case to one row of Table A Tables 181 to 210
Compounds of the formula I.7 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 1 to 30, and $R^1$, $R^2$, $R^3$, $R^6$ and $R^7$ for a compound corresponds in each case to one row of Table A Tables 211 to 240
Compounds of the formula I.8 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 31 to 60, and $R^1$, $R^2$, $R^3$, $R^6$ and $R^7$ for a compound corresponds in each case to one row of Table A Tables 241 to 270
Compounds of the formula I.9 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 61 to 90, and $R^1$, $R^2$, $R^3$, $R^6$ and $R^7$ for a compound corresponds in each case to one row of Table A Tables 271 to 300
Compounds of the formula I.10 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 1 to 30, and $R^1$, $R^2$, $R^3$, $R^6$ and $R^7$ for a compound corresponds in each case to one row of Table A Tables 301 to 330
Compounds of the formula I.11 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 31 to 60, and $R^1$, $R^2$, $R^3$, $R^6$ and $R^7$ for a compound corresponds in each case to one row of Table A Tables 331 to 360
Compounds of the formula I.12 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 61 to 90, and $R^1$, $R^2$, $R^3$, $R^6$ and $R^7$ for a compound corresponds in each case to one row of Table A Tables 361 to 390
Compounds of the formula I.13 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 1 to 30, and $R^1$, $R^2$, $R^3$, $R^6$ and $R^7$ for a compound corresponds in each case to one row of Table A Tables 391 to 420
Compounds of the formula I.14 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 31 to 60, and $R^1$, $R^2$, $R^3$, $R^6$ and $R^7$ for a compound corresponds in each case to one row of Table A Tables 421 to 450
Compounds of the formula I.15 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 61 to 90, and $R^1$, $R^2$, $R^3$, $R^6$ and $R^7$ for a compound corresponds in each case to one row of Table A Tables 451 to 480
Compounds of the formula I.16 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 1 to 30, and $R^1$, $R^2$, $R^3$, $R^6$ and $R^7$ for a compound corresponds in each case to one row of Table A Tables 481 to 510
Compounds of the formula I.17 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 31 to 60, and $R^1$, $R^2$, $R^3$, $R^6$ and $R^7$ for a compound corresponds in each case to one row of Table A Tables 511 to 540

Compounds of the formula I.18 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 61 to 90, and $R^1$, $R^2$, $R^3$, $R^6$ and $R^7$ for a compound corresponds in each case to one row of Table A Tables 541 to 570

Compounds of the formula I.19 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 1 to 30, and $R^2$, $R^3$, $R^6$ and $R^7$ for a compound corresponds in each case to one row of Table B Tables 571 to 600

Compounds of the formula I.20 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 31 to 60, and $R^2$, $R^3$, $R^6$ and $R^7$ for a compound corresponds in each case to one row of Table B Tables 601 to 630

Compounds of the formula I.21 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 61 to 90, and $R^2$, $R^3$, $R^6$ and $R^7$ for a compound corresponds in each case to one row of Table B Tables 631 to 660

Compounds of the formula I.22 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 1 to 30, and $R^2$, $R^3$, $R^6$ and $R^7$ for a compound corresponds in each case to one row of Table B Tables 661 to 690

Compounds of the formula I.23 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 31 to 60, and $R^2$, $R^3$, $R^6$ and $R^7$ for a compound corresponds in each case to one row of Table B Tables 691 to 720

Compounds of the formula I.24 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 61 to 90, and $R^2$, $R^3$, $R^6$ and $R^7$ for a compound corresponds in each case to one row of Table B Tables 721 to 750

Compounds of the formula I.25 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 1 to 30, and $R^2$, $R^3$, $R^6$ and $R^7$ for a compound corresponds in each case to one row of Table B Tables 751 to 780

Compounds of the formula I.26 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 31 to 60, and $R^2$, $R^3$, $R^6$ and $R^7$ for a compound corresponds in each case to one row of Table B Tables 781 to 810

Compounds of the formula I.27 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 61 to 90, and $R^2$, $R^3$, $R^6$ and $R^7$ for a compound corresponds in each case to one row of Table B Tables 811 to 840

Compounds of the formula I.28 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 1 to 30, and $R^2$, $R^3$, $R^6$ and $R^7$ for a compound corresponds in each case to one row of Table B Tables 841 to 870

Compounds of the formula I.29 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 31 to 60, and $R^2$, $R^3$, $R^6$ and $R^7$ for a compound corresponds in each case to one row of Table B Tables 871 to 900

Compounds of the formula I.30 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 61 to 90, and $R^2$, $R^3$, $R^6$ and $R^7$ for a compound corresponds in each case to one row of Table B Tables 901 to 930

Compounds of the formula I.31 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 1 to 30, and $R^2$, $R^3$, $R^6$ and $R^7$ for a compound corresponds in each case to one row of Table B Tables 931 to 960

Compounds of the formula I.32 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 31 to 60, and $R^2$, $R^3$, $R^6$ and $R^7$ for a compound corresponds in each case to one row of Table B Tables 961 to 990

Compounds of the formula I.33 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 61 to 90, and $R^2$, $R^3$, $R^6$ and $R^7$ for a compound corresponds in each case to one row of Table B Tables 991 to 1020

Compounds of the formula I.34 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 1 to 30, and $R^2$, $R^3$, $R^6$ and $R^7$ for a compound corresponds in each case to one row of Table B Tables 1021 to 1050

Compounds of the formula I.35 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 31 to 60, and $R^2$, $R^3$, $R^6$ and $R^7$ for a compound corresponds in each case to one row of Table B Tables 1051 to 1080

Compounds of the formula I.36 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 61 to 90, and $R^2$, $R^3$, $R^6$ and $R^7$ for a compound corresponds in each case to one row of Table B Tables 1081 to 1110

Compounds of the formula I.37 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 1 to 30, and $R^1$, $R^2$, $R^3$, $R^6$ and $R^7$ for a compound corresponds in each case to one row of Table A Tables 1111 to 1140

Compounds of the formula I.38 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 31 to 60, and $R^1$, $R^2$, $R^3$, $R^6$ and $R^7$ for a compound corresponds in each case to one row of Table A Tables 1141 to 1170

Compounds of the formula I.39 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and Tables 1171 to 1200

Compounds of the formula I.40 in which the combination of $R^{8a}, R^{8b}, R^{8c}, R^{8d}, R^{9a}, R^{9b}, R^{9c}, R^{9d}, R^{10a}, R^{10b}, R^{10c}$ and $R^{10d}$ is as defined in any of Tables 1 to 30, and $R^1, R^2, R^3, R^6$ and $R^7$ for a compound corresponds in each case to one row of Table A Tables 1201 to 1230

Compounds of the formula I.41 in which the combination of $R^{8a}, R^{8b}, R^{8c}, R^{8d}, R^{9a}, R^{9b}, R^{9c}, R^{9d}, R^{10a}, R^{10b}, R^{10c}$ and $R^{10d}$ is as defined in any of Tables 31 to 60, and $R^1, R^2, R^3, R^6$ and $R^7$ for a compound corresponds in each case to one row of Table A Tables 1231 to 1260

Compounds of the formula I.42 in which the combination of $R^{8a}, R^{8b}, R^{8c}, R^{8d}, R^{9a}, R^{9b}, R^{9c}, R^{9b}, R^{10a}, R^{10b}, R^{10c}$ and $R^{10d}$ is as defined in any of Tables 61 to 90, and $R^1, R^2, R^3, R^6$ and $R^7$ for a compound corresponds in each case to one row of Table A Tables 1261 to 1290

Compounds of the formula I.43 in which the combination of $R^{8a}, R^{8b}, R^{8c}, R^{8d}, R^{9a}, R^{9b}, R^{9c}, R^{9d}, R^{10a}, R^{10b}, R^{10c}$ and $R^{10d}$ is as defined in any of Tables 1 to 30, and $R^1, R^2, R^3, R^6$ and $R^7$ for a compound corresponds in each case to one row of Table A Tables 1291 to 1320

Compounds of the formula I.44 in which the combination of $R^{8a}, R^{8b}, R^{8c}, R^{8d}, R^{9a}, R^{9b}, R^{9c}, R^{9d}, R^{10a}, R^{10b}, R^{10c}$ and $R^{10d}$ is as defined in any of Tables 31 to 60, and $R^1, R^2, R^3, R^6$ and $R^7$ for a compound corresponds in each case to one row of Table A Tables 1321 to 1350

Compounds of the formula I.45 in which the combination of $R^{8a}, R^{8b}, R^{8c}, R^{8d}, R^{9a}, R^{9b}, R^{9c}, R^{9d}, R^{10a}, R^{10b}, R^{10c}$ and $R^{10d}$ is as defined in any of Tables 61 to 90, and $R^1, R^2, R^3, R^6$ and $R^7$ for a compound corresponds in each case to one row of Table A Tables 1351 to 1380

Compounds of the formula I.46 in which the combination of $R^{8a}, R^{8b}, R^{8c}, R^{8d}, R^{9a}, R^{9b}, R^{9c}, R^{9d}, R^{10a}, R^{10b}, R^{10c}$ and $R^{10d}$ is as defined in any of Tables 1 to 30, and $R^1, R^2, R^3, R^6$ and $R^7$ for a compound corresponds in each case to one row of Table A Tables 1381 to 1410

Compounds of the formula I.47 in which the combination of $R^{8a}, R^{8b}, R^{8c}, R^{8d}, R^{9a}, R^{9b}, R^{9c}, R^{9d}, R^{10a}, R^{10b}, R^{10c}$ and $R^{10d}$ is as defined in any of Tables 31 to 60, and $R^1, R^2, R^3, R^6$ and $R^7$ for a compound corresponds in each case to one row of Table A Tables 1411 to 1440

Compounds of the formula I.48 in which the combination of $R^{8a}, R^{8b}, R^{8c}, R^{8d}, R^{9a}, R^{9b}, R^{9c}, R^{9d}, R^{10a}, R^{10b}, R^{10c}$ and $R^{10d}$ is as defined in any of Tables 61 to 90, and $R^1, R^2, R^3, R^6$ and $R^7$ for a compound corresponds in each case to one row of Table A Tables 1441 to 1470

Compounds of the formula I.49 in which the combination of $R^{8a}, R^{8b}, R^{8c}, R^{8d}, R^{9a}, R^{9b}, R^{9c}, R^{9d}, R^{10a}, R^{10b}, R^{10c}$ and $R^{10d}$ is as defined in any of Tables 1 to 30, and $R^1, R^2, R^3, R^6$ and $R^7$ for a compound corresponds in each case to one row of Table A Tables 1471 to 1500

Compounds of the formula I.50 in which the combination of $R^{8a}, R^{8b}, R^{8c}, R^{8d}, R^{9a}, R^{9b}, R^{9c}, R^{9d}, R^{10a}, R^{10b}, R^{10c}$ and $R^{10d}$ is as defined in any of Tables 31 to 60, and $R^1, R^2, R^3, R^6$ and $R^7$ for a compound corresponds in each case to one row of Table A Tables 1501 to 1530

Compounds of the formula I.51 in which the combination of $R^{8a}, R^{8b}, R^{8c}, R^{8d}, R^{9a}, R^{9b}, R^{9c}, R^{9d}, R^{10a}, R^{10b}, R^{10c}$ and $R^{10d}$ is as defined in any of Tables 61 to 90, and $R^1, R^2, R^3, R^6$ and $R^7$ for a compound corresponds in each case to one row of Table A Tables 1531 to 1560

Compounds of the formula I.52 in which the combination of $R^{8a}, R^{8b}, R^{8c}, R^{8d}, R^{9a}, R^{9b}, R^{9c}, R^{9d}, R^{10a}, R^{10b}, R^{10c}$ and $R^{10d}$ is as defined in any of Tables 1 to 30, and $R^1, R^2, R^3, R^6$ and $R^7$ for a compound corresponds in each case to one row of Table A Tables 1561 to 1590

Compounds of the formula I.53 in which the combination of $R^{8a}, R^{8b}, R^{8c}, R^{8d}, R^{9a}, R^{9b}, R^{9c}, R^{9d}, R^{10a}, R^{10b}, R^{10c}$ and $R^{10d}$ is as defined in any of Tables 31 to 60, and $R^1, R^2, R^3, R^6$ and $R^7$ for a compound corresponds in each case to one row of Table A Tables 1591 to 1620

Compounds of the formula I.54 in which the combination of $R^{8a}, R^{8b}, R^{8c}, R^{8d}, R^{9a}, R^{9b}, R^{9c}, R^{9d}, R^{10a}, R^{10b}, R^{10c}$ and $R^{10d}$ is as defined in any of Tables 61 to 90, and $R^1, R^2, R^3, R^6$ and $R^7$ for a compound corresponds in each case to one row of Table A Tables 1621 to 1650

Compounds of the formula I.55 in which the combination of $R^{8a}, R^{8b}, R^{8c}, R^{8d}, R^{9a}, R^{9b}, R^{9c}, R^{9d}, R^{10a}, R^{10b}, R^{10c}$ and $R^{10d}$ is as defined in any of Tables 1 to 30, and $R^2, R^3, R^6$ and $R^7$ for a compound corresponds in each case to one row of Table B Tables 1651 to 1680

Compounds of the formula I.56 in which the combination of $R^{8a}, R^{8b}, R^{8c}, R^{8d}, R^{9a}, R^{9b}, R^{9c}, R^{9d}, R^{10a}, R^{10b}, R^{10c}$ and $R^{10d}$ is as defined in any of Tables 31 to 60, and $R^2, R^3, R^6$ and $R^7$ for a compound corresponds in each case to one row of Table B Tables 1681 to 1710

Compounds of the formula I.57 in which the combination of $R^{8a}, R^{8b}, R^{8c}, R^{8d}, R^{9a}, R^{9b}, R^{9c}, R^{9d}, R^{10a}, R^{10b}, R^{10c}$ and $R^{10d}$ is as defined in any of Tables 61 to 90, and $R^2, R^3, R^6$ and $R^7$ for a compound corresponds in each case to one row of Table B Tables 1711 to 1740

Compounds of the formula I.58 in which the combination of $R^{8a}, R^{8b}, R^{8c}, R^{8d}, R^{9a}, R^{9b}, R^{9c}, R^{9d}, R^{10a}, R^{10b}, R^{10c}$ and $R^{10d}$ is as defined in any of Tables 1 to 30, and $R^2, R^3, R^6$ and $R^7$ for a compound corresponds in each case to one row of Table B Tables 1741 to 1770

Compounds of the formula I.59 in which the combination of $R^{8a}, R^{8b}, R^{8c}, R^{8d}, R^{9a}, R^{9b}, R^{9c}, R^{9d}, R^{10a}, R^{10b}, R^{10c}$ and $R^{10d}$ is as defined in any of Tables 31 to 60, and $R^2, R^3, R^6$ and $R^7$ for a compound corresponds in each case to one row of Table B Tables 1771 to 1800

Compounds of the formula I.60 in which the combination of $R^{8a}, R^{8b}, R^{8c}, R^{8d}, R^{9a}, R^{9b}, R^{9c}, R^{9d}, R^{10a}, R^{10b}, R^{10c}$ and $R^{10d}$ is as defined in any of Tables 61 to 90, and $R^2, R^3, R^6$ and $R^7$ for a compound corresponds in each case to one row of Table B Tables 1801 to 1830

Compounds of the formula I.61 in which the combination of $R^{8a}, R^{8b}, R^{8c}, R^{8d}, R^{9a}, R^{9b}, R^{9c}, R^{9d}, R^{10a}, R^{10b}, R^{10c}$ and $R^{10d}$ is as defined in any of Tables 1 to 30, and $R^2$, $R^3$, $R^6$ and $R^7$ for a compound corresponds in each case to one row of Table B Tables 1831 to 1860

Compounds of the formula I.62 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 31 to 60, and $R^2$, $R^3$, $R^6$ and $R^7$ for a compound corresponds in each case to one row of Table B Tables 1861 to 1890

Compounds of the formula I.63 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 61 to 90, and $R^2$, $R^3$, $R^6$ and $R^7$ for a compound corresponds in each case to one row of Table B Tables 1891 to 1920

Compounds of the formula I.64 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 1 to 30, and $R^2$, $R^3$, $R^6$ and $R^7$ for a compound corresponds in each case to one row of Table B Tables 1921 to 1950

Compounds of the formula I.65 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 31 to 60, and $R^2$, $R^3$, $R^6$ and $R^7$ for a compound corresponds in each case to one row of Table B Tables 1951 to 1980

Compounds of the formula I.66 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 61 to 90, and $R^2$, $R^3$, $R^6$ and $R^7$ for a compound corresponds in each case to one row of Table B Tables 1981 to 2010

Compounds of the formula I.67 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 1 to 30, and $R^2$, $R^3$, $R^6$ and $R^7$ for a compound corresponds in each case to one row of Table B Tables 2011 to 2040

Compounds of the formula I.68 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 31 to 60, and $R^2$, $R^3$, $R^6$ and $R^7$ for a compound corresponds in each case to one row of Table B Tables 2041 to 2070

Compounds of the formula I.69 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 61 to 90, and $R^2$, $R^3$, $R^6$ and $R^7$ for a compound corresponds in each case to one row of Table B Tables 2071 to 2100

Compounds of the formula I.70 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 1 to 30, and $R^1$, $R^2$, $R^3$, $R^6$ and $R^7$ for a compound corresponds in each case to one row of Table A Tables 2101 to 2130

Compounds of the formula I.71 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 31 to 60, and $R^2$, $R^3$, $R^6$ and $R^7$ for a compound corresponds in each case to one row of Table B Tables 2131 to 2160

Compounds of the formula I.72 in which the combination of $R^{8a}$, $R^{8b}$, $R^{8c}$, $R^{8d}$, $R^{9a}$, $R^{9b}$, $R^{9c}$, $R^{9d}$, $R^{10a}$, $R^{10b}$, $R^{10c}$ and $R^{10d}$ is as defined in any of Tables 61 to 90, and $R^2$, $R^3$, $R^6$ and $R^7$ for a compound corresponds in each case to one row of Table B

TABLE A

| Example No. | $R^1$ | $R^2$ | $R^3$ | $R^6$ | $R^7$ |
|---|---|---|---|---|---|
| A-1. | H | H | H | CN | H |
| A-2. | F | H | H | CN | H |
| A-3. | $CH_3$ | H | H | CN | H |
| A-4. | $OCH_3$ | H | H | CN | H |
| A-5. | $CH_2F$ | H | H | CN | H |
| A-6. | $CHF_2$ | H | H | CN | H |
| A-7. | $CF_3$ | H | H | CN | H |
| A-8. | $OCH_2F$ | H | H | CN | H |
| A-9. | $OCHF_2$ | H | H | CN | H |
| A-10. | $OCF_3$ | H | H | CN | H |
| A-11. | H | F | H | CN | H |
| A-12. | H | $CH_3$ | H | CN | H |
| A-13. | H | $OCH_3$ | H | CN | H |
| A-14. | H | CN | H | CN | H |
| A-15. | H | $CH_2F$ | H | CN | H |
| A-16. | H | $CHF_2$ | H | CN | H |
| A-17. | H | $CF_3$ | H | CN | H |
| A-18. | H | $OCH_2F$ | H | CN | H |
| A-19. | H | $OCHF_2$ | H | CN | H |
| A-20. | H | $OCF_3$ | H | CN | H |
| A-21. | H | H | 3-F | CN | H |
| A-22. | H | H | 3-$CH_3$ | CN | H |
| A-23. | H | H | 3-$OCH_3$ | CN | H |
| A-24. | H | H | 5-F | CN | H |
| A-25. | H | H | 5-$CH_3$ | CN | H |
| A-26. | H | H | 5-$OCH_3$ | CN | H |
| A-27. | F | F | H | CN | H |
| A-28. | F | $CH_3$ | H | CN | H |
| A-29. | F | $OCH_3$ | H | CN | H |
| A-30. | F | CN | H | CN | H |
| A-31. | F | $CH_2F$ | H | CN | H |
| A-32. | F | $CHF_2$ | H | CN | H |
| A-33. | F | $CF_3$ | H | CN | H |
| A-34. | F | $OCH_2F$ | H | CN | H |
| A-35. | F | $OCHF_2$ | H | CN | H |
| A-36. | F | $OCF_3$ | H | CN | H |
| A-37. | F | H | 3-F | CN | H |
| A-38. | F | H | 3-$CH_3$ | CN | H |
| A-39. | F | H | 3-$OCH_3$ | CN | H |
| A-40. | F | H | 5-F | CN | H |
| A-41. | F | H | 5-$CH_3$ | CN | H |
| A-42. | F | H | 5-$OCH_3$ | CN | H |
| A-43. | $CH_3$ | F | H | CN | H |
| A-44. | $CH_3$ | $CH_3$ | H | CN | H |
| A-45. | $CH_3$ | $OCH_3$ | H | CN | H |
| A-46. | $CH_3$ | CN | H | CN | H |
| A-47. | $CH_3$ | $CH_2F$ | H | CN | H |
| A-48. | $CH_3$ | $CHF_2$ | H | CN | H |
| A-49. | $CH_3$ | $CF_3$ | H | CN | H |
| A-50. | $CH_3$ | $OCH_2F$ | H | CN | H |
| A-51. | $CH_3$ | $OCHF_2$ | H | CN | H |
| A-52. | $CH_3$ | $OCF_3$ | H | CN | H |
| A-53. | $CH_3$ | H | 3-F | CN | H |
| A-54. | $CH_3$ | H | 3-$CH_3$ | CN | H |
| A-55. | $CH_3$ | H | 3-$OCH_3$ | CN | H |
| A-56. | $CH_3$ | H | 5-F | CN | H |
| A-57. | $CH_3$ | H | 5-$CH_3$ | CN | H |
| A-58. | $CH_3$ | H | 5-$OCH_3$ | CN | H |
| A-59. | $OCH_3$ | F | H | CN | H |
| A-60. | $OCH_3$ | $CH_3$ | H | CN | H |
| A-61. | $OCH_3$ | $OCH_3$ | H | CN | H |
| A-62. | $OCH_3$ | CN | H | CN | H |
| A-63. | $OCH_3$ | $CH_2F$ | H | CN | H |
| A-64. | $OCH_3$ | $CHF_2$ | H | CN | H |
| A-65. | $OCH_3$ | $CF_3$ | H | CN | H |
| A-66. | $OCH_3$ | $OCH_2F$ | H | CN | H |
| A-67. | $OCH_3$ | $OCHF_2$ | H | CN | H |
| A-68. | $OCH_3$ | $OCF_3$ | H | CN | H |
| A-69. | $OCH_3$ | H | 3-F | CN | H |
| A-70. | $OCH_3$ | H | 3-$CH_3$ | CN | H |
| A-71. | $OCH_3$ | H | 3-$OCH_3$ | CN | H |
| A-72. | $OCH_3$ | H | 5-F | CN | H |
| A-73. | $OCH_3$ | H | 5-$CH_3$ | CN | H |

TABLE A-continued

| Example No. | R¹ | R² | R³ | R⁶ | R⁷ |
|---|---|---|---|---|---|
| A-74. | OCH₃ | H | 5-OCH₃ | CN | H |
| A-75. | H | F | 3-F | CN | H |
| A-76. | H | F | 3-CH₃ | CN | H |
| A-77. | H | F | 3-OCH₃ | CN | H |
| A-78. | H | F | 5-F | CN | H |
| A-79. | H | F | 5-CH₃ | CN | H |
| A-80. | H | F | 5-OCH₃ | CN | H |
| A-81. | H | CH₃ | 3-F | CN | H |
| A-82. | H | CH₃ | 3-CH₃ | CN | H |
| A-83. | H | CH₃ | 3-OCH₃ | CN | H |
| A-84. | H | CH₃ | 5-F | CN | H |
| A-85. | H | CH₃ | 5-CH₃ | CN | H |
| A-86. | H | CH₃ | 5-OCH₃ | CN | H |
| A-87. | H | OCH₃ | 3-F | CN | H |
| A-88. | H | OCH₃ | 3-CH₃ | CN | H |
| A-89. | H | OCH₃ | 3-OCH₃ | CN | H |
| A-90. | H | OCH₃ | 5-F | CN | H |
| A-91. | H | OCH₃ | 5-CH₃ | CN | H |
| A-92. | H | OCH₃ | 5-OCH₃ | CN | H |
| A-93. | H | CN | 3-F | CN | H |
| A-94. | H | CN | 3-CH₃ | CN | H |
| A-95. | H | CN | 3-OCH₃ | CN | H |
| A-96. | H | CN | 5-F | CN | H |
| A-97. | H | CN | 5-CH₃ | CN | H |
| A-98. | H | CN | 5-OCH₃ | CN | H |
| A-99. | H | CH₂F | 3-F | CN | H |
| A-100. | H | CH₂F | 3-CH₃ | CN | H |
| A-101. | H | CH₂F | 3-OCH₃ | CN | H |
| A-102. | H | CH₂F | 5-F | CN | H |
| A-103. | H | CH₂F | 5-CH₃ | CN | H |
| A-104. | H | CH₂F | 5-OCH₃ | CN | H |
| A-105. | H | CHF₂ | 3-F | CN | H |
| A-106. | H | CHF₂ | 3-CH₃ | CN | H |
| A-107. | H | CHF₂ | 3-OCH₃ | CN | H |
| A-108. | H | CHF₂ | 5-F | CN | H |
| A-109. | H | CHF₂ | 5-CH₃ | CN | H |
| A-110. | H | CHF₂ | 5-OCH₃ | CN | H |
| A-111. | H | CF₃ | 3-F | CN | H |
| A-112. | H | CF₃ | 3-CH₃ | CN | H |
| A-113. | H | CF₃ | 3-OCH₃ | CN | H |
| A-114. | H | CF₃ | 5-F | CN | H |
| A-115. | H | CF₃ | 5-CH₃ | CN | H |
| A-116. | H | CF₃ | 5-OCH₃ | CN | H |
| A-117. | H | OCH₂F | 3-F | CN | H |
| A-118. | H | OCH₂F | 3-CH₃ | CN | H |
| A-119. | H | OCH₂F | 3-OCH₃ | CN | H |
| A-120. | H | OCH₂F | 5-F | CN | H |
| A-121. | H | OCH₂F | 5-CH₃ | CN | H |
| A-122. | H | OCH₂F | 5-OCH₃ | CN | H |
| A-123. | H | OCHF₂ | 3-F | CN | H |
| A-124. | H | OCHF₂ | 3-CH₃ | CN | H |
| A-125. | H | OCHF₂ | 3-OCH₃ | CN | H |
| A-126. | H | OCHF₂ | 5-F | CN | H |
| A-127. | H | OCHF₂ | 5-CH₃ | CN | H |
| A-128. | H | OCHF₂ | 5-OCH₃ | CN | H |
| A-129. | H | OCF₃ | 3-F | CN | H |
| A-130. | H | OCF₃ | 3-CH₃ | CN | H |
| A-131. | H | OCF₃ | 3-OCH₃ | CN | H |
| A-132. | H | OCF₃ | 5-F | CN | H |
| A-133. | H | OCF₃ | 5-CH₃ | CN | H |
| A-134. | H | OCF₃ | 5-OCH₃ | CN | H |
| A-135. | F | F | 3-F | CN | H |
| A-136. | F | F | 3-CH₃ | CN | H |
| A-137. | F | F | 3-OCH₃ | CN | H |
| A-138. | F | F | 5-F | CN | H |
| A-139. | F | F | 5-CH₃ | CN | H |
| A-140. | F | F | 5-OCH₃ | CN | H |
| A-141. | F | CH₃ | 3-F | CN | H |
| A-142. | F | CH₃ | 3-CH₃ | CN | H |
| A-143. | F | CH₃ | 3-OCH₃ | CN | H |
| A-144. | F | CH₃ | 5-F | CN | H |
| A-145. | F | CH₃ | 5-CH₃ | CN | H |
| A-146. | F | CH₃ | 5-OCH₃ | CN | H |
| A-147. | F | OCH₃ | 3-F | CN | H |
| A-148. | F | OCH₃ | 3-CH₃ | CN | H |
| A-149. | F | OCH₃ | 3-OCH₃ | CN | H |
| A-150. | F | OCH₃ | 5-F | CN | H |
| A-151. | F | OCH₃ | 5-CH₃ | CN | H |
| A-152. | F | OCH₃ | 5-OCH₃ | CN | H |
| A-153. | F | CN | 3-F | CN | H |
| A-154. | F | CN | 3-CH₃ | CN | H |
| A-155. | F | CN | 3-OCH₃ | CN | H |
| A-156. | F | CN | 5-F | CN | H |
| A-157. | F | CN | 5-CH₃ | CN | H |
| A-158. | F | CN | 5-OCH₃ | CN | H |
| A-159. | F | CH₂F | 3-F | CN | H |
| A-160. | F | CH₂F | 3-CH₃ | CN | H |
| A-161. | F | CH₂F | 3-OCH₃ | CN | H |
| A-162. | F | CH₂F | 5-F | CN | H |
| A-163. | F | CH₂F | 5-CH₃ | CN | H |
| A-164. | F | CH₂F | 5-OCH₃ | CN | H |
| A-165. | F | CHF₂ | 3-F | CN | H |
| A-166. | F | CHF₂ | 3-CH₃ | CN | H |
| A-167. | F | CHF₂ | 3-OCH₃ | CN | H |
| A-168. | F | CHF₂ | 5-F | CN | H |
| A-169. | F | CHF₂ | 5-CH₃ | CN | H |
| A-170. | F | CHF₂ | 5-OCH₃ | CN | H |
| A-171. | F | CF₃ | 3-F | CN | H |
| A-172. | F | CF₃ | 3-CH₃ | CN | H |
| A-173. | F | CF₃ | 3-OCH₃ | CN | H |
| A-174. | F | CF₃ | 5-F | CN | H |
| A-175. | F | CF₃ | 5-CH₃ | CN | H |
| A-176. | F | CF₃ | 5-OCH₃ | CN | H |
| A-177. | F | OCH₂F | 3-F | CN | H |
| A-178. | F | OCH₂F | 3-CH₃ | CN | H |
| A-179. | F | OCH₂F | 3-OCH₃ | CN | H |
| A-180. | F | OCH₂F | 5-F | CN | H |
| A-181. | F | OCH₂F | 5-CH₃ | CN | H |
| A-182. | F | OCH₂F | 5-OCH₃ | CN | H |
| A-183. | F | OCHF₂ | 3-F | CN | H |
| A-184. | F | OCHF₂ | 3-CH₃ | CN | H |
| A-185. | F | OCHF₂ | 3-OCH₃ | CN | H |
| A-186. | F | OCHF₂ | 5-F | CN | H |
| A-187. | F | OCHF₂ | 5-CH₃ | CN | H |
| A-188. | F | OCHF₂ | 5-OCH₃ | CN | H |
| A-189. | F | OCF₃ | 3-F | CN | H |
| A-190. | F | OCF₃ | 3-CH₃ | CN | H |
| A-191. | F | OCF₃ | 3-OCH₃ | CN | H |
| A-192. | F | OCF₃ | 5-F | CN | H |
| A-193. | F | OCF₃ | 5-CH₃ | CN | H |
| A-194. | F | OCF₃ | 5-OCH₃ | CN | H |
| A-195. | CH₃ | F | 3-F | CN | H |
| A-196. | CH₃ | F | 3-CH₃ | CN | H |
| A-197. | CH₃ | F | 3-OCH₃ | CN | H |
| A-198. | CH₃ | F | 5-F | CN | H |
| A-199. | CH₃ | F | 5-CH₃ | CN | H |
| A-200. | CH₃ | F | 5-OCH₃ | CN | H |
| A-201. | CH₃ | CH₃ | 3-F | CN | H |
| A-202. | CH₃ | CH₃ | 3-CH₃ | CN | H |
| A-203. | CH₃ | CH₃ | 3-OCH₃ | CN | H |
| A-204. | CH₃ | CH₃ | 5-F | CN | H |
| A-205. | CH₃ | CH₃ | 5-CH₃ | CN | H |
| A-206. | CH₃ | CH₃ | 5-OCH₃ | CN | H |
| A-207. | CH₃ | OCH₃ | 3-F | CN | H |
| A-208. | CH₃ | OCH₃ | 3-CH₃ | CN | H |
| A-209. | CH₃ | OCH₃ | 3-OCH₃ | CN | H |
| A-210. | CH₃ | OCH₃ | 5-F | CN | H |
| A-211. | CH₃ | OCH₃ | 5-CH₃ | CN | H |
| A-212. | CH₃ | OCH₃ | 5-OCH₃ | CN | H |
| A-213. | CH₃ | CN | 3-F | CN | H |
| A-214. | CH₃ | CN | 3-CH₃ | CN | H |
| A-215. | CH₃ | CN | 3-OCH₃ | CN | H |
| A-216. | CH₃ | CN | 5-F | CN | H |
| A-217. | CH₃ | CN | 5-CH₃ | CN | H |
| A-218. | CH₃ | CN | 5-OCH₃ | CN | H |
| A-219. | CH₃ | CH₂F | 3-F | CN | H |
| A-220. | CH₃ | CH₂F | 3-CH₃ | CN | H |
| A-221. | CH₃ | CH₂F | 3-OCH₃ | CN | H |
| A-222. | CH₃ | CH₂F | 5-F | CN | H |
| A-223. | CH₃ | CH₂F | 5-CH₃ | CN | H |
| A-224. | CH₃ | CH₂F | 5-OCH₃ | CN | H |
| A-225. | CH₃ | CHF₂ | 3-F | CN | H |
| A-226. | CH₃ | CHF₂ | 3-CH₃ | CN | H |
| A-227. | CH₃ | CHF₂ | 3-OCH₃ | CN | H |
| A-228. | CH₃ | CHF₂ | 5-F | CN | H |
| A-229. | CH₃ | CHF₂ | 5-CH₃ | CN | H |

TABLE A-continued

| Example No. | R¹ | R² | R³ | R⁶ | R⁷ |
|---|---|---|---|---|---|
| A-230. | CH₃ | CHF₂ | 5-OCH₃ | CN | H |
| A-231. | CH₃ | CF₃ | 3-F | CN | H |
| A-232. | CH₃ | CF₃ | 3-CH₃ | CN | H |
| A-233. | CH₃ | CF₃ | 3-OCH₃ | CN | H |
| A-234. | CH₃ | CF₃ | 5-F | CN | H |
| A-235. | CH₃ | CF₃ | 5-CH₃ | CN | H |
| A-236. | CH₃ | CF₃ | 5-OCH₃ | CN | H |
| A-237. | CH₃ | OCH₂F | 3-F | CN | H |
| A-238. | CH₃ | OCH₂F | 3-CH₃ | CN | H |
| A-239. | CH₃ | OCH₂F | 3-OCH₃ | CN | H |
| A-240. | CH₃ | OCH₂F | 5-F | CN | H |
| A-241. | CH₃ | OCH₂F | 5-CH₃ | CN | H |
| A-242. | CH₃ | OCH₂F | 5-OCH₃ | CN | H |
| A-243. | CH₃ | OCHF₂ | 3-F | CN | H |
| A-244. | CH₃ | OCHF₂ | 3-CH₃ | CN | H |
| A-245. | CH₃ | OCHF₂ | 3-OCH₃ | CN | H |
| A-246. | CH₃ | OCHF₂ | 5-F | CN | H |
| A-247. | CH₃ | OCHF₂ | 5-CH₃ | CN | H |
| A-248. | CH₃ | OCHF₂ | 5-OCH₃ | CN | H |
| A-249. | CH₃ | OCF₃ | 3-F | CN | H |
| A-250. | CH₃ | OCF₃ | 3-CH₃ | CN | H |
| A-251. | CH₃ | OCF₃ | 3-OCH₃ | CN | H |
| A-252. | CH₃ | OCF₃ | 5-F | CN | H |
| A-253. | CH₃ | OCF₃ | 5-CH₃ | CN | H |
| A-254. | CH₃ | OCF₃ | 5-OCH₃ | CN | H |
| A-255. | OCH₃ | F | 3-F | CN | H |
| A-256. | OCH₃ | F | 3-CH₃ | CN | H |
| A-257. | OCH₃ | F | 3-OCH₃ | CN | H |
| A-258. | OCH₃ | F | 5-F | CN | H |
| A-259. | OCH₃ | F | 5-CH₃ | CN | H |
| A-260. | OCH₃ | F | 5-OCH₃ | CN | H |
| A-261. | OCH₃ | CH₃ | 3-F | CN | H |
| A-262. | OCH₃ | CH₃ | 3-CH₃ | CN | H |
| A-263. | OCH₃ | CH₃ | 3-OCH₃ | CN | H |
| A-264. | OCH₃ | CH₃ | 5-F | CN | H |
| A-265. | OCH₃ | CH₃ | 5-CH₃ | CN | H |
| A-266. | OCH₃ | CH₃ | 5-OCH₃ | CN | H |
| A-267. | OCH₃ | OCH₃ | 3-F | CN | H |
| A-268. | OCH₃ | OCH₃ | 3-CH₃ | CN | H |
| A-269. | OCH₃ | OCH₃ | 3-OCH₃ | CN | H |
| A-270. | OCH₃ | OCH₃ | 5-F | CN | H |
| A-271. | OCH₃ | OCH₃ | 5-CH₃ | CN | H |
| A-272. | OCH₃ | OCH₃ | 5-OCH₃ | CN | H |
| A-273. | OCH₃ | CN | 3-F | CN | H |
| A-274. | OCH₃ | CN | 3-CH₃ | CN | H |
| A-275. | OCH₃ | CN | 3-OCH₃ | CN | H |
| A-276. | OCH₃ | CN | 5-F | CN | H |
| A-277. | OCH₃ | CN | 5-CH₃ | CN | H |
| A-278. | OCH₃ | CN | 5-OCH₃ | CN | H |
| A-279. | OCH₃ | CH₂F | 3-F | CN | H |
| A-280. | OCH₃ | CH₂F | 3-CH₃ | CN | H |
| A-281. | OCH₃ | CH₂F | 3-OCH₃ | CN | H |
| A-282. | OCH₃ | CH₂F | 5-F | CN | H |
| A-283. | OCH₃ | CH₂F | 5-CH₃ | CN | H |
| A-284. | OCH₃ | CH₂F | 5-OCH₃ | CN | H |
| A-285. | OCH₃ | CHF₂ | 3-F | CN | H |
| A-286. | OCH₃ | CHF₂ | 3-CH₃ | CN | H |
| A-287. | OCH₃ | CHF₂ | 3-OCH₃ | CN | H |
| A-288. | OCH₃ | CHF₂ | 5-F | CN | H |
| A-289. | OCH₃ | CHF₂ | 5-CH₃ | CN | H |
| A-290. | OCH₃ | CHF₂ | 5-OCH₃ | CN | H |
| A-291. | OCH₃ | CF₃ | 3-F | CN | H |
| A-292. | OCH₃ | CF₃ | 3-CH₃ | CN | H |
| A-293. | OCH₃ | CF₃ | 3-OCH₃ | CN | H |
| A-294. | OCH₃ | CF₃ | 5-F | CN | H |
| A-295. | OCH₃ | CF₃ | 5-CH₃ | CN | H |
| A-296. | OCH₃ | CF₃ | 5-OCH₃ | CN | H |
| A-297. | OCH₃ | OCH₂F | 3-F | CN | H |
| A-298. | OCH₃ | OCH₂F | 3-CH₃ | CN | H |
| A-299. | OCH₃ | OCH₂F | 3-OCH₃ | CN | H |
| A-300. | OCH₃ | OCH₂F | 5-F | CN | H |
| A-301. | OCH₃ | OCH₂F | 5-CH₃ | CN | H |
| A-302. | OCH₃ | OCH₂F | 5-OCH₃ | CN | H |
| A-303. | OCH₃ | OCHF₂ | 3-F | CN | H |
| A-304. | OCH₃ | OCHF₂ | 3-CH₃ | CN | H |
| A-305. | OCH₃ | OCHF₂ | 3-OCH₃ | CN | H |
| A-306. | OCH₃ | OCHF₂ | 5-F | CN | H |
| A-307. | OCH₃ | OCHF₂ | 5-CH₃ | CN | H |
| A-308. | OCH₃ | OCHF₂ | 5-OCH₃ | CN | H |
| A-309. | OCH₃ | OCF₃ | 3-F | CN | H |
| A-310. | OCH₃ | OCF₃ | 3-CH₃ | CN | H |
| A-311. | OCH₃ | OCF₃ | 3-OCH₃ | CN | H |
| A-312. | OCH₃ | OCF₃ | 5-F | CN | H |
| A-313. | OCH₃ | OCF₃ | 5-CH₃ | CN | H |
| A-314. | OCH₃ | OCF₃ | 5-OCH₃ | CN | H |
| A-315. | CH₂F | F | 3-F | CN | H |
| A-316. | CH₂F | F | 3-CH₃ | CN | H |
| A-317. | CH₂F | F | 3-OCH₃ | CN | H |
| A-318. | CH₂F | F | 5-F | CN | H |
| A-319. | CH₂F | F | 5-CH₃ | CN | H |
| A-320. | CH₂F | F | 5-OCH₃ | CN | H |
| A-321. | CH₂F | CH₃ | 3-F | CN | H |
| A-322. | CH₂F | CH₃ | 3-CH₃ | CN | H |
| A-323. | CH₂F | CH₃ | 3-OCH₃ | CN | H |
| A-324. | CH₂F | CH₃ | 5-F | CN | H |
| A-325. | CH₂F | CH₃ | 5-CH₃ | CN | H |
| A-326. | CH₂F | CH₃ | 5-OCH₃ | CN | H |
| A-327. | CH₂F | OCH₃ | 3-F | CN | H |
| A-328. | CH₂F | OCH₃ | 3-CH₃ | CN | H |
| A-329. | CH₂F | OCH₃ | 3-OCH₃ | CN | H |
| A-330. | CH₂F | OCH₃ | 5-F | CN | H |
| A-331. | CH₂F | OCH₃ | 5-CH₃ | CN | H |
| A-332. | CH₂F | OCH₃ | 5-OCH₃ | CN | H |
| A-333. | CH₂F | CN | 3-F | CN | H |
| A-334. | CH₂F | CN | 3-CH₃ | CN | H |
| A-335. | CH₂F | CN | 3-OCH₃ | CN | H |
| A-336. | CH₂F | CN | 5-F | CN | H |
| A-337. | CH₂F | CN | 5-CH₃ | CN | H |
| A-338. | CH₂F | CN | 5-OCH₃ | CN | H |
| A-339. | CH₂F | CH₂F | 3-F | CN | H |
| A-340. | CH₂F | CH₂F | 3-CH₃ | CN | H |
| A-341. | CH₂F | CH₂F | 3-OCH₃ | CN | H |
| A-342. | CH₂F | CH₂F | 5-F | CN | H |
| A-343. | CH₂F | CH₂F | 5-CH₃ | CN | H |
| A-344. | CH₂F | CH₂F | 5-OCH₃ | CN | H |
| A-345. | CH₂F | CHF₂ | 3-F | CN | H |
| A-346. | CH₂F | CHF₂ | 3-CH₃ | CN | H |
| A-347. | CH₂F | CHF₂ | 3-OCH₃ | CN | H |
| A-348. | CH₂F | CHF₂ | 5-F | CN | H |
| A-349. | CH₂F | CHF₂ | 5-CH₃ | CN | H |
| A-350. | CH₂F | CHF₂ | 5-OCH₃ | CN | H |
| A-351. | CH₂F | CF₃ | 3-F | CN | H |
| A-352. | CH₂F | CF₃ | 3-CH₃ | CN | H |
| A-353. | CH₂F | CF₃ | 3-OCH₃ | CN | H |
| A-354. | CH₂F | CF₃ | 5-F | CN | H |
| A-355. | CH₂F | CF₃ | 5-CH₃ | CN | H |
| A-356. | CH₂F | CF₃ | 5-OCH₃ | CN | H |
| A-357. | CH₂F | OCH₂F | 3-F | CN | H |
| A-358. | CH₂F | OCH₂F | 3-CH₃ | CN | H |
| A-359. | CH₂F | OCH₂F | 3-OCH₃ | CN | H |
| A-360. | CH₂F | OCH₂F | 5-F | CN | H |
| A-361. | CH₂F | OCH₂F | 5-CH₃ | CN | H |
| A-362. | CH₂F | OCH₂F | 5-OCH₃ | CN | H |
| A-363. | CH₂F | OCHF₂ | 3-F | CN | H |
| A-364. | CH₂F | OCHF₂ | 3-CH₃ | CN | H |
| A-365. | CH₂F | OCHF₂ | 3-OCH₃ | CN | H |
| A-366. | CH₂F | OCHF₂ | 5-F | CN | H |
| A-367. | CH₂F | OCHF₂ | 5-CH₃ | CN | H |
| A-368. | CH₂F | OCHF₂ | 5-OCH₃ | CN | H |
| A-369. | CH₂F | OCF₃ | 3-F | CN | H |
| A-370. | CH₂F | OCF₃ | 3-CH₃ | CN | H |
| A-371. | CH₂F | OCF₃ | 3-OCH₃ | CN | H |
| A-372. | CH₂F | OCF₃ | 5-F | CN | H |
| A-373. | CH₂F | OCF₃ | 5-CH₃ | CN | H |
| A-374. | CH₂F | OCF₃ | 5-OCH₃ | CN | H |
| A-375. | CHF₂ | F | 3-F | CN | H |
| A-376. | CHF₂ | F | 3-CH₃ | CN | H |
| A-377. | CHF₂ | F | 3-OCH₃ | CN | H |
| A-378. | CHF₂ | F | 5-F | CN | H |
| A-379. | CHF₂ | F | 5-CH₃ | CN | H |
| A-380. | CHF₂ | F | 5-OCH₃ | CN | H |
| A-381. | CHF₂ | CH₃ | 3-F | CN | H |
| A-382. | CHF₂ | CH₃ | 3-CH₃ | CN | H |
| A-383. | CHF₂ | CH₃ | 3-OCH₃ | CN | H |
| A-384. | CHF₂ | CH₃ | 5-F | CN | H |
| A-385. | CHF₂ | CH₃ | 5-CH₃ | CN | H |

TABLE A-continued

| Example No. | R¹ | R² | R³ | R⁶ | R⁷ |
|---|---|---|---|---|---|
| A-386. | CHF₂ | CH₃ | 5-OCH₃ | CN | H |
| A-387. | CHF₂ | OCH₃ | 3-F | CN | H |
| A-388. | CHF₂ | OCH₃ | 3-CH₃ | CN | H |
| A-389. | CHF₂ | OCH₃ | 3-OCH₃ | CN | H |
| A-390. | CHF₂ | OCH₃ | 5-F | CN | H |
| A-391. | CHF₂ | OCH₃ | 5-CH₃ | CN | H |
| A-392. | CHF₂ | OCH₃ | 5-OCH₃ | CN | H |
| A-393. | CHF₂ | CN | 3-F | CN | H |
| A-394. | CHF₂ | CN | 3-CH₃ | CN | H |
| A-395. | CHF₂ | CN | 3-OCH₃ | CN | H |
| A-396. | CHF₂ | CN | 5-F | CN | H |
| A-397. | CHF₂ | CN | 5-CH₃ | CN | H |
| A-398. | CHF₂ | CN | 5-OCH₃ | CN | H |
| A-399. | CHF₂ | CH₂F | 3-F | CN | H |
| A-400. | CHF₂ | CH₂F | 3-CH₃ | CN | H |
| A-401. | CHF₂ | CH₂F | 3-OCH₃ | CN | H |
| A-402. | CHF₂ | CH₂F | 5-F | CN | H |
| A-403. | CHF₂ | CH₂F | 5-CH₃ | CN | H |
| A-404. | CHF₂ | CH₂F | 5-OCH₃ | CN | H |
| A-405. | CHF₂ | CHF₂ | 3-F | CN | H |
| A-406. | CHF₂ | CHF₂ | 3-CH₃ | CN | H |
| A-407. | CHF₂ | CHF₂ | 3-OCH₃ | CN | H |
| A-408. | CHF₂ | CHF₂ | 5-F | CN | H |
| A-409. | CHF₂ | CHF₂ | 5-CH₃ | CN | H |
| A-410. | CHF₂ | CHF₂ | 5-OCH₃ | CN | H |
| A-411. | CHF₂ | CF₃ | 3-F | CN | H |
| A-412. | CHF₂ | CF₃ | 3-CH₃ | CN | H |
| A-413. | CHF₂ | CF₃ | 3-OCH₃ | CN | H |
| A-414. | CHF₂ | CF₃ | 5-F | CN | H |
| A-415. | CHF₂ | CF₃ | 5-CH₃ | CN | H |
| A-416. | CHF₂ | CF₃ | 5-OCH₃ | CN | H |
| A-417. | CHF₂ | OCH₂F | 3-F | CN | H |
| A-418. | CHF₂ | OCH₂F | 3-CH₃ | CN | H |
| A-419. | CHF₂ | OCH₂F | 3-OCH₃ | CN | H |
| A-420. | CHF₂ | OCH₂F | 5-F | CN | H |
| A-421. | CHF₂ | OCH₂F | 5-CH₃ | CN | H |
| A-422. | CHF₂ | OCH₂F | 5-OCH₃ | CN | H |
| A-423. | CHF₂ | OCHF₂ | 3-F | CN | H |
| A-424. | CHF₂ | OCHF₂ | 3-CH₃ | CN | H |
| A-425. | CHF₂ | OCHF₂ | 3-OCH₃ | CN | H |
| A-426. | CHF₂ | OCHF₂ | 5-F | CN | H |
| A-427. | CHF₂ | OCHF₂ | 5-CH₃ | CN | H |
| A-428. | CHF₂ | OCHF₂ | 5-OCH₃ | CN | H |
| A-429. | CHF₂ | OCF₃ | 3-F | CN | H |
| A-430. | CHF₂ | OCF₃ | 3-CH₃ | CN | H |
| A-431. | CHF₂ | OCF₃ | 3-OCH₃ | CN | H |
| A-432. | CHF₂ | OCF₃ | 5-F | CN | H |
| A-433. | CHF₂ | OCF₃ | 5-CH₃ | CN | H |
| A-434. | CHF₂ | OCF₃ | 5-OCH₃ | CN | H |
| A-435. | CF₃ | F | 3-F | CN | H |
| A-436. | CF₃ | F | 3-CH₃ | CN | H |
| A-437. | CF₃ | F | 3-OCH₃ | CN | H |
| A-438. | CF₃ | F | 5-F | CN | H |
| A-439. | CF₃ | F | 5-CH₃ | CN | H |
| A-440. | CF₃ | F | 5-OCH₃ | CN | H |
| A-441. | CF₃ | CH₃ | 3-F | CN | H |
| A-442. | CF₃ | CH₃ | 3-CH₃ | CN | H |
| A-443. | CF₃ | CH₃ | 3-OCH₃ | CN | H |
| A-444. | CF₃ | CH₃ | 5-F | CN | H |
| A-445. | CF₃ | CH₃ | 5-CH₃ | CN | H |
| A-446. | CF₃ | CH₃ | 5-OCH₃ | CN | H |
| A-447. | CF₃ | OCH₃ | 3-F | CN | H |
| A-448. | CF₃ | OCH₃ | 3-CH₃ | CN | H |
| A-449. | CF₃ | OCH₃ | 3-OCH₃ | CN | H |
| A-450. | CF₃ | OCH₃ | 5-F | CN | H |
| A-451. | CF₃ | OCH₃ | 5-CH₃ | CN | H |
| A-452. | CF₃ | OCH₃ | 5-OCH₃ | CN | H |
| A-453. | CF₃ | CN | 3-F | CN | H |
| A-454. | CF₃ | CN | 3-CH₃ | CN | H |
| A-455. | CF₃ | CN | 3-OCH₃ | CN | H |
| A-456. | CF₃ | CN | 5-F | CN | H |
| A-457. | CF₃ | CN | 5-CH₃ | CN | H |
| A-458. | CF₃ | CN | 5-OCH₃ | CN | H |
| A-459. | CF₃ | CH₂F | 3-F | CN | H |
| A-460. | CF₃ | CH₂F | 3-CH₃ | CN | H |
| A-461. | CF₃ | CH₂F | 3-OCH₃ | CN | H |
| A-462. | CF₃ | CH₂F | 5-F | CN | H |
| A-463. | CF₃ | CH₂F | 5-CH₃ | CN | H |
| A-464. | CF₃ | CH₂F | 5-OCH₃ | CN | H |
| A-465. | CF₃ | CHF₂ | 3-F | CN | H |
| A-466. | CF₃ | CHF₂ | 3-CH₃ | CN | H |
| A-467. | CF₃ | CHF₂ | 3-OCH₃ | CN | H |
| A-468. | CF₃ | CHF₂ | 5-F | CN | H |
| A-469. | CF₃ | CHF₂ | 5-CH₃ | CN | H |
| A-470. | CF₃ | CHF₂ | 5-OCH₃ | CN | H |
| A-471. | CF₃ | CF₃ | 3-F | CN | H |
| A-472. | CF₃ | CF₃ | 3-CH₃ | CN | H |
| A-473. | CF₃ | CF₃ | 3-OCH₃ | CN | H |
| A-474. | CF₃ | CF₃ | 5-F | CN | H |
| A-475. | CF₃ | CF₃ | 5-CH₃ | CN | H |
| A-476. | CF₃ | CF₃ | 5-OCH₃ | CN | H |
| A-477. | CF₃ | OCH₂F | 3-F | CN | H |
| A-478. | CF₃ | OCH₂F | 3-CH₃ | CN | H |
| A-479. | CF₃ | OCH₂F | 3-OCH₃ | CN | H |
| A-480. | CF₃ | OCH₂F | 5-F | CN | H |
| A-481. | CF₃ | OCH₂F | 5-CH₃ | CN | H |
| A-482. | CF₃ | OCH₂F | 5-OCH₃ | CN | H |
| A-483. | CF₃ | OCHF₂ | 3-F | CN | H |
| A-484. | CF₃ | OCHF₂ | 3-CH₃ | CN | H |
| A-485. | CF₃ | OCHF₂ | 3-OCH₃ | CN | H |
| A-486. | CF₃ | OCHF₂ | 5-F | CN | H |
| A-487. | CF₃ | OCHF₂ | 5-CH₃ | CN | H |
| A-488. | CF₃ | OCHF₂ | 5-OCH₃ | CN | H |
| A-489. | CF₃ | OCF₃ | 3-F | CN | H |
| A-490. | CF₃ | OCF₃ | 3-CH₃ | CN | H |
| A-491. | CF₃ | OCF₃ | 3-OCH₃ | CN | H |
| A-492. | CF₃ | OCF₃ | 5-F | CN | H |
| A-493. | CF₃ | OCF₃ | 5-CH₃ | CN | H |
| A-494. | CF₃ | OCF₃ | 5-OCH₃ | CN | H |
| A-495. | OCH₂F | F | 3-F | CN | H |
| A-496. | OCH₂F | F | 3-CH₃ | CN | H |
| A-497. | OCH₂F | F | 3-OCH₃ | CN | H |
| A-498. | OCH₂F | F | 5-F | CN | H |
| A-499. | OCH₂F | F | 5-CH₃ | CN | H |
| A-500. | OCH₂F | F | 5-OCH₃ | CN | H |
| A-501. | OCH₂F | CH₃ | 3-F | CN | H |
| A-502. | OCH₂F | CH₃ | 3-CH₃ | CN | H |
| A-503. | OCH₂F | CH₃ | 3-OCH₃ | CN | H |
| A-504. | OCH₂F | CH₃ | 5-F | CN | H |
| A-505. | OCH₂F | CH₃ | 5-CH₃ | CN | H |
| A-506. | OCH₂F | CH₃ | 5-OCH₃ | CN | H |
| A-507. | OCH₂F | OCH₃ | 3-F | CN | H |
| A-508. | OCH₂F | OCH₃ | 3-CH₃ | CN | H |
| A-509. | OCH₂F | OCH₃ | 3-OCH₃ | CN | H |
| A-510. | OCH₂F | OCH₃ | 5-F | CN | H |
| A-511. | OCH₂F | OCH₃ | 5-CH₃ | CN | H |
| A-512. | OCH₂F | OCH₃ | 5-OCH₃ | CN | H |
| A-513. | OCH₂F | CN | 3-F | CN | H |
| A-514. | OCH₂F | CN | 3-CH₃ | CN | H |
| A-515. | OCH₂F | CN | 3-OCH₃ | CN | H |
| A-516. | OCH₂F | CN | 5-F | CN | H |
| A-517. | OCH₂F | CN | 5-CH₃ | CN | H |
| A-518. | OCH₂F | CN | 5-OCH₃ | CN | H |
| A-519. | OCH₂F | CH₂F | 3-F | CN | H |
| A-520. | OCH₂F | CH₂F | 3-CH₃ | CN | H |
| A-521. | OCH₂F | CH₂F | 3-OCH₃ | CN | H |
| A-522. | OCH₂F | CH₂F | 5-F | CN | H |
| A-523. | OCH₂F | CH₂F | 5-CH₃ | CN | H |
| A-524. | OCH₂F | CH₂F | 5-OCH₃ | CN | H |
| A-525. | OCH₂F | CHF₂ | 3-F | CN | H |
| A-526. | OCH₂F | CHF₂ | 3-CH₃ | CN | H |
| A-527. | OCH₂F | CHF₂ | 3-OCH₃ | CN | H |
| A-528. | OCH₂F | CHF₂ | 5-F | CN | H |
| A-529. | OCH₂F | CHF₂ | 5-CH₃ | CN | H |
| A-530. | OCH₂F | CHF₂ | 5-OCH₃ | CN | H |
| A-531. | OCH₂F | CF₃ | 3-F | CN | H |
| A-532. | OCH₂F | CF₃ | 3-CH₃ | CN | H |
| A-533. | OCH₂F | CF₃ | 3-OCH₃ | CN | H |
| A-534. | OCH₂F | CF₃ | 5-F | CN | H |
| A-535. | OCH₂F | CF₃ | 5-CH₃ | CN | H |
| A-536. | OCH₂F | CF₃ | 5-OCH₃ | CN | H |
| A-537. | OCH₂F | OCH₂F | 3-F | CN | H |
| A-538. | OCH₂F | OCH₂F | 3-CH₃ | CN | H |
| A-539. | OCH₂F | OCH₂F | 3-OCH₃ | CN | H |
| A-540. | OCH₂F | OCH₂F | 5-F | CN | H |
| A-541. | OCH₂F | OCH₂F | 5-CH₃ | CN | H |

TABLE A-continued

| Example No. | R¹ | R² | R³ | R⁶ | R⁷ |
|---|---|---|---|---|---|
| A-542. | OCH₂F | OCH₂F | 5-OCH₃ | CN | H |
| A-543. | OCH₂F | OCHF₂ | 3-F | CN | H |
| A-544. | OCH₂F | OCHF₂ | 3-CH₃ | CN | H |
| A-545. | OCH₂F | OCHF₂ | 3-OCH₃ | CN | H |
| A-546. | OCH₂F | OCHF₂ | 5-F | CN | H |
| A-547. | OCH₂F | OCHF₂ | 5-CH₃ | CN | H |
| A-548. | OCH₂F | OCHF₂ | 5-OCH₃ | CN | H |
| A-549. | OCH₂F | OCF₃ | 3-F | CN | H |
| A-550. | OCH₂F | OCF₃ | 3-CH₃ | CN | H |
| A-551. | OCH₂F | OCF₃ | 3-OCH₃ | CN | H |
| A-552. | OCH₂F | OCF₃ | 5-F | CN | H |
| A-553. | OCH₂F | OCF₃ | 5-CH₃ | CN | H |
| A-554. | OCH₂F | OCF₃ | 5-OCH₃ | CN | H |
| A-555. | OCHF₂ | F | 3-F | CN | H |
| A-556. | OCHF₂ | F | 3-CH₃ | CN | H |
| A-557. | OCHF₂ | F | 3-OCH₃ | CN | H |
| A-558. | OCHF₂ | F | 5-F | CN | H |
| A-559. | OCHF₂ | F | 5-CH₃ | CN | H |
| A-560. | OCHF₂ | F | 5-OCH₃ | CN | H |
| A-561. | OCHF₂ | CH₃ | 3-F | CN | H |
| A-562. | OCHF₂ | CH₃ | 3-CH₃ | CN | H |
| A-563. | OCHF₂ | CH₃ | 3-OCH₃ | CN | H |
| A-564. | OCHF₂ | CH₃ | 5-F | CN | H |
| A-565. | OCHF₂ | CH₃ | 5-CH₃ | CN | H |
| A-566. | OCHF₂ | CH₃ | 5-OCH₃ | CN | H |
| A-567. | OCHF₂ | OCH₃ | 3-F | CN | H |
| A-568. | OCHF₂ | OCH₃ | 3-CH₃ | CN | H |
| A-569. | OCHF₂ | OCH₃ | 3-OCH₃ | CN | H |
| A-570. | OCHF₂ | OCH₃ | 5-F | CN | H |
| A-571. | OCHF₂ | OCH₃ | 5-CH₃ | CN | H |
| A-572. | OCHF₂ | OCH₃ | 5-OCH₃ | CN | H |
| A-573. | OCHF₂ | CN | 3-F | CN | H |
| A-574. | OCHF₂ | CN | 3-CH₃ | CN | H |
| A-575. | OCHF₂ | CN | 3-OCH₃ | CN | H |
| A-576. | OCHF₂ | CN | 5-F | CN | H |
| A-577. | OCHF₂ | CN | 5-CH₃ | CN | H |
| A-578. | OCHF₂ | CN | 5-OCH₃ | CN | H |
| A-579. | OCHF₂ | CH₂F | 3-F | CN | H |
| A-580. | OCHF₂ | CH₂F | 3-CH₃ | CN | H |
| A-581. | OCHF₂ | CH₂F | 3-OCH₃ | CN | H |
| A-582. | OCHF₂ | CH₂F | 5-F | CN | H |
| A-583. | OCHF₂ | CH₂F | 5-CH₃ | CN | H |
| A-584. | OCHF₂ | CH₂F | 5-OCH₃ | CN | H |
| A-585. | OCHF₂ | CHF₂ | 3-F | CN | H |
| A-586. | OCHF₂ | CHF₂ | 3-CH₃ | CN | H |
| A-587. | OCHF₂ | CHF₂ | 3-OCH₃ | CN | H |
| A-588. | OCHF₂ | CHF₂ | 5-F | CN | H |
| A-589. | OCHF₂ | CHF₂ | 5-CH₃ | CN | H |
| A-590. | OCHF₂ | CHF₂ | 5-OCH₃ | CN | H |
| A-591. | OCHF₂ | CF₃ | 3-F | CN | H |
| A-592. | OCHF₂ | CF₃ | 3-CH₃ | CN | H |
| A-593. | OCHF₂ | CF₃ | 3-OCH₃ | CN | H |
| A-594. | OCHF₂ | CF₃ | 5-F | CN | H |
| A-595. | OCHF₂ | CF₃ | 5-CH₃ | CN | H |
| A-596. | OCHF₂ | CF₃ | 5-OCH₃ | CN | H |
| A-597. | OCHF₂ | OCH₂F | 3-F | CN | H |
| A-598. | OCHF₂ | OCH₂F | 3-CH₃ | CN | H |
| A-599. | OCHF₂ | OCH₂F | 3-OCH₃ | CN | H |
| A-600. | OCHF₂ | OCH₂F | 5-F | CN | H |
| A-601. | OCHF₂ | OCH₂F | 5-CH₃ | CN | H |
| A-602. | OCHF₂ | OCH₂F | 5-OCH₃ | CN | H |
| A-603. | OCHF₂ | OCHF₂ | 3-F | CN | H |
| A-604. | OCHF₂ | OCHF₂ | 3-CH₃ | CN | H |
| A-605. | OCHF₂ | OCHF₂ | 3-OCH₃ | CN | H |
| A-606. | OCHF₂ | OCHF₂ | 5-F | CN | H |
| A-607. | OCHF₂ | OCHF₂ | 5-CH₃ | CN | H |
| A-608. | OCHF₂ | OCHF₂ | 5-OCH₃ | CN | H |
| A-609. | OCHF₂ | OCF₃ | 3-F | CN | H |
| A-610. | OCHF₂ | OCF₃ | 3-CH₃ | CN | H |
| A-611. | OCHF₂ | OCF₃ | 3-OCH₃ | CN | H |
| A-612. | OCHF₂ | OCF₃ | 5-F | CN | H |
| A-613. | OCHF₂ | OCF₃ | 5-CH₃ | CN | H |
| A-614. | OCHF₂ | OCF₃ | 5-OCH₃ | CN | H |
| A-615. | OCF₃ | F | 3-F | CN | H |
| A-616. | OCF₃ | F | 3-CH₃ | CN | H |
| A-617. | OCF₃ | F | 3-OCH₃ | CN | H |
| A-618. | OCF₃ | F | 5-F | CN | H |
| A-619. | OCF₃ | F | 5-CH₃ | CN | H |
| A-620. | OCF₃ | F | 5-OCH₃ | CN | H |
| A-621. | OCF₃ | CH₃ | 3-F | CN | H |
| A-622. | OCF₃ | CH₃ | 3-CH₃ | CN | H |
| A-623. | OCF₃ | CH₃ | 3-OCH₃ | CN | H |
| A-624. | OCF₃ | CH₃ | 5-F | CN | H |
| A-625. | OCF₃ | CH₃ | 5-CH₃ | CN | H |
| A-626. | OCF₃ | CH₃ | 5-OCH₃ | CN | H |
| A-627. | OCF₃ | OCH₃ | 3-F | CN | H |
| A-628. | OCF₃ | OCH₃ | 3-CH₃ | CN | H |
| A-629. | OCF₃ | OCH₃ | 3-OCH₃ | CN | H |
| A-630. | OCF₃ | OCH₃ | 5-F | CN | H |
| A-631. | OCF₃ | OCH₃ | 5-CH₃ | CN | H |
| A-632. | OCF₃ | OCH₃ | 5-OCH₃ | CN | H |
| A-633. | OCF₃ | CN | 3-F | CN | H |
| A-634. | OCF₃ | CN | 3-CH₃ | CN | H |
| A-635. | OCF₃ | CN | 3-OCH₃ | CN | H |
| A-636. | OCF₃ | CN | 5-F | CN | H |
| A-637. | OCF₃ | CN | 5-CH₃ | CN | H |
| A-638. | OCF₃ | CN | 5-OCH₃ | CN | H |
| A-639. | OCF₃ | CH₂F | 3-F | CN | H |
| A-640. | OCF₃ | CH₂F | 3-CH₃ | CN | H |
| A-641. | OCF₃ | CH₂F | 3-OCH₃ | CN | H |
| A-642. | OCF₃ | CH₂F | 5-F | CN | H |
| A-643. | OCF₃ | CH₂F | 5-CH₃ | CN | H |
| A-644. | OCF₃ | CH₂F | 5-OCH₃ | CN | H |
| A-645. | OCF₃ | CHF₂ | 3-F | CN | H |
| A-646. | OCF₃ | CHF₂ | 3-CH₃ | CN | H |
| A-647. | OCF₃ | CHF₂ | 3-OCH₃ | CN | H |
| A-648. | OCF₃ | CHF₂ | 5-F | CN | H |
| A-649. | OCF₃ | CHF₂ | 5-CH₃ | CN | H |
| A-650. | OCF₃ | CHF₂ | 5-OCH₃ | CN | H |
| A-651. | OCF₃ | CF₃ | 3-F | CN | H |
| A-652. | OCF₃ | CF₃ | 3-CH₃ | CN | H |
| A-653. | OCF₃ | CF₃ | 3-OCH₃ | CN | H |
| A-654. | OCF₃ | CF₃ | 5-F | CN | H |
| A-655. | OCF₃ | CF₃ | 5-CH₃ | CN | H |
| A-656. | OCF₃ | CF₃ | 5-OCH₃ | CN | H |
| A-657. | OCF₃ | OCH₂F | 3-F | CN | H |
| A-658. | OCF₃ | OCH₂F | 3-CH₃ | CN | H |
| A-659. | OCF₃ | OCH₂F | 3-OCH₃ | CN | H |
| A-660. | OCF₃ | OCH₂F | 5-F | CN | H |
| A-661. | OCF₃ | OCH₂F | 5-CH₃ | CN | H |
| A-662. | OCF₃ | OCH₂F | 5-OCH₃ | CN | H |
| A-663. | OCF₃ | OCHF₂ | 3-F | CN | H |
| A-664. | OCF₃ | OCHF₂ | 3-CH₃ | CN | H |
| A-665. | OCF₃ | OCHF₂ | 3-OCH₃ | CN | H |
| A-666. | OCF₃ | OCHF₂ | 5-F | CN | H |
| A-667. | OCF₃ | OCHF₂ | 5-CH₃ | CN | H |
| A-668. | OCF₃ | OCHF₂ | 5-OCH₃ | CN | H |
| A-669. | OCF₃ | OCF₃ | 3-F | CN | H |
| A-670. | OCF₃ | OCF₃ | 3-CH₃ | CN | H |
| A-671. | OCF₃ | OCF₃ | 3-OCH₃ | CN | H |
| A-672. | OCF₃ | OCF₃ | 5-F | CN | H |
| A-673. | OCF₃ | OCF₃ | 5-CH₃ | CN | H |
| A-674. | OCF₃ | OCF₃ | 5-OCH₃ | CN | H |
| A-675. | H | H | H | F | H |
| A-676. | F | H | H | F | H |
| A-677. | CH₃ | H | H | F | H |
| A-678. | OCH₃ | H | H | F | H |
| A-679. | CH₂F | H | H | F | H |
| A-680. | CHF₂ | H | H | F | H |
| A-681. | CF₃ | H | H | F | H |
| A-682. | OCH₂F | H | H | F | H |
| A-683. | OCHF₂ | H | H | F | H |
| A-684. | OCF₃ | H | H | F | H |
| A-685. | H | F | H | F | H |
| A-686. | H | CH₃ | H | F | H |
| A-687. | H | OCH₃ | H | F | H |
| A-688. | H | CN | H | F | H |
| A-689. | H | CH₂F | H | F | H |
| A-690. | H | CHF₂ | H | F | H |
| A-691. | H | CF₃ | H | F | H |
| A-692. | H | OCH₂F | H | F | H |
| A-693. | H | OCHF₂ | H | F | H |
| A-694. | H | OCF₃ | H | F | H |
| A-695. | H | H | 3-F | F | H |
| A-696. | H | H | 3-CH₃ | F | H |
| A-697. | H | H | 3-OCH₃ | F | H |

TABLE A-continued

| Example No. | R¹ | R² | R³ | R⁶ | R⁷ |
|---|---|---|---|---|---|
| A-698. | H | H | 5-F | F | H |
| A-699. | H | H | 5-CH₃ | F | H |
| A-700. | H | H | 5-OCH₃ | F | H |
| A-701. | F | F | H | F | H |
| A-702. | F | CH₃ | H | F | H |
| A-703. | F | OCH₃ | H | F | H |
| A-704. | F | CN | H | F | H |
| A-705. | F | CH₂F | H | F | H |
| A-706. | F | CHF₂ | H | F | H |
| A-707. | F | CF₃ | H | F | H |
| A-708. | F | OCH₂F | H | F | H |
| A-709. | F | OCHF₂ | H | F | H |
| A-710. | F | OCF₃ | H | F | H |
| A-711. | F | H | 3-F | F | H |
| A-712. | F | H | 3-CH₃ | F | H |
| A-713. | F | H | 3-OCH₃ | F | H |
| A-714. | F | H | 5-F | F | H |
| A-715. | F | H | 5-CH₃ | F | H |
| A-716. | F | H | 5-OCH₃ | F | H |
| A-717. | CH₃ | F | H | F | H |
| A-718. | CH₃ | CH₃ | H | F | H |
| A-719. | CH₃ | OCH₃ | H | F | H |
| A-720. | CH₃ | CN | H | F | H |
| A-721. | CH₃ | CH₂F | H | F | H |
| A-722. | CH₃ | CHF₂ | H | F | H |
| A-723. | CH₃ | CF₃ | H | F | H |
| A-724. | CH₃ | OCH₂F | H | F | H |
| A-725. | CH₃ | OCHF₂ | H | F | H |
| A-726. | CH₃ | OCF₃ | H | F | H |
| A-727. | CH₃ | H | 3-F | F | H |
| A-728. | CH₃ | H | 3-CH₃ | F | H |
| A-729. | CH₃ | H | 3-OCH₃ | F | H |
| A-730. | CH₃ | H | 5-F | F | H |
| A-731. | CH₃ | H | 5-CH₃ | F | H |
| A-732. | CH₃ | H | 5-OCH₃ | F | H |
| A-733. | OCH₃ | F | H | F | H |
| A-734. | OCH₃ | CH₃ | H | F | H |
| A-735. | OCH₃ | OCH₃ | H | F | H |
| A-736. | OCH₃ | CN | H | F | H |
| A-737. | OCH₃ | CH₂F | H | F | H |
| A-738. | OCH₃ | CHF₂ | H | F | H |
| A-739. | OCH₃ | CF₃ | H | F | H |
| A-740. | OCH₃ | OCH₂F | H | F | H |
| A-741. | OCH₃ | OCHF₂ | H | F | H |
| A-742. | OCH₃ | OCF₃ | H | F | H |
| A-743. | OCH₃ | H | 3-F | F | H |
| A-744. | OCH₃ | H | 3-CH₃ | F | H |
| A-745. | OCH₃ | H | 3-OCH₃ | F | H |
| A-746. | OCH₃ | H | 5-F | F | H |
| A-747. | OCH₃ | H | 5-CH₃ | F | H |
| A-748. | OCH₃ | H | 5-OCH₃ | F | H |
| A-749. | H | F | 3-F | F | H |
| A-750. | H | F | 3-CH₃ | F | H |
| A-751. | H | F | 3-OCH₃ | F | H |
| A-752. | H | F | 5-F | F | H |
| A-753. | H | F | 5-CH₃ | F | H |
| A-754. | H | F | 5-OCH₃ | F | H |
| A-755. | H | CH₃ | 3-F | F | H |
| A-756. | H | CH₃ | 3-CH₃ | F | H |
| A-757. | H | CH₃ | 3-OCH₃ | F | H |
| A-758. | H | CH₃ | 5-F | F | H |
| A-759. | H | CH₃ | 5-CH₃ | F | H |
| A-760. | H | CH₃ | 5-OCH₃ | F | H |
| A-761. | H | OCH₃ | 3-F | F | H |
| A-762. | H | OCH₃ | 3-CH₃ | F | H |
| A-763. | H | OCH₃ | 3-OCH₃ | F | H |
| A-764. | H | OCH₃ | 5-F | F | H |
| A-765. | H | OCH₃ | 5-CH₃ | F | H |
| A-766. | H | OCH₃ | 5-OCH₃ | F | H |
| A-767. | H | CN | 3-F | F | H |
| A-768. | H | CN | 3-CH₃ | F | H |
| A-769. | H | CN | 3-OCH₃ | F | H |
| A-770. | H | CN | 5-F | F | H |
| A-771. | H | CN | 5-CH₃ | F | H |
| A-772. | H | CN | 5-OCH₃ | F | H |
| A-773. | H | CH₂F | 3-F | F | H |
| A-774. | H | CH₂F | 3-CH₃ | F | H |
| A-775. | H | CH₂F | 3-OCH₃ | F | H |
| A-776. | H | CH₂F | 5-F | F | H |
| A-777. | H | CH₂F | 5-CH₃ | F | H |
| A-778. | H | CH₂F | 5-OCH₃ | F | H |
| A-779. | H | CHF₂ | 3-F | F | H |
| A-780. | H | CHF₂ | 3-CH₃ | F | H |
| A-781. | H | CHF₂ | 3-OCH₃ | F | H |
| A-782. | H | CHF₂ | 5-F | F | H |
| A-783. | H | CHF₂ | 5-CH₃ | F | H |
| A-784. | H | CHF₂ | 5-OCH₃ | F | H |
| A-785. | H | CF₃ | 3-F | F | H |
| A-786. | H | CF₃ | 3-CH₃ | F | H |
| A-787. | H | CF₃ | 3-OCH₃ | F | H |
| A-788. | H | CF₃ | 5-F | F | H |
| A-789. | H | CF₃ | 5-CH₃ | F | H |
| A-790. | H | CF₃ | 5-OCH₃ | F | H |
| A-791. | H | OCH₂F | 3-F | F | H |
| A-792. | H | OCH₂F | 3-CH₃ | F | H |
| A-793. | H | OCH₂F | 3-OCH₃ | F | H |
| A-794. | H | OCH₂F | 5-F | F | H |
| A-795. | H | OCH₂F | 5-CH₃ | F | H |
| A-796. | H | OCH₂F | 5-OCH₃ | F | H |
| A-797. | H | OCHF₂ | 3-F | F | H |
| A-798. | H | OCHF₂ | 3-CH₃ | F | H |
| A-799. | H | OCHF₂ | 3-OCH₃ | F | H |
| A-800. | H | OCHF₂ | 5-F | F | H |
| A-801. | H | OCHF₂ | 5-CH₃ | F | H |
| A-802. | H | OCHF₂ | 5-OCH₃ | F | H |
| A-803. | H | OCF₃ | 3-F | F | H |
| A-804. | H | OCF₃ | 3-CH₃ | F | H |
| A-805. | H | OCF₃ | 3-OCH₃ | F | H |
| A-806. | H | OCF₃ | 5-F | F | H |
| A-807. | H | OCF₃ | 5-CH₃ | F | H |
| A-808. | H | OCF₃ | 5-OCH₃ | F | H |
| A-809. | F | F | 3-F | F | H |
| A-810. | F | F | 3-CH₃ | F | H |
| A-811. | F | F | 3-OCH₃ | F | H |
| A-812. | F | F | 5-F | F | H |
| A-813. | F | F | 5-CH₃ | F | H |
| A-814. | F | F | 5-OCH₃ | F | H |
| A-815. | F | CH₃ | 3-F | F | H |
| A-816. | F | CH₃ | 3-CH₃ | F | H |
| A-817. | F | CH₃ | 3-OCH₃ | F | H |
| A-818. | F | CH₃ | 5-F | F | H |
| A-819. | F | CH₃ | 5-CH₃ | F | H |
| A-820. | F | CH₃ | 5-OCH₃ | F | H |
| A-821. | F | OCH₃ | 3-F | F | H |
| A-822. | F | OCH₃ | 3-CH₃ | F | H |
| A-823. | F | OCH₃ | 3-OCH₃ | F | H |
| A-824. | F | OCH₃ | 5-F | F | H |
| A-825. | F | OCH₃ | 5-CH₃ | F | H |
| A-826. | F | OCH₃ | 5-OCH₃ | F | H |
| A-827. | F | CN | 3-F | F | H |
| A-828. | F | CN | 3-CH₃ | F | H |
| A-829. | F | CN | 3-OCH₃ | F | H |
| A-830. | F | CN | 5-F | F | H |
| A-831. | F | CN | 5-CH₃ | F | H |
| A-832. | F | CN | 5-OCH₃ | F | H |
| A-833. | F | CH₂F | 3-F | F | H |
| A-834. | F | CH₂F | 3-CH₃ | F | H |
| A-835. | F | CH₂F | 3-OCH₃ | F | H |
| A-836. | F | CH₂F | 5-F | F | H |
| A-837. | F | CH₂F | 5-CH₃ | F | H |
| A-838. | F | CH₂F | 5-OCH₃ | F | H |
| A-839. | F | CHF₂ | 3-F | F | H |
| A-840. | F | CHF₂ | 3-CH₃ | F | H |
| A-841. | F | CHF₂ | 3-OCH₃ | F | H |
| A-842. | F | CHF₂ | 5-F | F | H |
| A-843. | F | CHF₂ | 5-CH₃ | F | H |
| A-844. | F | CHF₂ | 5-OCH₃ | F | H |
| A-845. | F | CF₃ | 3-F | F | H |
| A-846. | F | CF₃ | 3-CH₃ | F | H |
| A-847. | F | CF₃ | 3-OCH₃ | F | H |
| A-848. | F | CF₃ | 5-F | F | H |
| A-849. | F | CF₃ | 5-CH₃ | F | H |
| A-850. | F | CF₃ | 5-OCH₃ | F | H |
| A-851. | F | OCH₂F | 3-F | F | H |
| A-852. | F | OCH₂F | 3-CH₃ | F | H |
| A-853. | F | OCH₂F | 3-OCH₃ | F | H |

TABLE A-continued

| Example No. | R¹ | R² | R³ | R⁶ | R⁷ |
|---|---|---|---|---|---|
| A-854. | F | OCH₂F | 5-F | F | H |
| A-855. | F | OCH₂F | 5-CH₃ | F | H |
| A-856. | F | OCH₂F | 5-OCH₃ | F | H |
| A-857. | F | OCHF₂ | 3-F | F | H |
| A-858. | F | OCHF₂ | 3-CH₃ | F | H |
| A-859. | F | OCHF₂ | 3-OCH₃ | F | H |
| A-860. | F | OCHF₂ | 5-F | F | H |
| A-861. | F | OCHF₂ | 5-CH₃ | F | H |
| A-862. | F | OCHF₂ | 5-OCH₃ | F | H |
| A-863. | F | OCF₃ | 3-F | F | H |
| A-864. | F | OCF₃ | 3-CH₃ | F | H |
| A-865. | F | OCF₃ | 3-OCH₃ | F | H |
| A-866. | F | OCF₃ | 5-F | F | H |
| A-867. | F | OCF₃ | 5-CH₃ | F | H |
| A-868. | F | OCF₃ | 5-OCH₃ | F | H |
| A-869. | CH₃ | F | 3-F | F | H |
| A-870. | CH₃ | F | 3-CH₃ | F | H |
| A-871. | CH₃ | F | 3-OCH₃ | F | H |
| A-872. | CH₃ | F | 5-F | F | H |
| A-873. | CH₃ | F | 5-CH₃ | F | H |
| A-874. | CH₃ | F | 5-OCH₃ | F | H |
| A-875. | CH₃ | CH₃ | 3-F | F | H |
| A-876. | CH₃ | CH₃ | 3-CH₃ | F | H |
| A-877. | CH₃ | CH₃ | 3-OCH₃ | F | H |
| A-878. | CH₃ | CH₃ | 5-F | F | H |
| A-879. | CH₃ | CH₃ | 5-CH₃ | F | H |
| A-880. | CH₃ | CH₃ | 5-OCH₃ | F | H |
| A-881. | CH₃ | OCH₃ | 3-F | F | H |
| A-882. | CH₃ | OCH₃ | 3-CH₃ | F | H |
| A-883. | CH₃ | OCH₃ | 3-OCH₃ | F | H |
| A-884. | CH₃ | OCH₃ | 5-F | F | H |
| A-885. | CH₃ | OCH₃ | 5-CH₃ | F | H |
| A-886. | CH₃ | OCH₃ | 5-OCH₃ | F | H |
| A-887. | CH₃ | CN | 3-F | F | H |
| A-888. | CH₃ | CN | 3-CH₃ | F | H |
| A-889. | CH₃ | CN | 3-OCH₃ | F | H |
| A-890. | CH₃ | CN | 5-F | F | H |
| A-891. | CH₃ | CN | 5-CH₃ | F | H |
| A-892. | CH₃ | CN | 5-OCH₃ | F | H |
| A-893. | CH₃ | CH₂F | 3-F | F | H |
| A-894. | CH₃ | CH₂F | 3-CH₃ | F | H |
| A-895. | CH₃ | CH₂F | 3-OCH₃ | F | H |
| A-896. | CH₃ | CH₂F | 5-F | F | H |
| A-897. | CH₃ | CH₂F | 5-CH₃ | F | H |
| A-898. | CH₃ | CH₂F | 5-OCH₃ | F | H |
| A-899. | CH₃ | CHF₂ | 3-F | F | H |
| A-900. | CH₃ | CHF₂ | 3-CH₃ | F | H |
| A-901. | CH₃ | CHF₂ | 3-OCH₃ | F | H |
| A-902. | CH₃ | CHF₂ | 5-F | F | H |
| A-903. | CH₃ | CHF₂ | 5-CH₃ | F | H |
| A-904. | CH₃ | CHF₂ | 5-OCH₃ | F | H |
| A-905. | CH₃ | CF₃ | 3-F | F | H |
| A-906. | CH₃ | CF₃ | 3-CH₃ | F | H |
| A-907. | CH₃ | CF₃ | 3-OCH₃ | F | H |
| A-908. | CH₃ | CF₃ | 5-F | F | H |
| A-909. | CH₃ | CF₃ | 5-CH₃ | F | H |
| A-910. | CH₃ | CF₃ | 5-OCH₃ | F | H |
| A-911. | CH₃ | OCH₂F | 3-F | F | H |
| A-912. | CH₃ | OCH₂F | 3-CH₃ | F | H |
| A-913. | CH₃ | OCH₂F | 3-OCH₃ | F | H |
| A-914. | CH₃ | OCH₂F | 5-F | F | H |
| A-915. | CH₃ | OCH₂F | 5-CH₃ | F | H |
| A-916. | CH₃ | OCH₂F | 5-OCH₃ | F | H |
| A-917. | CH₃ | OCHF₂ | 3-F | F | H |
| A-918. | CH₃ | OCHF₂ | 3-CH₃ | F | H |
| A-919. | CH₃ | OCHF₂ | 3-OCH₃ | F | H |
| A-920. | CH₃ | OCHF₂ | 5-F | F | H |
| A-921. | CH₃ | OCHF₂ | 5-CH₃ | F | H |
| A-922. | CH₃ | OCHF₂ | 5-OCH₃ | F | H |
| A-923. | CH₃ | OCF₃ | 3-F | F | H |
| A-924. | CH₃ | OCF₃ | 3-CH₃ | F | H |
| A-925. | CH₃ | OCF₃ | 3-OCH₃ | F | H |
| A-926. | CH₃ | OCF₃ | 5-F | F | H |
| A-927. | CH₃ | OCF₃ | 5-CH₃ | F | H |
| A-928. | CH₃ | OCF₃ | 5-OCH₃ | F | H |
| A-929. | OCH₃ | F | 3-F | F | H |
| A-930. | OCH₃ | F | 3-CH₃ | F | H |
| A-931. | OCH₃ | F | 3-OCH₃ | F | H |
| A-932. | OCH₃ | F | 5-F | F | H |
| A-933. | OCH₃ | F | 5-CH₃ | F | H |
| A-934. | OCH₃ | F | 5-OCH₃ | F | H |
| A-935. | OCH₃ | CH₃ | 3-F | F | H |
| A-936. | OCH₃ | CH₃ | 3-CH₃ | F | H |
| A-937. | OCH₃ | CH₃ | 3-OCH₃ | F | H |
| A-938. | OCH₃ | CH₃ | 5-F | F | H |
| A-939. | OCH₃ | CH₃ | 5-CH₃ | F | H |
| A-940. | OCH₃ | CH₃ | 5-OCH₃ | F | H |
| A-941. | OCH₃ | OCH₃ | 3-F | F | H |
| A-942. | OCH₃ | OCH₃ | 3-CH₃ | F | H |
| A-943. | OCH₃ | OCH₃ | 3-OCH₃ | F | H |
| A-944. | OCH₃ | OCH₃ | 5-F | F | H |
| A-945. | OCH₃ | OCH₃ | 5-CH₃ | F | H |
| A-946. | OCH₃ | OCH₃ | 5-OCH₃ | F | H |
| A-947. | OCH₃ | CN | 3-F | F | H |
| A-948. | OCH₃ | CN | 3-CH₃ | F | H |
| A-949. | OCH₃ | CN | 3-OCH₃ | F | H |
| A-950. | OCH₃ | CN | 5-F | F | H |
| A-951. | OCH₃ | CN | 5-CH₃ | F | H |
| A-952. | OCH₃ | CN | 5-OCH₃ | F | H |
| A-953. | OCH₃ | CH₂F | 3-F | F | H |
| A-954. | OCH₃ | CH₂F | 3-CH₃ | F | H |
| A-955. | OCH₃ | CH₂F | 3-OCH₃ | F | H |
| A-956. | OCH₃ | CH₂F | 5-F | F | H |
| A-957. | OCH₃ | CH₂F | 5-CH₃ | F | H |
| A-958. | OCH₃ | CH₂F | 5-OCH₃ | F | H |
| A-959. | OCH₃ | CHF₂ | 3-F | F | H |
| A-960. | OCH₃ | CHF₂ | 3-CH₃ | F | H |
| A-961. | OCH₃ | CHF₂ | 3-OCH₃ | F | H |
| A-962. | OCH₃ | CHF₂ | 5-F | F | H |
| A-963. | OCH₃ | CHF₂ | 5-CH₃ | F | H |
| A-964. | OCH₃ | CHF₂ | 5-OCH₃ | F | H |
| A-965. | OCH₃ | CF₃ | 3-F | F | H |
| A-966. | OCH₃ | CF₃ | 3-CH₃ | F | H |
| A-967. | OCH₃ | CF₃ | 3-OCH₃ | F | H |
| A-968. | OCH₃ | CF₃ | 5-F | F | H |
| A-969. | OCH₃ | CF₃ | 5-CH₃ | F | H |
| A-970. | OCH₃ | CF₃ | 5-OCH₃ | F | H |
| A-971. | OCH₃ | OCH₂F | 3-F | F | H |
| A-972. | OCH₃ | OCH₂F | 3-CH₃ | F | H |
| A-973. | OCH₃ | OCH₂F | 3-OCH₃ | F | H |
| A-974. | OCH₃ | OCH₂F | 5-F | F | H |
| A-975. | OCH₃ | OCH₂F | 5-CH₃ | F | H |
| A-976. | OCH₃ | OCH₂F | 5-OCH₃ | F | H |
| A-977. | OCH₃ | OCHF₂ | 3-F | F | H |
| A-978. | OCH₃ | OCHF₂ | 3-CH₃ | F | H |
| A-979. | OCH₃ | OCHF₂ | 3-OCH₃ | F | H |
| A-980. | OCH₃ | OCHF₂ | 5-F | F | H |
| A-981. | OCH₃ | OCHF₂ | 5-CH₃ | F | H |
| A-982. | OCH₃ | OCHF₂ | 5-OCH₃ | F | H |
| A-983. | OCH₃ | OCF₃ | 3-F | F | H |
| A-984. | OCH₃ | OCF₃ | 3-CH₃ | F | H |
| A-985. | OCH₃ | OCF₃ | 3-OCH₃ | F | H |
| A-986. | OCH₃ | OCF₃ | 5-F | F | H |
| A-987. | OCH₃ | OCF₃ | 5-CH₃ | F | H |
| A-988. | OCH₃ | OCF₃ | 5-OCH₃ | F | H |
| A-989. | CH₂F | F | 3-F | F | H |
| A-990. | CH₂F | F | 3-CH₃ | F | H |
| A-991. | CH₂F | F | 3-OCH₃ | F | H |
| A-992. | CH₂F | F | 5-F | F | H |
| A-993. | CH₂F | F | 5-CH₃ | F | H |
| A-994. | CH₂F | F | 5-OCH₃ | F | H |
| A-995. | CH₂F | CH₃ | 3-F | F | H |
| A-996. | CH₂F | CH₃ | 3-CH₃ | F | H |
| A-997. | CH₂F | CH₃ | 3-OCH₃ | F | H |
| A-998. | CH₂F | CH₃ | 5-F | F | H |
| A-999. | CH₂F | CH₃ | 5-CH₃ | F | H |
| A-1000. | CH₂F | CH₃ | 5-OCH₃ | F | H |
| A-1001. | CH₂F | OCH₃ | 3-F | F | H |
| A-1002. | CH₂F | OCH₃ | 3-CH₃ | F | H |
| A-1003. | CH₂F | OCH₃ | 3-OCH₃ | F | H |
| A-1004. | CH₂F | OCH₃ | 5-F | F | H |
| A-1005. | CH₂F | OCH₃ | 5-CH₃ | F | H |
| A-1006. | CH₂F | OCH₃ | 5-OCH₃ | F | H |
| A-1007. | CH₂F | CN | 3-F | F | H |
| A-1008. | CH₂F | CN | 3-CH₃ | F | H |
| A-1009. | CH₂F | CN | 3-OCH₃ | F | H |

TABLE A-continued

| Example No. | $R^1$ | $R^2$ | $R^3$ | $R^6$ | $R^7$ |
|---|---|---|---|---|---|
| A-1010. | $CH_2F$ | CN | 5-F | F | H |
| A-1011. | $CH_2F$ | CN | 5-$CH_3$ | F | H |
| A-1012. | $CH_2F$ | CN | 5-$OCH_3$ | F | H |
| A-1013. | $CH_2F$ | $CH_2F$ | 3-F | F | H |
| A-1014. | $CH_2F$ | $CH_2F$ | 3-$CH_3$ | F | H |
| A-1015. | $CH_2F$ | $CH_2F$ | 3-$OCH_3$ | F | H |
| A-1016. | $CH_2F$ | $CH_2F$ | 5-F | F | H |
| A-1017. | $CH_2F$ | $CH_2F$ | 5-$CH_3$ | F | H |
| A-1018. | $CH_2F$ | $CH_2F$ | 5-$OCH_3$ | F | H |
| A-1019. | $CH_2F$ | $CHF_2$ | 3-F | F | H |
| A-1020. | $CH_2F$ | $CHF_2$ | 3-$CH_3$ | F | H |
| A-1021. | $CH_2F$ | $CHF_2$ | 3-$OCH_3$ | F | H |
| A-1022. | $CH_2F$ | $CHF_2$ | 5-F | F | H |
| A-1023. | $CH_2F$ | $CHF_2$ | 5-$CH_3$ | F | H |
| A-1024. | $CH_2F$ | $CHF_2$ | 5-$OCH_3$ | F | H |
| A-1025. | $CH_2F$ | $CF_3$ | 3-F | F | H |
| A-1026. | $CH_2F$ | $CF_3$ | 3-$CH_3$ | F | H |
| A-1027. | $CH_2F$ | $CF_3$ | 3-$OCH_3$ | F | H |
| A-1028. | $CH_2F$ | $CF_3$ | 5-F | F | H |
| A-1029. | $CH_2F$ | $CF_3$ | 5-$CH_3$ | F | H |
| A-1030. | $CH_2F$ | $CF_3$ | 5-$OCH_3$ | F | H |
| A-1031. | $CH_2F$ | $OCH_2F$ | 3-F | F | H |
| A-1032. | $CH_2F$ | $OCH_2F$ | 3-$CH_3$ | F | H |
| A-1033. | $CH_2F$ | $OCH_2F$ | 3-$OCH_3$ | F | H |
| A-1034. | $CH_2F$ | $OCH_2F$ | 5-F | F | H |
| A-1035. | $CH_2F$ | $OCH_2F$ | 5-$CH_3$ | F | H |
| A-1036. | $CH_2F$ | $OCH_2F$ | 5-$OCH_3$ | F | H |
| A-1037. | $CH_2F$ | $OCHF_2$ | 3-F | F | H |
| A-1038. | $CH_2F$ | $OCHF_2$ | 3-$CH_3$ | F | H |
| A-1039. | $CH_2F$ | $OCHF_2$ | 3-$OCH_3$ | F | H |
| A-1040. | $CH_2F$ | $OCHF_2$ | 5-F | F | H |
| A-1041. | $CH_2F$ | $OCHF_2$ | 5-$CH_3$ | F | H |
| A-1042. | $CH_2F$ | $OCHF_2$ | 5-$OCH_3$ | F | H |
| A-1043. | $CH_2F$ | $OCF_3$ | 3-F | F | H |
| A-1044. | $CH_2F$ | $OCF_3$ | 3-$CH_3$ | F | H |
| A-1045. | $CH_2F$ | $OCF_3$ | 3-$OCH_3$ | F | H |
| A-1046. | $CH_2F$ | $OCF_3$ | 5-F | F | H |
| A-1047. | $CH_2F$ | $OCF_3$ | 5-$CH_3$ | F | H |
| A-1048. | $CH_2F$ | $OCF_3$ | 5-$OCH_3$ | F | H |
| A-1049. | $CHF_2$ | F | 3-F | F | H |
| A-1050. | $CHF_2$ | F | 3-$CH_3$ | F | H |
| A-1051. | $CHF_2$ | F | 3-$OCH_3$ | F | H |
| A-1052. | $CHF_2$ | F | 5-F | F | H |
| A-1053. | $CHF_2$ | F | 5-$CH_3$ | F | H |
| A-1054. | $CHF_2$ | F | 5-$OCH_3$ | F | H |
| A-1055. | $CHF_2$ | $CH_3$ | 3-F | F | H |
| A-1056. | $CHF_2$ | $CH_3$ | 3-$CH_3$ | F | H |
| A-1057. | $CHF_2$ | $CH_3$ | 3-$OCH_3$ | F | H |
| A-1058. | $CHF_2$ | $CH_3$ | 5-F | F | H |
| A-1059. | $CHF_2$ | $CH_3$ | 5-$CH_3$ | F | H |
| A-1060. | $CHF_2$ | $CH_3$ | 5-$OCH_3$ | F | H |
| A-1061. | $CHF_2$ | $OCH_3$ | 3-F | F | H |
| A-1062. | $CHF_2$ | $OCH_3$ | 3-$CH_3$ | F | H |
| A-1063. | $CHF_2$ | $OCH_3$ | 3-$OCH_3$ | F | H |
| A-1064. | $CHF_2$ | $OCH_3$ | 5-F | F | H |
| A-1065. | $CHF_2$ | $OCH_3$ | 5-$CH_3$ | F | H |
| A-1066. | $CHF_2$ | $OCH_3$ | 5-$OCH_3$ | F | H |
| A-1067. | $CHF_2$ | CN | 3-F | F | H |
| A-1068. | $CHF_2$ | CN | 3-$CH_3$ | F | H |
| A-1069. | $CHF_2$ | CN | 3-$OCH_3$ | F | H |
| A-1070. | $CHF_2$ | CN | 5-F | F | H |
| A-1071. | $CHF_2$ | CN | 5-$CH_3$ | F | H |
| A-1072. | $CHF_2$ | CN | 5-$OCH_3$ | F | H |
| A-1073. | $CHF_2$ | $CH_2F$ | 3-F | F | H |
| A-1074. | $CHF_2$ | $CH_2F$ | 3-$CH_3$ | F | H |
| A-1075. | $CHF_2$ | $CH_2F$ | 3-$OCH_3$ | F | H |
| A-1076. | $CHF_2$ | $CH_2F$ | 5-F | F | H |
| A-1077. | $CHF_2$ | $CH_2F$ | 5-$CH_3$ | F | H |
| A-1078. | $CHF_2$ | $CH_2F$ | 5-$OCH_3$ | F | H |
| A-1079. | $CHF_2$ | $CHF_2$ | 3-F | F | H |
| A-1080. | $CHF_2$ | $CHF_2$ | 3-$CH_3$ | F | H |
| A-1081. | $CHF_2$ | $CHF_2$ | 3-$OCH_3$ | F | H |
| A-1082. | $CHF_2$ | $CHF_2$ | 5-F | F | H |
| A-1083. | $CHF_2$ | $CHF_2$ | 5-$CH_3$ | F | H |
| A-1084. | $CHF_2$ | $CHF_2$ | 5-$OCH_3$ | F | H |
| A-1085. | $CHF_2$ | $CF_3$ | 3-F | F | H |
| A-1086. | $CHF_2$ | $CF_3$ | 3-$CH_3$ | F | H |
| A-1087. | $CHF_2$ | $CF_3$ | 3-$OCH_3$ | F | H |
| A-1088. | $CHF_2$ | $CF_3$ | 5-F | F | H |
| A-1089. | $CHF_2$ | $CF_3$ | 5-$CH_3$ | F | H |
| A-1090. | $CHF_2$ | $CF_3$ | 5-$OCH_3$ | F | H |
| A-1091. | $CHF_2$ | $OCH_2F$ | 3-F | F | H |
| A-1092. | $CHF_2$ | $OCH_2F$ | 3-$CH_3$ | F | H |
| A-1093. | $CHF_2$ | $OCH_2F$ | 3-$OCH_3$ | F | H |
| A-1094. | $CHF_2$ | $OCH_2F$ | 5-F | F | H |
| A-1095. | $CHF_2$ | $OCH_2F$ | 5-$CH_3$ | F | H |
| A-1096. | $CHF_2$ | $OCH_2F$ | 5-$OCH_3$ | F | H |
| A-1097. | $CHF_2$ | $OCHF_2$ | 3-F | F | H |
| A-1098. | $CHF_2$ | $OCHF_2$ | 3-$CH_3$ | F | H |
| A-1099. | $CHF_2$ | $OCHF_2$ | 3-$OCH_3$ | F | H |
| A-1100. | $CHF_2$ | $OCHF_2$ | 5-F | F | H |
| A-1101. | $CHF_2$ | $OCHF_2$ | 5-$CH_3$ | F | H |
| A-1102. | $CHF_2$ | $OCHF_2$ | 5-$OCH_3$ | F | H |
| A-1103. | $CHF_2$ | $OCF_3$ | 3-F | F | H |
| A-1104. | $CHF_2$ | $OCF_3$ | 3-$CH_3$ | F | H |
| A-1105. | $CHF_2$ | $OCF_3$ | 3-$OCH_3$ | F | H |
| A-1106. | $CHF_2$ | $OCF_3$ | 5-F | F | H |
| A-1107. | $CHF_2$ | $OCF_3$ | 5-$CH_3$ | F | H |
| A-1108. | $CHF_2$ | $OCF_3$ | 5-$OCH_3$ | F | H |
| A-1109. | $CF_3$ | F | 3-F | F | H |
| A-1110. | $CF_3$ | F | 3-$CH_3$ | F | H |
| A-1111. | $CF_3$ | F | 3-$OCH_3$ | F | H |
| A-1112. | $CF_3$ | F | 5-F | F | H |
| A-1113. | $CF_3$ | F | 5-$CH_3$ | F | H |
| A-1114. | $CF_3$ | F | 5-$OCH_3$ | F | H |
| A-1115. | $CF_3$ | $CH_3$ | 3-F | F | H |
| A-1116. | $CF_3$ | $CH_3$ | 3-$CH_3$ | F | H |
| A-1117. | $CF_3$ | $CH_3$ | 3-$OCH_3$ | F | H |
| A-1118. | $CF_3$ | $CH_3$ | 5-F | F | H |
| A-1119. | $CF_3$ | $CH_3$ | 5-$CH_3$ | F | H |
| A-1120. | $CF_3$ | $CH_3$ | 5-$OCH_3$ | F | H |
| A-1121. | $CF_3$ | $OCH_3$ | 3-F | F | H |
| A-1122. | $CF_3$ | $OCH_3$ | 3-$CH_3$ | F | H |
| A-1123. | $CF_3$ | $OCH_3$ | 3-$OCH_3$ | F | H |
| A-1124. | $CF_3$ | $OCH_3$ | 5-F | F | H |
| A-1125. | $CF_3$ | $OCH_3$ | 5-$CH_3$ | F | H |
| A-1126. | $CF_3$ | $OCH_3$ | 5-$OCH_3$ | F | H |
| A-1127. | $CF_3$ | CN | 3-F | F | H |
| A-1128. | $CF_3$ | CN | 3-$CH_3$ | F | H |
| A-1129. | $CF_3$ | CN | 3-$OCH_3$ | F | H |
| A-1130. | $CF_3$ | CN | 5-F | F | H |
| A-1131. | $CF_3$ | CN | 5-$CH_3$ | F | H |
| A-1132. | $CF_3$ | CN | 5-$OCH_3$ | F | H |
| A-1133. | $CF_3$ | $CH_2F$ | 3-F | F | H |
| A-1134. | $CF_3$ | $CH_2F$ | 3-$CH_3$ | F | H |
| A-1135. | $CF_3$ | $CH_2F$ | 3-$OCH_3$ | F | H |
| A-1136. | $CF_3$ | $CH_2F$ | 5-F | F | H |
| A-1137. | $CF_3$ | $CH_2F$ | 5-$CH_3$ | F | H |
| A-1138. | $CF_3$ | $CH_2F$ | 5-$OCH_3$ | F | H |
| A-1139. | $CF_3$ | $CHF_2$ | 3-F | F | H |
| A-1140. | $CF_3$ | $CHF_2$ | 3-$CH_3$ | F | H |
| A-1141. | $CF_3$ | $CHF_2$ | 3-$OCH_3$ | F | H |
| A-1142. | $CF_3$ | $CHF_2$ | 5-F | F | H |
| A-1143. | $CF_3$ | $CHF_2$ | 5-$CH_3$ | F | H |
| A-1144. | $CF_3$ | $CHF_2$ | 5-$OCH_3$ | F | H |
| A-1145. | $CF_3$ | $CF_3$ | 3-F | F | H |
| A-1146. | $CF_3$ | $CF_3$ | 3-$CH_3$ | F | H |
| A-1147. | $CF_3$ | $CF_3$ | 3-$OCH_3$ | F | H |
| A-1148. | $CF_3$ | $CF_3$ | 5-F | F | H |
| A-1149. | $CF_3$ | $CF_3$ | 5-$CH_3$ | F | H |
| A-1150. | $CF_3$ | $CF_3$ | 5-$OCH_3$ | F | H |
| A-1151. | $CF_3$ | $OCH_2F$ | 3-F | F | H |
| A-1152. | $CF_3$ | $OCH_2F$ | 3-$CH_3$ | F | H |
| A-1153. | $CF_3$ | $OCH_2F$ | 3-$OCH_3$ | F | H |
| A-1154. | $CF_3$ | $OCH_2F$ | 5-F | F | H |
| A-1155. | $CF_3$ | $OCH_2F$ | 5-$CH_3$ | F | H |
| A-1156. | $CF_3$ | $OCH_2F$ | 5-$OCH_3$ | F | H |
| A-1157. | $CF_3$ | $OCHF_2$ | 3-F | F | H |
| A-1158. | $CF_3$ | $OCHF_2$ | 3-$CH_3$ | F | H |
| A-1159. | $CF_3$ | $OCHF_2$ | 3-$OCH_3$ | F | H |
| A-1160. | $CF_3$ | $OCHF_2$ | 5-F | F | H |
| A-1161. | $CF_3$ | $OCHF_2$ | 5-$CH_3$ | F | H |
| A-1162. | $CF_3$ | $OCHF_2$ | 5-$OCH_3$ | F | H |
| A-1163. | $CF_3$ | $OCF_3$ | 3-F | F | H |
| A-1164. | $CF_3$ | $OCF_3$ | 3-$CH_3$ | F | H |
| A-1165. | $CF_3$ | $OCF_3$ | 3-$OCH_3$ | F | H |

TABLE A-continued

| Example No. | $R^1$ | $R^2$ | $R^3$ | $R^6$ | $R^7$ |
|---|---|---|---|---|---|
| A-1166. | $CF_3$ | $OCF_3$ | 5-F | F | H |
| A-1167. | $CF_3$ | $OCF_3$ | 5-$CH_3$ | F | H |
| A-1168. | $CF_3$ | $OCF_3$ | 5-$OCH_3$ | F | H |
| A-1169. | $OCH_2F$ | F | 3-F | F | H |
| A-1170. | $OCH_2F$ | F | 3-$CH_3$ | F | H |
| A-1171. | $OCH_2F$ | F | 3-$OCH_3$ | F | H |
| A-1172. | $OCH_2F$ | F | 5-F | F | H |
| A-1173. | $OCH_2F$ | F | 5-$CH_3$ | F | H |
| A-1174. | $OCH_2F$ | F | 5-$OCH_3$ | F | H |
| A-1175. | $OCH_2F$ | $CH_3$ | 3-F | F | H |
| A-1176. | $OCH_2F$ | $CH_3$ | 3-$CH_3$ | F | H |
| A-1177. | $OCH_2F$ | $CH_3$ | 3-$OCH_3$ | F | H |
| A-1178. | $OCH_2F$ | $CH_3$ | 5-F | F | H |
| A-1179. | $OCH_2F$ | $CH_3$ | 5-$CH_3$ | F | H |
| A-1180. | $OCH_2F$ | $CH_3$ | 5-$OCH_3$ | F | H |
| A-1181. | $OCH_2F$ | $OCH_3$ | 3-F | F | H |
| A-1182. | $OCH_2F$ | $OCH_3$ | 3-$CH_3$ | F | H |
| A-1183. | $OCH_2F$ | $OCH_3$ | 3-$OCH_3$ | F | H |
| A-1184. | $OCH_2F$ | $OCH_3$ | 5-F | F | H |
| A-1185. | $OCH_2F$ | $OCH_3$ | 5-$CH_3$ | F | H |
| A-1186. | $OCH_2F$ | $OCH_3$ | 5-$OCH_3$ | F | H |
| A-1187. | $OCH_2F$ | CN | 3-F | F | H |
| A-1188. | $OCH_2F$ | CN | 3-$CH_3$ | F | H |
| A-1189. | $OCH_2F$ | CN | 3-$OCH_3$ | F | H |
| A-1190. | $OCH_2F$ | CN | 5-F | F | H |
| A-1191. | $OCH_2F$ | CN | 5-$CH_3$ | F | H |
| A-1192. | $OCH_2F$ | CN | 5-$OCH_3$ | F | H |
| A-1193. | $OCH_2F$ | $CH_2F$ | 3-F | F | H |
| A-1194. | $OCH_2F$ | $CH_2F$ | 3-$CH_3$ | F | H |
| A-1195. | $OCH_2F$ | $CH_2F$ | 3-$OCH_3$ | F | H |
| A-1196. | $OCH_2F$ | $CH_2F$ | 5-F | F | H |
| A-1197. | $OCH_2F$ | $CH_2F$ | 5-$CH_3$ | F | H |
| A-1198. | $OCH_2F$ | $CH_2F$ | 5-$OCH_3$ | F | H |
| A-1199. | $OCH_2F$ | $CHF_2$ | 3-F | F | H |
| A-1200. | $OCH_2F$ | $CHF_2$ | 3-$CH_3$ | F | H |
| A-1201. | $OCH_2F$ | $CHF_2$ | 3-$OCH_3$ | F | H |
| A-1202. | $OCH_2F$ | $CHF_2$ | 5-F | F | H |
| A-1203. | $OCH_2F$ | $CHF_2$ | 5-$CH_3$ | F | H |
| A-1204. | $OCH_2F$ | $CHF_2$ | 5-$OCH_3$ | F | H |
| A-1205. | $OCH_2F$ | $CF_3$ | 3-F | F | H |
| A-1206. | $OCH_2F$ | $CF_3$ | 3-$CH_3$ | F | H |
| A-1207. | $OCH_2F$ | $CF_3$ | 3-$OCH_3$ | F | H |
| A-1208. | $OCH_2F$ | $CF_3$ | 5-F | F | H |
| A-1209. | $OCH_2F$ | $CF_3$ | 5-$CH_3$ | F | H |
| A-1210. | $OCH_2F$ | $CF_3$ | 5-$OCH_3$ | F | H |
| A-1211. | $OCH_2F$ | $OCH_2F$ | 3-F | F | H |
| A-1212. | $OCH_2F$ | $OCH_2F$ | 3-$CH_3$ | F | H |
| A-1213. | $OCH_2F$ | $OCH_2F$ | 3-$OCH_3$ | F | H |
| A-1214. | $OCH_2F$ | $OCH_2F$ | 5-F | F | H |
| A-1215. | $OCH_2F$ | $OCH_2F$ | 5-$CH_3$ | F | H |
| A-1216. | $OCH_2F$ | $OCH_2F$ | 5-$OCH_3$ | F | H |
| A-1217. | $OCH_2F$ | $OCHF_2$ | 3-F | F | H |
| A-1218. | $OCH_2F$ | $OCHF_2$ | 3-$CH_3$ | F | H |
| A-1219. | $OCH_2F$ | $OCHF_2$ | 3-$OCH_3$ | F | H |
| A-1220. | $OCH_2F$ | $OCHF_2$ | 5-F | F | H |
| A-1221. | $OCH_2F$ | $OCHF_2$ | 5-$CH_3$ | F | H |
| A-1222. | $OCH_2F$ | $OCHF_2$ | 5-$OCH_3$ | F | H |
| A-1223. | $OCH_2F$ | $OCF_3$ | 3-F | F | H |
| A-1224. | $OCH_2F$ | $OCF_3$ | 3-$CH_3$ | F | H |
| A-1225. | $OCH_2F$ | $OCF_3$ | 3-$OCH_3$ | F | H |
| A-1226. | $OCH_2F$ | $OCF_3$ | 5-F | F | H |
| A-1227. | $OCH_2F$ | $OCF_3$ | 5-$CH_3$ | F | H |
| A-1228. | $OCH_2F$ | $OCF_3$ | 5-$OCH_3$ | F | H |
| A-1229. | $OCHF_2$ | F | 3-F | F | H |
| A-1230. | $OCHF_2$ | F | 3-$CH_3$ | F | H |
| A-1231. | $OCHF_2$ | F | 3-$OCH_3$ | F | H |
| A-1232. | $OCHF_2$ | F | 5-F | F | H |
| A-1233. | $OCHF_2$ | F | 5-$CH_3$ | F | H |
| A-1234. | $OCHF_2$ | F | 5-$OCH_3$ | F | H |
| A-1235. | $OCHF_2$ | $CH_3$ | 3-F | F | H |
| A-1236. | $OCHF_2$ | $CH_3$ | 3-$CH_3$ | F | H |
| A-1237. | $OCHF_2$ | $CH_3$ | 3-$OCH_3$ | F | H |
| A-1238. | $OCHF_2$ | $CH_3$ | 5-F | F | H |
| A-1239. | $OCHF_2$ | $CH_3$ | 5-$CH_3$ | F | H |
| A-1240. | $OCHF_2$ | $CH_3$ | 5-$OCH_3$ | F | H |
| A-1241. | $OCHF_2$ | $OCH_3$ | 3-F | F | H |
| A-1242. | $OCHF_2$ | $OCH_3$ | 3-$CH_3$ | F | H |
| A-1243. | $OCHF_2$ | $OCH_3$ | 3-$OCH_3$ | F | H |
| A-1244. | $OCHF_2$ | $OCH_3$ | 5-F | F | H |
| A-1245. | $OCHF_2$ | $OCH_3$ | 5-$CH_3$ | F | H |
| A-1246. | $OCHF_2$ | $OCH_3$ | 5-$OCH_3$ | F | H |
| A-1247. | $OCHF_2$ | CN | 3-F | F | H |
| A-1248. | $OCHF_2$ | CN | 3-$CH_3$ | F | H |
| A-1249. | $OCHF_2$ | CN | 3-$OCH_3$ | F | H |
| A-1250. | $OCHF_2$ | CN | 5-F | F | H |
| A-1251. | $OCHF_2$ | CN | 5-$CH_3$ | F | H |
| A-1252. | $OCHF_2$ | CN | 5-$OCH_3$ | F | H |
| A-1253. | $OCHF_2$ | $CH_2F$ | 3-F | F | H |
| A-1254. | $OCHF_2$ | $CH_2F$ | 3-$CH_3$ | F | H |
| A-1255. | $OCHF_2$ | $CH_2F$ | 3-$OCH_3$ | F | H |
| A-1256. | $OCHF_2$ | $CH_2F$ | 5-F | F | H |
| A-1257. | $OCHF_2$ | $CH_2F$ | 5-$CH_3$ | F | H |
| A-1258. | $OCHF_2$ | $CH_2F$ | 5-$OCH_3$ | F | H |
| A-1259. | $OCHF_2$ | $CHF_2$ | 3-F | F | H |
| A-1260. | $OCHF_2$ | $CHF_2$ | 3-$CH_3$ | F | H |
| A-1261. | $OCHF_2$ | $CHF_2$ | 3-$OCH_3$ | F | H |
| A-1262. | $OCHF_2$ | $CHF_2$ | 5-F | F | H |
| A-1263. | $OCHF_2$ | $CHF_2$ | 5-$CH_3$ | F | H |
| A-1264. | $OCHF_2$ | $CHF_2$ | 5-$OCH_3$ | F | H |
| A-1265. | $OCHF_2$ | $CF_3$ | 3-F | F | H |
| A-1266. | $OCHF_2$ | $CF_3$ | 3-$CH_3$ | F | H |
| A-1267. | $OCHF_2$ | $CF_3$ | 3-$OCH_3$ | F | H |
| A-1268. | $OCHF_2$ | $CF_3$ | 5-F | F | H |
| A-1269. | $OCHF_2$ | $CF_3$ | 5-$CH_3$ | F | H |
| A-1270. | $OCHF_2$ | $CF_3$ | 5-$OCH_3$ | F | H |
| A-1271. | $OCHF_2$ | $OCH_2F$ | 3-F | F | H |
| A-1272. | $OCHF_2$ | $OCH_2F$ | 3-$CH_3$ | F | H |
| A-1273. | $OCHF_2$ | $OCH_2F$ | 3-$OCH_3$ | F | H |
| A-1274. | $OCHF_2$ | $OCH_2F$ | 5-F | F | H |
| A-1275. | $OCHF_2$ | $OCH_2F$ | 5-$CH_3$ | F | H |
| A-1276. | $OCHF_2$ | $OCH_2F$ | 5-$OCH_3$ | F | H |
| A-1277. | $OCHF_2$ | $OCHF_2$ | 3-F | F | H |
| A-1278. | $OCHF_2$ | $OCHF_2$ | 3-$CH_3$ | F | H |
| A-1279. | $OCHF_2$ | $OCHF_2$ | 3-$OCH_3$ | F | H |
| A-1280. | $OCHF_2$ | $OCHF_2$ | 5-F | F | H |
| A-1281. | $OCHF_2$ | $OCHF_2$ | 5-$CH_3$ | F | H |
| A-1282. | $OCHF_2$ | $OCHF_2$ | 5-$OCH_3$ | F | H |
| A-1283. | $OCHF_2$ | $OCF_3$ | 3-F | F | H |
| A-1284. | $OCHF_2$ | $OCF_3$ | 3-$CH_3$ | F | H |
| A-1285. | $OCHF_2$ | $OCF_3$ | 3-$OCH_3$ | F | H |
| A-1286. | $OCHF_2$ | $OCF_3$ | 5-F | F | H |
| A-1287. | $OCHF_2$ | $OCF_3$ | 5-$CH_3$ | F | H |
| A-1288. | $OCHF_2$ | $OCF_3$ | 5-$OCH_3$ | F | H |
| A-1289. | $OCF_3$ | F | 3-F | F | H |
| A-1290. | $OCF_3$ | F | 3-$CH_3$ | F | H |
| A-1291. | $OCF_3$ | F | 3-$OCH_3$ | F | H |
| A-1292. | $OCF_3$ | F | 5-F | F | H |
| A-1293. | $OCF_3$ | F | 5-$CH_3$ | F | H |
| A-1294. | $OCF_3$ | F | 5-$OCH_3$ | F | H |
| A-1295. | $OCF_3$ | $CH_3$ | 3-F | F | H |
| A-1296. | $OCF_3$ | $CH_3$ | 3-$CH_3$ | F | H |
| A-1297. | $OCF_3$ | $CH_3$ | 3-$OCH_3$ | F | H |
| A-1298. | $OCF_3$ | $CH_3$ | 5-F | F | H |
| A-1299. | $OCF_3$ | $CH_3$ | 5-$CH_3$ | F | H |
| A-1300. | $OCF_3$ | $CH_3$ | 5-$OCH_3$ | F | H |
| A-1301. | $OCF_3$ | $OCH_3$ | 3-F | F | H |
| A-1302. | $OCF_3$ | $OCH_3$ | 3-$CH_3$ | F | H |
| A-1303. | $OCF_3$ | $OCH_3$ | 3-$OCH_3$ | F | H |
| A-1304. | $OCF_3$ | $OCH_3$ | 5-F | F | H |
| A-1305. | $OCF_3$ | $OCH_3$ | 5-$CH_3$ | F | H |
| A-1306. | $OCF_3$ | $OCH_3$ | 5-$OCH_3$ | F | H |
| A-1307. | $OCF_3$ | CN | 3-F | F | H |
| A-1308. | $OCF_3$ | CN | 3-$CH_3$ | F | H |
| A-1309. | $OCF_3$ | CN | 3-$OCH_3$ | F | H |
| A-1310. | $OCF_3$ | CN | 5-F | F | H |
| A-1311. | $OCF_3$ | CN | 5-$CH_3$ | F | H |
| A-1312. | $OCF_3$ | CN | 5-$OCH_3$ | F | H |
| A-1313. | $OCF_3$ | $CH_2F$ | 3-F | F | H |
| A-1314. | $OCF_3$ | $CH_2F$ | 3-$CH_3$ | F | H |
| A-1315. | $OCF_3$ | $CH_2F$ | 3-$OCH_3$ | F | H |
| A-1316. | $OCF_3$ | $CH_2F$ | 5-F | F | H |
| A-1317. | $OCF_3$ | $CH_2F$ | 5-$CH_3$ | F | H |
| A-1318. | $OCF_3$ | $CH_2F$ | 5-$OCH_3$ | F | H |
| A-1319. | $OCF_3$ | $CHF_2$ | 3-F | F | H |
| A-1320. | $OCF_3$ | $CHF_2$ | 3-$CH_3$ | F | H |
| A-1321. | $OCF_3$ | $CHF_2$ | 3-$OCH_3$ | F | H |

TABLE A-continued

| Example No. | R¹ | R² | R³ | R⁶ | R⁷ |
|---|---|---|---|---|---|
| A-1322. | OCF$_3$ | CHF$_2$ | 5-F | F | H |
| A-1323. | OCF$_3$ | CHF$_2$ | 5-CH$_3$ | F | H |
| A-1324. | OCF$_3$ | CHF$_2$ | 5-OCH$_3$ | F | H |
| A-1325. | OCF$_3$ | CF$_3$ | 3-F | F | H |
| A-1326. | OCF$_3$ | CF$_3$ | 3-CH$_3$ | F | H |
| A-1327. | OCF$_3$ | CF$_3$ | 3-OCH$_3$ | F | H |
| A-1328. | OCF$_3$ | CF$_3$ | 5-F | F | H |
| A-1329. | OCF$_3$ | CF$_3$ | 5-CH$_3$ | F | H |
| A-1330. | OCF$_3$ | CF$_3$ | 5-OCH$_3$ | F | H |
| A-1331. | OCF$_3$ | OCH$_2$F | 3-F | F | H |
| A-1332. | OCF$_3$ | OCH$_2$F | 3-CH$_3$ | F | H |
| A-1333. | OCF$_3$ | OCH$_2$F | 3-OCH$_3$ | F | H |
| A-1334. | OCF$_3$ | OCH$_2$F | 5-F | F | H |
| A-1335. | OCF$_3$ | OCH$_2$F | 5-CH$_3$ | F | H |
| A-1336. | OCF$_3$ | OCH$_2$F | 5-OCH$_3$ | F | H |
| A-1337. | OCF$_3$ | OCHF$_2$ | 3-F | F | H |
| A-1338. | OCF$_3$ | OCHF$_2$ | 3-CH$_3$ | F | H |
| A-1339. | OCF$_3$ | OCHF$_2$ | 3-OCH$_3$ | F | H |
| A-1340. | OCF$_3$ | OCHF$_2$ | 5-F | F | H |
| A-1341. | OCF$_3$ | OCHF$_2$ | 5-CH$_3$ | F | H |
| A-1342. | OCF$_3$ | OCHF$_2$ | 5-OCH$_3$ | F | H |
| A-1343. | OCF$_3$ | OCF$_3$ | 3-F | F | H |
| A-1344. | OCF$_3$ | OCF$_3$ | 3-CH$_3$ | F | H |
| A-1345. | OCF$_3$ | OCF$_3$ | 3-OCH$_3$ | F | H |
| A-1346. | OCF$_3$ | OCF$_3$ | 5-F | F | H |
| A-1347. | OCF$_3$ | OCF$_3$ | 5-CH$_3$ | F | H |
| A-1348. | OCF$_3$ | OCF$_3$ | 5-OCH$_3$ | F | H |
| A-1349. | H | H | H | Cl | H |
| A-1350. | F | H | H | Cl | H |
| A-1351. | CH$_3$ | H | H | Cl | H |
| A-1352. | OCH$_3$ | H | H | Cl | H |
| A-1353. | CH$_2$F | H | H | Cl | H |
| A-1354. | CHF$_2$ | H | H | Cl | H |
| A-1355. | CF$_3$ | H | H | Cl | H |
| A-1356. | OCH$_2$F | H | H | Cl | H |
| A-1357. | OCHF$_2$ | H | H | Cl | H |
| A-1358. | OCF$_3$ | H | H | Cl | H |
| A-1359. | H | F | H | Cl | H |
| A-1360. | H | CH$_3$ | H | Cl | H |
| A-1361. | H | OCH$_3$ | H | Cl | H |
| A-1362. | H | CN | H | Cl | H |
| A-1363. | H | CH$_2$F | H | Cl | H |
| A-1364. | H | CHF$_2$ | H | Cl | H |
| A-1365. | H | CF$_3$ | H | Cl | H |
| A-1366. | H | OCH$_2$F | H | Cl | H |
| A-1367. | H | OCHF$_2$ | H | Cl | H |
| A-1368. | H | OCF$_3$ | H | Cl | H |
| A-1369. | H | H | 3-F | Cl | H |
| A-1370. | H | H | 3-CH$_3$ | Cl | H |
| A-1371. | H | H | 3-OCH$_3$ | Cl | H |
| A-1372. | H | H | 5-F | Cl | H |
| A-1373. | H | H | 5-CH$_3$ | Cl | H |
| A-1374. | H | H | 5-OCH$_3$ | Cl | H |
| A-1375. | F | F | H | Cl | H |
| A-1376. | F | CH$_3$ | H | Cl | H |
| A-1377. | F | OCH$_3$ | H | Cl | H |
| A-1378. | F | CN | H | Cl | H |
| A-1379. | F | CH$_2$F | H | Cl | H |
| A-1380. | F | CHF$_2$ | H | Cl | H |
| A-1381. | F | CF$_3$ | H | Cl | H |
| A-1382. | F | OCH$_2$F | H | Cl | H |
| A-1383. | F | OCHF$_2$ | H | Cl | H |
| A-1384. | F | OCF$_3$ | H | Cl | H |
| A-1385. | F | H | 3-F | Cl | H |
| A-1386. | F | H | 3-CH$_3$ | Cl | H |
| A-1387. | F | H | 3-OCH$_3$ | Cl | H |
| A-1388. | F | H | 5-F | Cl | H |
| A-1389. | F | H | 5-CH$_3$ | Cl | H |
| A-1390. | F | H | 5-OCH$_3$ | Cl | H |
| A-1391. | CH$_3$ | F | H | Cl | H |
| A-1392. | CH$_3$ | CH$_3$ | H | Cl | H |
| A-1393. | CH$_3$ | OCH$_3$ | H | Cl | H |
| A-1394. | CH$_3$ | CN | H | Cl | H |
| A-1395. | CH$_3$ | CH$_2$F | H | Cl | H |
| A-1396. | CH$_3$ | CHF$_2$ | H | Cl | H |
| A-1397. | CH$_3$ | CF$_3$ | H | Cl | H |
| A-1398. | CH$_3$ | OCH$_2$F | H | Cl | H |
| A-1399. | CH$_3$ | OCHF$_2$ | H | Cl | H |
| A-1400. | CH$_3$ | OCF$_3$ | H | Cl | H |
| A-1401. | CH$_3$ | H | 3-F | Cl | H |
| A-1402. | CH$_3$ | H | 3-CH$_3$ | Cl | H |
| A-1403. | CH$_3$ | H | 3-OCH$_3$ | Cl | H |
| A-1404. | CH$_3$ | H | 5-F | Cl | H |
| A-1405. | CH$_3$ | H | 5-CH$_3$ | Cl | H |
| A-1406. | CH$_3$ | H | 5-OCH$_3$ | Cl | H |
| A-1407. | OCH$_3$ | F | H | Cl | H |
| A-1408. | OCH$_3$ | CH$_3$ | H | Cl | H |
| A-1409. | OCH$_3$ | OCH$_3$ | H | Cl | H |
| A-1410. | OCH$_3$ | CN | H | Cl | H |
| A-1411. | OCH$_3$ | CH$_2$F | H | Cl | H |
| A-1412. | OCH$_3$ | CHF$_2$ | H | Cl | H |
| A-1413. | OCH$_3$ | CF$_3$ | H | Cl | H |
| A-1414. | OCH$_3$ | OCH$_2$F | H | Cl | H |
| A-1415. | OCH$_3$ | OCHF$_2$ | H | Cl | H |
| A-1416. | OCH$_3$ | OCF$_3$ | H | Cl | H |
| A-1417. | OCH$_3$ | H | 3-F | Cl | H |
| A-1418. | OCH$_3$ | H | 3-CH$_3$ | Cl | H |
| A-1419. | OCH$_3$ | H | 3-OCH$_3$ | Cl | H |
| A-1420. | OCH$_3$ | H | 5-F | Cl | H |
| A-1421. | OCH$_3$ | H | 5-CH$_3$ | Cl | H |
| A-1422. | OCH$_3$ | H | 5-OCH$_3$ | Cl | H |
| A-1423. | H | F | 3-F | Cl | H |
| A-1424. | H | F | 3-CH$_3$ | Cl | H |
| A-1425. | H | F | 3-OCH$_3$ | Cl | H |
| A-1426. | H | F | 5-F | Cl | H |
| A-1427. | H | F | 5-CH$_3$ | Cl | H |
| A-1428. | H | F | 5-OCH$_3$ | Cl | H |
| A-1429. | H | CH$_3$ | 3-F | Cl | H |
| A-1430. | H | CH$_3$ | 3-CH$_3$ | Cl | H |
| A-1431. | H | CH$_3$ | 3-OCH$_3$ | Cl | H |
| A-1432. | H | CH$_3$ | 5-F | Cl | H |
| A-1433. | H | CH$_3$ | 5-CH$_3$ | Cl | H |
| A-1434. | H | CH$_3$ | 5-OCH$_3$ | Cl | H |
| A-1435. | H | OCH$_3$ | 3-F | Cl | H |
| A-1436. | H | OCH$_3$ | 3-CH$_3$ | Cl | H |
| A-1437. | H | OCH$_3$ | 3-OCH$_3$ | Cl | H |
| A-1438. | H | OCH$_3$ | 5-F | Cl | H |
| A-1439. | H | OCH$_3$ | 5-CH$_3$ | Cl | H |
| A-1440. | H | OCH$_3$ | 5-OCH$_3$ | Cl | H |
| A-1441. | H | CN | 3-F | Cl | H |
| A-1442. | H | CN | 3-CH$_3$ | Cl | H |
| A-1443. | H | CN | 3-OCH$_3$ | Cl | H |
| A-1444. | H | CN | 5-F | Cl | H |
| A-1445. | H | CN | 5-CH$_3$ | Cl | H |
| A-1446. | H | CN | 5-OCH$_3$ | Cl | H |
| A-1447. | H | CH$_2$F | 3-F | Cl | H |
| A-1448. | H | CH$_2$F | 3-CH$_3$ | Cl | H |
| A-1449. | H | CH$_2$F | 3-OCH$_3$ | Cl | H |
| A-1450. | H | CH$_2$F | 5-F | Cl | H |
| A-1451. | H | CH$_2$F | 5-CH$_3$ | Cl | H |
| A-1452. | H | CH$_2$F | 5-OCH$_3$ | Cl | H |
| A-1453. | H | CHF$_2$ | 3-F | Cl | H |
| A-1454. | H | CHF$_2$ | 3-CH$_3$ | Cl | H |
| A-1455. | H | CHF$_2$ | 3-OCH$_3$ | Cl | H |
| A-1456. | H | CHF$_2$ | 5-F | Cl | H |
| A-1457. | H | CHF$_2$ | 5-CH$_3$ | Cl | H |
| A-1458. | H | CHF$_2$ | 5-OCH$_3$ | Cl | H |
| A-1459. | H | CF$_3$ | 3-F | Cl | H |
| A-1460. | H | CF$_3$ | 3-CH$_3$ | Cl | H |
| A-1461. | H | CF$_3$ | 3-OCH$_3$ | Cl | H |
| A-1462. | H | CF$_3$ | 5-F | Cl | H |
| A-1463. | H | CF$_3$ | 5-CH$_3$ | Cl | H |
| A-1464. | H | CF$_3$ | 5-OCH$_3$ | Cl | H |
| A-1465. | H | OCH$_2$F | 3-F | Cl | H |
| A-1466. | H | OCH$_2$F | 3-CH$_3$ | Cl | H |
| A-1467. | H | OCH$_2$F | 3-OCH$_3$ | Cl | H |
| A-1468. | H | OCH$_2$F | 5-F | Cl | H |
| A-1469. | H | OCH$_2$F | 5-CH$_3$ | Cl | H |
| A-1470. | H | OCH$_2$F | 5-OCH$_3$ | Cl | H |
| A-1471. | H | OCHF$_2$ | 3-F | Cl | H |
| A-1472. | H | OCHF$_2$ | 3-CH$_3$ | Cl | H |
| A-1473. | H | OCHF$_2$ | 3-OCH$_3$ | Cl | H |
| A-1474. | H | OCHF$_2$ | 5-F | Cl | H |
| A-1475. | H | OCHF$_2$ | 5-CH$_3$ | Cl | H |
| A-1476. | H | OCHF$_2$ | 5-OCH$_3$ | Cl | H |
| A-1477. | H | OCF$_3$ | 3-F | Cl | H |

TABLE A-continued

| Example No. | R¹ | R² | R³ | R⁶ | R⁷ |
|---|---|---|---|---|---|
| A-1478. | H | OCF₃ | 3-CH₃ | Cl | H |
| A-1479. | H | OCF₃ | 3-OCH₃ | Cl | H |
| A-1480. | H | OCF₃ | 5-F | Cl | H |
| A-1481. | H | OCF₃ | 5-CH₃ | Cl | H |
| A-1482. | H | OCF₃ | 5-OCH₃ | Cl | H |
| A-1483. | F | F | 3-F | Cl | H |
| A-1484. | F | F | 3-CH₃ | Cl | H |
| A-1485. | F | F | 3-OCH₃ | Cl | H |
| A-1486. | F | F | 5-F | Cl | H |
| A-1487. | F | F | 5-CH₃ | Cl | H |
| A-1488. | F | F | 5-OCH₃ | Cl | H |
| A-1489. | F | CH₃ | 3-F | Cl | H |
| A-1490. | F | CH₃ | 3-CH₃ | Cl | H |
| A-1491. | F | CH₃ | 3-OCH₃ | Cl | H |
| A-1492. | F | CH₃ | 5-F | Cl | H |
| A-1493. | F | CH₃ | 5-CH₃ | Cl | H |
| A-1494. | F | CH₃ | 5-OCH₃ | Cl | H |
| A-1495. | F | OCH₃ | 3-F | Cl | H |
| A-1496. | F | OCH₃ | 3-CH₃ | Cl | H |
| A-1497. | F | OCH₃ | 3-OCH₃ | Cl | H |
| A-1498. | F | OCH₃ | 5-F | Cl | H |
| A-1499. | F | OCH₃ | 5-CH₃ | Cl | H |
| A-1500. | F | OCH₃ | 5-OCH₃ | Cl | H |
| A-1501. | F | CN | 3-F | Cl | H |
| A-1502. | F | CN | 3-CH₃ | Cl | H |
| A-1503. | F | CN | 3-OCH₃ | Cl | H |
| A-1504. | F | CN | 5-F | Cl | H |
| A-1505. | F | CN | 5-CH₃ | Cl | H |
| A-1506. | F | CN | 5-OCH₃ | Cl | H |
| A-1507. | F | CH₂F | 3-F | Cl | H |
| A-1508. | F | CH₂F | 3-CH₃ | Cl | H |
| A-1509. | F | CH₂F | 3-OCH₃ | Cl | H |
| A-1510. | F | CH₂F | 5-F | Cl | H |
| A-1511. | F | CH₂F | 5-CH₃ | Cl | H |
| A-1512. | F | CH₂F | 5-OCH₃ | Cl | H |
| A-1513. | F | CHF₂ | 3-F | Cl | H |
| A-1514. | F | CHF₂ | 3-CH₃ | Cl | H |
| A-1515. | F | CHF₂ | 3-OCH₃ | Cl | H |
| A-1516. | F | CHF₂ | 5-F | Cl | H |
| A-1517. | F | CHF₂ | 5-CH₃ | Cl | H |
| A-1518. | F | CHF₂ | 5-OCH₃ | Cl | H |
| A-1519. | F | CF₃ | 3-F | Cl | H |
| A-1520. | F | CF₃ | 3-CH₃ | Cl | H |
| A-1521. | F | CF₃ | 3-OCH₃ | Cl | H |
| A-1522. | F | CF₃ | 5-F | Cl | H |
| A-1523. | F | CF₃ | 5-CH₃ | Cl | H |
| A-1524. | F | CF₃ | 5-OCH₃ | Cl | H |
| A-1525. | F | OCH₂F | 3-F | Cl | H |
| A-1526. | F | OCH₂F | 3-CH₃ | Cl | H |
| A-1527. | F | OCH₂F | 3-OCH₃ | Cl | H |
| A-1528. | F | OCH₂F | 5-F | Cl | H |
| A-1529. | F | OCH₂F | 5-CH₃ | Cl | H |
| A-1530. | F | OCH₂F | 5-OCH₃ | Cl | H |
| A-1531. | F | OCHF₂ | 3-F | Cl | H |
| A-1532. | F | OCHF₂ | 3-CH₃ | Cl | H |
| A-1533. | F | OCHF₂ | 3-OCH₃ | Cl | H |
| A-1534. | F | OCHF₂ | 5-F | Cl | H |
| A-1535. | F | OCHF₂ | 5-CH₃ | Cl | H |
| A-1536. | F | OCHF₂ | 5-OCH₃ | Cl | H |
| A-1537. | F | OCF₃ | 3-F | Cl | H |
| A-1538. | F | OCF₃ | 3-CH₃ | Cl | H |
| A-1539. | F | OCF₃ | 3-OCH₃ | Cl | H |
| A-1540. | F | OCF₃ | 5-F | Cl | H |
| A-1541. | F | OCF₃ | 5-CH₃ | Cl | H |
| A-1542. | F | OCF₃ | 5-OCH₃ | Cl | H |
| A-1543. | CH₃ | F | 3-F | Cl | H |
| A-1544. | CH₃ | F | 3-CH₃ | Cl | H |
| A-1545. | CH₃ | F | 3-OCH₃ | Cl | H |
| A-1546. | CH₃ | F | 5-F | Cl | H |
| A-1547. | CH₃ | F | 5-CH₃ | Cl | H |
| A-1548. | CH₃ | F | 5-OCH₃ | Cl | H |
| A-1549. | CH₃ | CH₃ | 3-F | Cl | H |
| A-1550. | CH₃ | CH₃ | 3-CH₃ | Cl | H |
| A-1551. | CH₃ | CH₃ | 3-OCH₃ | Cl | H |
| A-1552. | CH₃ | CH₃ | 5-F | Cl | H |
| A-1553. | CH₃ | CH₃ | 5-CH₃ | Cl | H |
| A-1554. | CH₃ | CH₃ | 5-OCH₃ | Cl | H |
| A-1555. | CH₃ | OCH₃ | 3-F | Cl | H |
| A-1556. | CH₃ | OCH₃ | 3-CH₃ | Cl | H |
| A-1557. | CH₃ | OCH₃ | 3-OCH₃ | Cl | H |
| A-1558. | CH₃ | OCH₃ | 5-F | Cl | H |
| A-1559. | CH₃ | OCH₃ | 5-CH₃ | Cl | H |
| A-1560. | CH₃ | OCH₃ | 5-OCH₃ | Cl | H |
| A-1561. | CH₃ | CN | 3-F | Cl | H |
| A-1562. | CH₃ | CN | 3-CH₃ | Cl | H |
| A-1563. | CH₃ | CN | 3-OCH₃ | Cl | H |
| A-1564. | CH₃ | CN | 5-F | Cl | H |
| A-1565. | CH₃ | CN | 5-CH₃ | Cl | H |
| A-1566. | CH₃ | CN | 5-OCH₃ | Cl | H |
| A-1567. | CH₃ | CH₂F | 3-F | Cl | H |
| A-1568. | CH₃ | CH₂F | 3-CH₃ | Cl | H |
| A-1569. | CH₃ | CH₂F | 3-OCH₃ | Cl | H |
| A-1570. | CH₃ | CH₂F | 5-F | Cl | H |
| A-1571. | CH₃ | CH₂F | 5-CH₃ | Cl | H |
| A-1572. | CH₃ | CH₂F | 5-OCH₃ | Cl | H |
| A-1573. | CH₃ | CHF₂ | 3-F | Cl | H |
| A-1574. | CH₃ | CHF₂ | 3-CH₃ | Cl | H |
| A-1575. | CH₃ | CHF₂ | 3-OCH₃ | Cl | H |
| A-1576. | CH₃ | CHF₂ | 5-F | Cl | H |
| A-1577. | CH₃ | CHF₂ | 5-CH₃ | Cl | H |
| A-1578. | CH₃ | CHF₂ | 5-OCH₃ | Cl | H |
| A-1579. | CH₃ | CF₃ | 3-F | Cl | H |
| A-1580. | CH₃ | CF₃ | 3-CH₃ | Cl | H |
| A-1581. | CH₃ | CF₃ | 3-OCH₃ | Cl | H |
| A-1582. | CH₃ | CF₃ | 5-F | Cl | H |
| A-1583. | CH₃ | CF₃ | 5-CH₃ | Cl | H |
| A-1584. | CH₃ | CF₃ | 5-OCH₃ | Cl | H |
| A-1585. | CH₃ | OCH₂F | 3-F | Cl | H |
| A-1586. | CH₃ | OCH₂F | 3-CH₃ | Cl | H |
| A-1587. | CH₃ | OCH₂F | 3-OCH₃ | Cl | H |
| A-1588. | CH₃ | OCH₂F | 5-F | Cl | H |
| A-1589. | CH₃ | OCH₂F | 5-CH₃ | Cl | H |
| A-1590. | CH₃ | OCH₂F | 5-OCH₃ | Cl | H |
| A-1591. | CH₃ | OCHF₂ | 3-F | Cl | H |
| A-1592. | CH₃ | OCHF₂ | 3-CH₃ | Cl | H |
| A-1593. | CH₃ | OCHF₂ | 3-OCH₃ | Cl | H |
| A-1594. | CH₃ | OCHF₂ | 5-F | Cl | H |
| A-1595. | CH₃ | OCHF₂ | 5-CH₃ | Cl | H |
| A-1596. | CH₃ | OCHF₂ | 5-OCH₃ | Cl | H |
| A-1597. | CH₃ | OCF₃ | 3-F | Cl | H |
| A-1598. | CH₃ | OCF₃ | 3-CH₃ | Cl | H |
| A-1599. | CH₃ | OCF₃ | 3-OCH₃ | Cl | H |
| A-1600. | CH₃ | OCF₃ | 5-F | Cl | H |
| A-1601. | CH₃ | OCF₃ | 5-CH₃ | Cl | H |
| A-1602. | CH₃ | OCF₃ | 5-OCH₃ | Cl | H |
| A-1603. | OCH₃ | F | 3-F | Cl | H |
| A-1604. | OCH₃ | F | 3-CH₃ | Cl | H |
| A-1605. | OCH₃ | F | 3-OCH₃ | Cl | H |
| A-1606. | OCH₃ | F | 5-F | Cl | H |
| A-1607. | OCH₃ | F | 5-CH₃ | Cl | H |
| A-1608. | OCH₃ | F | 5-OCH₃ | Cl | H |
| A-1609. | OCH₃ | CH₃ | 3-F | Cl | H |
| A-1610. | OCH₃ | CH₃ | 3-CH₃ | Cl | H |
| A-1611. | OCH₃ | CH₃ | 3-OCH₃ | Cl | H |
| A-1612. | OCH₃ | CH₃ | 5-F | Cl | H |
| A-1613. | OCH₃ | CH₃ | 5-CH₃ | Cl | H |
| A-1614. | OCH₃ | CH₃ | 5-OCH₃ | Cl | H |
| A-1615. | OCH₃ | OCH₃ | 3-F | Cl | H |
| A-1616. | OCH₃ | OCH₃ | 3-CH₃ | Cl | H |
| A-1617. | OCH₃ | OCH₃ | 3-OCH₃ | Cl | H |
| A-1618. | OCH₃ | OCH₃ | 5-F | Cl | H |
| A-1619. | OCH₃ | OCH₃ | 5-CH₃ | Cl | H |
| A-1620. | OCH₃ | OCH₃ | 5-OCH₃ | Cl | H |
| A-1621. | OCH₃ | CN | 3-F | Cl | H |
| A-1622. | OCH₃ | CN | 3-CH₃ | Cl | H |
| A-1623. | OCH₃ | CN | 3-OCH₃ | Cl | H |
| A-1624. | OCH₃ | CN | 5-F | Cl | H |
| A-1625. | OCH₃ | CN | 5-CH₃ | Cl | H |
| A-1626. | OCH₃ | CN | 5-OCH₃ | Cl | H |
| A-1627. | OCH₃ | CH₂F | 3-F | Cl | H |
| A-1628. | OCH₃ | CH₂F | 3-CH₃ | Cl | H |
| A-1629. | OCH₃ | CH₂F | 3-OCH₃ | Cl | H |
| A-1630. | OCH₃ | CH₂F | 5-F | Cl | H |
| A-1631. | OCH₃ | CH₂F | 5-CH₃ | Cl | H |
| A-1632. | OCH₃ | CH₂F | 5-OCH₃ | Cl | H |
| A-1633. | OCH₃ | CHF₂ | 3-F | Cl | H |

TABLE A-continued

| Example No. | R¹ | R² | R³ | R⁶ | R⁷ |
|---|---|---|---|---|---|
| A-1634. | OCH₃ | CHF₂ | 3-CH₃ | Cl | H |
| A-1635. | OCH₃ | CHF₂ | 3-OCH₃ | Cl | H |
| A-1636. | OCH₃ | CHF₂ | 5-F | Cl | H |
| A-1637. | OCH₃ | CHF₂ | 5-CH₃ | Cl | H |
| A-1638. | OCH₃ | CHF₂ | 5-OCH₃ | Cl | H |
| A-1639. | OCH₃ | CF₃ | 3-F | Cl | H |
| A-1640. | OCH₃ | CF₃ | 3-CH₃ | Cl | H |
| A-1641. | OCH₃ | CF₃ | 3-OCH₃ | Cl | H |
| A-1642. | OCH₃ | CF₃ | 5-F | Cl | H |
| A-1643. | OCH₃ | CF₃ | 5-CH₃ | Cl | H |
| A-1644. | OCH₃ | CF₃ | 5-OCH₃ | Cl | H |
| A-1645. | OCH₃ | OCH₂F | 3-F | Cl | H |
| A-1646. | OCH₃ | OCH₂F | 3-CH₃ | Cl | H |
| A-1647. | OCH₃ | OCH₂F | 3-OCH₃ | Cl | H |
| A-1648. | OCH₃ | OCH₂F | 5-F | Cl | H |
| A-1649. | OCH₃ | OCH₂F | 5-CH₃ | Cl | H |
| A-1650. | OCH₃ | OCH₂F | 5-OCH₃ | Cl | H |
| A-1651. | OCH₃ | OCHF₂ | 3-F | Cl | H |
| A-1652. | OCH₃ | OCHF₂ | 3-CH₃ | Cl | H |
| A-1653. | OCH₃ | OCHF₂ | 3-OCH₃ | Cl | H |
| A-1654. | OCH₃ | OCHF₂ | 5-F | Cl | H |
| A-1655. | OCH₃ | OCHF₂ | 5-CH₃ | Cl | H |
| A-1656. | OCH₃ | OCHF₂ | 5-OCH₃ | Cl | H |
| A-1657. | OCH₃ | OCF₃ | 3-F | Cl | H |
| A-1658. | OCH₃ | OCF₃ | 3-CH₃ | Cl | H |
| A-1659. | OCH₃ | OCF₃ | 3-OCH₃ | Cl | H |
| A-1660. | OCH₃ | OCF₃ | 5-F | Cl | H |
| A-1661. | OCH₃ | OCF₃ | 5-CH₃ | Cl | H |
| A-1662. | OCH₃ | OCF₃ | 5-OCH₃ | Cl | H |
| A-1663. | CH₂F | F | 3-F | Cl | H |
| A-1664. | CH₂F | F | 3-CH₃ | Cl | H |
| A-1665. | CH₂F | F | 3-OCH₃ | Cl | H |
| A-1666. | CH₂F | F | 5-F | Cl | H |
| A-1667. | CH₂F | F | 5-CH₃ | Cl | H |
| A-1668. | CH₂F | F | 5-OCH₃ | Cl | H |
| A-1669. | CH₂F | CH₃ | 3-F | Cl | H |
| A-1670. | CH₂F | CH₃ | 3-CH₃ | Cl | H |
| A-1671. | CH₂F | CH₃ | 3-OCH₃ | Cl | H |
| A-1672. | CH₂F | CH₃ | 5-F | Cl | H |
| A-1673. | CH₂F | CH₃ | 5-CH₃ | Cl | H |
| A-1674. | CH₂F | CH₃ | 5-OCH₃ | Cl | H |
| A-1675. | CH₂F | OCH₃ | 3-F | Cl | H |
| A-1676. | CH₂F | OCH₃ | 3-CH₃ | Cl | H |
| A-1677. | CH₂F | OCH₃ | 3-OCH₃ | Cl | H |
| A-1678. | CH₂F | OCH₃ | 5-F | Cl | H |
| A-1679. | CH₂F | OCH₃ | 5-CH₃ | Cl | H |
| A-1680. | CH₂F | OCH₃ | 5-OCH₃ | Cl | H |
| A-1681. | CH₂F | CN | 3-F | Cl | H |
| A-1682. | CH₂F | CN | 3-CH₃ | Cl | H |
| A-1683. | CH₂F | CN | 3-OCH₃ | Cl | H |
| A-1684. | CH₂F | CN | 5-F | Cl | H |
| A-1685. | CH₂F | CN | 5-CH₃ | Cl | H |
| A-1686. | CH₂F | CN | 5-OCH₃ | Cl | H |
| A-1687. | CH₂F | CH₂F | 3-F | Cl | H |
| A-1688. | CH₂F | CH₂F | 3-CH₃ | Cl | H |
| A-1689. | CH₂F | CH₂F | 3-OCH₃ | Cl | H |
| A-1690. | CH₂F | CH₂F | 5-F | Cl | H |
| A-1691. | CH₂F | CH₂F | 5-CH₃ | Cl | H |
| A-1692. | CH₂F | CH₂F | 5-OCH₃ | Cl | H |
| A-1693. | CH₂F | CHF₂ | 3-F | Cl | H |
| A-1694. | CH₂F | CHF₂ | 3-CH₃ | Cl | H |
| A-1695. | CH₂F | CHF₂ | 3-OCH₃ | Cl | H |
| A-1696. | CH₂F | CHF₂ | 5-F | Cl | H |
| A-1697. | CH₂F | CHF₂ | 5-CH₃ | Cl | H |
| A-1698. | CH₂F | CHF₂ | 5-OCH₃ | Cl | H |
| A-1699. | CH₂F | CF₃ | 3-F | Cl | H |
| A-1700. | CH₂F | CF₃ | 3-CH₃ | Cl | H |
| A-1701. | CH₂F | CF₃ | 3-OCH₃ | Cl | H |
| A-1702. | CH₂F | CF₃ | 5-F | Cl | H |
| A-1703. | CH₂F | CF₃ | 5-CH₃ | Cl | H |
| A-1704. | CH₂F | CF₃ | 5-OCH₃ | Cl | H |
| A-1705. | CH₂F | OCH₂F | 3-F | Cl | H |
| A-1706. | CH₂F | OCH₂F | 3-CH₃ | Cl | H |
| A-1707. | CH₂F | OCH₂F | 3-OCH₃ | Cl | H |
| A-1708. | CH₂F | OCH₂F | 5-F | Cl | H |
| A-1709. | CH₂F | OCH₂F | 5-CH₃ | Cl | H |
| A-1710. | CH₂F | OCH₂F | 5-OCH₃ | Cl | H |
| A-1711. | CH₂F | OCHF₂ | 3-F | Cl | H |
| A-1712. | CH₂F | OCHF₂ | 3-CH₃ | Cl | H |
| A-1713. | CH₂F | OCHF₂ | 3-OCH₃ | Cl | H |
| A-1714. | CH₂F | OCHF₂ | 5-F | Cl | H |
| A-1715. | CH₂F | OCHF₂ | 5-CH₃ | Cl | H |
| A-1716. | CH₂F | OCHF₂ | 5-OCH₃ | Cl | H |
| A-1717. | CH₂F | OCF₃ | 3-F | Cl | H |
| A-1718. | CH₂F | OCF₃ | 3-CH₃ | Cl | H |
| A-1719. | CH₂F | OCF₃ | 3-OCH₃ | Cl | H |
| A-1720. | CH₂F | OCF₃ | 5-F | Cl | H |
| A-1721. | CH₂F | OCF₃ | 5-CH₃ | Cl | H |
| A-1722. | CH₂F | OCF₃ | 5-OCH₃ | Cl | H |
| A-1723. | CHF₂ | F | 3-F | Cl | H |
| A-1724. | CHF₂ | F | 3-CH₃ | Cl | H |
| A-1725. | CHF₂ | F | 3-OCH₃ | Cl | H |
| A-1726. | CHF₂ | F | 5-F | Cl | H |
| A-1727. | CHF₂ | F | 5-CH₃ | Cl | H |
| A-1728. | CHF₂ | F | 5-OCH₃ | Cl | H |
| A-1729. | CHF₂ | CH₃ | 3-F | Cl | H |
| A-1730. | CHF₂ | CH₃ | 3-CH₃ | Cl | H |
| A-1731. | CHF₂ | CH₃ | 3-OCH₃ | Cl | H |
| A-1732. | CHF₂ | CH₃ | 5-F | Cl | H |
| A-1733. | CHF₂ | CH₃ | 5-CH₃ | Cl | H |
| A-1734. | CHF₂ | CH₃ | 5-OCH₃ | Cl | H |
| A-1735. | CHF₂ | OCH₃ | 3-F | Cl | H |
| A-1736. | CHF₂ | OCH₃ | 3-CH₃ | Cl | H |
| A-1737. | CHF₂ | OCH₃ | 3-OCH₃ | Cl | H |
| A-1738. | CHF₂ | OCH₃ | 5-F | Cl | H |
| A-1739. | CHF₂ | OCH₃ | 5-CH₃ | Cl | H |
| A-1740. | CHF₂ | OCH₃ | 5-OCH₃ | Cl | H |
| A-1741. | CHF₂ | CN | 3-F | Cl | H |
| A-1742. | CHF₂ | CN | 3-CH₃ | Cl | H |
| A-1743. | CHF₂ | CN | 3-OCH₃ | Cl | H |
| A-1744. | CHF₂ | CN | 5-F | Cl | H |
| A-1745. | CHF₂ | CN | 5-CH₃ | Cl | H |
| A-1746. | CHF₂ | CN | 5-OCH₃ | Cl | H |
| A-1747. | CHF₂ | CH₂F | 3-F | Cl | H |
| A-1748. | CHF₂ | CH₂F | 3-CH₃ | Cl | H |
| A-1749. | CHF₂ | CH₂F | 3-OCH₃ | Cl | H |
| A-1750. | CHF₂ | CH₂F | 5-F | Cl | H |
| A-1751. | CHF₂ | CH₂F | 5-CH₃ | Cl | H |
| A-1752. | CHF₂ | CH₂F | 5-OCH₃ | Cl | H |
| A-1753. | CHF₂ | CHF₂ | 3-F | Cl | H |
| A-1754. | CHF₂ | CHF₂ | 3-CH₃ | Cl | H |
| A-1755. | CHF₂ | CHF₂ | 3-OCH₃ | Cl | H |
| A-1756. | CHF₂ | CHF₂ | 5-F | Cl | H |
| A-1757. | CHF₂ | CHF₂ | 5-CH₃ | Cl | H |
| A-1758. | CHF₂ | CHF₂ | 5-OCH₃ | Cl | H |
| A-1759. | CHF₂ | CF₃ | 3-F | Cl | H |
| A-1760. | CHF₂ | CF₃ | 3-CH₃ | Cl | H |
| A-1761. | CHF₂ | CF₃ | 3-OCH₃ | Cl | H |
| A-1762. | CHF₂ | CF₃ | 5-F | Cl | H |
| A-1763. | CHF₂ | CF₃ | 5-CH₃ | Cl | H |
| A-1764. | CHF₂ | CF₃ | 5-OCH₃ | Cl | H |
| A-1765. | CHF₂ | OCH₂F | 3-F | Cl | H |
| A-1766. | CHF₂ | OCH₂F | 3-CH₃ | Cl | H |
| A-1767. | CHF₂ | OCH₂F | 3-OCH₃ | Cl | H |
| A-1768. | CHF₂ | OCH₂F | 5-F | Cl | H |
| A-1769. | CHF₂ | OCH₂F | 5-CH₃ | Cl | H |
| A-1770. | CHF₂ | OCH₂F | 5-OCH₃ | Cl | H |
| A-1771. | CHF₂ | OCHF₂ | 3-F | Cl | H |
| A-1772. | CHF₂ | OCHF₂ | 3-CH₃ | Cl | H |
| A-1773. | CHF₂ | OCHF₂ | 3-OCH₃ | Cl | H |
| A-1774. | CHF₂ | OCHF₂ | 5-F | Cl | H |
| A-1775. | CHF₂ | OCHF₂ | 5-CH₃ | Cl | H |
| A-1776. | CHF₂ | OCHF₂ | 5-OCH₃ | Cl | H |
| A-1777. | CHF₂ | OCF₃ | 3-F | Cl | H |
| A-1778. | CHF₂ | OCF₃ | 3-CH₃ | Cl | H |
| A-1779. | CHF₂ | OCF₃ | 3-OCH₃ | Cl | H |
| A-1780. | CHF₂ | OCF₃ | 5-F | Cl | H |
| A-1781. | CHF₂ | OCF₃ | 5-CH₃ | Cl | H |
| A-1782. | CHF₂ | OCF₃ | 5-OCH₃ | Cl | H |
| A-1783. | CF₃ | F | 3-F | Cl | H |
| A-1784. | CF₃ | F | 3-CH₃ | Cl | H |
| A-1785. | CF₃ | F | 3-OCH₃ | Cl | H |
| A-1786. | CF₃ | F | 5-F | Cl | H |
| A-1787. | CF₃ | F | 5-CH₃ | Cl | H |
| A-1788. | CF₃ | F | 5-OCH₃ | Cl | H |
| A-1789. | CF₃ | CH₃ | 3-F | Cl | H |

TABLE A-continued

| Example No. | R$^1$ | R$^2$ | R$^3$ | R$^6$ | R$^7$ |
|---|---|---|---|---|---|
| A-1790. | CF$_3$ | CH$_3$ | 3-CH$_3$ | Cl | H |
| A-1791. | CF$_3$ | CH$_3$ | 3-OCH$_3$ | Cl | H |
| A-1792. | CF$_3$ | CH$_3$ | 5-F | Cl | H |
| A-1793. | CF$_3$ | CH$_3$ | 5-CH$_3$ | Cl | H |
| A-1794. | CF$_3$ | CH$_3$ | 5-OCH$_3$ | Cl | H |
| A-1795. | CF$_3$ | OCH$_3$ | 3-F | Cl | H |
| A-1796. | CF$_3$ | OCH$_3$ | 3-CH$_3$ | Cl | H |
| A-1797. | CF$_3$ | OCH$_3$ | 3-OCH$_3$ | Cl | H |
| A-1798. | CF$_3$ | OCH$_3$ | 5-F | Cl | H |
| A-1799. | CF$_3$ | OCH$_3$ | 5-CH$_3$ | Cl | H |
| A-1800. | CF$_3$ | OCH$_3$ | 5-OCH$_3$ | Cl | H |
| A-1801. | CF$_3$ | CN | 3-F | Cl | H |
| A-1802. | CF$_3$ | CN | 3-CH$_3$ | Cl | H |
| A-1803. | CF$_3$ | CN | 3-OCH$_3$ | Cl | H |
| A-1804. | CF$_3$ | CN | 5-F | Cl | H |
| A-1805. | CF$_3$ | CN | 5-CH$_3$ | Cl | H |
| A-1806. | CF$_3$ | CN | 5-OCH$_3$ | Cl | H |
| A-1807. | CF$_3$ | CH$_2$F | 3-F | Cl | H |
| A-1808. | CF$_3$ | CH$_2$F | 3-CH$_3$ | Cl | H |
| A-1809. | CF$_3$ | CH$_2$F | 3-OCH$_3$ | Cl | H |
| A-1810. | CF$_3$ | CH$_2$F | 5-F | Cl | H |
| A-1811. | CF$_3$ | CH$_2$F | 5-CH$_3$ | Cl | H |
| A-1812. | CF$_3$ | CH$_2$F | 5-OCH$_3$ | Cl | H |
| A-1813. | CF$_3$ | CHF$_2$ | 3-F | Cl | H |
| A-1814. | CF$_3$ | CHF$_2$ | 3-CH$_3$ | Cl | H |
| A-1815. | CF$_3$ | CHF$_2$ | 3-OCH$_3$ | Cl | H |
| A-1816. | CF$_3$ | CHF$_2$ | 5-F | Cl | H |
| A-1817. | CF$_3$ | CHF$_2$ | 5-CH$_3$ | Cl | H |
| A-1818. | CF$_3$ | CHF$_2$ | 5-OCH$_3$ | Cl | H |
| A-1819. | CF$_3$ | CF$_3$ | 3-F | Cl | H |
| A-1820. | CF$_3$ | CF$_3$ | 3-CH$_3$ | Cl | H |
| A-1821. | CF$_3$ | CF$_3$ | 3-OCH$_3$ | Cl | H |
| A-1822. | CF$_3$ | CF$_3$ | 5-F | Cl | H |
| A-1823. | CF$_3$ | CF$_3$ | 5-CH$_3$ | Cl | H |
| A-1824. | CF$_3$ | CF$_3$ | 5-OCH$_3$ | Cl | H |
| A-1825. | CF$_3$ | OCH$_2$F | 3-F | Cl | H |
| A-1826. | CF$_3$ | OCH$_2$F | 3-CH$_3$ | Cl | H |
| A-1827. | CF$_3$ | OCH$_2$F | 3-OCH$_3$ | Cl | H |
| A-1828. | CF$_3$ | OCH$_2$F | 5-F | Cl | H |
| A-1829. | CF$_3$ | OCH$_2$F | 5-CH$_3$ | Cl | H |
| A-1830. | CF$_3$ | OCH$_2$F | 5-OCH$_3$ | Cl | H |
| A-1831. | CF$_3$ | OCHF$_2$ | 3-F | Cl | H |
| A-1832. | CF$_3$ | OCHF$_2$ | 3-CH$_3$ | Cl | H |
| A-1833. | CF$_3$ | OCHF$_2$ | 3-OCH$_3$ | Cl | H |
| A-1834. | CF$_3$ | OCHF$_2$ | 5-F | Cl | H |
| A-1835. | CF$_3$ | OCHF$_2$ | 5-CH$_3$ | Cl | H |
| A-1836. | CF$_3$ | OCHF$_2$ | 5-OCH$_3$ | Cl | H |
| A-1837. | CF$_3$ | OCF$_3$ | 3-F | Cl | H |
| A-1838. | CF$_3$ | OCF$_3$ | 3-CH$_3$ | Cl | H |
| A-1839. | CF$_3$ | OCF$_3$ | 3-OCH$_3$ | Cl | H |
| A-1840. | CF$_3$ | OCF$_3$ | 5-F | Cl | H |
| A-1841. | CF$_3$ | OCF$_3$ | 5-CH$_3$ | Cl | H |
| A-1842. | CF$_3$ | OCF$_3$ | 5-OCH$_3$ | Cl | H |
| A-1843. | OCH$_2$F | F | 3-F | Cl | H |
| A-1844. | OCH$_2$F | F | 3-CH$_3$ | Cl | H |
| A-1845. | OCH$_2$F | F | 3-OCH$_3$ | Cl | H |
| A-1846. | OCH$_2$F | F | 5-F | Cl | H |
| A-1847. | OCH$_2$F | F | 5-CH$_3$ | Cl | H |
| A-1848. | OCH$_2$F | F | 5-OCH$_3$ | Cl | H |
| A-1849. | OCH$_2$F | CH$_3$ | 3-F | Cl | H |
| A-1850. | OCH$_2$F | CH$_3$ | 3-CH$_3$ | Cl | H |
| A-1851. | OCH$_2$F | CH$_3$ | 3-OCH$_3$ | Cl | H |
| A-1852. | OCH$_2$F | CH$_3$ | 5-F | Cl | H |
| A-1853. | OCH$_2$F | CH$_3$ | 5-CH$_3$ | Cl | H |
| A-1854. | OCH$_2$F | CH$_3$ | 5-OCH$_3$ | Cl | H |
| A-1855. | OCH$_2$F | OCH$_3$ | 3-F | Cl | H |
| A-1856. | OCH$_2$F | OCH$_3$ | 3-CH$_3$ | Cl | H |
| A-1857. | OCH$_2$F | OCH$_3$ | 3-OCH$_3$ | Cl | H |
| A-1858. | OCH$_2$F | OCH$_3$ | 5-F | Cl | H |
| A-1859. | OCH$_2$F | OCH$_3$ | 5-CH$_3$ | Cl | H |
| A-1860. | OCH$_2$F | OCH$_3$ | 5-OCH$_3$ | Cl | H |
| A-1861. | OCH$_2$F | CN | 3-F | Cl | H |
| A-1862. | OCH$_2$F | CN | 3-CH$_3$ | Cl | H |
| A-1863. | OCH$_2$F | CN | 3-OCH$_3$ | Cl | H |
| A-1864. | OCH$_2$F | CN | 5-F | Cl | H |
| A-1865. | OCH$_2$F | CN | 5-CH$_3$ | Cl | H |
| A-1866. | OCH$_2$F | CN | 5-OCH$_3$ | Cl | H |
| A-1867. | OCH$_2$F | CH$_2$F | 3-F | Cl | H |
| A-1868. | OCH$_2$F | CH$_2$F | 3-CH$_3$ | Cl | H |
| A-1869. | OCH$_2$F | CH$_2$F | 3-OCH$_3$ | Cl | H |
| A-1870. | OCH$_2$F | CH$_2$F | 5-F | Cl | H |
| A-1871. | OCH$_2$F | CH$_2$F | 5-CH$_3$ | Cl | H |
| A-1872. | OCH$_2$F | CH$_2$F | 5-OCH$_3$ | Cl | H |
| A-1873. | OCH$_2$F | CHF$_2$ | 3-F | Cl | H |
| A-1874. | OCH$_2$F | CHF$_2$ | 3-CH$_3$ | Cl | H |
| A-1875. | OCH$_2$F | CHF$_2$ | 3-OCH$_3$ | Cl | H |
| A-1876. | OCH$_2$F | CHF$_2$ | 5-F | Cl | H |
| A-1877. | OCH$_2$F | CHF$_2$ | 5-CH$_3$ | Cl | H |
| A-1878. | OCH$_2$F | CHF$_2$ | 5-OCH$_3$ | Cl | H |
| A-1879. | OCH$_2$F | CF$_3$ | 3-F | Cl | H |
| A-1880. | OCH$_2$F | CF$_3$ | 3-CH$_3$ | Cl | H |
| A-1881. | OCH$_2$F | CF$_3$ | 3-OCH$_3$ | Cl | H |
| A-1882. | OCH$_2$F | CF$_3$ | 5-F | Cl | H |
| A-1883. | OCH$_2$F | CF$_3$ | 5-CH$_3$ | Cl | H |
| A-1884. | OCH$_2$F | CF$_3$ | 5-OCH$_3$ | Cl | H |
| A-1885. | OCH$_2$F | OCH$_2$F | 3-F | Cl | H |
| A-1886. | OCH$_2$F | OCH$_2$F | 3-CH$_3$ | Cl | H |
| A-1887. | OCH$_2$F | OCH$_2$F | 3-OCH$_3$ | Cl | H |
| A-1888. | OCH$_2$F | OCH$_2$F | 5-F | Cl | H |
| A-1889. | OCH$_2$F | OCH$_2$F | 5-CH$_3$ | Cl | H |
| A-1890. | OCH$_2$F | OCH$_2$F | 5-OCH$_3$ | Cl | H |
| A-1891. | OCH$_2$F | OCHF$_2$ | 3-F | Cl | H |
| A-1892. | OCH$_2$F | OCHF$_2$ | 3-CH$_3$ | Cl | H |
| A-1893. | OCH$_2$F | OCHF$_2$ | 3-OCH$_3$ | Cl | H |
| A-1894. | OCH$_2$F | OCHF$_2$ | 5-F | Cl | H |
| A-1895. | OCH$_2$F | OCHF$_2$ | 5-CH$_3$ | Cl | H |
| A-1896. | OCH$_2$F | OCHF$_2$ | 5-OCH$_3$ | Cl | H |
| A-1897. | OCH$_2$F | OCF$_3$ | 3-F | Cl | H |
| A-1898. | OCH$_2$F | OCF$_3$ | 3-CH$_3$ | Cl | H |
| A-1899. | OCH$_2$F | OCF$_3$ | 3-OCH$_3$ | Cl | H |
| A-1900. | OCH$_2$F | OCF$_3$ | 5-F | Cl | H |
| A-1901. | OCH$_2$F | OCF$_3$ | 5-CH$_3$ | Cl | H |
| A-1902. | OCH$_2$F | OCF$_3$ | 5-OCH$_3$ | Cl | H |
| A-1903. | OCHF$_2$ | F | 3-F | Cl | H |
| A-1904. | OCHF$_2$ | F | 3-CH$_3$ | Cl | H |
| A-1905. | OCHF$_2$ | F | 3-OCH$_3$ | Cl | H |
| A-1906. | OCHF$_2$ | F | 5-F | Cl | H |
| A-1907. | OCHF$_2$ | F | 5-CH$_3$ | Cl | H |
| A-1908. | OCHF$_2$ | F | 5-OCH$_3$ | Cl | H |
| A-1909. | OCHF$_2$ | CH$_3$ | 3-F | Cl | H |
| A-1910. | OCHF$_2$ | CH$_3$ | 3-CH$_3$ | Cl | H |
| A-1911. | OCHF$_2$ | CH$_3$ | 3-OCH$_3$ | Cl | H |
| A-1912. | OCHF$_2$ | CH$_3$ | 5-F | Cl | H |
| A-1913. | OCHF$_2$ | CH$_3$ | 5-CH$_3$ | Cl | H |
| A-1914. | OCHF$_2$ | CH$_3$ | 5-OCH$_3$ | Cl | H |
| A-1915. | OCHF$_2$ | OCH$_3$ | 3-F | Cl | H |
| A-1916. | OCHF$_2$ | OCH$_3$ | 3-CH$_3$ | Cl | H |
| A-1917. | OCHF$_2$ | OCH$_3$ | 3-OCH$_3$ | Cl | H |
| A-1918. | OCHF$_2$ | OCH$_3$ | 5-F | Cl | H |
| A-1919. | OCHF$_2$ | OCH$_3$ | 5-CH$_3$ | Cl | H |
| A-1920. | OCHF$_2$ | OCH$_3$ | 5-OCH$_3$ | Cl | H |
| A-1921. | OCHF$_2$ | CN | 3-F | Cl | H |
| A-1922. | OCHF$_2$ | CN | 3-CH$_3$ | Cl | H |
| A-1923. | OCHF$_2$ | CN | 3-OCH$_3$ | Cl | H |
| A-1924. | OCHF$_2$ | CN | 5-F | Cl | H |
| A-1925. | OCHF$_2$ | CN | 5-CH$_3$ | Cl | H |
| A-1926. | OCHF$_2$ | CN | 5-OCH$_3$ | Cl | H |
| A-1927. | OCHF$_2$ | CH$_2$F | 3-F | Cl | H |
| A-1928. | OCHF$_2$ | CH$_2$F | 3-CH$_3$ | Cl | H |
| A-1929. | OCHF$_2$ | CH$_2$F | 3-OCH$_3$ | Cl | H |
| A-1930. | OCHF$_2$ | CH$_2$F | 5-F | Cl | H |
| A-1931. | OCHF$_2$ | CH$_2$F | 5-CH$_3$ | Cl | H |
| A-1932. | OCHF$_2$ | CH$_2$F | 5-OCH$_3$ | Cl | H |
| A-1933. | OCHF$_2$ | CHF$_2$ | 3-F | Cl | H |
| A-1934. | OCHF$_2$ | CHF$_2$ | 3-CH$_3$ | Cl | H |
| A-1935. | OCHF$_2$ | CHF$_2$ | 3-OCH$_3$ | Cl | H |
| A-1936. | OCHF$_2$ | CHF$_2$ | 5-F | Cl | H |
| A-1937. | OCHF$_2$ | CHF$_2$ | 5-CH$_3$ | Cl | H |
| A-1938. | OCHF$_2$ | CHF$_2$ | 5-OCH$_3$ | Cl | H |
| A-1939. | OCHF$_2$ | CF$_3$ | 3-F | Cl | H |
| A-1940. | OCHF$_2$ | CF$_3$ | 3-CH$_3$ | Cl | H |
| A-1941. | OCHF$_2$ | CF$_3$ | 3-OCH$_3$ | Cl | H |
| A-1942. | OCHF$_2$ | CF$_3$ | 5-F | Cl | H |
| A-1943. | OCHF$_2$ | CF$_3$ | 5-CH$_3$ | Cl | H |
| A-1944. | OCHF$_2$ | CF$_3$ | 5-OCH$_3$ | Cl | H |
| A-1945. | OCHF$_2$ | OCH$_2$F | 3-F | Cl | H |

TABLE A-continued

| Example No. | R¹ | R² | R³ | R⁶ | R⁷ |
| --- | --- | --- | --- | --- | --- |
| A-1946. | OCHF₂ | OCH₂F | 3-CH₃ | Cl | H |
| A-1947. | OCHF₂ | OCH₂F | 3-OCH₃ | Cl | H |
| A-1948. | OCHF₂ | OCH₂F | 5-F | Cl | H |
| A-1949. | OCHF₂ | OCH₂F | 5-CH₃ | Cl | H |
| A-1950. | OCHF₂ | OCH₂F | 5-OCH₃ | Cl | H |
| A-1951. | OCHF₂ | OCHF₂ | 3-F | Cl | H |
| A-1952. | OCHF₂ | OCHF₂ | 3-CH₃ | Cl | H |
| A-1953. | OCHF₂ | OCHF₂ | 3-OCH₃ | Cl | H |
| A-1954. | OCHF₂ | OCHF₂ | 5-F | Cl | H |
| A-1955. | OCHF₂ | OCHF₂ | 5-CH₃ | Cl | H |
| A-1956. | OCHF₂ | OCHF₂ | 5-OCH₃ | Cl | H |
| A-1957. | OCHF₂ | OCF₃ | 3-F | Cl | H |
| A-1958. | OCHF₂ | OCF₃ | 3-CH₃ | Cl | H |
| A-1959. | OCHF₂ | OCF₃ | 3-OCH₃ | Cl | H |
| A-1960. | OCHF₂ | OCF₃ | 5-F | Cl | H |
| A-1961. | OCHF₂ | OCF₃ | 5-CH₃ | Cl | H |
| A-1962. | OCHF₂ | OCF₃ | 5-OCH₃ | Cl | H |
| A-1963. | OCF₃ | F | 3-F | Cl | H |
| A-1964. | OCF₃ | F | 3-CH₃ | Cl | H |
| A-1965. | OCF₃ | F | 3-OCH₃ | Cl | H |
| A-1966. | OCF₃ | F | 5-F | Cl | H |
| A-1967. | OCF₃ | F | 5-CH₃ | Cl | H |
| A-1968. | OCF₃ | F | 5-OCH₃ | Cl | H |
| A-1969. | OCF₃ | CH₃ | 3-F | Cl | H |
| A-1970. | OCF₃ | CH₃ | 3-CH₃ | Cl | H |
| A-1971. | OCF₃ | CH₃ | 3-OCH₃ | Cl | H |
| A-1972. | OCF₃ | CH₃ | 5-F | Cl | H |
| A-1973. | OCF₃ | CH₃ | 5-CH₃ | Cl | H |
| A-1974. | OCF₃ | CH₃ | 5-OCH₃ | Cl | H |
| A-1975. | OCF₃ | OCH₃ | 3-F | Cl | H |
| A-1976. | OCF₃ | OCH₃ | 3-CH₃ | Cl | H |
| A-1977. | OCF₃ | OCH₃ | 3-OCH₃ | Cl | H |
| A-1978. | OCF₃ | OCH₃ | 5-F | Cl | H |
| A-1979. | OCF₃ | OCH₃ | 5-CH₃ | Cl | H |
| A-1980. | OCF₃ | OCH₃ | 5-OCH₃ | Cl | H |
| A-1981. | OCF₃ | CN | 3-F | Cl | H |
| A-1982. | OCF₃ | CN | 3-CH₃ | Cl | H |
| A-1983. | OCF₃ | CN | 3-OCH₃ | Cl | H |
| A-1984. | OCF₃ | CN | 5-F | Cl | H |
| A-1985. | OCF₃ | CN | 5-CH₃ | Cl | H |
| A-1986. | OCF₃ | CN | 5-OCH₃ | Cl | H |
| A-1987. | OCF₃ | CH₂F | 3-F | Cl | H |
| A-1988. | OCF₃ | CH₂F | 3-CH₃ | Cl | H |
| A-1989. | OCF₃ | CH₂F | 3-OCH₃ | Cl | H |
| A-1990. | OCF₃ | CH₂F | 5-F | Cl | H |
| A-1991. | OCF₃ | CH₂F | 5-CH₃ | Cl | H |
| A-1992. | OCF₃ | CH₂F | 5-OCH₃ | Cl | H |
| A-1993. | OCF₃ | CHF₂ | 3-F | Cl | H |
| A-1994. | OCF₃ | CHF₂ | 3-CH₃ | Cl | H |
| A-1995. | OCF₃ | CHF₂ | 3-OCH₃ | Cl | H |
| A-1996. | OCF₃ | CHF₂ | 5-F | Cl | H |
| A-1997. | OCF₃ | CHF₂ | 5-CH₃ | Cl | H |
| A-1998. | OCF₃ | CHF₂ | 5-OCH₃ | Cl | H |
| A-1999. | OCF₃ | CF₃ | 3-F | Cl | H |
| A-2000. | OCF₃ | CF₃ | 3-CH₃ | Cl | H |
| A-2001. | OCF₃ | CF₃ | 3-OCH₃ | Cl | H |
| A-2002. | OCF₃ | CF₃ | 5-F | Cl | H |
| A-2003. | OCF₃ | CF₃ | 5-CH₃ | Cl | H |
| A-2004. | OCF₃ | CF₃ | 5-OCH₃ | Cl | H |
| A-2005. | OCF₃ | OCH₂F | 3-F | Cl | H |
| A-2006. | OCF₃ | OCH₂F | 3-CH₃ | Cl | H |
| A-2007. | OCF₃ | OCH₂F | 3-OCH₃ | Cl | H |
| A-2008. | OCF₃ | OCH₂F | 5-F | Cl | H |
| A-2009. | OCF₃ | OCH₂F | 5-CH₃ | Cl | H |
| A-2010. | OCF₃ | OCH₂F | 5-OCH₃ | Cl | H |
| A-2011. | OCF₃ | OCHF₂ | 3-F | Cl | H |
| A-2012. | OCF₃ | OCHF₂ | 3-CH₃ | Cl | H |
| A-2013. | OCF₃ | OCHF₂ | 3-OCH₃ | Cl | H |
| A-2014. | OCF₃ | OCHF₂ | 5-F | Cl | H |
| A-2015. | OCF₃ | OCHF₂ | 5-CH₃ | Cl | H |
| A-2016. | OCF₃ | OCHF₂ | 5-OCH₃ | Cl | H |
| A-2017. | OCF₃ | OCF₃ | 3-F | Cl | H |
| A-2018. | OCF₃ | OCF₃ | 3-CH₃ | Cl | H |
| A-2019. | OCF₃ | OCF₃ | 3-OCH₃ | Cl | H |
| A-2020. | OCF₃ | OCF₃ | 5-F | Cl | H |
| A-2021. | OCF₃ | OCF₃ | 5-CH₃ | Cl | H |
| A-2022. | OCF₃ | OCF₃ | 5-OCH₃ | Cl | H |
| A-2023. | H | H | H | CN | F |
| A-2024. | F | H | H | CN | F |
| A-2025. | CH₃ | H | H | CN | F |
| A-2026. | OCH₃ | H | H | CN | F |
| A-2027. | CH₂F | H | H | CN | F |
| A-2028. | CHF₂ | H | H | CN | F |
| A-2029. | CF₃ | H | H | CN | F |
| A-2030. | OCH₂F | H | H | CN | F |
| A-2031. | OCHF₂ | H | H | CN | F |
| A-2032. | OCF₃ | H | H | CN | F |
| A-2033. | H | F | H | CN | F |
| A-2034. | H | CH₃ | H | CN | F |
| A-2035. | H | OCH₃ | H | CN | F |
| A-2036. | H | CN | H | CN | F |
| A-2037. | H | CH₂F | H | CN | F |
| A-2038. | H | CHF₂ | H | CN | F |
| A-2039. | H | CF₃ | H | CN | F |
| A-2040. | H | OCH₂F | H | CN | F |
| A-2041. | H | OCHF₂ | H | CN | F |
| A-2042. | H | OCF₃ | H | CN | F |
| A-2043. | H | H | 3-F | CN | F |
| A-2044. | H | H | 3-CH₃ | CN | F |
| A-2045. | H | H | 3-OCH₃ | CN | F |
| A-2046. | H | H | 5-F | CN | F |
| A-2047. | H | H | 5-CH₃ | CN | F |
| A-2048. | H | H | 5-OCH₃ | CN | F |
| A-2049. | F | F | H | CN | F |
| A-2050. | F | CH₃ | H | CN | F |
| A-2051. | F | OCH₃ | H | CN | F |
| A-2052. | F | CN | H | CN | F |
| A-2053. | F | CH₂F | H | CN | F |
| A-2054. | F | CHF₂ | H | CN | F |
| A-2055. | F | CF₃ | H | CN | F |
| A-2056. | F | OCH₂F | H | CN | F |
| A-2057. | F | OCHF₂ | H | CN | F |
| A-2058. | F | OCF₃ | H | CN | F |
| A-2059. | F | H | 3-F | CN | F |
| A-2060. | F | H | 3-CH₃ | CN | F |
| A-2061. | F | H | 3-OCH₃ | CN | F |
| A-2062. | F | H | 5-F | CN | F |
| A-2063. | F | H | 5-CH₃ | CN | F |
| A-2064. | F | H | 5-OCH₃ | CN | F |
| A-2065. | CH₃ | F | H | CN | F |
| A-2066. | CH₃ | CH₃ | H | CN | F |
| A-2067. | CH₃ | OCH₃ | H | CN | F |
| A-2068. | CH₃ | CN | H | CN | F |
| A-2069. | CH₃ | CH₂F | H | CN | F |
| A-2070. | CH₃ | CHF₂ | H | CN | F |
| A-2071. | CH₃ | CF₃ | H | CN | F |
| A-2072. | CH₃ | OCH₂F | H | CN | F |
| A-2073. | CH₃ | OCHF₂ | H | CN | F |
| A-2074. | CH₃ | OCF₃ | H | CN | F |
| A-2075. | CH₃ | H | 3-F | CN | F |
| A-2076. | CH₃ | H | 3-CH₃ | CN | F |
| A-2077. | CH₃ | H | 3-OCH₃ | CN | F |
| A-2078. | CH₃ | H | 5-F | CN | F |
| A-2079. | CH₃ | H | 5-CH₃ | CN | F |
| A-2080. | CH₃ | H | 5-OCH₃ | CN | F |
| A-2081. | OCH₃ | F | H | CN | F |
| A-2082. | OCH₃ | CH₃ | H | CN | F |
| A-2083. | OCH₃ | OCH₃ | H | CN | F |
| A-2084. | OCH₃ | CN | H | CN | F |
| A-2085. | OCH₃ | CH₂F | H | CN | F |
| A-2086. | OCH₃ | CHF₂ | H | CN | F |
| A-2087. | OCH₃ | CF₃ | H | CN | F |
| A-2088. | OCH₃ | OCH₂F | H | CN | F |
| A-2089. | OCH₃ | OCHF₂ | H | CN | F |
| A-2090. | OCH₃ | OCF₃ | H | CN | F |
| A-2091. | OCH₃ | H | 3-F | CN | F |
| A-2092. | OCH₃ | H | 3-CH₃ | CN | F |
| A-2093. | OCH₃ | H | 3-OCH₃ | CN | F |
| A-2094. | OCH₃ | H | 5-F | CN | F |
| A-2095. | OCH₃ | H | 5-CH₃ | CN | F |
| A-2096. | OCH₃ | H | 5-OCH₃ | CN | F |
| A-2097. | H | F | 3-F | CN | F |
| A-2098. | H | F | 3-CH₃ | CN | F |
| A-2099. | H | F | 3-OCH₃ | CN | F |
| A-2100. | H | F | 5-F | CN | F |
| A-2101. | H | F | 5-CH₃ | CN | F |

TABLE A-continued

| Example No. | R¹ | R² | R³ | R⁶ | R⁷ |
|---|---|---|---|---|---|
| A-2102. | H | F | 5-OCH₃ | CN | F |
| A-2103. | H | CH₃ | 3-F | CN | F |
| A-2104. | H | CH₃ | 3-CH₃ | CN | F |
| A-2105. | H | CH₃ | 3-OCH₃ | CN | F |
| A-2106. | H | CH₃ | 5-F | CN | F |
| A-2107. | H | CH₃ | 5-CH₃ | CN | F |
| A-2108. | H | CH₃ | 5-OCH₃ | CN | F |
| A-2109. | H | OCH₃ | 3-F | CN | F |
| A-2110. | H | OCH₃ | 3-CH₃ | CN | F |
| A-2111. | H | OCH₃ | 3-OCH₃ | CN | F |
| A-2112. | H | OCH₃ | 5-F | CN | F |
| A-2113. | H | OCH₃ | 5-CH₃ | CN | F |
| A-2114. | H | OCH₃ | 5-OCH₃ | CN | F |
| A-2115. | H | CN | 3-F | CN | F |
| A-2116. | H | CN | 3-CH₃ | CN | F |
| A-2117. | H | CN | 3-OCH₃ | CN | F |
| A-2118. | H | CN | 5-F | CN | F |
| A-2119. | H | CN | 5-CH₃ | CN | F |
| A-2120. | H | CN | 5-OCH₃ | CN | F |
| A-2121. | H | CH₂F | 3-F | CN | F |
| A-2122. | H | CH₂F | 3-CH₃ | CN | F |
| A-2123. | H | CH₂F | 3-OCH₃ | CN | F |
| A-2124. | H | CH₂F | 5-F | CN | F |
| A-2125. | H | CH₂F | 5-CH₃ | CN | F |
| A-2126. | H | CH₂F | 5-OCH₃ | CN | F |
| A-2127. | H | CHF₂ | 3-F | CN | F |
| A-2128. | H | CHF₂ | 3-CH₃ | CN | F |
| A-2129. | H | CHF₂ | 3-OCH₃ | CN | F |
| A-2130. | H | CHF₂ | 5-F | CN | F |
| A-2131. | H | CHF₂ | 5-CH₃ | CN | F |
| A-2132. | H | CHF₂ | 5-OCH₃ | CN | F |
| A-2133. | H | CF₃ | 3-F | CN | F |
| A-2134. | H | CF₃ | 3-CH₃ | CN | F |
| A-2135. | H | CF₃ | 3-OCH₃ | CN | F |
| A-2136. | H | CF₃ | 5-F | CN | F |
| A-2137. | H | CF₃ | 5-CH₃ | CN | F |
| A-2138. | H | CF₃ | 5-OCH₃ | CN | F |
| A-2139. | H | OCH₂F | 3-F | CN | F |
| A-2140. | H | OCH₂F | 3-CH₃ | CN | F |
| A-2141. | H | OCH₂F | 3-OCH₃ | CN | F |
| A-2142. | H | OCH₂F | 5-F | CN | F |
| A-2143. | H | OCH₂F | 5-CH₃ | CN | F |
| A-2144. | H | OCH₂F | 5-OCH₃ | CN | F |
| A-2145. | H | OCHF₂ | 3-F | CN | F |
| A-2146. | H | OCHF₂ | 3-CH₃ | CN | F |
| A-2147. | H | OCHF₂ | 3-OCH₃ | CN | F |
| A-2148. | H | OCHF₂ | 5-F | CN | F |
| A-2149. | H | OCHF₂ | 5-CH₃ | CN | F |
| A-2150. | H | OCHF₂ | 5-OCH₃ | CN | F |
| A-2151. | H | OCF₃ | 3-F | CN | F |
| A-2152. | H | OCF₃ | 3-CH₃ | CN | F |
| A-2153. | H | OCF₃ | 3-OCH₃ | CN | F |
| A-2154. | H | OCF₃ | 5-F | CN | F |
| A-2155. | H | OCF₃ | 5-CH₃ | CN | F |
| A-2156. | H | OCF₃ | 5-OCH₃ | CN | F |
| A-2157. | F | F | 3-F | CN | F |
| A-2158. | F | F | 3-CH₃ | CN | F |
| A-2159. | F | F | 3-OCH₃ | CN | F |
| A-2160. | F | F | 5-F | CN | F |
| A-2161. | F | F | 5-CH₃ | CN | F |
| A-2162. | F | F | 5-OCH₃ | CN | F |
| A-2163. | F | CH₃ | 3-F | CN | F |
| A-2164. | F | CH₃ | 3-CH₃ | CN | F |
| A-2165. | F | CH₃ | 3-OCH₃ | CN | F |
| A-2166. | F | CH₃ | 5-F | CN | F |
| A-2167. | F | CH₃ | 5-CH₃ | CN | F |
| A-2168. | F | CH₃ | 5-OCH₃ | CN | F |
| A-2169. | F | OCH₃ | 3-F | CN | F |
| A-2170. | F | OCH₃ | 3-CH₃ | CN | F |
| A-2171. | F | OCH₃ | 3-OCH₃ | CN | F |
| A-2172. | F | OCH₃ | 5-F | CN | F |
| A-2173. | F | OCH₃ | 5-CH₃ | CN | F |
| A-2174. | F | OCH₃ | 5-OCH₃ | CN | F |
| A-2175. | F | CN | 3-F | CN | F |
| A-2176. | F | CN | 3-CH₃ | CN | F |
| A-2177. | F | CN | 3-OCH₃ | CN | F |
| A-2178. | F | CN | 5-F | CN | F |
| A-2179. | F | CN | 5-CH₃ | CN | F |
| A-2180. | F | CN | 5-OCH₃ | CN | F |
| A-2181. | F | CH₂F | 3-F | CN | F |
| A-2182. | F | CH₂F | 3-CH₃ | CN | F |
| A-2183. | F | CH₂F | 3-OCH₃ | CN | F |
| A-2184. | F | CH₂F | 5-F | CN | F |
| A-2185. | F | CH₂F | 5-CH₃ | CN | F |
| A-2186. | F | CH₂F | 5-OCH₃ | CN | F |
| A-2187. | F | CHF₂ | 3-F | CN | F |
| A-2188. | F | CHF₂ | 3-CH₃ | CN | F |
| A-2189. | F | CHF₂ | 3-OCH₃ | CN | F |
| A-2190. | F | CHF₂ | 5-F | CN | F |
| A-2191. | F | CHF₂ | 5-CH₃ | CN | F |
| A-2192. | F | CHF₂ | 5-OCH₃ | CN | F |
| A-2193. | F | CF₃ | 3-F | CN | F |
| A-2194. | F | CF₃ | 3-CH₃ | CN | F |
| A-2195. | F | CF₃ | 3-OCH₃ | CN | F |
| A-2196. | F | CF₃ | 5-F | CN | F |
| A-2197. | F | CF₃ | 5-CH₃ | CN | F |
| A-2198. | F | CF₃ | 5-OCH₃ | CN | F |
| A-2199. | F | OCH₂F | 3-F | CN | F |
| A-2200. | F | OCH₂F | 3-CH₃ | CN | F |
| A-2201. | F | OCH₂F | 3-OCH₃ | CN | F |
| A-2202. | F | OCH₂F | 5-F | CN | F |
| A-2203. | F | OCH₂F | 5-CH₃ | CN | F |
| A-2204. | F | OCH₂F | 5-OCH₃ | CN | F |
| A-2205. | F | OCHF₂ | 3-F | CN | F |
| A-2206. | F | OCHF₂ | 3-CH₃ | CN | F |
| A-2207. | F | OCHF₂ | 3-OCH₃ | CN | F |
| A-2208. | F | OCHF₂ | 5-F | CN | F |
| A-2209. | F | OCHF₂ | 5-CH₃ | CN | F |
| A-2210. | F | OCHF₂ | 5-OCH₃ | CN | F |
| A-2211. | F | OCF₃ | 3-F | CN | F |
| A-2212. | F | OCF₃ | 3-CH₃ | CN | F |
| A-2213. | F | OCF₃ | 3-OCH₃ | CN | F |
| A-2214. | F | OCF₃ | 5-F | CN | F |
| A-2215. | F | OCF₃ | 5-CH₃ | CN | F |
| A-2216. | F | OCF₃ | 5-OCH₃ | CN | F |
| A-2217. | CH₃ | F | 3-F | CN | F |
| A-2218. | CH₃ | F | 3-CH₃ | CN | F |
| A-2219. | CH₃ | F | 3-OCH₃ | CN | F |
| A-2220. | CH₃ | F | 5-F | CN | F |
| A-2221. | CH₃ | F | 5-CH₃ | CN | F |
| A-2222. | CH₃ | F | 5-OCH₃ | CN | F |
| A-2223. | CH₃ | CH₃ | 3-F | CN | F |
| A-2224. | CH₃ | CH₃ | 3-CH₃ | CN | F |
| A-2225. | CH₃ | CH₃ | 3-OCH₃ | CN | F |
| A-2226. | CH₃ | CH₃ | 5-F | CN | F |
| A-2227. | CH₃ | CH₃ | 5-CH₃ | CN | F |
| A-2228. | CH₃ | CH₃ | 5-OCH₃ | CN | F |
| A-2229. | CH₃ | OCH₃ | 3-F | CN | F |
| A-2230. | CH₃ | OCH₃ | 3-CH₃ | CN | F |
| A-2231. | CH₃ | OCH₃ | 3-OCH₃ | CN | F |
| A-2232. | CH₃ | OCH₃ | 5-F | CN | F |
| A-2233. | CH₃ | OCH₃ | 5-CH₃ | CN | F |
| A-2234. | CH₃ | OCH₃ | 5-OCH₃ | CN | F |
| A-2235. | CH₃ | CN | 3-F | CN | F |
| A-2236. | CH₃ | CN | 3-CH₃ | CN | F |
| A-2237. | CH₃ | CN | 3-OCH₃ | CN | F |
| A-2238. | CH₃ | CN | 5-F | CN | F |
| A-2239. | CH₃ | CN | 5-CH₃ | CN | F |
| A-2240. | CH₃ | CN | 5-OCH₃ | CN | F |
| A-2241. | CH₃ | CH₂F | 3-F | CN | F |
| A-2242. | CH₃ | CH₂F | 3-CH₃ | CN | F |
| A-2243. | CH₃ | CH₂F | 3-OCH₃ | CN | F |
| A-2244. | CH₃ | CH₂F | 5-F | CN | F |
| A-2245. | CH₃ | CH₂F | 5-CH₃ | CN | F |
| A-2246. | CH₃ | CH₂F | 5-OCH₃ | CN | F |
| A-2247. | CH₃ | CHF₂ | 3-F | CN | F |
| A-2248. | CH₃ | CHF₂ | 3-CH₃ | CN | F |
| A-2249. | CH₃ | CHF₂ | 3-OCH₃ | CN | F |
| A-2250. | CH₃ | CHF₂ | 5-F | CN | F |
| A-2251. | CH₃ | CHF₂ | 5-CH₃ | CN | F |
| A-2252. | CH₃ | CHF₂ | 5-OCH₃ | CN | F |
| A-2253. | CH₃ | CF₃ | 3-F | CN | F |
| A-2254. | CH₃ | CF₃ | 3-CH₃ | CN | F |
| A-2255. | CH₃ | CF₃ | 3-OCH₃ | CN | F |
| A-2256. | CH₃ | CF₃ | 5-F | CN | F |
| A-2257. | CH₃ | CF₃ | 5-CH₃ | CN | F |

TABLE A-continued

| Example No. | R¹ | R² | R³ | R⁶ | R⁷ |
|---|---|---|---|---|---|
| A-2258. | CH₃ | CF₃ | 5-OCH₃ | CN | F |
| A-2259. | CH₃ | OCH₂F | 3-F | CN | F |
| A-2260. | CH₃ | OCH₂F | 3-CH₃ | CN | F |
| A-2261. | CH₃ | OCH₂F | 3-OCH₃ | CN | F |
| A-2262. | CH₃ | OCH₂F | 5-F | CN | F |
| A-2263. | CH₃ | OCH₂F | 5-CH₃ | CN | F |
| A-2264. | CH₃ | OCH₂F | 5-OCH₃ | CN | F |
| A-2265. | CH₃ | OCHF₂ | 3-F | CN | F |
| A-2266. | CH₃ | OCHF₂ | 3-CH₃ | CN | F |
| A-2267. | CH₃ | OCHF₂ | 3-OCH₃ | CN | F |
| A-2268. | CH₃ | OCHF₂ | 5-F | CN | F |
| A-2269. | CH₃ | OCHF₂ | 5-CH₃ | CN | F |
| A-2270. | CH₃ | OCHF₂ | 5-OCH₃ | CN | F |
| A-2271. | CH₃ | OCF₃ | 3-F | CN | F |
| A-2272. | CH₃ | OCF₃ | 3-CH₃ | CN | F |
| A-2273. | CH₃ | OCF₃ | 3-OCH₃ | CN | F |
| A-2274. | CH₃ | OCF₃ | 5-F | CN | F |
| A-2275. | CH₃ | OCF₃ | 5-CH₃ | CN | F |
| A-2276. | CH₃ | OCF₃ | 5-OCH₃ | CN | F |
| A-2277. | OCH₃ | F | 3-F | CN | F |
| A-2278. | OCH₃ | F | 3-CH₃ | CN | F |
| A-2279. | OCH₃ | F | 3-OCH₃ | CN | F |
| A-2280. | OCH₃ | F | 5-F | CN | F |
| A-2281. | OCH₃ | F | 5-CH₃ | CN | F |
| A-2282. | OCH₃ | F | 5-OCH₃ | CN | F |
| A-2283. | OCH₃ | CH₃ | 3-F | CN | F |
| A-2284. | OCH₃ | CH₃ | 3-CH₃ | CN | F |
| A-2285. | OCH₃ | CH₃ | 3-OCH₃ | CN | F |
| A-2286. | OCH₃ | CH₃ | 5-F | CN | F |
| A-2287. | OCH₃ | CH₃ | 5-CH₃ | CN | F |
| A-2288. | OCH₃ | CH₃ | 5-OCH₃ | CN | F |
| A-2289. | OCH₃ | OCH₃ | 3-F | CN | F |
| A-2290. | OCH₃ | OCH₃ | 3-CH₃ | CN | F |
| A-2291. | OCH₃ | OCH₃ | 3-OCH₃ | CN | F |
| A-2292. | OCH₃ | OCH₃ | 5-F | CN | F |
| A-2293. | OCH₃ | OCH₃ | 5-CH₃ | CN | F |
| A-2294. | OCH₃ | OCH₃ | 5-OCH₃ | CN | F |
| A-2295. | OCH₃ | CN | 3-F | CN | F |
| A-2296. | OCH₃ | CN | 3-CH₃ | CN | F |
| A-2297. | OCH₃ | CN | 3-OCH₃ | CN | F |
| A-2298. | OCH₃ | CN | 5-F | CN | F |
| A-2299. | OCH₃ | CN | 5-CH₃ | CN | F |
| A-2300. | OCH₃ | CN | 5-OCH₃ | CN | F |
| A-2301. | OCH₃ | CH₂F | 3-F | CN | F |
| A-2302. | OCH₃ | CH₂F | 3-CH₃ | CN | F |
| A-2303. | OCH₃ | CH₂F | 3-OCH₃ | CN | F |
| A-2304. | OCH₃ | CH₂F | 5-F | CN | F |
| A-2305. | OCH₃ | CH₂F | 5-CH₃ | CN | F |
| A-2306. | OCH₃ | CH₂F | 5-OCH₃ | CN | F |
| A-2307. | OCH₃ | CHF₂ | 3-F | CN | F |
| A-2308. | OCH₃ | CHF₂ | 3-CH₃ | CN | F |
| A-2309. | OCH₃ | CHF₂ | 3-OCH₃ | CN | F |
| A-2310. | OCH₃ | CHF₂ | 5-F | CN | F |
| A-2311. | OCH₃ | CHF₂ | 5-CH₃ | CN | F |
| A-2312. | OCH₃ | CHF₂ | 5-OCH₃ | CN | F |
| A-2313. | OCH₃ | CF₃ | 3-F | CN | F |
| A-2314. | OCH₃ | CF₃ | 3-CH₃ | CN | F |
| A-2315. | OCH₃ | CF₃ | 3-OCH₃ | CN | F |
| A-2316. | OCH₃ | CF₃ | 5-F | CN | F |
| A-2317. | OCH₃ | CF₃ | 5-CH₃ | CN | F |
| A-2318. | OCH₃ | CF₃ | 5-OCH₃ | CN | F |
| A-2319. | OCH₃ | OCH₂F | 3-F | CN | F |
| A-2320. | OCH₃ | OCH₂F | 3-CH₃ | CN | F |
| A-2321. | OCH₃ | OCH₂F | 3-OCH₃ | CN | F |
| A-2322. | OCH₃ | OCH₂F | 5-F | CN | F |
| A-2323. | OCH₃ | OCH₂F | 5-CH₃ | CN | F |
| A-2324. | OCH₃ | OCH₂F | 5-OCH₃ | CN | F |
| A-2325. | OCH₃ | OCHF₂ | 3-F | CN | F |
| A-2326. | OCH₃ | OCHF₂ | 3-CH₃ | CN | F |
| A-2327. | OCH₃ | OCHF₂ | 3-OCH₃ | CN | F |
| A-2328. | OCH₃ | OCHF₂ | 5-F | CN | F |
| A-2329. | OCH₃ | OCHF₂ | 5-CH₃ | CN | F |
| A-2330. | OCH₃ | OCHF₂ | 5-OCH₃ | CN | F |
| A-2331. | OCH₃ | OCF₃ | 3-F | CN | F |
| A-2332. | OCH₃ | OCF₃ | 3-CH₃ | CN | F |
| A-2333. | OCH₃ | OCF₃ | 3-OCH₃ | CN | F |
| A-2334. | OCH₃ | OCF₃ | 5-F | CN | F |
| A-2335. | OCH₃ | OCF₃ | 5-CH₃ | CN | F |
| A-2336. | OCH₃ | OCF₃ | 5-OCH₃ | CN | F |
| A-2337. | CH₂F | F | 3-F | CN | F |
| A-2338. | CH₂F | F | 3-CH₃ | CN | F |
| A-2339. | CH₂F | F | 3-OCH₃ | CN | F |
| A-2340. | CH₂F | F | 5-F | CN | F |
| A-2341. | CH₂F | F | 5-CH₃ | CN | F |
| A-2342. | CH₂F | F | 5-OCH₃ | CN | F |
| A-2343. | CH₂F | CH₃ | 3-F | CN | F |
| A-2344. | CH₂F | CH₃ | 3-CH₃ | CN | F |
| A-2345. | CH₂F | CH₃ | 3-OCH₃ | CN | F |
| A-2346. | CH₂F | CH₃ | 5-F | CN | F |
| A-2347. | CH₂F | CH₃ | 5-CH₃ | CN | F |
| A-2348. | CH₂F | CH₃ | 5-OCH₃ | CN | F |
| A-2349. | CH₂F | OCH₃ | 3-F | CN | F |
| A-2350. | CH₂F | OCH₃ | 3-CH₃ | CN | F |
| A-2351. | CH₂F | OCH₃ | 3-OCH₃ | CN | F |
| A-2352. | CH₂F | OCH₃ | 5-F | CN | F |
| A-2353. | CH₂F | OCH₃ | 5-CH₃ | CN | F |
| A-2354. | CH₂F | OCH₃ | 5-OCH₃ | CN | F |
| A-2355. | CH₂F | CN | 3-F | CN | F |
| A-2356. | CH₂F | CN | 3-CH₃ | CN | F |
| A-2357. | CH₂F | CN | 3-OCH₃ | CN | F |
| A-2358. | CH₂F | CN | 5-F | CN | F |
| A-2359. | CH₂F | CN | 5-CH₃ | CN | F |
| A-2360. | CH₂F | CN | 5-OCH₃ | CN | F |
| A-2361. | CH₂F | CH₂F | 3-F | CN | F |
| A-2362. | CH₂F | CH₂F | 3-CH₃ | CN | F |
| A-2363. | CH₂F | CH₂F | 3-OCH₃ | CN | F |
| A-2364. | CH₂F | CH₂F | 5-F | CN | F |
| A-2365. | CH₂F | CH₂F | 5-CH₃ | CN | F |
| A-2366. | CH₂F | CH₂F | 5-OCH₃ | CN | F |
| A-2367. | CH₂F | CHF₂ | 3-F | CN | F |
| A-2368. | CH₂F | CHF₂ | 3-CH₃ | CN | F |
| A-2369. | CH₂F | CHF₂ | 3-OCH₃ | CN | F |
| A-2370. | CH₂F | CHF₂ | 5-F | CN | F |
| A-2371. | CH₂F | CHF₂ | 5-CH₃ | CN | F |
| A-2372. | CH₂F | CHF₂ | 5-OCH₃ | CN | F |
| A-2373. | CH₂F | CF₃ | 3-F | CN | F |
| A-2374. | CH₂F | CF₃ | 3-CH₃ | CN | F |
| A-2375. | CH₂F | CF₃ | 3-OCH₃ | CN | F |
| A-2376. | CH₂F | CF₃ | 5-F | CN | F |
| A-2377. | CH₂F | CF₃ | 5-CH₃ | CN | F |
| A-2378. | CH₂F | CF₃ | 5-OCH₃ | CN | F |
| A-2379. | CH₂F | OCH₂F | 3-F | CN | F |
| A-2380. | CH₂F | OCH₂F | 3-CH₃ | CN | F |
| A-2381. | CH₂F | OCH₂F | 3-OCH₃ | CN | F |
| A-2382. | CH₂F | OCH₂F | 5-F | CN | F |
| A-2383. | CH₂F | OCH₂F | 5-CH₃ | CN | F |
| A-2384. | CH₂F | OCH₂F | 5-OCH₃ | CN | F |
| A-2385. | CH₂F | OCHF₂ | 3-F | CN | F |
| A-2386. | CH₂F | OCHF₂ | 3-CH₃ | CN | F |
| A-2387. | CH₂F | OCHF₂ | 3-OCH₃ | CN | F |
| A-2388. | CH₂F | OCHF₂ | 5-F | CN | F |
| A-2389. | CH₂F | OCHF₂ | 5-CH₃ | CN | F |
| A-2390. | CH₂F | OCHF₂ | 5-OCH₃ | CN | F |
| A-2391. | CH₂F | OCF₃ | 3-F | CN | F |
| A-2392. | CH₂F | OCF₃ | 3-CH₃ | CN | F |
| A-2393. | CH₂F | OCF₃ | 3-OCH₃ | CN | F |
| A-2394. | CH₂F | OCF₃ | 5-F | CN | F |
| A-2395. | CH₂F | OCF₃ | 5-CH₃ | CN | F |
| A-2396. | CH₂F | OCF₃ | 5-OCH₃ | CN | F |
| A-2397. | CHF₂ | F | 3-F | CN | F |
| A-2398. | CHF₂ | F | 3-CH₃ | CN | F |
| A-2399. | CHF₂ | F | 3-OCH₃ | CN | F |
| A-2400. | CHF₂ | F | 5-F | CN | F |
| A-2401. | CHF₂ | F | 5-CH₃ | CN | F |
| A-2402. | CHF₂ | F | 5-OCH₃ | CN | F |
| A-2403. | CHF₂ | CH₃ | 3-F | CN | F |
| A-2404. | CHF₂ | CH₃ | 3-CH₃ | CN | F |
| A-2405. | CHF₂ | CH₃ | 3-OCH₃ | CN | F |
| A-2406. | CHF₂ | CH₃ | 5-F | CN | F |
| A-2407. | CHF₂ | CH₃ | 5-CH₃ | CN | F |
| A-2408. | CHF₂ | CH₃ | 5-OCH₃ | CN | F |
| A-2409. | CHF₂ | OCH₃ | 3-F | CN | F |
| A-2410. | CHF₂ | OCH₃ | 3-CH₃ | CN | F |
| A-2411. | CHF₂ | OCH₃ | 3-OCH₃ | CN | F |
| A-2412. | CHF₂ | OCH₃ | 5-F | CN | F |
| A-2413. | CHF₂ | OCH₃ | 5-CH₃ | CN | F |

TABLE A-continued

| Example No. | R¹ | R² | R³ | R⁶ | R⁷ |
|---|---|---|---|---|---|
| A-2414. | CHF$_2$ | OCH$_3$ | 5-OCH$_3$ | CN | F |
| A-2415. | CHF$_2$ | CN | 3-F | CN | F |
| A-2416. | CHF$_2$ | CN | 3-CH$_3$ | CN | F |
| A-2417. | CHF$_2$ | CN | 3-OCH$_3$ | CN | F |
| A-2418. | CHF$_2$ | CN | 5-F | CN | F |
| A-2419. | CHF$_2$ | CN | 5-CH$_3$ | CN | F |
| A-2420. | CHF$_2$ | CN | 5-OCH$_3$ | CN | F |
| A-2421. | CHF$_2$ | CH$_2$F | 3-F | CN | F |
| A-2422. | CHF$_2$ | CH$_2$F | 3-CH$_3$ | CN | F |
| A-2423. | CHF$_2$ | CH$_2$F | 3-OCH$_3$ | CN | F |
| A-2424. | CHF$_2$ | CH$_2$F | 5-F | CN | F |
| A-2425. | CHF$_2$ | CH$_2$F | 5-CH$_3$ | CN | F |
| A-2426. | CHF$_2$ | CH$_2$F | 5-OCH$_3$ | CN | F |
| A-2427. | CHF$_2$ | CHF$_2$ | 3-F | CN | F |
| A-2428. | CHF$_2$ | CHF$_2$ | 3-CH$_3$ | CN | F |
| A-2429. | CHF$_2$ | CHF$_2$ | 3-OCH$_3$ | CN | F |
| A-2430. | CHF$_2$ | CHF$_2$ | 5-F | CN | F |
| A-2431. | CHF$_2$ | CHF$_2$ | 5-CH$_3$ | CN | F |
| A-2432. | CHF$_2$ | CHF$_2$ | 5-OCH$_3$ | CN | F |
| A-2433. | CHF$_2$ | CF$_3$ | 3-F | CN | F |
| A-2434. | CHF$_2$ | CF$_3$ | 3-CH$_3$ | CN | F |
| A-2435. | CHF$_2$ | CF$_3$ | 3-OCH$_3$ | CN | F |
| A-2436. | CHF$_2$ | CF$_3$ | 5-F | CN | F |
| A-2437. | CHF$_2$ | CF$_3$ | 5-CH$_3$ | CN | F |
| A-2438. | CHF$_2$ | CF$_3$ | 5-OCH$_3$ | CN | F |
| A-2439. | CHF$_2$ | OCH$_2$F | 3-F | CN | F |
| A-2440. | CHF$_2$ | OCH$_2$F | 3-CH$_3$ | CN | F |
| A-2441. | CHF$_2$ | OCH$_2$F | 3-OCH$_3$ | CN | F |
| A-2442. | CHF$_2$ | OCH$_2$F | 5-F | CN | F |
| A-2443. | CHF$_2$ | OCH$_2$F | 5-CH$_3$ | CN | F |
| A-2444. | CHF$_2$ | OCH$_2$F | 5-OCH$_3$ | CN | F |
| A-2445. | CHF$_2$ | OCHF$_2$ | 3-F | CN | F |
| A-2446. | CHF$_2$ | OCHF$_2$ | 3-CH$_3$ | CN | F |
| A-2447. | CHF$_2$ | OCHF$_2$ | 3-OCH$_3$ | CN | F |
| A-2448. | CHF$_2$ | OCHF$_2$ | 5-F | CN | F |
| A-2449. | CHF$_2$ | OCHF$_2$ | 5-CH$_3$ | CN | F |
| A-2450. | CHF$_2$ | OCHF$_2$ | 5-OCH$_3$ | CN | F |
| A-2451. | CHF$_2$ | OCF$_3$ | 3-F | CN | F |
| A-2452. | CHF$_2$ | OCF$_3$ | 3-CH$_3$ | CN | F |
| A-2453. | CHF$_2$ | OCF$_3$ | 3-OCH$_3$ | CN | F |
| A-2454. | CHF$_2$ | OCF$_3$ | 5-F | CN | F |
| A-2455. | CHF$_2$ | OCF$_3$ | 5-CH$_3$ | CN | F |
| A-2456. | CHF$_2$ | OCF$_3$ | 5-OCH$_3$ | CN | F |
| A-2457. | CF$_3$ | F | 3-F | CN | F |
| A-2458. | CF$_3$ | F | 3-CH$_3$ | CN | F |
| A-2459. | CF$_3$ | F | 3-OCH$_3$ | CN | F |
| A-2460. | CF$_3$ | F | 5-F | CN | F |
| A-2461. | CF$_3$ | F | 5-CH$_3$ | CN | F |
| A-2462. | CF$_3$ | F | 5-OCH$_3$ | CN | F |
| A-2463. | CF$_3$ | CH$_3$ | 3-F | CN | F |
| A-2464. | CF$_3$ | CH$_3$ | 3-CH$_3$ | CN | F |
| A-2465. | CF$_3$ | CH$_3$ | 3-OCH$_3$ | CN | F |
| A-2466. | CF$_3$ | CH$_3$ | 5-F | CN | F |
| A-2467. | CF$_3$ | CH$_3$ | 5-CH$_3$ | CN | F |
| A-2468. | CF$_3$ | CH$_3$ | 5-OCH$_3$ | CN | F |
| A-2469. | CF$_3$ | OCH$_3$ | 3-F | CN | F |
| A-2470. | CF$_3$ | OCH$_3$ | 3-CH$_3$ | CN | F |
| A-2471. | CF$_3$ | OCH$_3$ | 3-OCH$_3$ | CN | F |
| A-2472. | CF$_3$ | OCH$_3$ | 5-F | CN | F |
| A-2473. | CF$_3$ | OCH$_3$ | 5-CH$_3$ | CN | F |
| A-2474. | CF$_3$ | OCH$_3$ | 5-OCH$_3$ | CN | F |
| A-2475. | CF$_3$ | CN | 3-F | CN | F |
| A-2476. | CF$_3$ | CN | 3-CH$_3$ | CN | F |
| A-2477. | CF$_3$ | CN | 3-OCH$_3$ | CN | F |
| A-2478. | CF$_3$ | CN | 5-F | CN | F |
| A-2479. | CF$_3$ | CN | 5-CH$_3$ | CN | F |
| A-2480. | CF$_3$ | CN | 5-OCH$_3$ | CN | F |
| A-2481. | CF$_3$ | CH$_2$F | 3-F | CN | F |
| A-2482. | CF$_3$ | CH$_2$F | 3-CH$_3$ | CN | F |
| A-2483. | CF$_3$ | CH$_2$F | 3-OCH$_3$ | CN | F |
| A-2484. | CF$_3$ | CH$_2$F | 5-F | CN | F |
| A-2485. | CF$_3$ | CH$_2$F | 5-CH$_3$ | CN | F |
| A-2486. | CF$_3$ | CH$_2$F | 5-OCH$_3$ | CN | F |
| A-2487. | CF$_3$ | CHF$_2$ | 3-F | CN | F |
| A-2488. | CF$_3$ | CHF$_2$ | 3-CH$_3$ | CN | F |
| A-2489. | CF$_3$ | CHF$_2$ | 3-OCH$_3$ | CN | F |
| A-2490. | CF$_3$ | CHF$_2$ | 5-F | CN | F |
| A-2491. | CF$_3$ | CHF$_2$ | 5-CH$_3$ | CN | F |
| A-2492. | CF$_3$ | CHF$_2$ | 5-OCH$_3$ | CN | F |
| A-2493. | CF$_3$ | CF$_3$ | 3-F | CN | F |
| A-2494. | CF$_3$ | CF$_3$ | 3-CH$_3$ | CN | F |
| A-2495. | CF$_3$ | CF$_3$ | 3-OCH$_3$ | CN | F |
| A-2496. | CF$_3$ | CF$_3$ | 5-F | CN | F |
| A-2497. | CF$_3$ | CF$_3$ | 5-CH$_3$ | CN | F |
| A-2498. | CF$_3$ | CF$_3$ | 5-OCH$_3$ | CN | F |
| A-2499. | CF$_3$ | OCH$_2$F | 3-F | CN | F |
| A-2500. | CF$_3$ | OCH$_2$F | 3-CH$_3$ | CN | F |
| A-2501. | CF$_3$ | OCH$_2$F | 3-OCH$_3$ | CN | F |
| A-2502. | CF$_3$ | OCH$_2$F | 5-F | CN | F |
| A-2503. | CF$_3$ | OCH$_2$F | 5-CH$_3$ | CN | F |
| A-2504. | CF$_3$ | OCH$_2$F | 5-OCH$_3$ | CN | F |
| A-2505. | CF$_3$ | OCHF$_2$ | 3-F | CN | F |
| A-2506. | CF$_3$ | OCHF$_2$ | 3-CH$_3$ | CN | F |
| A-2507. | CF$_3$ | OCHF$_2$ | 3-OCH$_3$ | CN | F |
| A-2508. | CF$_3$ | OCHF$_2$ | 5-F | CN | F |
| A-2509. | CF$_3$ | OCHF$_2$ | 5-CH$_3$ | CN | F |
| A-2510. | CF$_3$ | OCHF$_2$ | 5-OCH$_3$ | CN | F |
| A-2511. | CF$_3$ | OCF$_3$ | 3-F | CN | F |
| A-2512. | CF$_3$ | OCF$_3$ | 3-CH$_3$ | CN | F |
| A-2513. | CF$_3$ | OCF$_3$ | 3-OCH$_3$ | CN | F |
| A-2514. | CF$_3$ | OCF$_3$ | 5-F | CN | F |
| A-2515. | CF$_3$ | OCF$_3$ | 5-CH$_3$ | CN | F |
| A-2516. | CF$_3$ | OCF$_3$ | 5-OCH$_3$ | CN | F |
| A-2517. | OCH$_2$F | F | 3-F | CN | F |
| A-2518. | OCH$_2$F | F | 3-CH$_3$ | CN | F |
| A-2519. | OCH$_2$F | F | 3-OCH$_3$ | CN | F |
| A-2520. | OCH$_2$F | F | 5-F | CN | F |
| A-2521. | OCH$_2$F | F | 5-CH$_3$ | CN | F |
| A-2522. | OCH$_2$F | F | 5-OCH$_3$ | CN | F |
| A-2523. | OCH$_2$F | CH$_3$ | 3-F | CN | F |
| A-2524. | OCH$_2$F | CH$_3$ | 3-CH$_3$ | CN | F |
| A-2525. | OCH$_2$F | CH$_3$ | 3-OCH$_3$ | CN | F |
| A-2526. | OCH$_2$F | CH$_3$ | 5-F | CN | F |
| A-2527. | OCH$_2$F | CH$_3$ | 5-CH$_3$ | CN | F |
| A-2528. | OCH$_2$F | CH$_3$ | 5-OCH$_3$ | CN | F |
| A-2529. | OCH$_2$F | OCH$_3$ | 3-F | CN | F |
| A-2530. | OCH$_2$F | OCH$_3$ | 3-CH$_3$ | CN | F |
| A-2531. | OCH$_2$F | OCH$_3$ | 3-OCH$_3$ | CN | F |
| A-2532. | OCH$_2$F | OCH$_3$ | 5-F | CN | F |
| A-2533. | OCH$_2$F | OCH$_3$ | 5-CH$_3$ | CN | F |
| A-2534. | OCH$_2$F | OCH$_3$ | 5-OCH$_3$ | CN | F |
| A-2535. | OCH$_2$F | CN | 3-F | CN | F |
| A-2536. | OCH$_2$F | CN | 3-CH$_3$ | CN | F |
| A-2537. | OCH$_2$F | CN | 3-OCH$_3$ | CN | F |
| A-2538. | OCH$_2$F | CN | 5-F | CN | F |
| A-2539. | OCH$_2$F | CN | 5-CH$_3$ | CN | F |
| A-2540. | OCH$_2$F | CN | 5-OCH$_3$ | CN | F |
| A-2541. | OCH$_2$F | CH$_2$F | 3-F | CN | F |
| A-2542. | OCH$_2$F | CH$_2$F | 3-CH$_3$ | CN | F |
| A-2543. | OCH$_2$F | CH$_2$F | 3-OCH$_3$ | CN | F |
| A-2544. | OCH$_2$F | CH$_2$F | 5-F | CN | F |
| A-2545. | OCH$_2$F | CH$_2$F | 5-CH$_3$ | CN | F |
| A-2546. | OCH$_2$F | CH$_2$F | 5-OCH$_3$ | CN | F |
| A-2547. | OCH$_2$F | CHF$_2$ | 3-F | CN | F |
| A-2548. | OCH$_2$F | CHF$_2$ | 3-CH$_3$ | CN | F |
| A-2549. | OCH$_2$F | CHF$_2$ | 3-OCH$_3$ | CN | F |
| A-2550. | OCH$_2$F | CHF$_2$ | 5-F | CN | F |
| A-2551. | OCH$_2$F | CHF$_2$ | 5-CH$_3$ | CN | F |
| A-2552. | OCH$_2$F | CHF$_2$ | 5-OCH$_3$ | CN | F |
| A-2553. | OCH$_2$F | CF$_3$ | 3-F | CN | F |
| A-2554. | OCH$_2$F | CF$_3$ | 3-CH$_3$ | CN | F |
| A-2555. | OCH$_2$F | CF$_3$ | 3-OCH$_3$ | CN | F |
| A-2556. | OCH$_2$F | CF$_3$ | 5-F | CN | F |
| A-2557. | OCH$_2$F | CF$_3$ | 5-CH$_3$ | CN | F |
| A-2558. | OCH$_2$F | CF$_3$ | 5-OCH$_3$ | CN | F |
| A-2559. | OCH$_2$F | OCH$_2$F | 3-F | CN | F |
| A-2560. | OCH$_2$F | OCH$_2$F | 3-CH$_3$ | CN | F |
| A-2561. | OCH$_2$F | OCH$_2$F | 3-OCH$_3$ | CN | F |
| A-2562. | OCH$_2$F | OCH$_2$F | 5-F | CN | F |
| A-2563. | OCH$_2$F | OCH$_2$F | 5-CH$_3$ | CN | F |
| A-2564. | OCH$_2$F | OCH$_2$F | 5-OCH$_3$ | CN | F |
| A-2565. | OCH$_2$F | OCHF$_2$ | 3-F | CN | F |
| A-2566. | OCH$_2$F | OCHF$_2$ | 3-CH$_3$ | CN | F |
| A-2567. | OCH$_2$F | OCHF$_2$ | 3-OCH$_3$ | CN | F |
| A-2568. | OCH$_2$F | OCHF$_2$ | 5-F | CN | F |
| A-2569. | OCH$_2$F | OCHF$_2$ | 5-CH$_3$ | CN | F |

TABLE A-continued

| Example No. | R¹ | R² | R³ | R⁶ | R⁷ |
|---|---|---|---|---|---|
| A-2570. | OCH₂F | OCHF₂ | 5-OCH₃ | CN | F |
| A-2571. | OCH₂F | OCF₃ | 3-F | CN | F |
| A-2572. | OCH₂F | OCF₃ | 3-CH₃ | CN | F |
| A-2573. | OCH₂F | OCF₃ | 3-OCH₃ | CN | F |
| A-2574. | OCH₂F | OCF₃ | 5-F | CN | F |
| A-2575. | OCH₂F | OCF₃ | 5-CH₃ | CN | F |
| A-2576. | OCH₂F | OCF₃ | 5-OCH₃ | CN | F |
| A-2577. | OCHF₂ | F | 3-F | CN | F |
| A-2578. | OCHF₂ | F | 3-CH₃ | CN | F |
| A-2579. | OCHF₂ | F | 3-OCH₃ | CN | F |
| A-2580. | OCHF₂ | F | 5-F | CN | F |
| A-2581. | OCHF₂ | F | 5-CH₃ | CN | F |
| A-2582. | OCHF₂ | F | 5-OCH₃ | CN | F |
| A-2583. | OCHF₂ | CH₃ | 3-F | CN | F |
| A-2584. | OCHF₂ | CH₃ | 3-CH₃ | CN | F |
| A-2585. | OCHF₂ | CH₃ | 3-OCH₃ | CN | F |
| A-2586. | OCHF₂ | CH₃ | 5-F | CN | F |
| A-2587. | OCHF₂ | CH₃ | 5-CH₃ | CN | F |
| A-2588. | OCHF₂ | CH₃ | 5-OCH₃ | CN | F |
| A-2589. | OCHF₂ | OCH₃ | 3-F | CN | F |
| A-2590. | OCHF₂ | OCH₃ | 3-CH₃ | CN | F |
| A-2591. | OCHF₂ | OCH₃ | 3-OCH₃ | CN | F |
| A-2592. | OCHF₂ | OCH₃ | 5-F | CN | F |
| A-2593. | OCHF₂ | OCH₃ | 5-CH₃ | CN | F |
| A-2594. | OCHF₂ | OCH₃ | 5-OCH₃ | CN | F |
| A-2595. | OCHF₂ | CN | 3-F | CN | F |
| A-2596. | OCHF₂ | CN | 3-CH₃ | CN | F |
| A-2597. | OCHF₂ | CN | 3-OCH₃ | CN | F |
| A-2598. | OCHF₂ | CN | 5-F | CN | F |
| A-2599. | OCHF₂ | CN | 5-CH₃ | CN | F |
| A-2600. | OCHF₂ | CN | 5-OCH₃ | CN | F |
| A-2601. | OCHF₂ | CH₂F | 3-F | CN | F |
| A-2602. | OCHF₂ | CH₂F | 3-CH₃ | CN | F |
| A-2603. | OCHF₂ | CH₂F | 3-OCH₃ | CN | F |
| A-2604. | OCHF₂ | CH₂F | 5-F | CN | F |
| A-2605. | OCHF₂ | CH₂F | 5-CH₃ | CN | F |
| A-2606. | OCHF₂ | CH₂F | 5-OCH₃ | CN | F |
| A-2607. | OCHF₂ | CHF₂ | 3-F | CN | F |
| A-2608. | OCHF₂ | CHF₂ | 3-CH₃ | CN | F |
| A-2609. | OCHF₂ | CHF₂ | 3-OCH₃ | CN | F |
| A-2610. | OCHF₂ | CHF₂ | 5-F | CN | F |
| A-2611. | OCHF₂ | CHF₂ | 5-CH₃ | CN | F |
| A-2612. | OCHF₂ | CHF₂ | 5-OCH₃ | CN | F |
| A-2613. | OCHF₂ | CF₃ | 3-F | CN | F |
| A-2614. | OCHF₂ | CF₃ | 3-CH₃ | CN | F |
| A-2615. | OCHF₂ | CF₃ | 3-OCH₃ | CN | F |
| A-2616. | OCHF₂ | CF₃ | 5-F | CN | F |
| A-2617. | OCHF₂ | CF₃ | 5-CH₃ | CN | F |
| A-2618. | OCHF₂ | CF₃ | 5-OCH₃ | CN | F |
| A-2619. | OCHF₂ | OCH₂F | 3-F | CN | F |
| A-2620. | OCHF₂ | OCH₂F | 3-CH₃ | CN | F |
| A-2621. | OCHF₂ | OCH₂F | 3-OCH₃ | CN | F |
| A-2622. | OCHF₂ | OCH₂F | 5-F | CN | F |
| A-2623. | OCHF₂ | OCH₂F | 5-CH₃ | CN | F |
| A-2624. | OCHF₂ | OCH₂F | 5-OCH₃ | CN | F |
| A-2625. | OCHF₂ | OCHF₂ | 3-F | CN | F |
| A-2626. | OCHF₂ | OCHF₂ | 3-CH₃ | CN | F |
| A-2627. | OCHF₂ | OCHF₂ | 3-OCH₃ | CN | F |
| A-2628. | OCHF₂ | OCHF₂ | 5-F | CN | F |
| A-2629. | OCHF₂ | OCHF₂ | 5-CH₃ | CN | F |
| A-2630. | OCHF₂ | OCHF₂ | 5-OCH₃ | CN | F |
| A-2631. | OCHF₂ | OCF₃ | 3-F | CN | F |
| A-2632. | OCHF₂ | OCF₃ | 3-CH₃ | CN | F |
| A-2633. | OCHF₂ | OCF₃ | 3-OCH₃ | CN | F |
| A-2634. | OCHF₂ | OCF₃ | 5-F | CN | F |
| A-2635. | OCHF₂ | OCF₃ | 5-CH₃ | CN | F |
| A-2636. | OCHF₂ | OCF₃ | 5-OCH₃ | CN | F |
| A-2637. | OCF₃ | F | 3-F | CN | F |
| A-2638. | OCF₃ | F | 3-CH₃ | CN | F |
| A-2639. | OCF₃ | F | 3-OCH₃ | CN | F |
| A-2640. | OCF₃ | F | 5-F | CN | F |
| A-2641. | OCF₃ | F | 5-CH₃ | CN | F |
| A-2642. | OCF₃ | F | 5-OCH₃ | CN | F |
| A-2643. | OCF₃ | CH₃ | 3-F | CN | F |
| A-2644. | OCF₃ | CH₃ | 3-CH₃ | CN | F |
| A-2645. | OCF₃ | CH₃ | 3-OCH₃ | CN | F |
| A-2646. | OCF₃ | CH₃ | 5-F | CN | F |
| A-2647. | OCF₃ | CH₃ | 5-CH₃ | CN | F |
| A-2648. | OCF₃ | CH₃ | 5-OCH₃ | CN | F |
| A-2649. | OCF₃ | OCH₃ | 3-F | CN | F |
| A-2650. | OCF₃ | OCH₃ | 3-CH₃ | CN | F |
| A-2651. | OCF₃ | OCH₃ | 3-OCH₃ | CN | F |
| A-2652. | OCF₃ | OCH₃ | 5-F | CN | F |
| A-2653. | OCF₃ | OCH₃ | 5-CH₃ | CN | F |
| A-2654. | OCF₃ | OCH₃ | 5-OCH₃ | CN | F |
| A-2655. | OCF₃ | CN | 3-F | CN | F |
| A-2656. | OCF₃ | CN | 3-CH₃ | CN | F |
| A-2657. | OCF₃ | CN | 3-OCH₃ | CN | F |
| A-2658. | OCF₃ | CN | 5-F | CN | F |
| A-2659. | OCF₃ | CN | 5-CH₃ | CN | F |
| A-2660. | OCF₃ | CN | 5-OCH₃ | CN | F |
| A-2661. | OCF₃ | CH₂F | 3-F | CN | F |
| A-2662. | OCF₃ | CH₂F | 3-CH₃ | CN | F |
| A-2663. | OCF₃ | CH₂F | 3-OCH₃ | CN | F |
| A-2664. | OCF₃ | CH₂F | 5-F | CN | F |
| A-2665. | OCF₃ | CH₂F | 5-CH₃ | CN | F |
| A-2666. | OCF₃ | CH₂F | 5-OCH₃ | CN | F |
| A-2667. | OCF₃ | CHF₂ | 3-F | CN | F |
| A-2668. | OCF₃ | CHF₂ | 3-CH₃ | CN | F |
| A-2669. | OCF₃ | CHF₂ | 3-OCH₃ | CN | F |
| A-2670. | OCF₃ | CHF₂ | 5-F | CN | F |
| A-2671. | OCF₃ | CHF₂ | 5-CH₃ | CN | F |
| A-2672. | OCF₃ | CHF₂ | 5-OCH₃ | CN | F |
| A-2673. | OCF₃ | CF₃ | 3-F | CN | F |
| A-2674. | OCF₃ | CF₃ | 3-CH₃ | CN | F |
| A-2675. | OCF₃ | CF₃ | 3-OCH₃ | CN | F |
| A-2676. | OCF₃ | CF₃ | 5-F | CN | F |
| A-2677. | OCF₃ | CF₃ | 5-CH₃ | CN | F |
| A-2678. | OCF₃ | CF₃ | 5-OCH₃ | CN | F |
| A-2679. | OCF₃ | OCH₂F | 3-F | CN | F |
| A-2680. | OCF₃ | OCH₂F | 3-CH₃ | CN | F |
| A-2681. | OCF₃ | OCH₂F | 3-OCH₃ | CN | F |
| A-2682. | OCF₃ | OCH₂F | 5-F | CN | F |
| A-2683. | OCF₃ | OCH₂F | 5-CH₃ | CN | F |
| A-2684. | OCF₃ | OCH₂F | 5-OCH₃ | CN | F |
| A-2685. | OCF₃ | OCHF₂ | 3-F | CN | F |
| A-2686. | OCF₃ | OCHF₂ | 3-CH₃ | CN | F |
| A-2687. | OCF₃ | OCHF₂ | 3-OCH₃ | CN | F |
| A-2688. | OCF₃ | OCHF₂ | 5-F | CN | F |
| A-2689. | OCF₃ | OCHF₂ | 5-CH₃ | CN | F |
| A-2690. | OCF₃ | OCHF₂ | 5-OCH₃ | CN | F |
| A-2691. | OCF₃ | OCF₃ | 3-F | CN | F |
| A-2692. | OCF₃ | OCF₃ | 3-CH₃ | CN | F |
| A-2693. | OCF₃ | OCF₃ | 3-OCH₃ | CN | F |
| A-2694. | OCF₃ | OCF₃ | 5-F | CN | F |
| A-2695. | OCF₃ | OCF₃ | 5-CH₃ | CN | F |
| A-2696. | OCF₃ | OCF₃ | 5-OCH₃ | CN | F |
| A-2697. | H | H | H | F | F |
| A-2698. | F | H | H | F | F |
| A-2699. | CH₃ | H | H | F | F |
| A-2700. | OCH₃ | H | H | F | F |
| A-2701. | CH₂F | H | H | F | F |
| A-2702. | CHF₂ | H | H | F | F |
| A-2703. | CF₃ | H | H | F | F |
| A-2704. | OCH₂F | H | H | F | F |
| A-2705. | OCHF₂ | H | H | F | F |
| A-2706. | OCF₃ | H | H | F | F |
| A-2707. | H | F | H | F | F |
| A-2708. | H | CH₃ | H | F | F |
| A-2709. | H | OCH₃ | H | F | F |
| A-2710. | H | CN | H | F | F |
| A-2711. | H | CH₂F | H | F | F |
| A-2712. | H | CHF₂ | H | F | F |
| A-2713. | H | CF₃ | H | F | F |
| A-2714. | H | OCH₂F | H | F | F |
| A-2715. | H | OCHF₂ | H | F | F |
| A-2716. | H | OCF₃ | H | F | F |
| A-2717. | H | H | 3-F | F | F |
| A-2718. | H | H | 3-CH₃ | F | F |
| A-2719. | H | H | 3-OCH₃ | F | F |
| A-2720. | H | H | 5-F | F | F |
| A-2721. | H | H | 5-CH₃ | F | F |
| A-2722. | H | H | 5-OCH₃ | F | F |
| A-2723. | F | F | H | F | F |
| A-2724. | F | CH₃ | H | F | F |
| A-2725. | F | OCH₃ | H | F | F |

TABLE A-continued

| Example No. | R¹ | R² | R³ | R⁶ | R⁷ |
|---|---|---|---|---|---|
| A-2726. | F | CN | H | F | F |
| A-2727. | F | CH₂F | H | F | F |
| A-2728. | F | CHF₂ | H | F | F |
| A-2729. | F | CF₃ | H | F | F |
| A-2730. | F | OCH₂F | H | F | F |
| A-2731. | F | OCHF₂ | H | F | F |
| A-2732. | F | OCF₃ | H | F | F |
| A-2733. | F | H | 3-F | F | F |
| A-2734. | F | H | 3-CH₃ | F | F |
| A-2735. | F | H | 3-OCH₃ | F | F |
| A-2736. | F | H | 5-F | F | F |
| A-2737. | F | H | 5-CH₃ | F | F |
| A-2738. | F | H | 5-OCH₃ | F | F |
| A-2739. | CH₃ | F | H | F | F |
| A-2740. | CH₃ | CH₃ | H | F | F |
| A-2741. | CH₃ | OCH₃ | H | F | F |
| A-2742. | CH₃ | CN | H | F | F |
| A-2743. | CH₃ | CH₂F | H | F | F |
| A-2744. | CH₃ | CHF₂ | H | F | F |
| A-2745. | CH₃ | CF₃ | H | F | F |
| A-2746. | CH₃ | OCH₂F | H | F | F |
| A-2747. | CH₃ | OCHF₂ | H | F | F |
| A-2748. | CH₃ | OCF₃ | H | F | F |
| A-2749. | CH₃ | H | 3-F | F | F |
| A-2750. | CH₃ | H | 3-CH₃ | F | F |
| A-2751. | CH₃ | H | 3-OCH₃ | F | F |
| A-2752. | CH₃ | H | 5-F | F | F |
| A-2753. | CH₃ | H | 5-CH₃ | F | F |
| A-2754. | CH₃ | H | 5-OCH₃ | F | F |
| A-2755. | OCH₃ | F | H | F | F |
| A-2756. | OCH₃ | CH₃ | H | F | F |
| A-2757. | OCH₃ | OCH₃ | H | F | F |
| A-2758. | OCH₃ | CN | H | F | F |
| A-2759. | OCH₃ | CH₂F | H | F | F |
| A-2760. | OCH₃ | CHF₂ | H | F | F |
| A-2761. | OCH₃ | CF₃ | H | F | F |
| A-2762. | OCH₃ | OCH₂F | H | F | F |
| A-2763. | OCH₃ | OCHF₂ | H | F | F |
| A-2764. | OCH₃ | OCF₃ | H | F | F |
| A-2765. | OCH₃ | H | 3-F | F | F |
| A-2766. | OCH₃ | H | 3-CH₃ | F | F |
| A-2767. | OCH₃ | H | 3-OCH₃ | F | F |
| A-2768. | OCH₃ | H | 5-F | F | F |
| A-2769. | OCH₃ | H | 5-CH₃ | F | F |
| A-2770. | OCH₃ | H | 5-OCH₃ | F | F |
| A-2771. | H | F | 3-F | F | F |
| A-2772. | H | F | 3-CH₃ | F | F |
| A-2773. | H | F | 3-OCH₃ | F | F |
| A-2774. | H | F | 5-F | F | F |
| A-2775. | H | F | 5-CH₃ | F | F |
| A-2776. | H | F | 5-OCH₃ | F | F |
| A-2777. | H | CH₃ | 3-F | F | F |
| A-2778. | H | CH₃ | 3-CH₃ | F | F |
| A-2779. | H | CH₃ | 3-OCH₃ | F | F |
| A-2780. | H | CH₃ | 5-F | F | F |
| A-2781. | H | CH₃ | 5-CH₃ | F | F |
| A-2782. | H | CH₃ | 5-OCH₃ | F | F |
| A-2783. | H | OCH₃ | 3-F | F | F |
| A-2784. | H | OCH₃ | 3-CH₃ | F | F |
| A-2785. | H | OCH₃ | 3-OCH₃ | F | F |
| A-2786. | H | OCH₃ | 5-F | F | F |
| A-2787. | H | OCH₃ | 5-CH₃ | F | F |
| A-2788. | H | OCH₃ | 5-OCH₃ | F | F |
| A-2789. | H | CN | 3-F | F | F |
| A-2790. | H | CN | 3-CH₃ | F | F |
| A-2791. | H | CN | 3-OCH₃ | F | F |
| A-2792. | H | CN | 5-F | F | F |
| A-2793. | H | CN | 5-CH₃ | F | F |
| A-2794. | H | CN | 5-OCH₃ | F | F |
| A-2795. | H | CH₂F | 3-F | F | F |
| A-2796. | H | CH₂F | 3-CH₃ | F | F |
| A-2797. | H | CH₂F | 3-OCH₃ | F | F |
| A-2798. | H | CH₂F | 5-F | F | F |
| A-2799. | H | CH₂F | 5-CH₃ | F | F |
| A-2800. | H | CH₂F | 5-OCH₃ | F | F |
| A-2801. | H | CHF₂ | 3-F | F | F |
| A-2802. | H | CHF₂ | 3-CH₃ | F | F |
| A-2803. | H | CHF₂ | 3-OCH₃ | F | F |
| A-2804. | H | CHF₂ | 5-F | F | F |
| A-2805. | H | CHF₂ | 5-CH₃ | F | F |
| A-2806. | H | CHF₂ | 5-OCH₃ | F | F |
| A-2807. | H | CF₃ | 3-F | F | F |
| A-2808. | H | CF₃ | 3-CH₃ | F | F |
| A-2809. | H | CF₃ | 3-OCH₃ | F | F |
| A-2810. | H | CF₃ | 5-F | F | F |
| A-2811. | H | CF₃ | 5-CH₃ | F | F |
| A-2812. | H | CF₃ | 5-OCH₃ | F | F |
| A-2813. | H | OCH₂F | 3-F | F | F |
| A-2814. | H | OCH₂F | 3-CH₃ | F | F |
| A-2815. | H | OCH₂F | 3-OCH₃ | F | F |
| A-2816. | H | OCH₂F | 5-F | F | F |
| A-2817. | H | OCH₂F | 5-CH₃ | F | F |
| A-2818. | H | OCH₂F | 5-OCH₃ | F | F |
| A-2819. | H | OCHF₂ | 3-F | F | F |
| A-2820. | H | OCHF₂ | 3-CH₃ | F | F |
| A-2821. | H | OCHF₂ | 3-OCH₃ | F | F |
| A-2822. | H | OCHF₂ | 5-F | F | F |
| A-2823. | H | OCHF₂ | 5-CH₃ | F | F |
| A-2824. | H | OCHF₂ | 5-OCH₃ | F | F |
| A-2825. | H | OCF₃ | 3-F | F | F |
| A-2826. | H | OCF₃ | 3-CH₃ | F | F |
| A-2827. | H | OCF₃ | 3-OCH₃ | F | F |
| A-2828. | H | OCF₃ | 5-F | F | F |
| A-2829. | H | OCF₃ | 5-CH₃ | F | F |
| A-2830. | H | OCF₃ | 5-OCH₃ | F | F |
| A-2831. | F | F | 3-F | F | F |
| A-2832. | F | F | 3-CH₃ | F | F |
| A-2833. | F | F | 3-OCH₃ | F | F |
| A-2834. | F | F | 5-F | F | F |
| A-2835. | F | F | 5-CH₃ | F | F |
| A-2836. | F | F | 5-OCH₃ | F | F |
| A-2837. | F | CH₃ | 3-F | F | F |
| A-2838. | F | CH₃ | 3-CH₃ | F | F |
| A-2839. | F | CH₃ | 3-OCH₃ | F | F |
| A-2840. | F | CH₃ | 5-F | F | F |
| A-2841. | F | CH₃ | 5-CH₃ | F | F |
| A-2842. | F | CH₃ | 5-OCH₃ | F | F |
| A-2843. | F | OCH₃ | 3-F | F | F |
| A-2844. | F | OCH₃ | 3-CH₃ | F | F |
| A-2845. | F | OCH₃ | 3-OCH₃ | F | F |
| A-2846. | F | OCH₃ | 5-F | F | F |
| A-2847. | F | OCH₃ | 5-CH₃ | F | F |
| A-2848. | F | OCH₃ | 5-OCH₃ | F | F |
| A-2849. | F | CN | 3-F | F | F |
| A-2850. | F | CN | 3-CH₃ | F | F |
| A-2851. | F | CN | 3-OCH₃ | F | F |
| A-2852. | F | CN | 5-F | F | F |
| A-2853. | F | CN | 5-CH₃ | F | F |
| A-2854. | F | CN | 5-OCH₃ | F | F |
| A-2855. | F | CH₂F | 3-F | F | F |
| A-2856. | F | CH₂F | 3-CH₃ | F | F |
| A-2857. | F | CH₂F | 3-OCH₃ | F | F |
| A-2858. | F | CH₂F | 5-F | F | F |
| A-2859. | F | CH₂F | 5-CH₃ | F | F |
| A-2860. | F | CH₂F | 5-OCH₃ | F | F |
| A-2861. | F | CHF₂ | 3-F | F | F |
| A-2862. | F | CHF₂ | 3-CH₃ | F | F |
| A-2863. | F | CHF₂ | 3-OCH₃ | F | F |
| A-2864. | F | CHF₂ | 5-F | F | F |
| A-2865. | F | CHF₂ | 5-CH₃ | F | F |
| A-2866. | F | CHF₂ | 5-OCH₃ | F | F |
| A-2867. | F | CF₃ | 3-F | F | F |
| A-2868. | F | CF₃ | 3-CH₃ | F | F |
| A-2869. | F | CF₃ | 3-OCH₃ | F | F |
| A-2870. | F | CF₃ | 5-F | F | F |
| A-2871. | F | CF₃ | 5-CH₃ | F | F |
| A-2872. | F | CF₃ | 5-OCH₃ | F | F |
| A-2873. | F | OCH₂F | 3-F | F | F |
| A-2874. | F | OCH₂F | 3-CH₃ | F | F |
| A-2875. | F | OCH₂F | 3-OCH₃ | F | F |
| A-2876. | F | OCH₂F | 5-F | F | F |
| A-2877. | F | OCH₂F | 5-CH₃ | F | F |
| A-2878. | F | OCH₂F | 5-OCH₃ | F | F |
| A-2879. | F | OCHF₂ | 3-F | F | F |
| A-2880. | F | OCHF₂ | 3-CH₃ | F | F |
| A-2881. | F | OCHF₂ | 3-OCH₃ | F | F |

TABLE A-continued

| Example No. | R¹ | R² | R³ | R⁶ | R⁷ |
|---|---|---|---|---|---|
| A-2882. | F | OCHF₂ | 5-F | F | F |
| A-2883. | F | OCHF₂ | 5-CH₃ | F | F |
| A-2884. | F | OCHF₂ | 5-OCH₃ | F | F |
| A-2885. | F | OCF₃ | 3-F | F | F |
| A-2886. | F | OCF₃ | 3-CH₃ | F | F |
| A-2887. | F | OCF₃ | 3-OCH₃ | F | F |
| A-2888. | F | OCF₃ | 5-F | F | F |
| A-2889. | F | OCF₃ | 5-CH₃ | F | F |
| A-2890. | F | OCF₃ | 5-OCH₃ | F | F |
| A-2891. | CH₃ | F | 3-F | F | F |
| A-2892. | CH₃ | F | 3-CH₃ | F | F |
| A-2893. | CH₃ | F | 3-OCH₃ | F | F |
| A-2894. | CH₃ | F | 5-F | F | F |
| A-2895. | CH₃ | F | 5-CH₃ | F | F |
| A-2896. | CH₃ | F | 5-OCH₃ | F | F |
| A-2897. | CH₃ | CH₃ | 3-F | F | F |
| A-2898. | CH₃ | CH₃ | 3-CH₃ | F | F |
| A-2899. | CH₃ | CH₃ | 3-OCH₃ | F | F |
| A-2900. | CH₃ | CH₃ | 5-F | F | F |
| A-2901. | CH₃ | CH₃ | 5-CH₃ | F | F |
| A-2902. | CH₃ | CH₃ | 5-OCH₃ | F | F |
| A-2903. | CH₃ | OCH₃ | 3-F | F | F |
| A-2904. | CH₃ | OCH₃ | 3-CH₃ | F | F |
| A-2905. | CH₃ | OCH₃ | 3-OCH₃ | F | F |
| A-2906. | CH₃ | OCH₃ | 5-F | F | F |
| A-2907. | CH₃ | OCH₃ | 5-CH₃ | F | F |
| A-2908. | CH₃ | OCH₃ | 5-OCH₃ | F | F |
| A-2909. | CH₃ | CN | 3-F | F | F |
| A-2910. | CH₃ | CN | 3-CH₃ | F | F |
| A-2911. | CH₃ | CN | 3-OCH₃ | F | F |
| A-2912. | CH₃ | CN | 5-F | F | F |
| A-2913. | CH₃ | CN | 5-CH₃ | F | F |
| A-2914. | CH₃ | CN | 5-OCH₃ | F | F |
| A-2915. | CH₃ | CH₂F | 3-F | F | F |
| A-2916. | CH₃ | CH₂F | 3-CH₃ | F | F |
| A-2917. | CH₃ | CH₂F | 3-OCH₃ | F | F |
| A-2918. | CH₃ | CH₂F | 5-F | F | F |
| A-2919. | CH₃ | CH₂F | 5-CH₃ | F | F |
| A-2920. | CH₃ | CH₂F | 5-OCH₃ | F | F |
| A-2921. | CH₃ | CHF₂ | 3-F | F | F |
| A-2922. | CH₃ | CHF₂ | 3-CH₃ | F | F |
| A-2923. | CH₃ | CHF₂ | 3-OCH₃ | F | F |
| A-2924. | CH₃ | CHF₂ | 5-F | F | F |
| A-2925. | CH₃ | CHF₂ | 5-CH₃ | F | F |
| A-2926. | CH₃ | CHF₂ | 5-OCH₃ | F | F |
| A-2927. | CH₃ | CF₃ | 3-F | F | F |
| A-2928. | CH₃ | CF₃ | 3-CH₃ | F | F |
| A-2929. | CH₃ | CF₃ | 3-OCH₃ | F | F |
| A-2930. | CH₃ | CF₃ | 5-F | F | F |
| A-2931. | CH₃ | CF₃ | 5-CH₃ | F | F |
| A-2932. | CH₃ | CF₃ | 5-OCH₃ | F | F |
| A-2933. | CH₃ | OCH₂F | 3-F | F | F |
| A-2934. | CH₃ | OCH₂F | 3-CH₃ | F | F |
| A-2935. | CH₃ | OCH₂F | 3-OCH₃ | F | F |
| A-2936. | CH₃ | OCH₂F | 5-F | F | F |
| A-2937. | CH₃ | OCH₂F | 5-CH₃ | F | F |
| A-2938. | CH₃ | OCH₂F | 5-OCH₃ | F | F |
| A-2939. | CH₃ | OCHF₂ | 3-F | F | F |
| A-2940. | CH₃ | OCHF₂ | 3-CH₃ | F | F |
| A-2941. | CH₃ | OCHF₂ | 3-OCH₃ | F | F |
| A-2942. | CH₃ | OCHF₂ | 5-F | F | F |
| A-2943. | CH₃ | OCHF₂ | 5-CH₃ | F | F |
| A-2944. | CH₃ | OCHF₂ | 5-OCH₃ | F | F |
| A-2945. | CH₃ | OCF₃ | 3-F | F | F |
| A-2946. | CH₃ | OCF₃ | 3-CH₃ | F | F |
| A-2947. | CH₃ | OCF₃ | 3-OCH₃ | F | F |
| A-2948. | CH₃ | OCF₃ | 5-F | F | F |
| A-2949. | CH₃ | OCF₃ | 5-CH₃ | F | F |
| A-2950. | CH₃ | OCF₃ | 5-OCH₃ | F | F |
| A-2951. | OCH₃ | F | 3-F | F | F |
| A-2952. | OCH₃ | F | 3-CH₃ | F | F |
| A-2953. | OCH₃ | F | 3-OCH₃ | F | F |
| A-2954. | OCH₃ | F | 5-F | F | F |
| A-2955. | OCH₃ | F | 5-CH₃ | F | F |
| A-2956. | OCH₃ | F | 5-OCH₃ | F | F |
| A-2957. | OCH₃ | CH₃ | 3-F | F | F |
| A-2958. | OCH₃ | CH₃ | 3-CH₃ | F | F |
| A-2959. | OCH₃ | CH₃ | 3-OCH₃ | F | F |
| A-2960. | OCH₃ | CH₃ | 5-F | F | F |
| A-2961. | OCH₃ | CH₃ | 5-CH₃ | F | F |
| A-2962. | OCH₃ | CH₃ | 5-OCH₃ | F | F |
| A-2963. | OCH₃ | OCH₃ | 3-F | F | F |
| A-2964. | OCH₃ | OCH₃ | 3-CH₃ | F | F |
| A-2965. | OCH₃ | OCH₃ | 3-OCH₃ | F | F |
| A-2966. | OCH₃ | OCH₃ | 5-F | F | F |
| A-2967. | OCH₃ | OCH₃ | 5-CH₃ | F | F |
| A-2968. | OCH₃ | OCH₃ | 5-OCH₃ | F | F |
| A-2969. | OCH₃ | CN | 3-F | F | F |
| A-2970. | OCH₃ | CN | 3-CH₃ | F | F |
| A-2971. | OCH₃ | CN | 3-OCH₃ | F | F |
| A-2972. | OCH₃ | CN | 5-F | F | F |
| A-2973. | OCH₃ | CN | 5-CH₃ | F | F |
| A-2974. | OCH₃ | CN | 5-OCH₃ | F | F |
| A-2975. | OCH₃ | CH₂F | 3-F | F | F |
| A-2976. | OCH₃ | CH₂F | 3-CH₃ | F | F |
| A-2977. | OCH₃ | CH₂F | 3-OCH₃ | F | F |
| A-2978. | OCH₃ | CH₂F | 5-F | F | F |
| A-2979. | OCH₃ | CH₂F | 5-CH₃ | F | F |
| A-2980. | OCH₃ | CH₂F | 5-OCH₃ | F | F |
| A-2981. | OCH₃ | CHF₂ | 3-F | F | F |
| A-2982. | OCH₃ | CHF₂ | 3-CH₃ | F | F |
| A-2983. | OCH₃ | CHF₂ | 3-OCH₃ | F | F |
| A-2984. | OCH₃ | CHF₂ | 5-F | F | F |
| A-2985. | OCH₃ | CHF₂ | 5-CH₃ | F | F |
| A-2986. | OCH₃ | CHF₂ | 5-OCH₃ | F | F |
| A-2987. | OCH₃ | CF₃ | 3-F | F | F |
| A-2988. | OCH₃ | CF₃ | 3-CH₃ | F | F |
| A-2989. | OCH₃ | CF₃ | 3-OCH₃ | F | F |
| A-2990. | OCH₃ | CF₃ | 5-F | F | F |
| A-2991. | OCH₃ | CF₃ | 5-CH₃ | F | F |
| A-2992. | OCH₃ | CF₃ | 5-OCH₃ | F | F |
| A-2993. | OCH₃ | OCH₂F | 3-F | F | F |
| A-2994. | OCH₃ | OCH₂F | 3-CH₃ | F | F |
| A-2995. | OCH₃ | OCH₂F | 3-OCH₃ | F | F |
| A-2996. | OCH₃ | OCH₂F | 5-F | F | F |
| A-2997. | OCH₃ | OCH₂F | 5-CH₃ | F | F |
| A-2998. | OCH₃ | OCH₂F | 5-OCH₃ | F | F |
| A-2999. | OCH₃ | OCHF₂ | 3-F | F | F |
| A-3000. | OCH₃ | OCHF₂ | 3-CH₃ | F | F |
| A-3001. | OCH₃ | OCHF₂ | 3-OCH₃ | F | F |
| A-3002. | OCH₃ | OCHF₂ | 5-F | F | F |
| A-3003. | OCH₃ | OCHF₂ | 5-CH₃ | F | F |
| A-3004. | OCH₃ | OCHF₂ | 5-OCH₃ | F | F |
| A-3005. | OCH₃ | OCF₃ | 3-F | F | F |
| A-3006. | OCH₃ | OCF₃ | 3-CH₃ | F | F |
| A-3007. | OCH₃ | OCF₃ | 3-OCH₃ | F | F |
| A-3008. | OCH₃ | OCF₃ | 5-F | F | F |
| A-3009. | OCH₃ | OCF₃ | 5-CH₃ | F | F |
| A-3010. | OCH₃ | OCF₃ | 5-OCH₃ | F | F |
| A-3011. | CH₂F | F | 3-F | F | F |
| A-3012. | CH₂F | F | 3-CH₃ | F | F |
| A-3013. | CH₂F | F | 3-OCH₃ | F | F |
| A-3014. | CH₂F | F | 5-F | F | F |
| A-3015. | CH₂F | F | 5-CH₃ | F | F |
| A-3016. | CH₂F | F | 5-OCH₃ | F | F |
| A-3017. | CH₂F | CH₃ | 3-F | F | F |
| A-3018. | CH₂F | CH₃ | 3-CH₃ | F | F |
| A-3019. | CH₂F | CH₃ | 3-OCH₃ | F | F |
| A-3020. | CH₂F | CH₃ | 5-F | F | F |
| A-3021. | CH₂F | CH₃ | 5-CH₃ | F | F |
| A-3022. | CH₂F | CH₃ | 5-OCH₃ | F | F |
| A-3023. | CH₂F | OCH₃ | 3-F | F | F |
| A-3024. | CH₂F | OCH₃ | 3-CH₃ | F | F |
| A-3025. | CH₂F | OCH₃ | 3-OCH₃ | F | F |
| A-3026. | CH₂F | OCH₃ | 5-F | F | F |
| A-3027. | CH₂F | OCH₃ | 5-CH₃ | F | F |
| A-3028. | CH₂F | OCH₃ | 5-OCH₃ | F | F |
| A-3029. | CH₂F | CN | 3-F | F | F |
| A-3030. | CH₂F | CN | 3-CH₃ | F | F |
| A-3031. | CH₂F | CN | 3-OCH₃ | F | F |
| A-3032. | CH₂F | CN | 5-F | F | F |
| A-3033. | CH₂F | CN | 5-CH₃ | F | F |
| A-3034. | CH₂F | CN | 5-OCH₃ | F | F |
| A-3035. | CH₂F | CH₂F | 3-F | F | F |
| A-3036. | CH₂F | CH₂F | 3-CH₃ | F | F |
| A-3037. | CH₂F | CH₂F | 3-OCH₃ | F | F |

TABLE A-continued

| Example No. | $R^1$ | $R^2$ | $R^3$ | $R^6$ | $R^7$ |
|---|---|---|---|---|---|
| A-3038. | $CH_2F$ | $CH_2F$ | 5-F | F | F |
| A-3039. | $CH_2F$ | $CH_2F$ | 5-$CH_3$ | F | F |
| A-3040. | $CH_2F$ | $CH_2F$ | 5-$OCH_3$ | F | F |
| A-3041. | $CH_2F$ | $CHF_2$ | 3-F | F | F |
| A-3042. | $CH_2F$ | $CHF_2$ | 3-$CH_3$ | F | F |
| A-3043. | $CH_2F$ | $CHF_2$ | 3-$OCH_3$ | F | F |
| A-3044. | $CH_2F$ | $CHF_2$ | 5-F | F | F |
| A-3045. | $CH_2F$ | $CHF_2$ | 5-$CH_3$ | F | F |
| A-3046. | $CH_2F$ | $CHF_2$ | 5-$OCH_3$ | F | F |
| A-3047. | $CH_2F$ | $CF_3$ | 3-F | F | F |
| A-3048. | $CH_2F$ | $CF_3$ | 3-$CH_3$ | F | F |
| A-3049. | $CH_2F$ | $CF_3$ | 3-$OCH_3$ | F | F |
| A-3050. | $CH_2F$ | $CF_3$ | 5-F | F | F |
| A-3051. | $CH_2F$ | $CF_3$ | 5-$CH_3$ | F | F |
| A-3052. | $CH_2F$ | $CF_3$ | 5-$OCH_3$ | F | F |
| A-3053. | $CH_2F$ | $OCH_2F$ | 3-F | F | F |
| A-3054. | $CH_2F$ | $OCH_2F$ | 3-$CH_3$ | F | F |
| A-3055. | $CH_2F$ | $OCH_2F$ | 3-$OCH_3$ | F | F |
| A-3056. | $CH_2F$ | $OCH_2F$ | 5-F | F | F |
| A-3057. | $CH_2F$ | $OCH_2F$ | 5-$CH_3$ | F | F |
| A-3058. | $CH_2F$ | $OCH_2F$ | 5-$OCH_3$ | F | F |
| A-3059. | $CH_2F$ | $OCHF_2$ | 3-F | F | F |
| A-3060. | $CH_2F$ | $OCHF_2$ | 3-$CH_3$ | F | F |
| A-3061. | $CH_2F$ | $OCHF_2$ | 3-$OCH_3$ | F | F |
| A-3062. | $CH_2F$ | $OCHF_2$ | 5-F | F | F |
| A-3063. | $CH_2F$ | $OCHF_2$ | 5-$CH_3$ | F | F |
| A-3064. | $CH_2F$ | $OCHF_2$ | 5-$OCH_3$ | F | F |
| A-3065. | $CH_2F$ | $OCF_3$ | 3-F | F | F |
| A-3066. | $CH_2F$ | $OCF_3$ | 3-$CH_3$ | F | F |
| A-3067. | $CH_2F$ | $OCF_3$ | 3-$OCH_3$ | F | F |
| A-3068. | $CH_2F$ | $OCF_3$ | 5-F | F | F |
| A-3069. | $CH_2F$ | $OCF_3$ | 5-$CH_3$ | F | F |
| A-3070. | $CH_2F$ | $OCF_3$ | 5-$OCH_3$ | F | F |
| A-3071. | $CHF_2$ | F | 3-F | F | F |
| A-3072. | $CHF_2$ | F | 3-$CH_3$ | F | F |
| A-3073. | $CHF_2$ | F | 3-$OCH_3$ | F | F |
| A-3074. | $CHF_2$ | F | 5-F | F | F |
| A-3075. | $CHF_2$ | F | 5-$CH_3$ | F | F |
| A-3076. | $CHF_2$ | F | 5-$OCH_3$ | F | F |
| A-3077. | $CHF_2$ | $CH_3$ | 3-F | F | F |
| A-3078. | $CHF_2$ | $CH_3$ | 3-$CH_3$ | F | F |
| A-3079. | $CHF_2$ | $CH_3$ | 3-$OCH_3$ | F | F |
| A-3080. | $CHF_2$ | $CH_3$ | 5-F | F | F |
| A-3081. | $CHF_2$ | $CH_3$ | 5-$CH_3$ | F | F |
| A-3082. | $CHF_2$ | $CH_3$ | 5-$OCH_3$ | F | F |
| A-3083. | $CHF_2$ | $OCH_3$ | 3-F | F | F |
| A-3084. | $CHF_2$ | $OCH_3$ | 3-$CH_3$ | F | F |
| A-3085. | $CHF_2$ | $OCH_3$ | 3-$OCH_3$ | F | F |
| A-3086. | $CHF_2$ | $OCH_3$ | 5-F | F | F |
| A-3087. | $CHF_2$ | $OCH_3$ | 5-$CH_3$ | F | F |
| A-3088. | $CHF_2$ | $OCH_3$ | 5-$OCH_3$ | F | F |
| A-3089. | $CHF_2$ | CN | 3-F | F | F |
| A-3090. | $CHF_2$ | CN | 3-$CH_3$ | F | F |
| A-3091. | $CHF_2$ | CN | 3-$OCH_3$ | F | F |
| A-3092. | $CHF_2$ | CN | 5-F | F | F |
| A-3093. | $CHF_2$ | CN | 5-$CH_3$ | F | F |
| A-3094. | $CHF_2$ | CN | 5-$OCH_3$ | F | F |
| A-3095. | $CHF_2$ | $CH_2F$ | 3-F | F | F |
| A-3096. | $CHF_2$ | $CH_2F$ | 3-$CH_3$ | F | F |
| A-3097. | $CHF_2$ | $CH_2F$ | 3-$OCH_3$ | F | F |
| A-3098. | $CHF_2$ | $CH_2F$ | 5-F | F | F |
| A-3099. | $CHF_2$ | $CH_2F$ | 5-$CH_3$ | F | F |
| A-3100. | $CHF_2$ | $CH_2F$ | 5-$OCH_3$ | F | F |
| A-3101. | $CHF_2$ | $CHF_2$ | 3-F | F | F |
| A-3102. | $CHF_2$ | $CHF_2$ | 3-$CH_3$ | F | F |
| A-3103. | $CHF_2$ | $CHF_2$ | 3-$OCH_3$ | F | F |
| A-3104. | $CHF_2$ | $CHF_2$ | 5-F | F | F |
| A-3105. | $CHF_2$ | $CHF_2$ | 5-$CH_3$ | F | F |
| A-3106. | $CHF_2$ | $CHF_2$ | 5-$OCH_3$ | F | F |
| A-3107. | $CHF_2$ | $CF_3$ | 3-F | F | F |
| A-3108. | $CHF_2$ | $CF_3$ | 3-$CH_3$ | F | F |
| A-3109. | $CHF_2$ | $CF_3$ | 3-$OCH_3$ | F | F |
| A-3110. | $CHF_2$ | $CF_3$ | 5-F | F | F |
| A-3111. | $CHF_2$ | $CF_3$ | 5-$CH_3$ | F | F |
| A-3112. | $CHF_2$ | $CF_3$ | 5-$OCH_3$ | F | F |
| A-3113. | $CHF_2$ | $OCH_2F$ | 3-F | F | F |
| A-3114. | $CHF_2$ | $OCH_2F$ | 3-$CH_3$ | F | F |
| A-3115. | $CHF_2$ | $OCH_2F$ | 3-$OCH_3$ | F | F |
| A-3116. | $CHF_2$ | $OCH_2F$ | 5-F | F | F |
| A-3117. | $CHF_2$ | $OCH_2F$ | 5-$CH_3$ | F | F |
| A-3118. | $CHF_2$ | $OCH_2F$ | 5-$OCH_3$ | F | F |
| A-3119. | $CHF_2$ | $OCHF_2$ | 3-F | F | F |
| A-3120. | $CHF_2$ | $OCHF_2$ | 3-$CH_3$ | F | F |
| A-3121. | $CHF_2$ | $OCHF_2$ | 3-$OCH_3$ | F | F |
| A-3122. | $CHF_2$ | $OCHF_2$ | 5-F | F | F |
| A-3123. | $CHF_2$ | $OCHF_2$ | 5-$CH_3$ | F | F |
| A-3124. | $CHF_2$ | $OCHF_2$ | 5-$OCH_3$ | F | F |
| A-3125. | $CHF_2$ | $OCF_3$ | 3-F | F | F |
| A-3126. | $CHF_2$ | $OCF_3$ | 3-$CH_3$ | F | F |
| A-3127. | $CHF_2$ | $OCF_3$ | 3-$OCH_3$ | F | F |
| A-3128. | $CHF_2$ | $OCF_3$ | 5-F | F | F |
| A-3129. | $CHF_2$ | $OCF_3$ | 5-$CH_3$ | F | F |
| A-3130. | $CHF_2$ | $OCF_3$ | 5-$OCH_3$ | F | F |
| A-3131. | $CF_3$ | F | 3-F | F | F |
| A-3132. | $CF_3$ | F | 3-$CH_3$ | F | F |
| A-3133. | $CF_3$ | F | 3-$OCH_3$ | F | F |
| A-3134. | $CF_3$ | F | 5-F | F | F |
| A-3135. | $CF_3$ | F | 5-$CH_3$ | F | F |
| A-3136. | $CF_3$ | F | 5-$OCH_3$ | F | F |
| A-3137. | $CF_3$ | $CH_3$ | 3-F | F | F |
| A-3138. | $CF_3$ | $CH_3$ | 3-$CH_3$ | F | F |
| A-3139. | $CF_3$ | $CH_3$ | 3-$OCH_3$ | F | F |
| A-3140. | $CF_3$ | $CH_3$ | 5-F | F | F |
| A-3141. | $CF_3$ | $CH_3$ | 5-$CH_3$ | F | F |
| A-3142. | $CF_3$ | $CH_3$ | 5-$OCH_3$ | F | F |
| A-3143. | $CF_3$ | $OCH_3$ | 3-F | F | F |
| A-3144. | $CF_3$ | $OCH_3$ | 3-$CH_3$ | F | F |
| A-3145. | $CF_3$ | $OCH_3$ | 3-$OCH_3$ | F | F |
| A-3146. | $CF_3$ | $OCH_3$ | 5-F | F | F |
| A-3147. | $CF_3$ | $OCH_3$ | 5-$CH_3$ | F | F |
| A-3148. | $CF_3$ | $OCH_3$ | 5-$OCH_3$ | F | F |
| A-3149. | $CF_3$ | CN | 3-F | F | F |
| A-3150. | $CF_3$ | CN | 3-$CH_3$ | F | F |
| A-3151. | $CF_3$ | CN | 3-$OCH_3$ | F | F |
| A-3152. | $CF_3$ | CN | 5-F | F | F |
| A-3153. | $CF_3$ | CN | 5-$CH_3$ | F | F |
| A-3154. | $CF_3$ | CN | 5-$OCH_3$ | F | F |
| A-3155. | $CF_3$ | $CH_2F$ | 3-F | F | F |
| A-3156. | $CF_3$ | $CH_2F$ | 3-$CH_3$ | F | F |
| A-3157. | $CF_3$ | $CH_2F$ | 3-$OCH_3$ | F | F |
| A-3158. | $CF_3$ | $CH_2F$ | 5-F | F | F |
| A-3159. | $CF_3$ | $CH_2F$ | 5-$CH_3$ | F | F |
| A-3160. | $CF_3$ | $CH_2F$ | 5-$OCH_3$ | F | F |
| A-3161. | $CF_3$ | $CHF_2$ | 3-F | F | F |
| A-3162. | $CF_3$ | $CHF_2$ | 3-$CH_3$ | F | F |
| A-3163. | $CF_3$ | $CHF_2$ | 3-$OCH_3$ | F | F |
| A-3164. | $CF_3$ | $CHF_2$ | 5-F | F | F |
| A-3165. | $CF_3$ | $CHF_2$ | 5-$CH_3$ | F | F |
| A-3166. | $CF_3$ | $CHF_2$ | 5-$OCH_3$ | F | F |
| A-3167. | $CF_3$ | $CF_3$ | 3-F | F | F |
| A-3168. | $CF_3$ | $CF_3$ | 3-$CH_3$ | F | F |
| A-3169. | $CF_3$ | $CF_3$ | 3-$OCH_3$ | F | F |
| A-3170. | $CF_3$ | $CF_3$ | 5-F | F | F |
| A-3171. | $CF_3$ | $CF_3$ | 5-$CH_3$ | F | F |
| A-3172. | $CF_3$ | $CF_3$ | 5-$OCH_3$ | F | F |
| A-3173. | $CF_3$ | $OCH_2F$ | 3-F | F | F |
| A-3174. | $CF_3$ | $OCH_2F$ | 3-$CH_3$ | F | F |
| A-3175. | $CF_3$ | $OCH_2F$ | 3-$OCH_3$ | F | F |
| A-3176. | $CF_3$ | $OCH_2F$ | 5-F | F | F |
| A-3177. | $CF_3$ | $OCH_2F$ | 5-$CH_3$ | F | F |
| A-3178. | $CF_3$ | $OCH_2F$ | 5-$OCH_3$ | F | F |
| A-3179. | $CF_3$ | $OCHF_2$ | 3-F | F | F |
| A-3180. | $CF_3$ | $OCHF_2$ | 3-$CH_3$ | F | F |
| A-3181. | $CF_3$ | $OCHF_2$ | 3-$OCH_3$ | F | F |
| A-3182. | $CF_3$ | $OCHF_2$ | 5-F | F | F |
| A-3183. | $CF_3$ | $OCHF_2$ | 5-$CH_3$ | F | F |
| A-3184. | $CF_3$ | $OCHF_2$ | 5-$OCH_3$ | F | F |
| A-3185. | $CF_3$ | $OCF_3$ | 3-F | F | F |
| A-3186. | $CF_3$ | $OCF_3$ | 3-$CH_3$ | F | F |
| A-3187. | $CF_3$ | $OCF_3$ | 3-$OCH_3$ | F | F |
| A-3188. | $CF_3$ | $OCF_3$ | 5-F | F | F |
| A-3189. | $CF_3$ | $OCF_3$ | 5-$CH_3$ | F | F |
| A-3190. | $CF_3$ | $OCF_3$ | 5-$OCH_3$ | F | F |
| A-3191. | $OCH_2F$ | F | 3-F | F | F |
| A-3192. | $OCH_2F$ | F | 3-$CH_3$ | F | F |
| A-3193. | $OCH_2F$ | F | 3-$OCH_3$ | F | F |

TABLE A-continued

| Example No. | R¹ | R² | R³ | R⁶ | R⁷ |
|---|---|---|---|---|---|
| A-3194. | OCH₂F | F | 5-F | F | F |
| A-3195. | OCH₂F | F | 5-CH₃ | F | F |
| A-3196. | OCH₂F | F | 5-OCH₃ | F | F |
| A-3197. | OCH₂F | CH₃ | 3-F | F | F |
| A-3198. | OCH₂F | CH₃ | 3-CH₃ | F | F |
| A-3199. | OCH₂F | CH₃ | 3-OCH₃ | F | F |
| A-3200. | OCH₂F | CH₃ | 5-F | F | F |
| A-3201. | OCH₂F | CH₃ | 5-CH₃ | F | F |
| A-3202. | OCH₂F | CH₃ | 5-OCH₃ | F | F |
| A-3203. | OCH₂F | OCH₃ | 3-F | F | F |
| A-3204. | OCH₂F | OCH₃ | 3-CH₃ | F | F |
| A-3205. | OCH₂F | OCH₃ | 3-OCH₃ | F | F |
| A-3206. | OCH₂F | OCH₃ | 5-F | F | F |
| A-3207. | OCH₂F | OCH₃ | 5-CH₃ | F | F |
| A-3208. | OCH₂F | OCH₃ | 5-OCH₃ | F | F |
| A-3209. | OCH₂F | CN | 3-F | F | F |
| A-3210. | OCH₂F | CN | 3-CH₃ | F | F |
| A-3211. | OCH₂F | CN | 3-OCH₃ | F | F |
| A-3212. | OCH₂F | CN | 5-F | F | F |
| A-3213. | OCH₂F | CN | 5-CH₃ | F | F |
| A-3214. | OCH₂F | CN | 5-OCH₃ | F | F |
| A-3215. | OCH₂F | CH₂F | 3-F | F | F |
| A-3216. | OCH₂F | CH₂F | 3-CH₃ | F | F |
| A-3217. | OCH₂F | CH₂F | 3-OCH₃ | F | F |
| A-3218. | OCH₂F | CH₂F | 5-F | F | F |
| A-3219. | OCH₂F | CH₂F | 5-CH₃ | F | F |
| A-3220. | OCH₂F | CH₂F | 5-OCH₃ | F | F |
| A-3221. | OCH₂F | CHF₂ | 3-F | F | F |
| A-3222. | OCH₂F | CHF₂ | 3-CH₃ | F | F |
| A-3223. | OCH₂F | CHF₂ | 3-OCH₃ | F | F |
| A-3224. | OCH₂F | CHF₂ | 5-F | F | F |
| A-3225. | OCH₂F | CHF₂ | 5-CH₃ | F | F |
| A-3226. | OCH₂F | CHF₂ | 5-OCH₃ | F | F |
| A-3227. | OCH₂F | CF₃ | 3-F | F | F |
| A-3228. | OCH₂F | CF₃ | 3-CH₃ | F | F |
| A-3229. | OCH₂F | CF₃ | 3-OCH₃ | F | F |
| A-3230. | OCH₂F | CF₃ | 5-F | F | F |
| A-3231. | OCH₂F | CF₃ | 5-CH₃ | F | F |
| A-3232. | OCH₂F | CF₃ | 5-OCH₃ | F | F |
| A-3233. | OCH₂F | OCH₂F | 3-F | F | F |
| A-3234. | OCH₂F | OCH₂F | 3-CH₃ | F | F |
| A-3235. | OCH₂F | OCH₂F | 3-OCH₃ | F | F |
| A-3236. | OCH₂F | OCH₂F | 5-F | F | F |
| A-3237. | OCH₂F | OCH₂F | 5-CH₃ | F | F |
| A-3238. | OCH₂F | OCH₂F | 5-OCH₃ | F | F |
| A-3239. | OCH₂F | OCHF₂ | 3-F | F | F |
| A-3240. | OCH₂F | OCHF₂ | 3-CH₃ | F | F |
| A-3241. | OCH₂F | OCHF₂ | 3-OCH₃ | F | F |
| A-3242. | OCH₂F | OCHF₂ | 5-F | F | F |
| A-3243. | OCH₂F | OCHF₂ | 5-CH₃ | F | F |
| A-3244. | OCH₂F | OCHF₂ | 5-OCH₃ | F | F |
| A-3245. | OCH₂F | OCF₃ | 3-F | F | F |
| A-3246. | OCH₂F | OCF₃ | 3-CH₃ | F | F |
| A-3247. | OCH₂F | OCF₃ | 3-OCH₃ | F | F |
| A-3248. | OCH₂F | OCF₃ | 5-F | F | F |
| A-3249. | OCH₂F | OCF₃ | 5-CH₃ | F | F |
| A-3250. | OCH₂F | OCF₃ | 5-OCH₃ | F | F |
| A-3251. | OCHF₂ | F | 3-F | F | F |
| A-3252. | OCHF₂ | F | 3-CH₃ | F | F |
| A-3253. | OCHF₂ | F | 3-OCH₃ | F | F |
| A-3254. | OCHF₂ | F | 5-F | F | F |
| A-3255. | OCHF₂ | F | 5-CH₃ | F | F |
| A-3256. | OCHF₂ | F | 5-OCH₃ | F | F |
| A-3257. | OCHF₂ | CH₃ | 3-F | F | F |
| A-3258. | OCHF₂ | CH₃ | 3-CH₃ | F | F |
| A-3259. | OCHF₂ | CH₃ | 3-OCH₃ | F | F |
| A-3260. | OCHF₂ | CH₃ | 5-F | F | F |
| A-3261. | OCHF₂ | CH₃ | 5-CH₃ | F | F |
| A-3262. | OCHF₂ | CH₃ | 5-OCH₃ | F | F |
| A-3263. | OCHF₂ | OCH₃ | 3-F | F | F |
| A-3264. | OCHF₂ | OCH₃ | 3-CH₃ | F | F |
| A-3265. | OCHF₂ | OCH₃ | 3-OCH₃ | F | F |
| A-3266. | OCHF₂ | OCH₃ | 5-F | F | F |
| A-3267. | OCHF₂ | OCH₃ | 5-CH₃ | F | F |
| A-3268. | OCHF₂ | OCH₃ | 5-OCH₃ | F | F |
| A-3269. | OCHF₂ | CN | 3-F | F | F |
| A-3270. | OCHF₂ | CN | 3-CH₃ | F | F |
| A-3271. | OCHF₂ | CN | 3-OCH₃ | F | F |
| A-3272. | OCHF₂ | CN | 5-F | F | F |
| A-3273. | OCHF₂ | CN | 5-CH₃ | F | F |
| A-3274. | OCHF₂ | CN | 5-OCH₃ | F | F |
| A-3275. | OCHF₂ | CH₂F | 3-F | F | F |
| A-3276. | OCHF₂ | CH₂F | 3-CH₃ | F | F |
| A-3277. | OCHF₂ | CH₂F | 3-OCH₃ | F | F |
| A-3278. | OCHF₂ | CH₂F | 5-F | F | F |
| A-3279. | OCHF₂ | CH₂F | 5-CH₃ | F | F |
| A-3280. | OCHF₂ | CH₂F | 5-OCH₃ | F | F |
| A-3281. | OCHF₂ | CHF₂ | 3-F | F | F |
| A-3282. | OCHF₂ | CHF₂ | 3-CH₃ | F | F |
| A-3283. | OCHF₂ | CHF₂ | 3-OCH₃ | F | F |
| A-3284. | OCHF₂ | CHF₂ | 5-F | F | F |
| A-3285. | OCHF₂ | CHF₂ | 5-CH₃ | F | F |
| A-3286. | OCHF₂ | CHF₂ | 5-OCH₃ | F | F |
| A-3287. | OCHF₂ | CF₃ | 3-F | F | F |
| A-3288. | OCHF₂ | CF₃ | 3-CH₃ | F | F |
| A-3289. | OCHF₂ | CF₃ | 3-OCH₃ | F | F |
| A-3290. | OCHF₂ | CF₃ | 5-F | F | F |
| A-3291. | OCHF₂ | CF₃ | 5-CH₃ | F | F |
| A-3292. | OCHF₂ | CF₃ | 5-OCH₃ | F | F |
| A-3293. | OCHF₂ | OCH₂F | 3-F | F | F |
| A-3294. | OCHF₂ | OCH₂F | 3-CH₃ | F | F |
| A-3295. | OCHF₂ | OCH₂F | 3-OCH₃ | F | F |
| A-3296. | OCHF₂ | OCH₂F | 5-F | F | F |
| A-3297. | OCHF₂ | OCH₂F | 5-CH₃ | F | F |
| A-3298. | OCHF₂ | OCH₂F | 5-OCH₃ | F | F |
| A-3299. | OCHF₂ | OCHF₂ | 3-F | F | F |
| A-3300. | OCHF₂ | OCHF₂ | 3-CH₃ | F | F |
| A-3301. | OCHF₂ | OCHF₂ | 3-OCH₃ | F | F |
| A-3302. | OCHF₂ | OCHF₂ | 5-F | F | F |
| A-3303. | OCHF₂ | OCHF₂ | 5-CH₃ | F | F |
| A-3304. | OCHF₂ | OCHF₂ | 5-OCH₃ | F | F |
| A-3305. | OCHF₂ | OCF₃ | 3-F | F | F |
| A-3306. | OCHF₂ | OCF₃ | 3-CH₃ | F | F |
| A-3307. | OCHF₂ | OCF₃ | 3-OCH₃ | F | F |
| A-3308. | OCHF₂ | OCF₃ | 5-F | F | F |
| A-3309. | OCHF₂ | OCF₃ | 5-CH₃ | F | F |
| A-3310. | OCHF₂ | OCF₃ | 5-OCH₃ | F | F |
| A-3311. | OCF₃ | F | 3-F | F | F |
| A-3312. | OCF₃ | F | 3-CH₃ | F | F |
| A-3313. | OCF₃ | F | 3-OCH₃ | F | F |
| A-3314. | OCF₃ | F | 5-F | F | F |
| A-3315. | OCF₃ | F | 5-CH₃ | F | F |
| A-3316. | OCF₃ | F | 5-OCH₃ | F | F |
| A-3317. | OCF₃ | CH₃ | 3-F | F | F |
| A-3318. | OCF₃ | CH₃ | 3-CH₃ | F | F |
| A-3319. | OCF₃ | CH₃ | 3-OCH₃ | F | F |
| A-3320. | OCF₃ | CH₃ | 5-F | F | F |
| A-3321. | OCF₃ | CH₃ | 5-CH₃ | F | F |
| A-3322. | OCF₃ | CH₃ | 5-OCH₃ | F | F |
| A-3323. | OCF₃ | OCH₃ | 3-F | F | F |
| A-3324. | OCF₃ | OCH₃ | 3-CH₃ | F | F |
| A-3325. | OCF₃ | OCH₃ | 3-OCH₃ | F | F |
| A-3326. | OCF₃ | OCH₃ | 5-F | F | F |
| A-3327. | OCF₃ | OCH₃ | 5-CH₃ | F | F |
| A-3328. | OCF₃ | OCH₃ | 5-OCH₃ | F | F |
| A-3329. | OCF₃ | CN | 3-F | F | F |
| A-3330. | OCF₃ | CN | 3-CH₃ | F | F |
| A-3331. | OCF₃ | CN | 3-OCH₃ | F | F |
| A-3332. | OCF₃ | CN | 5-F | F | F |
| A-3333. | OCF₃ | CN | 5-CH₃ | F | F |
| A-3334. | OCF₃ | CN | 5-OCH₃ | F | F |
| A-3335. | OCF₃ | CH₂F | 3-F | F | F |
| A-3336. | OCF₃ | CH₂F | 3-CH₃ | F | F |
| A-3337. | OCF₃ | CH₂F | 3-OCH₃ | F | F |
| A-3338. | OCF₃ | CH₂F | 5-F | F | F |
| A-3339. | OCF₃ | CH₂F | 5-CH₃ | F | F |
| A-3340. | OCF₃ | CH₂F | 5-OCH₃ | F | F |
| A-3341. | OCF₃ | CHF₂ | 3-F | F | F |
| A-3342. | OCF₃ | CHF₂ | 3-CH₃ | F | F |
| A-3343. | OCF₃ | CHF₂ | 3-OCH₃ | F | F |
| A-3344. | OCF₃ | CHF₂ | 5-F | F | F |
| A-3345. | OCF₃ | CHF₂ | 5-CH₃ | F | F |
| A-3346. | OCF₃ | CHF₂ | 5-OCH₃ | F | F |
| A-3347. | OCF₃ | CF₃ | 3-F | F | F |
| A-3348. | OCF₃ | CF₃ | 3-CH₃ | F | F |
| A-3349. | OCF₃ | CF₃ | 3-OCH₃ | F | F |

TABLE A-continued

| Example No. | R¹ | R² | R³ | R⁶ | R⁷ |
|---|---|---|---|---|---|
| A-3350. | OCF$_3$ | CF$_3$ | 5-F | F | F |
| A-3351. | OCF$_3$ | CF$_3$ | 5-CH$_3$ | F | F |
| A-3352. | OCF$_3$ | CF$_3$ | 5-OCH$_3$ | F | F |
| A-3353. | OCF$_3$ | OCH$_2$F | 3-F | F | F |
| A-3354. | OCF$_3$ | OCH$_2$F | 3-CH$_3$ | F | F |
| A-3355. | OCF$_3$ | OCH$_2$F | 3-OCH$_3$ | F | F |
| A-3356. | OCF$_3$ | OCH$_2$F | 5-F | F | F |
| A-3357. | OCF$_3$ | OCH$_2$F | 5-CH$_3$ | F | F |
| A-3358. | OCF$_3$ | OCH$_2$F | 5-OCH$_3$ | F | F |
| A-3359. | OCF$_3$ | OCHF$_2$ | 3-F | F | F |
| A-3360. | OCF$_3$ | OCHF$_2$ | 3-CH$_3$ | F | F |
| A-3361. | OCF$_3$ | OCHF$_2$ | 3-OCH$_3$ | F | F |
| A-3362. | OCF$_3$ | OCHF$_2$ | 5-F | F | F |
| A-3363. | OCF$_3$ | OCHF$_2$ | 5-CH$_3$ | F | F |
| A-3364. | OCF$_3$ | OCHF$_2$ | 5-OCH$_3$ | F | F |
| A-3365. | OCF$_3$ | OCF$_3$ | 3-F | F | F |
| A-3366. | OCF$_3$ | OCF$_3$ | 3-CH$_3$ | F | F |
| A-3367. | OCF$_3$ | OCF$_3$ | 3-OCH$_3$ | F | F |
| A-3368. | OCF$_3$ | OCF$_3$ | 5-F | F | F |
| A-3369. | OCF$_3$ | OCF$_3$ | 5-CH$_3$ | F | F |
| A-3370. | OCF$_3$ | OCF$_3$ | 5-OCH$_3$ | F | F |
| A-3371. | H | H | H | Cl | F |
| A-3372. | F | H | H | Cl | F |
| A-3373. | CH$_3$ | H | H | Cl | F |
| A-3374. | OCH$_3$ | H | H | Cl | F |
| A-3375. | CH$_2$F | H | H | Cl | F |
| A-3376. | CHF$_2$ | H | H | Cl | F |
| A-3377. | CF$_3$ | H | H | Cl | F |
| A-3378. | OCH$_2$F | H | H | Cl | F |
| A-3379. | OCHF$_2$ | H | H | Cl | F |
| A-3380. | OCF$_3$ | H | H | Cl | F |
| A-3381. | H | F | H | Cl | F |
| A-3382. | H | CH$_3$ | H | Cl | F |
| A-3383. | H | OCH$_3$ | H | Cl | F |
| A-3384. | H | CN | H | Cl | F |
| A-3385. | H | CH$_2$F | H | Cl | F |
| A-3386. | H | CHF$_2$ | H | Cl | F |
| A-3387. | H | CF$_3$ | H | Cl | F |
| A-3388. | H | OCH$_2$F | H | Cl | F |
| A-3389. | H | OCHF$_2$ | H | Cl | F |
| A-3390. | H | OCF$_3$ | H | Cl | F |
| A-3391. | H | H | 3-F | Cl | F |
| A-3392. | H | H | 3-CH$_3$ | Cl | F |
| A-3393. | H | H | 3-OCH$_3$ | Cl | F |
| A-3394. | H | H | 5-F | Cl | F |
| A-3395. | H | H | 5-CH$_3$ | Cl | F |
| A-3396. | H | H | 5-OCH$_3$ | Cl | F |
| A-3397. | F | F | H | Cl | F |
| A-3398. | F | CH$_3$ | H | Cl | F |
| A-3399. | F | OCH$_3$ | H | Cl | F |
| A-3400. | F | CN | H | Cl | F |
| A-3401. | F | CH$_2$F | H | Cl | F |
| A-3402. | F | CHF$_2$ | H | Cl | F |
| A-3403. | F | CF$_3$ | H | Cl | F |
| A-3404. | F | OCH$_2$F | H | Cl | F |
| A-3405. | F | OCHF$_2$ | H | Cl | F |
| A-3406. | F | OCF$_3$ | H | Cl | F |
| A-3407. | F | H | 3-F | Cl | F |
| A-3408. | F | H | 3-CH$_3$ | Cl | F |
| A-3409. | F | H | 3-OCH$_3$ | Cl | F |
| A-3410. | F | H | 5-F | Cl | F |
| A-3411. | F | H | 5-CH$_3$ | Cl | F |
| A-3412. | F | H | 5-OCH$_3$ | Cl | F |
| A-3413. | CH$_3$ | F | H | Cl | F |
| A-3414. | CH$_3$ | CH$_3$ | H | Cl | F |
| A-3415. | CH$_3$ | OCH$_3$ | H | Cl | F |
| A-3416. | CH$_3$ | CN | H | Cl | F |
| A-3417. | CH$_3$ | CH$_2$F | H | Cl | F |
| A-3418. | CH$_3$ | CHF$_2$ | H | Cl | F |
| A-3419. | CH$_3$ | CF$_3$ | H | Cl | F |
| A-3420. | CH$_3$ | OCH$_2$F | H | Cl | F |
| A-3421. | CH$_3$ | OCHF$_2$ | H | Cl | F |
| A-3422. | CH$_3$ | OCF$_3$ | H | Cl | F |
| A-3423. | CH$_3$ | H | 3-F | Cl | F |
| A-3424. | CH$_3$ | H | 3-CH$_3$ | Cl | F |
| A-3425. | CH$_3$ | H | 3-OCH$_3$ | Cl | F |
| A-3426. | CH$_3$ | H | 5-F | Cl | F |
| A-3427. | CH$_3$ | H | 5-CH$_3$ | Cl | F |
| A-3428. | CH$_3$ | H | 5-OCH$_3$ | Cl | F |
| A-3429. | OCH$_3$ | F | H | Cl | F |
| A-3430. | OCH$_3$ | CH$_3$ | H | Cl | F |
| A-3431. | OCH$_3$ | OCH$_3$ | H | Cl | F |
| A-3432. | OCH$_3$ | CN | H | Cl | F |
| A-3433. | OCH$_3$ | CH$_2$F | H | Cl | F |
| A-3434. | OCH$_3$ | CHF$_2$ | H | Cl | F |
| A-3435. | OCH$_3$ | CF$_3$ | H | Cl | F |
| A-3436. | OCH$_3$ | OCH$_2$F | H | Cl | F |
| A-3437. | OCH$_3$ | OCHF$_2$ | H | Cl | F |
| A-3438. | OCH$_3$ | OCF$_3$ | H | Cl | F |
| A-3439. | OCH$_3$ | H | 3-F | Cl | F |
| A-3440. | OCH$_3$ | H | 3-CH$_3$ | Cl | F |
| A-3441. | OCH$_3$ | H | 3-OCH$_3$ | Cl | F |
| A-3442. | OCH$_3$ | H | 5-F | Cl | F |
| A-3443. | OCH$_3$ | H | 5-CH$_3$ | Cl | F |
| A-3444. | OCH$_3$ | H | 5-OCH$_3$ | Cl | F |
| A-3445. | H | F | 3-F | Cl | F |
| A-3446. | H | F | 3-CH$_3$ | Cl | F |
| A-3447. | H | F | 3-OCH$_3$ | Cl | F |
| A-3448. | H | F | 5-F | Cl | F |
| A-3449. | H | F | 5-CH$_3$ | Cl | F |
| A-3450. | H | F | 5-OCH$_3$ | Cl | F |
| A-3451. | H | CH$_3$ | 3-F | Cl | F |
| A-3452. | H | CH$_3$ | 3-CH$_3$ | Cl | F |
| A-3453. | H | CH$_3$ | 3-OCH$_3$ | Cl | F |
| A-3454. | H | CH$_3$ | 5-F | Cl | F |
| A-3455. | H | CH$_3$ | 5-CH$_3$ | Cl | F |
| A-3456. | H | CH$_3$ | 5-OCH$_3$ | Cl | F |
| A-3457. | H | OCH$_3$ | 3-F | Cl | F |
| A-3458. | H | OCH$_3$ | 3-CH$_3$ | Cl | F |
| A-3459. | H | OCH$_3$ | 3-OCH$_3$ | Cl | F |
| A-3460. | H | OCH$_3$ | 5-F | Cl | F |
| A-3461. | H | OCH$_3$ | 5-CH$_3$ | Cl | F |
| A-3462. | H | OCH$_3$ | 5-OCH$_3$ | Cl | F |
| A-3463. | H | CN | 3-F | Cl | F |
| A-3464. | H | CN | 3-CH$_3$ | Cl | F |
| A-3465. | H | CN | 3-OCH$_3$ | Cl | F |
| A-3466. | H | CN | 5-F | Cl | F |
| A-3467. | H | CN | 5-CH$_3$ | Cl | F |
| A-3468. | H | CN | 5-OCH$_3$ | Cl | F |
| A-3469. | H | CH$_2$F | 3-F | Cl | F |
| A-3470. | H | CH$_2$F | 3-CH$_3$ | Cl | F |
| A-3471. | H | CH$_2$F | 3-OCH$_3$ | Cl | F |
| A-3472. | H | CH$_2$F | 5-F | Cl | F |
| A-3473. | H | CH$_2$F | 5-CH$_3$ | Cl | F |
| A-3474. | H | CH$_2$F | 5-OCH$_3$ | Cl | F |
| A-3475. | H | CHF$_2$ | 3-F | Cl | F |
| A-3476. | H | CHF$_2$ | 3-CH$_3$ | Cl | F |
| A-3477. | H | CHF$_2$ | 3-OCH$_3$ | Cl | F |
| A-3478. | H | CHF$_2$ | 5-F | Cl | F |
| A-3479. | H | CHF$_2$ | 5-CH$_3$ | Cl | F |
| A-3480. | H | CHF$_2$ | 5-OCH$_3$ | Cl | F |
| A-3481. | H | CF$_3$ | 3-F | Cl | F |
| A-3482. | H | CF$_3$ | 3-CH$_3$ | Cl | F |
| A-3483. | H | CF$_3$ | 3-OCH$_3$ | Cl | F |
| A-3484. | H | CF$_3$ | 5-F | Cl | F |
| A-3485. | H | CF$_3$ | 5-CH$_3$ | Cl | F |
| A-3486. | H | CF$_3$ | 5-OCH$_3$ | Cl | F |
| A-3487. | H | OCH$_2$F | 3-F | Cl | F |
| A-3488. | H | OCH$_2$F | 3-CH$_3$ | Cl | F |
| A-3489. | H | OCH$_2$F | 3-OCH$_3$ | Cl | F |
| A-3490. | H | OCH$_2$F | 5-F | Cl | F |
| A-3491. | H | OCH$_2$F | 5-CH$_3$ | Cl | F |
| A-3492. | H | OCH$_2$F | 5-OCH$_3$ | Cl | F |
| A-3493. | H | OCHF$_2$ | 3-F | Cl | F |
| A-3494. | H | OCHF$_2$ | 3-CH$_3$ | Cl | F |
| A-3495. | H | OCHF$_2$ | 3-OCH$_3$ | Cl | F |
| A-3496. | H | OCHF$_2$ | 5-F | Cl | F |
| A-3497. | H | OCHF$_2$ | 5-CH$_3$ | Cl | F |
| A-3498. | H | OCHF$_2$ | 5-OCH$_3$ | Cl | F |
| A-3499. | H | OCF$_3$ | 3-F | Cl | F |
| A-3500. | H | OCF$_3$ | 3-CH$_3$ | Cl | F |
| A-3501. | H | OCF$_3$ | 3-OCH$_3$ | Cl | F |
| A-3502. | H | OCF$_3$ | 5-F | Cl | F |
| A-3503. | H | OCF$_3$ | 5-CH$_3$ | Cl | F |
| A-3504. | H | OCF$_3$ | 5-OCH$_3$ | Cl | F |
| A-3505. | F | F | 3-F | Cl | F |

TABLE A-continued

| Example No. | R$^1$ | R$^2$ | R$^3$ | R$^6$ | R$^7$ |
|---|---|---|---|---|---|
| A-3506. | F | F | 3-CH$_3$ | Cl | F |
| A-3507. | F | F | 3-OCH$_3$ | Cl | F |
| A-3508. | F | F | 5-F | Cl | F |
| A-3509. | F | F | 5-CH$_3$ | Cl | F |
| A-3510. | F | F | 5-OCH$_3$ | Cl | F |
| A-3511. | F | CH$_3$ | 3-F | Cl | F |
| A-3512. | F | CH$_3$ | 3-CH$_3$ | Cl | F |
| A-3513. | F | CH$_3$ | 3-OCH$_3$ | Cl | F |
| A-3514. | F | CH$_3$ | 5-F | Cl | F |
| A-3515. | F | CH$_3$ | 5-CH$_3$ | Cl | F |
| A-3516. | F | CH$_3$ | 5-OCH$_3$ | Cl | F |
| A-3517. | F | OCH$_3$ | 3-F | Cl | F |
| A-3518. | F | OCH$_3$ | 3-CH$_3$ | Cl | F |
| A-3519. | F | OCH$_3$ | 3-OCH$_3$ | Cl | F |
| A-3520. | F | OCH$_3$ | 5-F | Cl | F |
| A-3521. | F | OCH$_3$ | 5-CH$_3$ | Cl | F |
| A-3522. | F | OCH$_3$ | 5-OCH$_3$ | Cl | F |
| A-3523. | F | CN | 3-F | Cl | F |
| A-3524. | F | CN | 3-CH$_3$ | Cl | F |
| A-3525. | F | CN | 3-OCH$_3$ | Cl | F |
| A-3526. | F | CN | 5-F | Cl | F |
| A-3527. | F | CN | 5-CH$_3$ | Cl | F |
| A-3528. | F | CN | 5-OCH$_3$ | Cl | F |
| A-3529. | F | CH$_2$F | 3-F | Cl | F |
| A-3530. | F | CH$_2$F | 3-CH$_3$ | Cl | F |
| A-3531. | F | CH$_2$F | 3-OCH$_3$ | Cl | F |
| A-3532. | F | CH$_2$F | 5-F | Cl | F |
| A-3533. | F | CH$_2$F | 5-CH$_3$ | Cl | F |
| A-3534. | F | CH$_2$F | 5-OCH$_3$ | Cl | F |
| A-3535. | F | CHF$_2$ | 3-F | Cl | F |
| A-3536. | F | CHF$_2$ | 3-CH$_3$ | Cl | F |
| A-3537. | F | CHF$_2$ | 3-OCH$_3$ | Cl | F |
| A-3538. | F | CHF$_2$ | 5-F | Cl | F |
| A-3539. | F | CHF$_2$ | 5-CH$_3$ | Cl | F |
| A-3540. | F | CHF$_2$ | 5-OCH$_3$ | Cl | F |
| A-3541. | F | CF$_3$ | 3-F | Cl | F |
| A-3542. | F | CF$_3$ | 3-CH$_3$ | Cl | F |
| A-3543. | F | CF$_3$ | 3-OCH$_3$ | Cl | F |
| A-3544. | F | CF$_3$ | 5-F | Cl | F |
| A-3545. | F | CF$_3$ | 5-CH$_3$ | Cl | F |
| A-3546. | F | CF$_3$ | 5-OCH$_3$ | Cl | F |
| A-3547. | F | OCH$_2$F | 3-F | Cl | F |
| A-3548. | F | OCH$_2$F | 3-CH$_3$ | Cl | F |
| A-3549. | F | OCH$_2$F | 3-OCH$_3$ | Cl | F |
| A-3550. | F | OCH$_2$F | 5-F | Cl | F |
| A-3551. | F | OCH$_2$F | 5-CH$_3$ | Cl | F |
| A-3552. | F | OCH$_2$F | 5-OCH$_3$ | Cl | F |
| A-3553. | F | OCHF$_2$ | 3-F | Cl | F |
| A-3554. | F | OCHF$_2$ | 3-CH$_3$ | Cl | F |
| A-3555. | F | OCHF$_2$ | 3-OCH$_3$ | Cl | F |
| A-3556. | F | OCHF$_2$ | 5-F | Cl | F |
| A-3557. | F | OCHF$_2$ | 5-CH$_3$ | Cl | F |
| A-3558. | F | OCHF$_2$ | 5-OCH$_3$ | Cl | F |
| A-3559. | F | OCF$_3$ | 3-F | Cl | F |
| A-3560. | F | OCF$_3$ | 3-CH$_3$ | Cl | F |
| A-3561. | F | OCF$_3$ | 3-OCH$_3$ | Cl | F |
| A-3562. | F | OCF$_3$ | 5-F | Cl | F |
| A-3563. | F | OCF$_3$ | 5-CH$_3$ | Cl | F |
| A-3564. | F | OCF$_3$ | 5-OCH$_3$ | Cl | F |
| A-3565. | CH$_3$ | F | 3-F | Cl | F |
| A-3566. | CH$_3$ | F | 3-CH$_3$ | Cl | F |
| A-3567. | CH$_3$ | F | 3-OCH$_3$ | Cl | F |
| A-3568. | CH$_3$ | F | 5-F | Cl | F |
| A-3569. | CH$_3$ | F | 5-CH$_3$ | Cl | F |
| A-3570. | CH$_3$ | F | 5-OCH$_3$ | Cl | F |
| A-3571. | CH$_3$ | CH$_3$ | 3-F | Cl | F |
| A-3572. | CH$_3$ | CH$_3$ | 3-CH$_3$ | Cl | F |
| A-3573. | CH$_3$ | CH$_3$ | 3-OCH$_3$ | Cl | F |
| A-3574. | CH$_3$ | CH$_3$ | 5-F | Cl | F |
| A-3575. | CH$_3$ | CH$_3$ | 5-CH$_3$ | Cl | F |
| A-3576. | CH$_3$ | CH$_3$ | 5-OCH$_3$ | Cl | F |
| A-3577. | CH$_3$ | OCH$_3$ | 3-F | Cl | F |
| A-3578. | CH$_3$ | OCH$_3$ | 3-CH$_3$ | Cl | F |
| A-3579. | CH$_3$ | OCH$_3$ | 3-OCH$_3$ | Cl | F |
| A-3580. | CH$_3$ | OCH$_3$ | 5-F | Cl | F |
| A-3581. | CH$_3$ | OCH$_3$ | 5-CH$_3$ | Cl | F |
| A-3582. | CH$_3$ | OCH$_3$ | 5-OCH$_3$ | Cl | F |
| A-3583. | CH$_3$ | CN | 3-F | Cl | F |
| A-3584. | CH$_3$ | CN | 3-CH$_3$ | Cl | F |
| A-3585. | CH$_3$ | CN | 3-OCH$_3$ | Cl | F |
| A-3586. | CH$_3$ | CN | 5-F | Cl | F |
| A-3587. | CH$_3$ | CN | 5-CH$_3$ | Cl | F |
| A-3588. | CH$_3$ | CN | 5-OCH$_3$ | Cl | F |
| A-3589. | CH$_3$ | CH$_2$F | 3-F | Cl | F |
| A-3590. | CH$_3$ | CH$_2$F | 3-CH$_3$ | Cl | F |
| A-3591. | CH$_3$ | CH$_2$F | 3-OCH$_3$ | Cl | F |
| A-3592. | CH$_3$ | CH$_2$F | 5-F | Cl | F |
| A-3593. | CH$_3$ | CH$_2$F | 5-CH$_3$ | Cl | F |
| A-3594. | CH$_3$ | CH$_2$F | 5-OCH$_3$ | Cl | F |
| A-3595. | CH$_3$ | CHF$_2$ | 3-F | Cl | F |
| A-3596. | CH$_3$ | CHF$_2$ | 3-CH$_3$ | Cl | F |
| A-3597. | CH$_3$ | CHF$_2$ | 3-OCH$_3$ | Cl | F |
| A-3598. | CH$_3$ | CHF$_2$ | 5-F | Cl | F |
| A-3599. | CH$_3$ | CHF$_2$ | 5-CH$_3$ | Cl | F |
| A-3600. | CH$_3$ | CHF$_2$ | 5-OCH$_3$ | Cl | F |
| A-3601. | CH$_3$ | CF$_3$ | 3-F | Cl | F |
| A-3602. | CH$_3$ | CF$_3$ | 3-CH$_3$ | Cl | F |
| A-3603. | CH$_3$ | CF$_3$ | 3-OCH$_3$ | Cl | F |
| A-3604. | CH$_3$ | CF$_3$ | 5-F | Cl | F |
| A-3605. | CH$_3$ | CF$_3$ | 5-CH$_3$ | Cl | F |
| A-3606. | CH$_3$ | CF$_3$ | 5-OCH$_3$ | Cl | F |
| A-3607. | CH$_3$ | OCH$_2$F | 3-F | Cl | F |
| A-3608. | CH$_3$ | OCH$_2$F | 3-CH$_3$ | Cl | F |
| A-3609. | CH$_3$ | OCH$_2$F | 3-OCH$_3$ | Cl | F |
| A-3610. | CH$_3$ | OCH$_2$F | 5-F | Cl | F |
| A-3611. | CH$_3$ | OCH$_2$F | 5-CH$_3$ | Cl | F |
| A-3612. | CH$_3$ | OCH$_2$F | 5-OCH$_3$ | Cl | F |
| A-3613. | CH$_3$ | OCHF$_2$ | 3-F | Cl | F |
| A-3614. | CH$_3$ | OCHF$_2$ | 3-CH$_3$ | Cl | F |
| A-3615. | CH$_3$ | OCHF$_2$ | 3-OCH$_3$ | Cl | F |
| A-3616. | CH$_3$ | OCHF$_2$ | 5-F | Cl | F |
| A-3617. | CH$_3$ | OCHF$_2$ | 5-CH$_3$ | Cl | F |
| A-3618. | CH$_3$ | OCHF$_2$ | 5-OCH$_3$ | Cl | F |
| A-3619. | CH$_3$ | OCF$_3$ | 3-F | Cl | F |
| A-3620. | CH$_3$ | OCF$_3$ | 3-CH$_3$ | Cl | F |
| A-3621. | CH$_3$ | OCF$_3$ | 3-OCH$_3$ | Cl | F |
| A-3622. | CH$_3$ | OCF$_3$ | 5-F | Cl | F |
| A-3623. | CH$_3$ | OCF$_3$ | 5-CH$_3$ | Cl | F |
| A-3624. | CH$_3$ | OCF$_3$ | 5-OCH$_3$ | Cl | F |
| A-3625. | OCH$_3$ | F | 3-F | Cl | F |
| A-3626. | OCH$_3$ | F | 3-CH$_3$ | Cl | F |
| A-3627. | OCH$_3$ | F | 3-OCH$_3$ | Cl | F |
| A-3628. | OCH$_3$ | F | 5-F | Cl | F |
| A-3629. | OCH$_3$ | F | 5-CH$_3$ | Cl | F |
| A-3630. | OCH$_3$ | F | 5-OCH$_3$ | Cl | F |
| A-3631. | OCH$_3$ | CH$_3$ | 3-F | Cl | F |
| A-3632. | OCH$_3$ | CH$_3$ | 3-CH$_3$ | Cl | F |
| A-3633. | OCH$_3$ | CH$_3$ | 3-OCH$_3$ | Cl | F |
| A-3634. | OCH$_3$ | CH$_3$ | 5-F | Cl | F |
| A-3635. | OCH$_3$ | CH$_3$ | 5-CH$_3$ | Cl | F |
| A-3636. | OCH$_3$ | CH$_3$ | 5-OCH$_3$ | Cl | F |
| A-3637. | OCH$_3$ | OCH$_3$ | 3-F | Cl | F |
| A-3638. | OCH$_3$ | OCH$_3$ | 3-CH$_3$ | Cl | F |
| A-3639. | OCH$_3$ | OCH$_3$ | 3-OCH$_3$ | Cl | F |
| A-3640. | OCH$_3$ | OCH$_3$ | 5-F | Cl | F |
| A-3641. | OCH$_3$ | OCH$_3$ | 5-CH$_3$ | Cl | F |
| A-3642. | OCH$_3$ | OCH$_3$ | 5-OCH$_3$ | Cl | F |
| A-3643. | OCH$_3$ | CN | 3-F | Cl | F |
| A-3644. | OCH$_3$ | CN | 3-CH$_3$ | Cl | F |
| A-3645. | OCH$_3$ | CN | 3-OCH$_3$ | Cl | F |
| A-3646. | OCH$_3$ | CN | 5-F | Cl | F |
| A-3647. | OCH$_3$ | CN | 5-CH$_3$ | Cl | F |
| A-3648. | OCH$_3$ | CN | 5-OCH$_3$ | Cl | F |
| A-3649. | OCH$_3$ | CH$_2$F | 3-F | Cl | F |
| A-3650. | OCH$_3$ | CH$_2$F | 3-CH$_3$ | Cl | F |
| A-3651. | OCH$_3$ | CH$_2$F | 3-OCH$_3$ | Cl | F |
| A-3652. | OCH$_3$ | CH$_2$F | 5-F | Cl | F |
| A-3653. | OCH$_3$ | CH$_2$F | 5-CH$_3$ | Cl | F |
| A-3654. | OCH$_3$ | CH$_2$F | 5-OCH$_3$ | Cl | F |
| A-3655. | OCH$_3$ | CHF$_2$ | 3-F | Cl | F |
| A-3656. | OCH$_3$ | CHF$_2$ | 3-CH$_3$ | Cl | F |
| A-3657. | OCH$_3$ | CHF$_2$ | 3-OCH$_3$ | Cl | F |
| A-3658. | OCH$_3$ | CHF$_2$ | 5-F | Cl | F |
| A-3659. | OCH$_3$ | CHF$_2$ | 5-CH$_3$ | Cl | F |
| A-3660. | OCH$_3$ | CHF$_2$ | 5-OCH$_3$ | Cl | F |
| A-3661. | OCH$_3$ | CF$_3$ | 3-F | Cl | F |

TABLE A-continued

| Example No. | R¹ | R² | R³ | R⁶ | R⁷ |
|---|---|---|---|---|---|
| A-3662. | OCH$_3$ | CF$_3$ | 3-CH$_3$ | Cl | F |
| A-3663. | OCH$_3$ | CF$_3$ | 3-OCH$_3$ | Cl | F |
| A-3664. | OCH$_3$ | CF$_3$ | 5-F | Cl | F |
| A-3665. | OCH$_3$ | CF$_3$ | 5-CH$_3$ | Cl | F |
| A-3666. | OCH$_3$ | CF$_3$ | 5-OCH$_3$ | Cl | F |
| A-3667. | OCH$_3$ | OCH$_2$F | 3-F | Cl | F |
| A-3668. | OCH$_3$ | OCH$_2$F | 3-CH$_3$ | Cl | F |
| A-3669. | OCH$_3$ | OCH$_2$F | 3-OCH$_3$ | Cl | F |
| A-3670. | OCH$_3$ | OCH$_2$F | 5-F | Cl | F |
| A-3671. | OCH$_3$ | OCH$_2$F | 5-CH$_3$ | Cl | F |
| A-3672. | OCH$_3$ | OCH$_2$F | 5-OCH$_3$ | Cl | F |
| A-3673. | OCH$_3$ | OCHF$_2$ | 3-F | Cl | F |
| A-3674. | OCH$_3$ | OCHF$_2$ | 3-CH$_3$ | Cl | F |
| A-3675. | OCH$_3$ | OCHF$_2$ | 3-OCH$_3$ | Cl | F |
| A-3676. | OCH$_3$ | OCHF$_2$ | 5-F | Cl | F |
| A-3677. | OCH$_3$ | OCHF$_2$ | 5-CH$_3$ | Cl | F |
| A-3678. | OCH$_3$ | OCHF$_2$ | 5-OCH$_3$ | Cl | F |
| A-3679. | OCH$_3$ | OCF$_3$ | 3-F | Cl | F |
| A-3680. | OCH$_3$ | OCF$_3$ | 3-CH$_3$ | Cl | F |
| A-3681. | OCH$_3$ | OCF$_3$ | 3-OCH$_3$ | Cl | F |
| A-3682. | OCH$_3$ | OCF$_3$ | 5-F | Cl | F |
| A-3683. | OCH$_3$ | OCF$_3$ | 5-CH$_3$ | Cl | F |
| A-3684. | OCH$_3$ | OCF$_3$ | 5-OCH$_3$ | Cl | F |
| A-3685. | CH$_2$F | F | 3-F | Cl | F |
| A-3686. | CH$_2$F | F | 3-CH$_3$ | Cl | F |
| A-3687. | CH$_2$F | F | 3-OCH$_3$ | Cl | F |
| A-3688. | CH$_2$F | F | 5-F | Cl | F |
| A-3689. | CH$_2$F | F | 5-CH$_3$ | Cl | F |
| A-3690. | CH$_2$F | F | 5-OCH$_3$ | Cl | F |
| A-3691. | CH$_2$F | CH$_3$ | 3-F | Cl | F |
| A-3692. | CH$_2$F | CH$_3$ | 3-CH$_3$ | Cl | F |
| A-3693. | CH$_2$F | CH$_3$ | 3-OCH$_3$ | Cl | F |
| A-3694. | CH$_2$F | CH$_3$ | 5-F | Cl | F |
| A-3695. | CH$_2$F | CH$_3$ | 5-CH$_3$ | Cl | F |
| A-3696. | CH$_2$F | CH$_3$ | 5-OCH$_3$ | Cl | F |
| A-3697. | CH$_2$F | OCH$_3$ | 3-F | Cl | F |
| A-3698. | CH$_2$F | OCH$_3$ | 3-CH$_3$ | Cl | F |
| A-3699. | CH$_2$F | OCH$_3$ | 3-OCH$_3$ | Cl | F |
| A-3700. | CH$_2$F | OCH$_3$ | 5-F | Cl | F |
| A-3701. | CH$_2$F | OCH$_3$ | 5-CH$_3$ | Cl | F |
| A-3702. | CH$_2$F | OCH$_3$ | 5-OCH$_3$ | Cl | F |
| A-3703. | CH$_2$F | CN | 3-F | Cl | F |
| A-3704. | CH$_2$F | CN | 3-CH$_3$ | Cl | F |
| A-3705. | CH$_2$F | CN | 3-OCH$_3$ | Cl | F |
| A-3706. | CH$_2$F | CN | 5-F | Cl | F |
| A-3707. | CH$_2$F | CN | 5-CH$_3$ | Cl | F |
| A-3708. | CH$_2$F | CN | 5-OCH$_3$ | Cl | F |
| A-3709. | CH$_2$F | CH$_2$F | 3-F | Cl | F |
| A-3710. | CH$_2$F | CH$_2$F | 3-CH$_3$ | Cl | F |
| A-3711. | CH$_2$F | CH$_2$F | 3-OCH$_3$ | Cl | F |
| A-3712. | CH$_2$F | CH$_2$F | 5-F | Cl | F |
| A-3713. | CH$_2$F | CH$_2$F | 5-CH$_3$ | Cl | F |
| A-3714. | CH$_2$F | CH$_2$F | 5-OCH$_3$ | Cl | F |
| A-3715. | CH$_2$F | CHF$_2$ | 3-F | Cl | F |
| A-3716. | CH$_2$F | CHF$_2$ | 3-CH$_3$ | Cl | F |
| A-3717. | CH$_2$F | CHF$_2$ | 3-OCH$_3$ | Cl | F |
| A-3718. | CH$_2$F | CHF$_2$ | 5-F | Cl | F |
| A-3719. | CH$_2$F | CHF$_2$ | 5-CH$_3$ | Cl | F |
| A-3720. | CH$_2$F | CHF$_2$ | 5-OCH$_3$ | Cl | F |
| A-3721. | CH$_2$F | CF$_3$ | 3-F | Cl | F |
| A-3722. | CH$_2$F | CF$_3$ | 3-CH$_3$ | Cl | F |
| A-3723. | CH$_2$F | CF$_3$ | 3-OCH$_3$ | Cl | F |
| A-3724. | CH$_2$F | CF$_3$ | 5-F | Cl | F |
| A-3725. | CH$_2$F | CF$_3$ | 5-CH$_3$ | Cl | F |
| A-3726. | CH$_2$F | CF$_3$ | 5-OCH$_3$ | Cl | F |
| A-3727. | CH$_2$F | OCH$_2$F | 3-F | Cl | F |
| A-3728. | CH$_2$F | OCH$_2$F | 3-CH$_3$ | Cl | F |
| A-3729. | CH$_2$F | OCH$_2$F | 3-OCH$_3$ | Cl | F |
| A-3730. | CH$_2$F | OCH$_2$F | 5-F | Cl | F |
| A-3731. | CH$_2$F | OCH$_2$F | 5-CH$_3$ | Cl | F |
| A-3732. | CH$_2$F | OCH$_2$F | 5-OCH$_3$ | Cl | F |
| A-3733. | CH$_2$F | OCHF$_2$ | 3-F | Cl | F |
| A-3734. | CH$_2$F | OCHF$_2$ | 3-CH$_3$ | Cl | F |
| A-3735. | CH$_2$F | OCHF$_2$ | 3-OCH$_3$ | Cl | F |
| A-3736. | CH$_2$F | OCHF$_2$ | 5-F | Cl | F |
| A-3737. | CH$_2$F | OCHF$_2$ | 5-CH$_3$ | Cl | F |
| A-3738. | CH$_2$F | OCHF$_2$ | 5-OCH$_3$ | Cl | F |
| A-3739. | CH$_2$F | OCF$_3$ | 3-F | Cl | F |
| A-3740. | CH$_2$F | OCF$_3$ | 3-CH$_3$ | Cl | F |
| A-3741. | CH$_2$F | OCF$_3$ | 3-OCH$_3$ | Cl | F |
| A-3742. | CH$_2$F | OCF$_3$ | 5-F | Cl | F |
| A-3743. | CH$_2$F | OCF$_3$ | 5-CH$_3$ | Cl | F |
| A-3744. | CH$_2$F | OCF$_3$ | 5-OCH$_3$ | Cl | F |
| A-3745. | CHF$_2$ | F | 3-F | Cl | F |
| A-3746. | CHF$_2$ | F | 3-CH$_3$ | Cl | F |
| A-3747. | CHF$_2$ | F | 3-OCH$_3$ | Cl | F |
| A-3748. | CHF$_2$ | F | 5-F | Cl | F |
| A-3749. | CHF$_2$ | F | 5-CH$_3$ | Cl | F |
| A-3750. | CHF$_2$ | F | 5-OCH$_3$ | Cl | F |
| A-3751. | CHF$_2$ | CH$_3$ | 3-F | Cl | F |
| A-3752. | CHF$_2$ | CH$_3$ | 3-CH$_3$ | Cl | F |
| A-3753. | CHF$_2$ | CH$_3$ | 3-OCH$_3$ | Cl | F |
| A-3754. | CHF$_2$ | CH$_3$ | 5-F | Cl | F |
| A-3755. | CHF$_2$ | CH$_3$ | 5-CH$_3$ | Cl | F |
| A-3756. | CHF$_2$ | CH$_3$ | 5-OCH$_3$ | Cl | F |
| A-3757. | CHF$_2$ | OCH$_3$ | 3-F | Cl | F |
| A-3758. | CHF$_2$ | OCH$_3$ | 3-CH$_3$ | Cl | F |
| A-3759. | CHF$_2$ | OCH$_3$ | 3-OCH$_3$ | Cl | F |
| A-3760. | CHF$_2$ | OCH$_3$ | 5-F | Cl | F |
| A-3761. | CHF$_2$ | OCH$_3$ | 5-CH$_3$ | Cl | F |
| A-3762. | CHF$_2$ | OCH$_3$ | 5-OCH$_3$ | Cl | F |
| A-3763. | CHF$_2$ | CN | 3-F | Cl | F |
| A-3764. | CHF$_2$ | CN | 3-CH$_3$ | Cl | F |
| A-3765. | CHF$_2$ | CN | 3-OCH$_3$ | Cl | F |
| A-3766. | CHF$_2$ | CN | 5-F | Cl | F |
| A-3767. | CHF$_2$ | CN | 5-CH$_3$ | Cl | F |
| A-3768. | CHF$_2$ | CN | 5-OCH$_3$ | Cl | F |
| A-3769. | CHF$_2$ | CH$_2$F | 3-F | Cl | F |
| A-3770. | CHF$_2$ | CH$_2$F | 3-CH$_3$ | Cl | F |
| A-3771. | CHF$_2$ | CH$_2$F | 3-OCH$_3$ | Cl | F |
| A-3772. | CHF$_2$ | CH$_2$F | 5-F | Cl | F |
| A-3773. | CHF$_2$ | CH$_2$F | 5-CH$_3$ | Cl | F |
| A-3774. | CHF$_2$ | CH$_2$F | 5-OCH$_3$ | Cl | F |
| A-3775. | CHF$_2$ | CHF$_2$ | 3-F | Cl | F |
| A-3776. | CHF$_2$ | CHF$_2$ | 3-CH$_3$ | Cl | F |
| A-3777. | CHF$_2$ | CHF$_2$ | 3-OCH$_3$ | Cl | F |
| A-3778. | CHF$_2$ | CHF$_2$ | 5-F | Cl | F |
| A-3779. | CHF$_2$ | CHF$_2$ | 5-CH$_3$ | Cl | F |
| A-3780. | CHF$_2$ | CHF$_2$ | 5-OCH$_3$ | Cl | F |
| A-3781. | CHF$_2$ | CF$_3$ | 3-F | Cl | F |
| A-3782. | CHF$_2$ | CF$_3$ | 3-CH$_3$ | Cl | F |
| A-3783. | CHF$_2$ | CF$_3$ | 3-OCH$_3$ | Cl | F |
| A-3784. | CHF$_2$ | CF$_3$ | 5-F | Cl | F |
| A-3785. | CHF$_2$ | CF$_3$ | 5-CH$_3$ | Cl | F |
| A-3786. | CHF$_2$ | CF$_3$ | 5-OCH$_3$ | Cl | F |
| A-3787. | CHF$_2$ | OCH$_2$F | 3-F | Cl | F |
| A-3788. | CHF$_2$ | OCH$_2$F | 3-CH$_3$ | Cl | F |
| A-3789. | CHF$_2$ | OCH$_2$F | 3-OCH$_3$ | Cl | F |
| A-3790. | CHF$_2$ | OCH$_2$F | 5-F | Cl | F |
| A-3791. | CHF$_2$ | OCH$_2$F | 5-CH$_3$ | Cl | F |
| A-3792. | CHF$_2$ | OCH$_2$F | 5-OCH$_3$ | Cl | F |
| A-3793. | CHF$_2$ | OCHF$_2$ | 3-F | Cl | F |
| A-3794. | CHF$_2$ | OCHF$_2$ | 3-CH$_3$ | Cl | F |
| A-3795. | CHF$_2$ | OCHF$_2$ | 3-OCH$_3$ | Cl | F |
| A-3796. | CHF$_2$ | OCHF$_2$ | 5-F | Cl | F |
| A-3797. | CHF$_2$ | OCHF$_2$ | 5-CH$_3$ | Cl | F |
| A-3798. | CHF$_2$ | OCHF$_2$ | 5-OCH$_3$ | Cl | F |
| A-3799. | CHF$_2$ | OCF$_3$ | 3-F | Cl | F |
| A-3800. | CHF$_2$ | OCF$_3$ | 3-CH$_3$ | Cl | F |
| A-3801. | CHF$_2$ | OCF$_3$ | 3-OCH$_3$ | Cl | F |
| A-3802. | CHF$_2$ | OCF$_3$ | 5-F | Cl | F |
| A-3803. | CHF$_2$ | OCF$_3$ | 5-CH$_3$ | Cl | F |
| A-3804. | CHF$_2$ | OCF$_3$ | 5-OCH$_3$ | Cl | F |
| A-3805. | CF$_3$ | F | 3-F | Cl | F |
| A-3806. | CF$_3$ | F | 3-CH$_3$ | Cl | F |
| A-3807. | CF$_3$ | F | 3-OCH$_3$ | Cl | F |
| A-3808. | CF$_3$ | F | 5-F | Cl | F |
| A-3809. | CF$_3$ | F | 5-CH$_3$ | Cl | F |
| A-3810. | CF$_3$ | F | 5-OCH$_3$ | Cl | F |
| A-3811. | CF$_3$ | CH$_3$ | 3-F | Cl | F |
| A-3812. | CF$_3$ | CH$_3$ | 3-CH$_3$ | Cl | F |
| A-3813. | CF$_3$ | CH$_3$ | 3-OCH$_3$ | Cl | F |
| A-3814. | CF$_3$ | CH$_3$ | 5-F | Cl | F |
| A-3815. | CF$_3$ | CH$_3$ | 5-CH$_3$ | Cl | F |
| A-3816. | CF$_3$ | CH$_3$ | 5-OCH$_3$ | Cl | F |
| A-3817. | CF$_3$ | OCH$_3$ | 3-F | Cl | F |

TABLE A-continued

| Example No. | R¹ | R² | R³ | R⁶ | R⁷ |
|---|---|---|---|---|---|
| A-3818. | CF₃ | OCH₃ | 3-CH₃ | Cl | F |
| A-3819. | CF₃ | OCH₃ | 3-OCH₃ | Cl | F |
| A-3820. | CF₃ | OCH₃ | 5-F | Cl | F |
| A-3821. | CF₃ | OCH₃ | 5-CH₃ | Cl | F |
| A-3822. | CF₃ | OCH₃ | 5-OCH₃ | Cl | F |
| A-3823. | CF₃ | CN | 3-F | Cl | F |
| A-3824. | CF₃ | CN | 3-CH₃ | Cl | F |
| A-3825. | CF₃ | CN | 3-OCH₃ | Cl | F |
| A-3826. | CF₃ | CN | 5-F | Cl | F |
| A-3827. | CF₃ | CN | 5-CH₃ | Cl | F |
| A-3828. | CF₃ | CN | 5-OCH₃ | Cl | F |
| A-3829. | CF₃ | CH₂F | 3-F | Cl | F |
| A-3830. | CF₃ | CH₂F | 3-CH₃ | Cl | F |
| A-3831. | CF₃ | CH₂F | 3-OCH₃ | Cl | F |
| A-3832. | CF₃ | CH₂F | 5-F | Cl | F |
| A-3833. | CF₃ | CH₂F | 5-CH₃ | Cl | F |
| A-3834. | CF₃ | CH₂F | 5-OCH₃ | Cl | F |
| A-3835. | CF₃ | CHF₂ | 3-F | Cl | F |
| A-3836. | CF₃ | CHF₂ | 3-CH₃ | Cl | F |
| A-3837. | CF₃ | CHF₂ | 3-OCH₃ | Cl | F |
| A-3838. | CF₃ | CHF₂ | 5-F | Cl | F |
| A-3839. | CF₃ | CHF₂ | 5-CH₃ | Cl | F |
| A-3840. | CF₃ | CHF₂ | 5-OCH₃ | Cl | F |
| A-3841. | CF₃ | CF₃ | 3-F | Cl | F |
| A-3842. | CF₃ | CF₃ | 3-CH₃ | Cl | F |
| A-3843. | CF₃ | CF₃ | 3-OCH₃ | Cl | F |
| A-3844. | CF₃ | CF₃ | 5-F | Cl | F |
| A-3845. | CF₃ | CF₃ | 5-CH₃ | Cl | F |
| A-3846. | CF₃ | CF₃ | 5-OCH₃ | Cl | F |
| A-3847. | CF₃ | OCH₂F | 3-F | Cl | F |
| A-3848. | CF₃ | OCH₂F | 3-CH₃ | Cl | F |
| A-3849. | CF₃ | OCH₂F | 3-OCH₃ | Cl | F |
| A-3850. | CF₃ | OCH₂F | 5-F | Cl | F |
| A-3851. | CF₃ | OCH₂F | 5-CH₃ | Cl | F |
| A-3852. | CF₃ | OCH₂F | 5-OCH₃ | Cl | F |
| A-3853. | CF₃ | OCHF₂ | 3-F | Cl | F |
| A-3854. | CF₃ | OCHF₂ | 3-CH₃ | Cl | F |
| A-3855. | CF₃ | OCHF₂ | 3-OCH₃ | Cl | F |
| A-3856. | CF₃ | OCHF₂ | 5-F | Cl | F |
| A-3857. | CF₃ | OCHF₂ | 5-CH₃ | Cl | F |
| A-3858. | CF₃ | OCHF₂ | 5-OCH₃ | Cl | F |
| A-3859. | CF₃ | OCF₃ | 3-F | Cl | F |
| A-3860. | CF₃ | OCF₃ | 3-CH₃ | Cl | F |
| A-3861. | CF₃ | OCF₃ | 3-OCH₃ | Cl | F |
| A-3862. | CF₃ | OCF₃ | 5-F | Cl | F |
| A-3863. | CF₃ | OCF₃ | 5-CH₃ | Cl | F |
| A-3864. | CF₃ | OCF₃ | 5-OCH₃ | Cl | F |
| A-3865. | OCH₂F | F | 3-F | Cl | F |
| A-3866. | OCH₂F | F | 3-CH₃ | Cl | F |
| A-3867. | OCH₂F | F | 3-OCH₃ | Cl | F |
| A-3868. | OCH₂F | F | 5-F | Cl | F |
| A-3869. | OCH₂F | F | 5-CH₃ | Cl | F |
| A-3870. | OCH₂F | F | 5-OCH₃ | Cl | F |
| A-3871. | OCH₂F | CH₃ | 3-F | Cl | F |
| A-3872. | OCH₂F | CH₃ | 3-CH₃ | Cl | F |
| A-3873. | OCH₂F | CH₃ | 3-OCH₃ | Cl | F |
| A-3874. | OCH₂F | CH₃ | 5-F | Cl | F |
| A-3875. | OCH₂F | CH₃ | 5-CH₃ | Cl | F |
| A-3876. | OCH₂F | CH₃ | 5-OCH₃ | Cl | F |
| A-3877. | OCH₂F | OCH₃ | 3-F | Cl | F |
| A-3878. | OCH₂F | OCH₃ | 3-CH₃ | Cl | F |
| A-3879. | OCH₂F | OCH₃ | 3-OCH₃ | Cl | F |
| A-3880. | OCH₂F | OCH₃ | 5-F | Cl | F |
| A-3881. | OCH₂F | OCH₃ | 5-CH₃ | Cl | F |
| A-3882. | OCH₂F | OCH₃ | 5-OCH₃ | Cl | F |
| A-3883. | OCH₂F | CN | 3-F | Cl | F |
| A-3884. | OCH₂F | CN | 3-CH₃ | Cl | F |
| A-3885. | OCH₂F | CN | 3-OCH₃ | Cl | F |
| A-3886. | OCH₂F | CN | 5-F | Cl | F |
| A-3887. | OCH₂F | CN | 5-CH₃ | Cl | F |
| A-3888. | OCH₂F | CN | 5-OCH₃ | Cl | F |
| A-3889. | OCH₂F | CH₂F | 3-F | Cl | F |
| A-3890. | OCH₂F | CH₂F | 3-CH₃ | Cl | F |
| A-3891. | OCH₂F | CH₂F | 3-OCH₃ | Cl | F |
| A-3892. | OCH₂F | CH₂F | 5-F | Cl | F |
| A-3893. | OCH₂F | CH₂F | 5-CH₃ | Cl | F |
| A-3894. | OCH₂F | CH₂F | 5-OCH₃ | Cl | F |
| A-3895. | OCH₂F | CHF₂ | 3-F | Cl | F |
| A-3896. | OCH₂F | CHF₂ | 3-CH₃ | Cl | F |
| A-3897. | OCH₂F | CHF₂ | 3-OCH₃ | Cl | F |
| A-3898. | OCH₂F | CHF₂ | 5-F | Cl | F |
| A-3899. | OCH₂F | CHF₂ | 5-CH₃ | Cl | F |
| A-3900. | OCH₂F | CHF₂ | 5-OCH₃ | Cl | F |
| A-3901. | OCH₂F | CF₃ | 3-F | Cl | F |
| A-3902. | OCH₂F | CF₃ | 3-CH₃ | Cl | F |
| A-3903. | OCH₂F | CF₃ | 3-OCH₃ | Cl | F |
| A-3904. | OCH₂F | CF₃ | 5-F | Cl | F |
| A-3905. | OCH₂F | CF₃ | 5-CH₃ | Cl | F |
| A-3906. | OCH₂F | CF₃ | 5-OCH₃ | Cl | F |
| A-3907. | OCH₂F | OCH₂F | 3-F | Cl | F |
| A-3908. | OCH₂F | OCH₂F | 3-CH₃ | Cl | F |
| A-3909. | OCH₂F | OCH₂F | 3-OCH₃ | Cl | F |
| A-3910. | OCH₂F | OCH₂F | 5-F | Cl | F |
| A-3911. | OCH₂F | OCH₂F | 5-CH₃ | Cl | F |
| A-3912. | OCH₂F | OCH₂F | 5-OCH₃ | Cl | F |
| A-3913. | OCH₂F | OCHF₂ | 3-F | Cl | F |
| A-3914. | OCH₂F | OCHF₂ | 3-CH₃ | Cl | F |
| A-3915. | OCH₂F | OCHF₂ | 3-OCH₃ | Cl | F |
| A-3916. | OCH₂F | OCHF₂ | 5-F | Cl | F |
| A-3917. | OCH₂F | OCHF₂ | 5-CH₃ | Cl | F |
| A-3918. | OCH₂F | OCHF₂ | 5-OCH₃ | Cl | F |
| A-3919. | OCH₂F | OCF₃ | 3-F | Cl | F |
| A-3920. | OCH₂F | OCF₃ | 3-CH₃ | Cl | F |
| A-3921. | OCH₂F | OCF₃ | 3-OCH₃ | Cl | F |
| A-3922. | OCH₂F | OCF₃ | 5-F | Cl | F |
| A-3923. | OCH₂F | OCF₃ | 5-CH₃ | Cl | F |
| A-3924. | OCH₂F | OCF₃ | 5-OCH₃ | Cl | F |
| A-3925. | OCHF₂ | F | 3-F | Cl | F |
| A-3926. | OCHF₂ | F | 3-CH₃ | Cl | F |
| A-3927. | OCHF₂ | F | 3-OCH₃ | Cl | F |
| A-3928. | OCHF₂ | F | 5-F | Cl | F |
| A-3929. | OCHF₂ | F | 5-CH₃ | Cl | F |
| A-3930. | OCHF₂ | F | 5-OCH₃ | Cl | F |
| A-3931. | OCHF₂ | CH₃ | 3-F | Cl | F |
| A-3932. | OCHF₂ | CH₃ | 3-CH₃ | Cl | F |
| A-3933. | OCHF₂ | CH₃ | 3-OCH₃ | Cl | F |
| A-3934. | OCHF₂ | CH₃ | 5-F | Cl | F |
| A-3935. | OCHF₂ | CH₃ | 5-CH₃ | Cl | F |
| A-3936. | OCHF₂ | CH₃ | 5-OCH₃ | Cl | F |
| A-3937. | OCHF₂ | OCH₃ | 3-F | Cl | F |
| A-3938. | OCHF₂ | OCH₃ | 3-CH₃ | Cl | F |
| A-3939. | OCHF₂ | OCH₃ | 3-OCH₃ | Cl | F |
| A-3940. | OCHF₂ | OCH₃ | 5-F | Cl | F |
| A-3941. | OCHF₂ | OCH₃ | 5-CH₃ | Cl | F |
| A-3942. | OCHF₂ | OCH₃ | 5-OCH₃ | Cl | F |
| A-3943. | OCHF₂ | CN | 3-F | Cl | F |
| A-3944. | OCHF₂ | CN | 3-CH₃ | Cl | F |
| A-3945. | OCHF₂ | CN | 3-OCH₃ | Cl | F |
| A-3946. | OCHF₂ | CN | 5-F | Cl | F |
| A-3947. | OCHF₂ | CN | 5-CH₃ | Cl | F |
| A-3948. | OCHF₂ | CN | 5-OCH₃ | Cl | F |
| A-3949. | OCHF₂ | CH₂F | 3-F | Cl | F |
| A-3950. | OCHF₂ | CH₂F | 3-CH₃ | Cl | F |
| A-3951. | OCHF₂ | CH₂F | 3-OCH₃ | Cl | F |
| A-3952. | OCHF₂ | CH₂F | 5-F | Cl | F |
| A-3953. | OCHF₂ | CH₂F | 5-CH₃ | Cl | F |
| A-3954. | OCHF₂ | CH₂F | 5-OCH₃ | Cl | F |
| A-3955. | OCHF₂ | CHF₂ | 3-F | Cl | F |
| A-3956. | OCHF₂ | CHF₂ | 3-CH₃ | Cl | F |
| A-3957. | OCHF₂ | CHF₂ | 3-OCH₃ | Cl | F |
| A-3958. | OCHF₂ | CHF₂ | 5-F | Cl | F |
| A-3959. | OCHF₂ | CHF₂ | 5-CH₃ | Cl | F |
| A-3960. | OCHF₂ | CHF₂ | 5-OCH₃ | Cl | F |
| A-3961. | OCHF₂ | CF₃ | 3-F | Cl | F |
| A-3962. | OCHF₂ | CF₃ | 3-CH₃ | Cl | F |
| A-3963. | OCHF₂ | CF₃ | 3-OCH₃ | Cl | F |
| A-3964. | OCHF₂ | CF₃ | 5-F | Cl | F |
| A-3965. | OCHF₂ | CF₃ | 5-CH₃ | Cl | F |
| A-3966. | OCHF₂ | CF₃ | 5-OCH₃ | Cl | F |
| A-3967. | OCHF₂ | OCH₂F | 3-F | Cl | F |
| A-3968. | OCHF₂ | OCH₂F | 3-CH₃ | Cl | F |
| A-3969. | OCHF₂ | OCH₂F | 3-OCH₃ | Cl | F |
| A-3970. | OCHF₂ | OCH₂F | 5-F | Cl | F |
| A-3971. | OCHF₂ | OCH₂F | 5-CH₃ | Cl | F |
| A-3972. | OCHF₂ | OCH₂F | 5-OCH₃ | Cl | F |
| A-3973. | OCHF₂ | OCHF₂ | 3-F | Cl | F |

TABLE A-continued

| Example No. | R¹ | R² | R³ | R⁶ | R⁷ |
|---|---|---|---|---|---|
| A-3974. | OCHF₂ | OCHF₂ | 3-CH₃ | Cl | F |
| A-3975. | OCHF₂ | OCHF₂ | 3-OCH₃ | Cl | F |
| A-3976. | OCHF₂ | OCHF₂ | 5-F | Cl | F |
| A-3977. | OCHF₂ | OCHF₂ | 5-CH₃ | Cl | F |
| A-3978. | OCHF₂ | OCHF₂ | 5-OCH₃ | Cl | F |
| A-3979. | OCHF₂ | OCF₃ | 3-F | Cl | F |
| A-3980. | OCHF₂ | OCF₃ | 3-CH₃ | Cl | F |
| A-3981. | OCHF₂ | OCF₃ | 3-OCH₃ | Cl | F |
| A-3982. | OCHF₂ | OCF₃ | 5-F | Cl | F |
| A-3983. | OCHF₂ | OCF₃ | 5-CH₃ | Cl | F |
| A-3984. | OCHF₂ | OCF₃ | 5-OCH₃ | Cl | F |
| A-3985. | OCF₃ | F | 3-F | Cl | F |
| A-3986. | OCF₃ | F | 3-CH₃ | Cl | F |
| A-3987. | OCF₃ | F | 3-OCH₃ | Cl | F |
| A-3988. | OCF₃ | F | 5-F | Cl | F |
| A-3989. | OCF₃ | F | 5-CH₃ | Cl | F |
| A-3990. | OCF₃ | F | 5-OCH₃ | Cl | F |
| A-3991. | OCF₃ | CH₃ | 3-F | Cl | F |
| A-3992. | OCF₃ | CH₃ | 3-CH₃ | Cl | F |
| A-3993. | OCF₃ | CH₃ | 3-OCH₃ | Cl | F |
| A-3994. | OCF₃ | CH₃ | 5-F | Cl | F |
| A-3995. | OCF₃ | CH₃ | 5-CH₃ | Cl | F |
| A-3996. | OCF₃ | CH₃ | 5-OCH₃ | Cl | F |
| A-3997. | OCF₃ | OCH₃ | 3-F | Cl | F |
| A-3998. | OCF₃ | OCH₃ | 3-CH₃ | Cl | F |
| A-3999. | OCF₃ | OCH₃ | 3-OCH₃ | Cl | F |
| A-4000. | OCF₃ | OCH₃ | 5-F | Cl | F |
| A-4001. | OCF₃ | OCH₃ | 5-CH₃ | Cl | F |
| A-4002. | OCF₃ | OCH₃ | 5-OCH₃ | Cl | F |
| A-4003. | OCF₃ | CN | 3-F | Cl | F |
| A-4004. | OCF₃ | CN | 3-CH₃ | Cl | F |
| A-4005. | OCF₃ | CN | 3-OCH₃ | Cl | F |
| A-4006. | OCF₃ | CN | 5-F | Cl | F |
| A-4007. | OCF₃ | CN | 5-CH₃ | Cl | F |
| A-4008. | OCF₃ | CN | 5-OCH₃ | Cl | F |
| A-4009. | OCF₃ | CH₂F | 3-F | Cl | F |
| A-4010. | OCF₃ | CH₂F | 3-CH₃ | Cl | F |
| A-4011. | OCF₃ | CH₂F | 3-OCH₃ | Cl | F |
| A-4012. | OCF₃ | CH₂F | 5-F | Cl | F |
| A-4013. | OCF₃ | CH₂F | 5-CH₃ | Cl | F |
| A-4014. | OCF₃ | CH₂F | 5-OCH₃ | Cl | F |
| A-4015. | OCF₃ | CHF₂ | 3-F | Cl | F |
| A-4016. | OCF₃ | CHF₂ | 3-CH₃ | Cl | F |
| A-4017. | OCF₃ | CHF₂ | 3-OCH₃ | Cl | F |
| A-4018. | OCF₃ | CHF₂ | 5-F | Cl | F |
| A-4019. | OCF₃ | CHF₂ | 5-CH₃ | Cl | F |
| A-4020. | OCF₃ | CHF₂ | 5-OCH₃ | Cl | F |
| A-4021. | OCF₃ | CF₃ | 3-F | Cl | F |
| A-4022. | OCF₃ | CF₃ | 3-CH₃ | Cl | F |
| A-4023. | OCF₃ | CF₃ | 3-OCH₃ | Cl | F |
| A-4024. | OCF₃ | CF₃ | 5-F | Cl | F |
| A-4025. | OCF₃ | CF₃ | 5-CH₃ | Cl | F |
| A-4026. | OCF₃ | CF₃ | 5-OCH₃ | Cl | F |
| A-4027. | OCF₃ | OCH₂F | 3-F | Cl | F |
| A-4028. | OCF₃ | OCH₂F | 3-CH₃ | Cl | F |
| A-4029. | OCF₃ | OCH₂F | 3-OCH₃ | Cl | F |
| A-4030. | OCF₃ | OCH₂F | 5-F | Cl | F |
| A-4031. | OCF₃ | OCH₂F | 5-CH₃ | Cl | F |
| A-4032. | OCF₃ | OCH₂F | 5-OCH₃ | Cl | F |
| A-4033. | OCF₃ | OCHF₂ | 3-F | Cl | F |
| A-4034. | OCF₃ | OCHF₂ | 3-CH₃ | Cl | F |
| A-4035. | OCF₃ | OCHF₂ | 3-OCH₃ | Cl | F |
| A-4036. | OCF₃ | OCHF₂ | 5-F | Cl | F |
| A-4037. | OCF₃ | OCHF₂ | 5-CH₃ | Cl | F |
| A-4038. | OCF₃ | OCHF₂ | 5-OCH₃ | Cl | F |
| A-4039. | OCF₃ | OCF₃ | 3-F | Cl | F |
| A-4040. | OCF₃ | OCF₃ | 3-CH₃ | Cl | F |
| A-4041. | OCF₃ | OCF₃ | 3-OCH₃ | Cl | F |
| A-4042. | OCF₃ | OCF₃ | 5-F | Cl | F |
| A-4043. | OCF₃ | OCF₃ | 5-CH₃ | Cl | F |
| A-4044. | OCF₃ | OCF₃ | 5-OCH₃ | Cl | F |

TABLE B

| Example No. | R² | R³ | R⁶ | R⁷ |
|---|---|---|---|---|
| B-1. | H | H | CN | H |
| B-2. | F | H | CN | H |
| B-3. | CH₃ | H | CN | H |
| B-4. | OCH₃ | H | CN | H |
| B-5. | CN | H | CN | H |
| B-6. | CH₂F | H | CN | H |
| B-7. | CHF₂ | H | CN | H |
| B-8. | CF₃ | H | CN | H |
| B-9. | OCH₂F | H | CN | H |
| B-10. | OCHF₂ | H | CN | H |
| B-11. | OCF₃ | H | CN | H |
| B-12. | H | 3-F | CN | H |
| B-13. | H | 3-CH₃ | CN | H |
| B-14. | H | 3-OCH₃ | CN | H |
| B-15. | H | 5-F | CN | H |
| B-16. | H | 5-CH₃ | CN | H |
| B-17. | H | 5-OCH₃ | CN | H |
| B-18. | H | 6-F | CN | H |
| B-19. | H | 6-CH₃ | CN | H |
| B-20. | H | 6-OCH₃ | CN | H |
| B-21. | F | 3-F | CN | H |
| B-22. | F | 3-CH₃ | CN | H |
| B-23. | F | 3-OCH₃ | CN | H |
| B-24. | F | 5-F | CN | H |
| B-25. | F | 5-CH₃ | CN | H |
| B-26. | F | 5-OCH₃ | CN | H |
| B-27. | F | 6-F | CN | H |
| B-28. | F | 6-CH₃ | CN | H |
| B-29. | F | 6-OCH₃ | CN | H |
| B-30. | CH₃ | 3-F | CN | H |
| B-31. | CH₃ | 3-CH₃ | CN | H |
| B-32. | CH₃ | 3-OCH₃ | CN | H |
| B-33. | CH₃ | 5-F | CN | H |
| B-34. | CH₃ | 5-CH₃ | CN | H |
| B-35. | CH₃ | 5-OCH₃ | CN | H |
| B-36. | CH₃ | 6-F | CN | H |
| B-37. | CH₃ | 6-CH₃ | CN | H |
| B-38. | CH₃ | 6-OCH₃ | CN | H |
| B-39. | OCH₃ | 3-F | CN | H |
| B-40. | OCH₃ | 3-CH₃ | CN | H |
| B-41. | OCH₃ | 3-OCH₃ | CN | H |
| B-42. | OCH₃ | 5-F | CN | H |
| B-43. | OCH₃ | 5-CH₃ | CN | H |
| B-44. | OCH₃ | 5-OCH₃ | CN | H |
| B-45. | OCH₃ | 6-F | CN | H |
| B-46. | OCH₃ | 6-CH₃ | CN | H |
| B-47. | OCH₃ | 6-OCH₃ | CN | H |
| B-48. | CN | 3-F | CN | H |
| B-49. | CN | 3-CH₃ | CN | H |
| B-50. | CN | 3-OCH₃ | CN | H |
| B-51. | CN | 5-F | CN | H |
| B-52. | CN | 5-CH₃ | CN | H |
| B-53. | CN | 5-OCH₃ | CN | H |
| B-54. | CN | 6-F | CN | H |
| B-55. | CN | 6-CH₃ | CN | H |
| B-56. | CN | 6-OCH₃ | CN | H |
| B-57. | CH₂F | 3-F | CN | H |
| B-58. | CH₂F | 3-CH₃ | CN | H |
| B-59. | CH₂F | 3-OCH₃ | CN | H |
| B-60. | CH₂F | 5-F | CN | H |
| B-61. | CH₂F | 5-CH₃ | CN | H |
| B-62. | CH₂F | 5-OCH₃ | CN | H |
| B-63. | CH₂F | 6-F | CN | H |
| B-64. | CH₂F | 6-CH₃ | CN | H |
| B-65. | CH₂F | 6-OCH₃ | CN | H |
| B-66. | CHF₂ | 3-F | CN | H |
| B-67. | CHF₂ | 3-CH₃ | CN | H |
| B-68. | CHF₂ | 3-OCH₃ | CN | H |
| B-69. | CHF₂ | 5-F | CN | H |
| B-70. | CHF₂ | 5-CH₃ | CN | H |
| B-71. | CHF₂ | 5-OCH₃ | CN | H |
| B-72. | CHF₂ | 6-F | CN | H |
| B-73. | CHF₂ | 6-CH₃ | CN | H |
| B-74. | CHF₂ | 6-OCH₃ | CN | H |
| B-75. | CF₃ | 3-F | CN | H |
| B-76. | CF₃ | 3-CH₃ | CN | H |
| B-77. | CF₃ | 3-OCH₃ | CN | H |
| B-78. | CF₃ | 5-F | CN | H |

TABLE B-continued

| Example No. | R² | R³ | R⁶ | R⁷ |
|---|---|---|---|---|
| B-79. | CF₃ | 5-CH₃ | CN | H |
| B-80. | CF₃ | 5-OCH₃ | CN | H |
| B-81. | CF₃ | 6-F | CN | H |
| B-82. | CF₃ | 6-CH₃ | CN | H |
| B-83. | CF₃ | 6-OCH₃ | CN | H |
| B-84. | OCH₂F | 3-F | CN | H |
| B-85. | OCH₂F | 3-CH₃ | CN | H |
| B-86. | OCH₂F | 3-OCH₃ | CN | H |
| B-87. | OCH₂F | 5-F | CN | H |
| B-88. | OCH₂F | 5-CH₃ | CN | H |
| B-89. | OCH₂F | 5-OCH₃ | CN | H |
| B-90. | OCH₂F | 6-F | CN | H |
| B-91. | OCH₂F | 6-CH₃ | CN | H |
| B-92. | OCH₂F | 6-OCH₃ | CN | H |
| B-93. | OCHF₂ | 3-F | CN | H |
| B-94. | OCHF₂ | 3-CH₃ | CN | H |
| B-95. | OCHF₂ | 3-OCH₃ | CN | H |
| B-96. | OCHF₂ | 5-F | CN | H |
| B-97. | OCHF₂ | 5-CH₃ | CN | H |
| B-98. | OCHF₂ | 5-OCH₃ | CN | H |
| B-99. | OCHF₂ | 6-F | CN | H |
| B-100. | OCHF₂ | 6-CH₃ | CN | H |
| B-101. | OCHF₂ | 6-OCH₃ | CN | H |
| B-102. | OCF₃ | 3-F | CN | H |
| B-103. | OCF₃ | 3-CH₃ | CN | H |
| B-104. | OCF₃ | 3-OCH₃ | CN | H |
| B-105. | OCF₃ | 5-F | CN | H |
| B-106. | OCF₃ | 5-CH₃ | CN | H |
| B-107. | OCF₃ | 5-OCH₃ | CN | H |
| B-108. | OCF₃ | 6-F | CN | H |
| B-109. | OCF₃ | 6-CH₃ | CN | H |
| B-110. | OCF₃ | 6-OCH₃ | CN | H |
| B-111. | H | H | F | H |
| B-112. | F | H | F | H |
| B-113. | CH₃ | H | F | H |
| B-114. | OCH₃ | H | F | H |
| B-115. | CN | H | F | H |
| B-116. | CH₂F | H | F | H |
| B-117. | CHF₂ | H | F | H |
| B-118. | CF₃ | H | F | H |
| B-119. | OCH₂F | H | F | H |
| B-120. | OCHF₂ | H | F | H |
| B-121. | OCF₃ | H | F | H |
| B-122. | H | 3-F | F | H |
| B-123. | H | 3-CH₃ | F | H |
| B-124. | H | 3-OCH₃ | F | H |
| B-125. | H | 5-F | F | H |
| B-126. | H | 5-CH₃ | F | H |
| B-127. | H | 5-OCH₃ | F | H |
| B-128. | H | 6-F | F | H |
| B-129. | H | 6-CH₃ | F | H |
| B-130. | H | 6-OCH₃ | F | H |
| B-131. | F | 3-F | F | H |
| B-132. | F | 3-CH₃ | F | H |
| B-133. | F | 3-OCH₃ | F | H |
| B-134. | F | 5-F | F | H |
| B-135. | F | 5-CH₃ | F | H |
| B-136. | F | 5-OCH₃ | F | H |
| B-137. | F | 6-F | F | H |
| B-138. | F | 6-CH₃ | F | H |
| B-139. | F | 6-OCH₃ | F | H |
| B-140. | CH₃ | 3-F | F | H |
| B-141. | CH₃ | 3-CH₃ | F | H |
| B-142. | CH₃ | 3-OCH₃ | F | H |
| B-143. | CH₃ | 5-F | F | H |
| B-144. | CH₃ | 5-CH₃ | F | H |
| B-145. | CH₃ | 5-OCH₃ | F | H |
| B-146. | CH₃ | 6-F | F | H |
| B-147. | CH₃ | 6-CH₃ | F | H |
| B-148. | CH₃ | 6-OCH₃ | F | H |
| B-149. | OCH₃ | 3-F | F | H |
| B-150. | OCH₃ | 3-CH₃ | F | H |
| B-151. | OCH₃ | 3-OCH₃ | F | H |
| B-152. | OCH₃ | 5-F | F | H |
| B-153. | OCH₃ | 5-CH₃ | F | H |
| B-154. | OCH₃ | 5-OCH₃ | F | H |
| B-155. | OCH₃ | 6-F | F | H |
| B-156. | OCH₃ | 6-CH₃ | F | H |
| B-157. | OCH₃ | 6-OCH₃ | F | H |
| B-158. | CN | 3-F | F | H |
| B-159. | CN | 3-CH₃ | F | H |
| B-160. | CN | 3-OCH₃ | F | H |
| B-161. | CN | 5-F | F | H |
| B-162. | CN | 5-CH₃ | F | H |
| B-163. | CN | 5-OCH₃ | F | H |
| B-164. | CN | 6-F | F | H |
| B-165. | CN | 6-CH₃ | F | H |
| B-166. | CN | 6-OCH₃ | F | H |
| B-167. | CH₂F | 3-F | F | H |
| B-168. | CH₂F | 3-CH₃ | F | H |
| B-169. | CH₂F | 3-OCH₃ | F | H |
| B-170. | CH₂F | 5-F | F | H |
| B-171. | CH₂F | 5-CH₃ | F | H |
| B-172. | CH₂F | 5-OCH₃ | F | H |
| B-173. | CH₂F | 6-F | F | H |
| B-174. | CH₂F | 6-CH₃ | F | H |
| B-175. | CH₂F | 6-OCH₃ | F | H |
| B-176. | CHF₂ | 3-F | F | H |
| B-177. | CHF₂ | 3-CH₃ | F | H |
| B-178. | CHF₂ | 3-OCH₃ | F | H |
| B-179. | CHF₂ | 5-F | F | H |
| B-180. | CHF₂ | 5-CH₃ | F | H |
| B-181. | CHF₂ | 5-OCH₃ | F | H |
| B-182. | CHF₂ | 6-F | F | H |
| B-183. | CHF₂ | 6-CH₃ | F | H |
| B-184. | CHF₂ | 6-OCH₃ | F | H |
| B-185. | CF₃ | 3-F | F | H |
| B-186. | CF₃ | 3-CH₃ | F | H |
| B-187. | CF₃ | 3-OCH₃ | F | H |
| B-188. | CF₃ | 5-F | F | H |
| B-189. | CF₃ | 5-CH₃ | F | H |
| B-190. | CF₃ | 5-OCH₃ | F | H |
| B-191. | CF₃ | 6-F | F | H |
| B-192. | CF₃ | 6-CH₃ | F | H |
| B-193. | CF₃ | 6-OCH₃ | F | H |
| B-194. | OCH₂F | 3-F | F | H |
| B-195. | OCH₂F | 3-CH₃ | F | H |
| B-196. | OCH₂F | 3-OCH₃ | F | H |
| B-197. | OCH₂F | 5-F | F | H |
| B-198. | OCH₂F | 5-CH₃ | F | H |
| B-199. | OCH₂F | 5-OCH₃ | F | H |
| B-200. | OCH₂F | 6-F | F | H |
| B-201. | OCH₂F | 6-CH₃ | F | H |
| B-202. | OCH₂F | 6-OCH₃ | F | H |
| B-203. | OCHF₂ | 3-F | F | H |
| B-204. | OCHF₂ | 3-CH₃ | F | H |
| B-205. | OCHF₂ | 3-OCH₃ | F | H |
| B-206. | OCHF₂ | 5-F | F | H |
| B-207. | OCHF₂ | 5-CH₃ | F | H |
| B-208. | OCHF₂ | 5-OCH₃ | F | H |
| B-209. | OCHF₂ | 6-F | F | H |
| B-210. | OCHF₂ | 6-CH₃ | F | H |
| B-211. | OCHF₂ | 6-OCH₃ | F | H |
| B-212. | OCF₃ | 3-F | F | H |
| B-213. | OCF₃ | 3-CH₃ | F | H |
| B-214. | OCF₃ | 3-OCH₃ | F | H |
| B-215. | OCF₃ | 5-F | F | H |
| B-216. | OCF₃ | 5-CH₃ | F | H |
| B-217. | OCF₃ | 5-OCH₃ | F | H |
| B-218. | OCF₃ | 6-F | F | H |
| B-219. | OCF₃ | 6-CH₃ | F | H |
| B-220. | OCF₃ | 6-OCH₃ | F | H |
| B-221. | H | H | Cl | H |
| B-222. | F | H | Cl | H |
| B-223. | CH₃ | H | Cl | H |
| B-224. | OCH₃ | H | Cl | H |
| B-225. | CN | H | Cl | H |
| B-226. | CH₂F | H | Cl | H |
| B-227. | CHF₂ | H | Cl | H |
| B-228. | CF₃ | H | Cl | H |
| B-229. | OCH₂F | H | Cl | H |
| B-230. | OCHF₂ | H | Cl | H |
| B-231. | OCF₃ | H | Cl | H |
| B-232. | H | 3-F | Cl | H |
| B-233. | H | 3-CH₃ | Cl | H |
| B-234. | H | 3-OCH₃ | Cl | H |

TABLE B-continued

| Example No. | R² | R³ | R⁶ | R⁷ |
|---|---|---|---|---|
| B-235. | H | 5-F | Cl | H |
| B-236. | H | 5-CH₃ | Cl | H |
| B-237. | H | 5-OCH₃ | Cl | H |
| B-238. | H | 6-F | Cl | H |
| B-239. | H | 6-CH₃ | Cl | H |
| B-240. | H | 6-OCH₃ | Cl | H |
| B-241. | F | 3-F | Cl | H |
| B-242. | F | 3-CH₃ | Cl | H |
| B-243. | F | 3-OCH₃ | Cl | H |
| B-244. | F | 5-F | Cl | H |
| B-245. | F | 5-CH₃ | Cl | H |
| B-246. | F | 5-OCH₃ | Cl | H |
| B-247. | F | 6-F | Cl | H |
| B-248. | F | 6-CH₃ | Cl | H |
| B-249. | F | 6-OCH₃ | Cl | H |
| B-250. | CH₃ | 3-F | Cl | H |
| B-251. | CH₃ | 3-CH₃ | Cl | H |
| B-252. | CH₃ | 3-OCH₃ | Cl | H |
| B-253. | CH₃ | 5-F | Cl | H |
| B-254. | CH₃ | 5-CH₃ | Cl | H |
| B-255. | CH₃ | 5-OCH₃ | Cl | H |
| B-256. | CH₃ | 6-F | Cl | H |
| B-257. | CH₃ | 6-CH₃ | Cl | H |
| B-258. | CH₃ | 6-OCH₃ | Cl | H |
| B-259. | OCH₃ | 3-F | Cl | H |
| B-260. | OCH₃ | 3-CH₃ | Cl | H |
| B-261. | OCH₃ | 3-OCH₃ | Cl | H |
| B-262. | OCH₃ | 5-F | Cl | H |
| B-263. | OCH₃ | 5-CH₃ | Cl | H |
| B-264. | OCH₃ | 5-OCH₃ | Cl | H |
| B-265. | OCH₃ | 6-F | Cl | H |
| B-266. | OCH₃ | 6-CH₃ | Cl | H |
| B-267. | OCH₃ | 6-OCH₃ | Cl | H |
| B-268. | CN | 3-F | Cl | H |
| B-269. | CN | 3-CH₃ | Cl | H |
| B-270. | CN | 3-OCH₃ | Cl | H |
| B-271. | CN | 5-F | Cl | H |
| B-272. | CN | 5-CH₃ | Cl | H |
| B-273. | CN | 5-OCH₃ | Cl | H |
| B-274. | CN | 6-F | Cl | H |
| B-275. | CN | 6-CH₃ | Cl | H |
| B-276. | CN | 6-OCH₃ | Cl | H |
| B-277. | CH₂F | 3-F | Cl | H |
| B-278. | CH₂F | 3-CH₃ | Cl | H |
| B-279. | CH₂F | 3-OCH₃ | Cl | H |
| B-280. | CH₂F | 5-F | Cl | H |
| B-281. | CH₂F | 5-CH₃ | Cl | H |
| B-282. | CH₂F | 5-OCH₃ | Cl | H |
| B-283. | CH₂F | 6-F | Cl | H |
| B-284. | CH₂F | 6-CH₃ | Cl | H |
| B-285. | CH₂F | 6-OCH₃ | Cl | H |
| B-286. | CHF₂ | 3-F | Cl | H |
| B-287. | CHF₂ | 3-CH₃ | Cl | H |
| B-288. | CHF₂ | 3-OCH₃ | Cl | H |
| B-289. | CHF₂ | 5-F | Cl | H |
| B-290. | CHF₂ | 5-CH₃ | Cl | H |
| B-291. | CHF₂ | 5-OCH₃ | Cl | H |
| B-292. | CHF₂ | 6-F | Cl | H |
| B-293. | CHF₂ | 6-CH₃ | Cl | H |
| B-294. | CHF₂ | 6-OCH₃ | Cl | H |
| B-295. | CF₃ | 3-F | Cl | H |
| B-296. | CF₃ | 3-CH₃ | Cl | H |
| B-297. | CF₃ | 3-OCH₃ | Cl | H |
| B-298. | CF₃ | 5-F | Cl | H |
| B-299. | CF₃ | 5-CH₃ | Cl | H |
| B-300. | CF₃ | 5-OCH₃ | Cl | H |
| B-301. | CF₃ | 6-F | Cl | H |
| B-302. | CF₃ | 6-CH₃ | Cl | H |
| B-303. | CF₃ | 6-OCH₃ | Cl | H |
| B-304. | OCH₂F | 3-F | Cl | H |
| B-305. | OCH₂F | 3-CH₃ | Cl | H |
| B-306. | OCH₂F | 3-OCH₃ | Cl | H |
| B-307. | OCH₂F | 5-F | Cl | H |
| B-308. | OCH₂F | 5-CH₃ | Cl | H |
| B-309. | OCH₂F | 5-OCH₃ | Cl | H |
| B-310. | OCH₂F | 6-F | Cl | H |
| B-311. | OCH₂F | 6-CH₃ | Cl | H |
| B-312. | OCH₂F | 6-OCH₃ | Cl | H |
| B-313. | OCHF₂ | 3-F | Cl | H |
| B-314. | OCHF₂ | 3-CH₃ | Cl | H |
| B-315. | OCHF₂ | 3-OCH₃ | Cl | H |
| B-316. | OCHF₂ | 5-F | Cl | H |
| B-317. | OCHF₂ | 5-CH₃ | Cl | H |
| B-318. | OCHF₂ | 5-OCH₃ | Cl | H |
| B-319. | OCHF₂ | 6-F | Cl | H |
| B-320. | OCHF₂ | 6-CH₃ | Cl | H |
| B-321. | OCHF₂ | 6-OCH₃ | Cl | H |
| B-322. | OCF₃ | 3-F | Cl | H |
| B-323. | OCF₃ | 3-CH₃ | Cl | H |
| B-324. | OCF₃ | 3-OCH₃ | Cl | H |
| B-325. | OCF₃ | 5-F | Cl | H |
| B-326. | OCF₃ | 5-CH₃ | Cl | H |
| B-327. | OCF₃ | 5-OCH₃ | Cl | H |
| B-328. | OCF₃ | 6-F | Cl | H |
| B-329. | OCF₃ | 6-CH₃ | Cl | H |
| B-330. | OCF₃ | 6-OCH₃ | Cl | H |
| B-331. | H | H | CN | F |
| B-332. | F | H | CN | F |
| B-333. | CH₃ | H | CN | F |
| B-334. | OCH₃ | H | CN | F |
| B-335. | CN | H | CN | F |
| B-336. | CH₂F | H | CN | F |
| B-337. | CHF₂ | H | CN | F |
| B-338. | CF₃ | H | CN | F |
| B-339. | OCH₂F | H | CN | F |
| B-340. | OCHF₂ | H | CN | F |
| B-341. | OCF₃ | H | CN | F |
| B-342. | H | 3-F | CN | F |
| B-343. | H | 3-CH₃ | CN | F |
| B-344. | H | 3-OCH₃ | CN | F |
| B-345. | H | 5-F | CN | F |
| B-346. | H | 5-CH₃ | CN | F |
| B-347. | H | 5-OCH₃ | CN | F |
| B-348. | H | 6-F | CN | F |
| B-349. | H | 6-CH₃ | CN | F |
| B-350. | H | 6-OCH₃ | CN | F |
| B-351. | F | 3-F | CN | F |
| B-352. | F | 3-CH₃ | CN | F |
| B-353. | F | 3-OCH₃ | CN | F |
| B-354. | F | 5-F | CN | F |
| B-355. | F | 5-CH₃ | CN | F |
| B-356. | F | 5-OCH₃ | CN | F |
| B-357. | F | 6-F | CN | F |
| B-358. | F | 6-CH₃ | CN | F |
| B-359. | F | 6-OCH₃ | CN | F |
| B-360. | CH₃ | 3-F | CN | F |
| B-361. | CH₃ | 3-CH₃ | CN | F |
| B-362. | CH₃ | 3-OCH₃ | CN | F |
| B-363. | CH₃ | 5-F | CN | F |
| B-364. | CH₃ | 5-CH₃ | CN | F |
| B-365. | CH₃ | 5-OCH₃ | CN | F |
| B-366. | CH₃ | 6-F | CN | F |
| B-367. | CH₃ | 6-CH₃ | CN | F |
| B-368. | CH₃ | 6-OCH₃ | CN | F |
| B-369. | OCH₃ | 3-F | CN | F |
| B-370. | OCH₃ | 3-CH₃ | CN | F |
| B-371. | OCH₃ | 3-OCH₃ | CN | F |
| B-372. | OCH₃ | 5-F | CN | F |
| B-373. | OCH₃ | 5-CH₃ | CN | F |
| B-374. | OCH₃ | 5-OCH₃ | CN | F |
| B-375. | OCH₃ | 6-F | CN | F |
| B-376. | OCH₃ | 6-CH₃ | CN | F |
| B-377. | OCH₃ | 6-OCH₃ | CN | F |
| B-378. | CN | 3-F | CN | F |
| B-379. | CN | 3-CH₃ | CN | F |
| B-380. | CN | 3-OCH₃ | CN | F |
| B-381. | CN | 5-F | CN | F |
| B-382. | CN | 5-CH₃ | CN | F |
| B-383. | CN | 5-OCH₃ | CN | F |
| B-384. | CN | 6-F | CN | F |
| B-385. | CN | 6-CH₃ | CN | F |
| B-386. | CN | 6-OCH₃ | CN | F |
| B-387. | CH₂F | 3-F | CN | F |
| B-388. | CH₂F | 3-CH₃ | CN | F |
| B-389. | CH₂F | 3-OCH₃ | CN | F |
| B-390. | CH₂F | 5-F | CN | F |

TABLE B-continued

| Example No. | R² | R³ | R⁶ | R⁷ |
|---|---|---|---|---|
| B-391. | CH₂F | 5-CH₃ | CN | F |
| B-392. | CH₂F | 5-OCH₃ | CN | F |
| B-393. | CH₂F | 6-F | CN | F |
| B-394. | CH₂F | 6-CH₃ | CN | F |
| B-395. | CH₂F | 6-OCH₃ | CN | F |
| B-396. | CHF₂ | 3-F | CN | F |
| B-397. | CHF₂ | 3-CH₃ | CN | F |
| B-398. | CHF₂ | 3-OCH₃ | CN | F |
| B-399. | CHF₂ | 5-F | CN | F |
| B-400. | CHF₂ | 5-CH₃ | CN | F |
| B-401. | CHF₂ | 5-OCH₃ | CN | F |
| B-402. | CHF₂ | 6-F | CN | F |
| B-403. | CHF₂ | 6-CH₃ | CN | F |
| B-404. | CHF₂ | 6-OCH₃ | CN | F |
| B-405. | CF₃ | 3-F | CN | F |
| B-406. | CF₃ | 3-CH₃ | CN | F |
| B-407. | CF₃ | 3-OCH₃ | CN | F |
| B-408. | CF₃ | 5-F | CN | F |
| B-409. | CF₃ | 5-CH₃ | CN | F |
| B-410. | CF₃ | 5-OCH₃ | CN | F |
| B-411. | CF₃ | 6-F | CN | F |
| B-412. | CF₃ | 6-CH₃ | CN | F |
| B-413. | CF₃ | 6-OCH₃ | CN | F |
| B-414. | OCH₂F | 3-F | CN | F |
| B-415. | OCH₂F | 3-CH₃ | CN | F |
| B-416. | OCH₂F | 3-OCH₃ | CN | F |
| B-417. | OCH₂F | 5-F | CN | F |
| B-418. | OCH₂F | 5-CH₃ | CN | F |
| B-419. | OCH₂F | 5-OCH₃ | CN | F |
| B-420. | OCH₂F | 6-F | CN | F |
| B-421. | OCH₂F | 6-CH₃ | CN | F |
| B-422. | OCH₂F | 6-OCH₃ | CN | F |
| B-423. | OCHF₂ | 3-F | CN | F |
| B-424. | OCHF₂ | 3-CH₃ | CN | F |
| B-425. | OCHF₂ | 3-OCH₃ | CN | F |
| B-426. | OCHF₂ | 5-F | CN | F |
| B-427. | OCHF₂ | 5-CH₃ | CN | F |
| B-428. | OCHF₂ | 5-OCH₃ | CN | F |
| B-429. | OCHF₂ | 6-F | CN | F |
| B-430. | OCHF₂ | 6-CH₃ | CN | F |
| B-431. | OCHF₂ | 6-OCH₃ | CN | F |
| B-432. | OCF₃ | 3-F | CN | F |
| B-433. | OCF₃ | 3-CH₃ | CN | F |
| B-434. | OCF₃ | 3-OCH₃ | CN | F |
| B-435. | OCF₃ | 5-F | CN | F |
| B-436. | OCF₃ | 5-CH₃ | CN | F |
| B-437. | OCF₃ | 5-OCH₃ | CN | F |
| B-438. | OCF₃ | 6-F | CN | F |
| B-439. | OCF₃ | 6-CH₃ | CN | F |
| B-440. | OCF₃ | 6-OCH₃ | CN | F |
| B-441. | H | H | F | F |
| B-442. | F | H | F | F |
| B-443. | CH₃ | H | F | F |
| B-444. | OCH₃ | H | F | F |
| B-445. | CN | H | F | F |
| B-446. | CH₂F | H | F | F |
| B-447. | CHF₂ | H | F | F |
| B-448. | CF₃ | H | F | F |
| B-449. | OCH₂F | H | F | F |
| B-450. | OCHF₂ | H | F | F |
| B-451. | OCF₃ | H | F | F |
| B-452. | H | 3-F | F | F |
| B-453. | H | 3-CH₃ | F | F |
| B-454. | H | 3-OCH₃ | F | F |
| B-455. | H | 5-F | F | F |
| B-456. | H | 5-CH₃ | F | F |
| B-457. | H | 5-OCH₃ | F | F |
| B-458. | H | 6-F | F | F |
| B-459. | H | 6-CH₃ | F | F |
| B-460. | H | 6-OCH₃ | F | F |
| B-461. | F | 3-F | F | F |
| B-462. | F | 3-CH₃ | F | F |
| B-463. | F | 3-OCH₃ | F | F |
| B-464. | F | 5-F | F | F |
| B-465. | F | 5-CH₃ | F | F |
| B-466. | F | 5-OCH₃ | F | F |
| B-467. | F | 6-F | F | F |
| B-468. | F | 6-CH₃ | F | F |
| B-469. | F | 6-OCH₃ | F | F |
| B-470. | CH₃ | 3-F | F | F |
| B-471. | CH₃ | 3-CH₃ | F | F |
| B-472. | CH₃ | 3-OCH₃ | F | F |
| B-473. | CH₃ | 5-F | F | F |
| B-474. | CH₃ | 5-CH₃ | F | F |
| B-475. | CH₃ | 5-OCH₃ | F | F |
| B-476. | CH₃ | 6-F | F | F |
| B-477. | CH₃ | 6-CH₃ | F | F |
| B-478. | CH₃ | 6-OCH₃ | F | F |
| B-479. | OCH₃ | 3-F | F | F |
| B-480. | OCH₃ | 3-CH₃ | F | F |
| B-481. | OCH₃ | 3-OCH₃ | F | F |
| B-482. | OCH₃ | 5-F | F | F |
| B-483. | OCH₃ | 5-CH₃ | F | F |
| B-484. | OCH₃ | 5-OCH₃ | F | F |
| B-485. | OCH₃ | 6-F | F | F |
| B-486. | OCH₃ | 6-CH₃ | F | F |
| B-487. | OCH₃ | 6-OCH₃ | F | F |
| B-488. | CN | 3-F | F | F |
| B-489. | CN | 3-CH₃ | F | F |
| B-490. | CN | 3-OCH₃ | F | F |
| B-491. | CN | 5-F | F | F |
| B-492. | CN | 5-CH₃ | F | F |
| B-493. | CN | 5-OCH₃ | F | F |
| B-494. | CN | 6-F | F | F |
| B-495. | CN | 6-CH₃ | F | F |
| B-496. | CN | 6-OCH₃ | F | F |
| B-497. | CH₂F | 3-F | F | F |
| B-498. | CH₂F | 3-CH₃ | F | F |
| B-499. | CH₂F | 3-OCH₃ | F | F |
| B-500. | CH₂F | 5-F | F | F |
| B-501. | CH₂F | 5-CH₃ | F | F |
| B-502. | CH₂F | 5-OCH₃ | F | F |
| B-503. | CH₂F | 6-F | F | F |
| B-504. | CH₂F | 6-CH₃ | F | F |
| B-505. | CH₂F | 6-OCH₃ | F | F |
| B-506. | CHF₂ | 3-F | F | F |
| B-507. | CHF₂ | 3-CH₃ | F | F |
| B-508. | CHF₂ | 3-OCH₃ | F | F |
| B-509. | CHF₂ | 5-F | F | F |
| B-510. | CHF₂ | 5-CH₃ | F | F |
| B-511. | CHF₂ | 5-OCH₃ | F | F |
| B-512. | CHF₂ | 6-F | F | F |
| B-513. | CHF₂ | 6-CH₃ | F | F |
| B-514. | CHF₂ | 6-OCH₃ | F | F |
| B-515. | CF₃ | 3-F | F | F |
| B-516. | CF₃ | 3-CH₃ | F | F |
| B-517. | CF₃ | 3-OCH₃ | F | F |
| B-518. | CF₃ | 5-F | F | F |
| B-519. | CF₃ | 5-CH₃ | F | F |
| B-520. | CF₃ | 5-OCH₃ | F | F |
| B-521. | CF₃ | 6-F | F | F |
| B-522. | CF₃ | 6-CH₃ | F | F |
| B-523. | CF₃ | 6-OCH₃ | F | F |
| B-524. | OCH₂F | 3-F | F | F |
| B-525. | OCH₂F | 3-CH₃ | F | F |
| B-526. | OCH₂F | 3-OCH₃ | F | F |
| B-527. | OCH₂F | 5-F | F | F |
| B-528. | OCH₂F | 5-CH₃ | F | F |
| B-529. | OCH₂F | 5-OCH₃ | F | F |
| B-530. | OCH₂F | 6-F | F | F |
| B-531. | OCH₂F | 6-CH₃ | F | F |
| B-532. | OCH₂F | 6-OCH₃ | F | F |
| B-533. | OCHF₂ | 3-F | F | F |
| B-534. | OCHF₂ | 3-CH₃ | F | F |
| B-535. | OCHF₂ | 3-OCH₃ | F | F |
| B-536. | OCHF₂ | 5-F | F | F |
| B-537. | OCHF₂ | 5-CH₃ | F | F |
| B-538. | OCHF₂ | 5-OCH₃ | F | F |
| B-539. | OCHF₂ | 6-F | F | F |
| B-540. | OCHF₂ | 6-CH₃ | F | F |
| B-541. | OCHF₂ | 6-OCH₃ | F | F |
| B-542. | OCF₃ | 3-F | F | F |
| B-543. | OCF₃ | 3-CH₃ | F | F |
| B-544. | OCF₃ | 3-OCH₃ | F | F |
| B-545. | OCF₃ | 5-F | F | F |
| B-546. | OCF₃ | 5-CH₃ | F | F |

TABLE B-continued

| Example No. | R² | R³ | R⁶ | R⁷ |
|---|---|---|---|---|
| B-547. | OCF₃ | 5-OCH₃ | F | F |
| B-548. | OCF₃ | 6-F | F | F |
| B-549. | OCF₃ | 6-CH₃ | F | F |
| B-550. | OCF₃ | 6-OCH₃ | F | F |
| B-551. | H | H | Cl | F |
| B-552. | F | H | Cl | F |
| B-553. | CH₃ | H | Cl | F |
| B-554. | OCH₃ | H | Cl | F |
| B-555. | CN | H | Cl | F |
| B-556. | CH₂F | H | Cl | F |
| B-557. | CHF₂ | H | Cl | F |
| B-558. | CF₃ | H | Cl | F |
| B-559. | OCH₂F | H | Cl | F |
| B-560. | OCHF₂ | H | Cl | F |
| B-561. | OCF₃ | H | Cl | F |
| B-562. | H | 3-F | Cl | F |
| B-563. | H | 3-CH₃ | Cl | F |
| B-564. | H | 3-OCH₃ | Cl | F |
| B-565. | H | 5-F | Cl | F |
| B-566. | H | 5-CH₃ | Cl | F |
| B-567. | H | 5-OCH₃ | Cl | F |
| B-568. | H | 6-F | Cl | F |
| B-569. | H | 6-CH₃ | Cl | F |
| B-570. | H | 6-OCH₃ | Cl | F |
| B-571. | F | 3-F | Cl | F |
| B-572. | F | 3-CH₃ | Cl | F |
| B-573. | F | 3-OCH₃ | Cl | F |
| B-574. | F | 5-F | Cl | F |
| B-575. | F | 5-CH₃ | Cl | F |
| B-576. | F | 5-OCH₃ | Cl | F |
| B-577. | F | 6-F | Cl | F |
| B-578. | F | 6-CH₃ | Cl | F |
| B-579. | F | 6-OCH₃ | Cl | F |
| B-580. | CH₃ | 3-F | Cl | F |
| B-581. | CH₃ | 3-CH₃ | Cl | F |
| B-582. | CH₃ | 3-OCH₃ | Cl | F |
| B-583. | CH₃ | 5-F | Cl | F |
| B-584. | CH₃ | 5-CH₃ | Cl | F |
| B-585. | CH₃ | 5-OCH₃ | Cl | F |
| B-586. | CH₃ | 6-F | Cl | F |
| B-587. | CH₃ | 6-CH₃ | Cl | F |
| B-588. | CH₃ | 6-OCH₃ | Cl | F |
| B-589. | OCH₃ | 3-F | Cl | F |
| B-590. | OCH₃ | 3-CH₃ | Cl | F |
| B-591. | OCH₃ | 3-OCH₃ | Cl | F |
| B-592. | OCH₃ | 5-F | Cl | F |
| B-593. | OCH₃ | 5-CH₃ | Cl | F |
| B-594. | OCH₃ | 5-OCH₃ | Cl | F |
| B-595. | OCH₃ | 6-F | Cl | F |
| B-596. | OCH₃ | 6-CH₃ | Cl | F |
| B-597. | OCH₃ | 6-OCH₃ | Cl | F |
| B-598. | CN | 3-F | Cl | F |
| B-599. | CN | 3-CH₃ | Cl | F |
| B-600. | CN | 3-OCH₃ | Cl | F |
| B-601. | CN | 5-F | Cl | F |
| B-602. | CN | 5-CH₃ | Cl | F |
| B-603. | CN | 5-OCH₃ | Cl | F |
| B-604. | CN | 6-F | Cl | F |
| B-605. | CN | 6-CH₃ | Cl | F |
| B-606. | CN | 6-OCH₃ | Cl | F |
| B-607. | CH₂F | 3-F | Cl | F |
| B-608. | CH₂F | 3-CH₃ | Cl | F |
| B-609. | CH₂F | 3-OCH₃ | Cl | F |
| B-610. | CH₂F | 5-F | Cl | F |
| B-611. | CH₂F | 5-CH₃ | Cl | F |
| B-612. | CH₂F | 5-OCH₃ | Cl | F |
| B-613. | CH₂F | 6-F | Cl | F |
| B-614. | CH₂F | 6-CH₃ | Cl | F |
| B-615. | CH₂F | 6-OCH₃ | Cl | F |
| B-616. | CHF₂ | 3-F | Cl | F |
| B-617. | CHF₂ | 3-CH₃ | Cl | F |
| B-618. | CHF₂ | 3-OCH₃ | Cl | F |
| B-619. | CHF₂ | 5-F | Cl | F |
| B-620. | CHF₂ | 5-CH₃ | Cl | F |
| B-621. | CHF₂ | 5-OCH₃ | Cl | F |
| B-622. | CHF₂ | 6-F | Cl | F |
| B-623. | CHF₂ | 6-CH₃ | Cl | F |
| B-624. | CHF₂ | 6-OCH₃ | Cl | F |
| B-625. | CF₃ | 3-F | Cl | F |
| B-626. | CF₃ | 3-CH₃ | Cl | F |
| B-627. | CF₃ | 3-OCH₃ | Cl | F |
| B-628. | CF₃ | 5-F | Cl | F |
| B-629. | CF₃ | 5-CH₃ | Cl | F |
| B-630. | CF₃ | 5-OCH₃ | Cl | F |
| B-631. | CF₃ | 6-F | Cl | F |
| B-632. | CF₃ | 6-CH₃ | Cl | F |
| B-633. | CF₃ | 6-OCH₃ | Cl | F |
| B-634. | OCH₂F | 3-F | Cl | F |
| B-635. | OCH₂F | 3-CH₃ | Cl | F |
| B-636. | OCH₂F | 3-OCH₃ | Cl | F |
| B-637. | OCH₂F | 5-F | Cl | F |
| B-638. | OCH₂F | 5-CH₃ | Cl | F |
| B-639. | OCH₂F | 5-OCH₃ | Cl | F |
| B-640. | OCH₂F | 6-F | Cl | F |
| B-641. | OCH₂F | 6-CH₃ | Cl | F |
| B-642. | OCH₂F | 6-OCH₃ | Cl | F |
| B-643. | OCHF₂ | 3-F | Cl | F |
| B-644. | OCHF₂ | 3-CH₃ | Cl | F |
| B-645. | OCHF₂ | 3-OCH₃ | Cl | F |
| B-646. | OCHF₂ | 5-F | Cl | F |
| B-647. | OCHF₂ | 5-CH₃ | Cl | F |
| B-648. | OCHF₂ | 5-OCH₃ | Cl | F |
| B-649. | OCHF₂ | 6-F | Cl | F |
| B-650. | OCHF₂ | 6-CH₃ | Cl | F |
| B-651. | OCHF₂ | 6-OCH₃ | Cl | F |
| B-652. | OCF₃ | 3-F | Cl | F |
| B-653. | OCF₃ | 3-CH₃ | Cl | F |
| B-654. | OCF₃ | 3-OCH₃ | Cl | F |
| B-655. | OCF₃ | 5-F | Cl | F |
| B-656. | OCF₃ | 5-CH₃ | Cl | F |
| B-657. | OCF₃ | 5-OCH₃ | Cl | F |
| B-658. | OCF₃ | 6-F | Cl | F |
| B-659. | OCF₃ | 6-CH₃ | Cl | F |
| B-660. | OCF₃ | 6-OCH₃ | Cl | F |

The positions (e.g. 3-/5-/6-) of $R^3$ are relative to the 2- and 4-positions of radicals $R^1$ and $R^2$ and to the 1-position of the attachment point of the ring to the $SO_2$ group.

The preferred compounds among the compounds I.1 to I.72 mentioned above are those of the formulae I.1 to I.6 and I.37 to I.42, and especially compounds of the formulae I.1 to I.6. Particularly preferred are compounds of the formulae I.1 to I.3.

The compounds I of the invention have a center of chirality in position 3 of the 2-oxindole ring. The compounds of the invention may therefore be in the form of a 1:1 mixture of enantiomers (racemate) or of a nonracemic mixture of enantiomers in which one of the two enantiomers, either the enantiomer which rotates the plane of vibration of linearly polarized light to the left (i.e. minus rotation) (hereinafter (−) enantiomer) or the enantiomer which rotates the plane of vibration of linearly polarized light to the right (i.e. plus rotation) (hereinafter (+) enantiomer), is enriched, or of substantially enantiopure compounds, that is to say of substantially enantiopure (−) enantiomer or (+) enantiomer. Since the compounds of the invention have a single center of asymmetry and no axis/plane of chirality, a nonracemic mixture can also be defined as a mixture of enantiomers in which either the R or the S enantiomer predominates. Substantially enantiopure compounds can accordingly also be defined as substantially enantiopure R enantiomer or substantially enantiopure S enantiomer.

"Substantially enantiopure compounds" means in the context of the present invention those compounds having an enantiomeric excess (ee; % ee=(R−S)/(R+S)×100 or (S−R)/(S+R)×100) of at least 80% ee, preferably at least 85% ee, more preferably at least 90% ee, even more preferably at least 95% ee and in particular at least 98% ee.

In one embodiment of the invention, the compounds of the invention are in the form of substantially enantiopure compounds. Particularly preferred compounds have an enantiomeric excess of at least 85% ee, more preferably of at least 90% ee, even more preferably of at least 95% ee and in particular of at least 98% ee.

The invention thus relates both to the pure enantiomers and to mixtures thereof, e.g. mixtures in which one enantiomer is present in enriched form, but also to the racemates. The invention also relates to the pharmaceutically acceptable salts of the pure enantiomers of compounds I, and the mixtures of enantiomers in the form of the pharmaceutically acceptable salts of compounds I.

Preferred embodiments of the invention are compounds of the formula I as detailed above which are characterized in that they are in optically active form, and the enantiomer of the relevant compound of the formula I is the S-enantiomner, in the form of a free base, or a pharmaceutically acceptable salt thereof.

Particularly preference is given to compounds of the general formula I and their pharmaceutically acceptable salts as detailed above in which the corresponding S-enantiomer is present in an optical purity (enantiomeric excess, ee) of more than 50% ee, particularly preferably of at least 80% ee, more preferably of at least 90% ee and even more preferably of at least 95% ee and in particular of at least 98% ee.

Likewise preferred embodiments of the invention are compounds of the general formula I as detailed above which are characterized in that they are in optically inactive form, i.e. in the form of the racemate, or in the form of a pharmaceutically acceptable salt of the racemate.

Examples of synthetic routes for preparing the oxindole derivatives of the invention are described below.

The compounds of the invention can be prepared by using methods described in WO 2005/030755, WO 2006/005609 and the other references mentioned in the outset for synthesizing analogous compounds, and the preparation is outlined by way of example in synthesis scheme 1. The variables in these synthetic schemes have the same meanings as in formula I.

The 3-hydroxy-1,3-dihydroindol-2-ones IV can be obtained by addition of metallated heterocycles III onto the 3-keto group of the isatins II. The metallated heterocycles, such as, for example, the corresponding Grignard (Mg) or organyllithium compound, can be obtained in any conventional way from halogen or hydrocarbon compounds. Examples of methods are present in Houben-Weyl, Methoden der Organischen Chemie, vol. 13, 1-2, chapter on Mg and Li compounds. The isatins II are either commercially available or were prepared in analogy to methods described in the literature (Advances in Heterocyclic Chemistry, A. R. Katritzky and A. J. Boulton, Academic Press, New York, 1975, 18, 2-58; J. Brazil. Chem. Soc. 12, 273-324, 2001).

The 3-hydroxyoxindoles IV can be converted into the compounds V which have a leaving group LG' in position 3, where the leaving group LG' is a conventional leaving group such as, for example, chlorine or bromide. The intermediate V with for example LG'=chlorine can be prepared by treating the alcohol IV with thionyl chloride in the presence of a base such as, for example, pyridine, in a suitable solvent such as, for example, dichloromethane.

The compounds V can subsequently be reacted with amines, such as, for example, ammonia, in a substitution reaction to give the amines VI. The compounds VI can subsequently be converted by treatment with sulfonyl chlorides VII after deprotonation with a strong base such as, for example, potassium tert-butoxide or sodium hydride in DMF into the sulfonylated product VIII. The sulfonyl chlorides VII employed can either be purchased or be prepared by known processes (for example J. Med. Chem. 40, 1149 (1997)). The compounds VIII are then reacted with phenyl chloroformate in the presence of a base such as, for example, pyridine to give the corresponding phenyl carbamate IX.

The compounds of the invention of the general formula I which have a urea group in position 3 can be prepared as described in WO 2005/030755 and WO 2006/005609, and shown in synthesis scheme 1, by two different sequences: In the first variant, compound IX is first reacted with amine X, where appropriate at elevated temperature and with the addition of auxiliary bases such as, for example, triethylamine or diisopropylethylamine. PG is a protective group, typically Boc. Subsequent deprotection (for Boc typically treatment with trifluoroacetic acid in dichloromethane) yields compound XII, which is then reacted with the oxetan-3-one XIII to give compound I with $X^3$ being a bond. The latter reaction is carried out in the presence of a suitable reduction agent, e.g. boron-based reduction agent, typically a boronic ester, such as sodium triacetoxyhydroborate, or cyanoborhydride. For obtaining compounds wherein $X^3$ is $CH_2$, oxetane-3-carbaldehyde optionally carrying c substituents $R^{10}$ is used instead of oxetanone XIII. For obtaining compounds wherein $X^3$ is CO, oxetane-3-carbonylchloride optionally carrying c substituents $R^{10}$ is used instead of oxetanone XIII.

In the second variant, compound IX is reacted with the amine XIV. The reaction is generally carried out in the presence of a base, such as triethylamine or diisopropylethylamine.

SYNTHESIS SCHEME 1

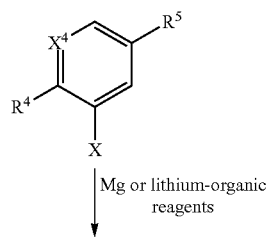

-continued
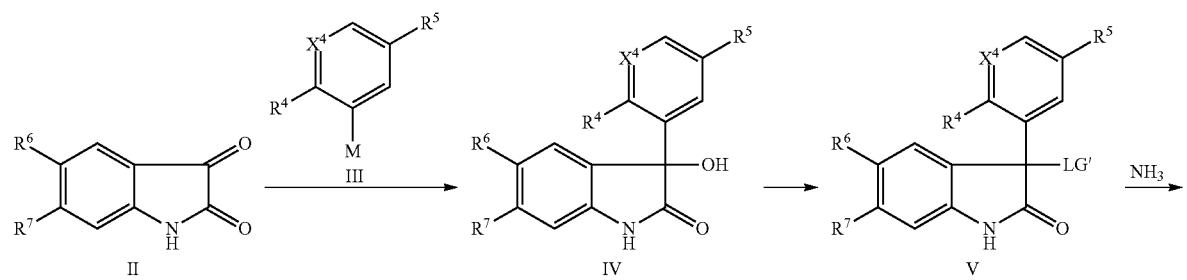
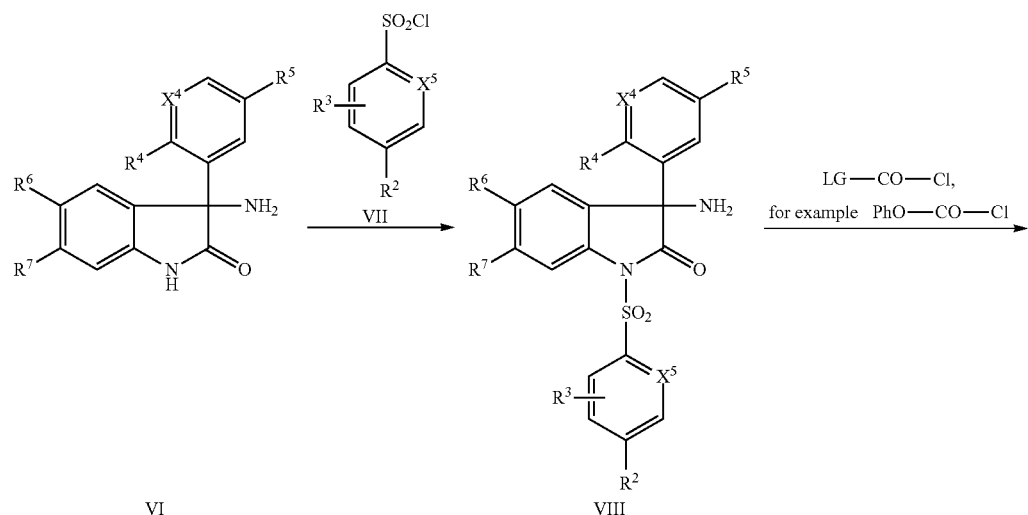
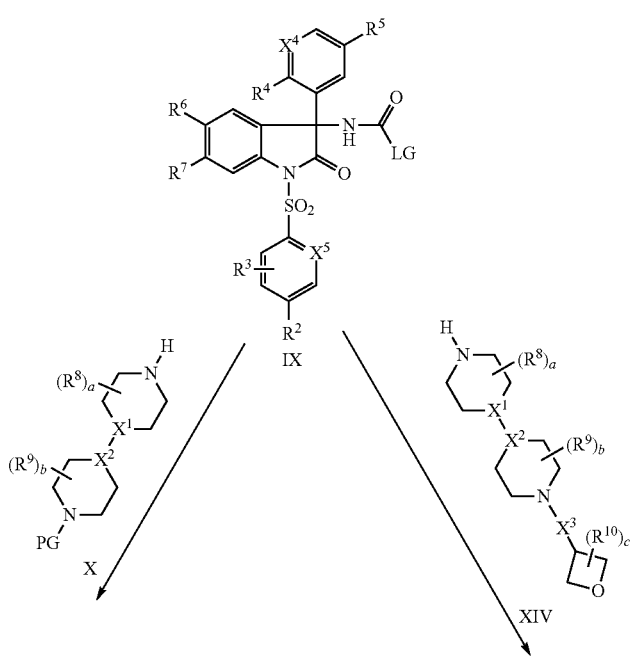

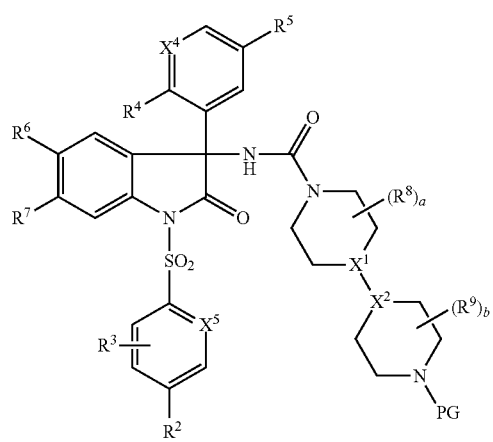 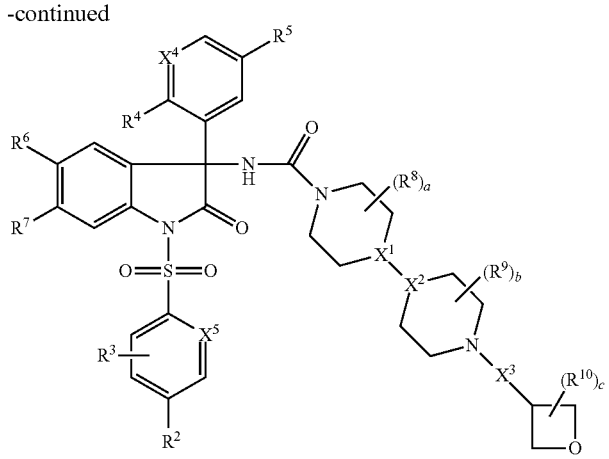

XI → I

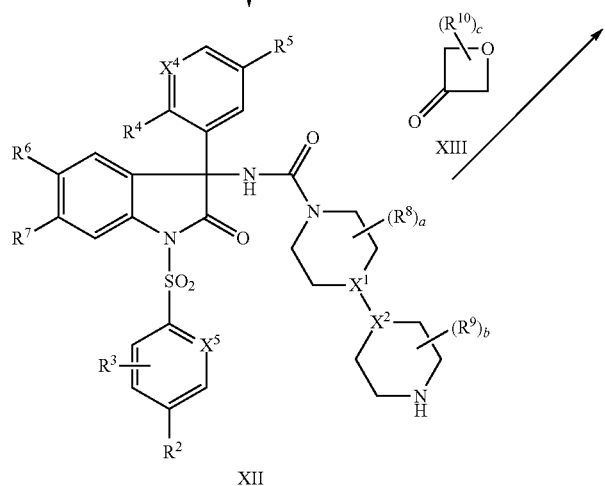 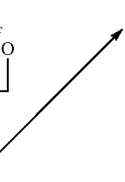

XII    XIII

X = I or Br
M = Mg or Li
LG' = Leaving group such as, for example, Cl
LG = Leaving group such as, for example, OPh
PG = Protective group such as, for example, boc
Ph = Phenyl The amines X can be either purchased or prepared by methods known from the literature.

Compounds XIV wherein $X^3$ is a bond can be prepared by reacting a compound X with oxetan-3-one carrying c substituents $R^{10}$ in the presence of a reduction agent such as sodium triacetoxyhydroborate or cyanoborhydride. For obtaining compounds XIV wherein $X^3$ is $CH_2$, oxetane-3-carbaldehyde carrying c substituents $R^{10}$ is used instead of the oxetan-3-one XIII. Analogously, for obtaining compounds XIV wherein $X^3$ is $C_2$-$C_4$-alkylene, oxetane carrying in the 3-position a $C_2$-$C_4$-keto or aldehyde group (e.g. a group $CH_2CHO$, $CH_2CH_2CHO$, $(CH_2)_3CHO$, $CH_2COCH_3$, $CH_2CH_2COCH_3$ etc.) and carrying c substituents $R^{10}$ is used instead of the oxetan-3-one XIII. Such oxetanes are either commercially available or can be prepared by routine methods. For obtaining compounds wherein $X^3$ is CO, oxetane-3-carbonylchloride carrying c substituents $R^{10}$ is used instead of the oxetan-3-one XIII.

If not indicated otherwise, the above-described reactions are generally carried out in a solvent at temperatures between room temperature and the boiling temperature of the solvent employed. Alternatively, the activation energy which is required for the reaction can be introduced into the reaction mixture using microwaves, something which has proved to be of value, in particular, in the case of the reactions catalyzed by transition metals (with regard to reactions using microwaves, see Tetrahedron 2001, 57, p. 9199 ff. p. 9225 ff. and also, in a general manner, "Microwaves in Organic Synthesis", André Loupy (Ed.), Wiley-VCH 2002.

The acid addition salts of compounds I are prepared in a customary manner by mixing the free base with a corresponding acid, where appropriate in solution in an organic solvent, for example a lower alcohol, such as methanol, ethanol or propanol, an ether, such as methyl tert-butyl ether or diisopropyl ether, a ketone, such as acetone or methyl ethyl ketone, or an ester, such as ethyl acetate.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the preparation methods are within routine techniques.

Suitable protecting groups and the methods for protecting and deprotecting different substituents using such suitable protecting groups are well known to those skilled in the art; examples of which may be found in T. Greene and P. Wuts, Protective Groups in Organic Synthesis (3rd ed.), John Wiley & Sons, NY (1999), which is incorporated herein by reference in its entirety. Synthesis of the compounds of the invention may be accomplished by methods analogous to those described in the synthetic scheme described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

The present invention moreover relates to compounds of formula I as defined above, wherein at least one of the atoms has been replaced by its stable, non-radioactive isotope (e.g., hydrogen by deuterium, $^{12}C$ by $^{13}C$, $^{14}N$ by $^{15}N$, $^{16}O$ by $^{18}O$) and preferably wherein at least one hydrogen atom has been replaced by a deuterium atom.

Of course, the compounds according to the invention contain more of the respective isotope than this naturally occurs and thus is anyway present in the compounds I.

Stable isotopes (e.g., deuterium, $^{13}C$, $^{15}N$, $^{18}O$) are nonradioactive isotopes which contain one additional neutron than the normally abundant isotope of the respective atom. Deuterated compounds have been used in pharmaceutical research to investigate the in vivo metabolic fate of the compounds by evaluation of the mechanism of action and metabolic pathway of the non deuterated parent compound (Blake et al. J. Pharm. Sci. 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., J. Labelled Comp. Radiopharmaceut., 36(10):927-932 (1995); Kushner et al., Can. J. Physiol. Pharmacol., 77, 79-88 (1999)).

Incorporation of a heavy atom, particularly substitution of deuterium for hydrogen, can give rise to an isotope effect that could alter the pharmacokinetics of the drug.

Stable isotope labeling of a drug can alter its physicochemical properties such as pKa and lipid solubility. These changes may influence the fate of the drug at different steps along its passage through the body. Absorption, distribution, metabolism or excretion can be changed. Absorption and distribution are processes that depend primarily on the molecular size and the lipophilicity of the substance. These effects and alterations can affect the pharmacodynamic response of the drug molecule if the isotopic substitution affects a region involved in a ligand-receptor interaction.

Drug metabolism can give rise to large isotopic effect if the breaking of a chemical bond to a deuterium atom is the rate limiting step in the process. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. In any reaction in which the breaking of this bond is the rate limiting step, the reaction will proceed slower for the molecule with the heavy isotope due to "kinetic isotope effect". A reaction involving breaking a C—D bond can be up to 700 percent slower than a similar reaction involving breaking a C—H bond. If the C—D bond is not involved in any of the steps leading to the metabolite, there may not be any effect to alter the behavior of the drug. If a deuterium is placed at a site involved in the metabolism of a drug, an isotope effect will be observed only if breaking of the C—D bond is the rate limiting step. There is evidence to suggest that whenever cleavage of an aliphatic C—H bond occurs, usually by oxidation catalyzed by a mixed-function oxidase, replacement of the hydrogen by deuterium will lead to observable isotope effect. It is also important to understand that the incorporation of deuterium at the site of metabolism slows its rate to the point where another metabolite produced by attack at a carbon atom not substituted by deuterium becomes the major pathway a process called "metabolic switching".

Deuterium tracers, such as deuterium-labeled drugs and doses, in some cases re-peatedly, of thousands of milligrams of deuterated water, are also used in healthy humans of all ages, including neonates and pregnant women, without reported incident (e.g. Pons G and Rey E, Pediatrics 1999 104: 633; Coward W A et al., Lancet 1979 7: 13; Schwarcz H P, Control. Clin. Trials 1984 5(4 Suppl): 573; Rodewald L E et al., J. Pediatr. 1989 114: 885; Butte N F et al. Br. J. Nutr. 1991 65: 3; MacLennan A H et al. Am. J. Obstet. Gynecol. 1981 139: 948). Thus, it is clear that any deuterium released, for instance, during the metabolism of compounds of this invention poses no health risk.

The weight percentage of hydrogen in a mammal (approximately 9%) and natural abundance of deuterium (approximately 0.015%) indicates that a 70 kg human normally contains nearly a gram of deuterium. Furthermore, replacement of up to about 15% of normal hydrogen with deuterium has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci. 1960 84: 736; Czakja D M et al., Am. J. Physiol. 1961 201: 357). Higher deuterium concentrations, usually in excess of 20%, can be toxic in animals. However, acute replacement of as high as 15%-23% of the hydrogen in humans' fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Increasing the amount of deuterium present in a compound above its natural abundance is called enrichment or deuterium-enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %.

The hydrogens present on a particular organic compound have different capacities for exchange with deuterium. Certain hydrogen atoms are easily exchangeable under physiological conditions and, if replaced by deuterium atoms, it is expected that they will readily exchange for protons after administration to a patient. Certain hydrogen atoms may be exchanged for deuterium atoms by the action of a deuteric acid such as $D_2SO_4/D_2O$. Alternatively, deuterium atoms may be incorporated in various combinations during the synthesis of compounds of the invention. Certain hydrogen atoms are not easily exchangeable for deuterium atoms. However, deuterium atoms at the remaining positions may be incorporated by the use of deuterated starting materials or intermediates during the construction of compounds of the invention.

Deuterated and deuterium-enriched compounds of the invention can be prepared by using known methods described in the literature. Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure. Relevant procedures and intermediates are disclosed, for instance in Lizondo, J et al., Drugs Fut, 21(11), 1116 (1996); Brickner, S J et al., J Med Chem, 39(3), 673 (1996); Mallesham, B et al., Org Lett, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; 20090082471, the methods are hereby incorporated by reference.

A further aspect of the present invention relates to a pharmaceutical composition comprising at least one compound of the general formula I and/or an N-oxide, a stereoisomer or a pharmaceutically acceptable salt thereof as detailed above, and a pharmaceutically acceptable carrier; or comprising at least one compound I wherein at least one of the atoms has been replaced by its stable, non-radioactive isotope, preferably wherein at least one hydrogen atom has been replaced by a deuterium atom, in combination with at least one pharmaceutically acceptable carrier and/or auxiliary substance. Suitable carriers depend inter alia on the dosage form of the composition and are known in principle to the skilled worker. Some suitable carriers are described hereinafter.

The present invention furthermore relates to a compound I as defined above or an N-oxide, a stereoisomer or a pharmaceutically acceptable salt thereof for use as a medicament. The present invention also relates to a compound I as defined above or an N-oxide, a stereoisomer or a pharmaceutically acceptable salt thereof for the treatment of vasopressin-related diseases, especially of disorders which respond to the modulation of the vasopressin receptor and in particular of the V1b receptor.

A further aspect of the present invention relates to the use of compounds of the formula I and/or of an N-oxide, a stereoisomer or of pharmaceutically acceptable salts thereof for the manufacture of a medicament for the treatment and/or prophylaxis of vasopressin-related diseases, especially of disorders which respond to the modulation of the vasopressin receptor and in particular of the V1b receptor.

Vasopressin-related diseases are those in which the progress of the disease is at least partly dependent on vasopressin, i.e. diseases which show an elevated vasopressin level which may contribute directly or indirectly to the pathological condition. In other words, vasopressin-related diseases are those which can be influenced by modulating the vasopressin receptor, for example by administration of a vasopressin receptor ligand (agonist, antagonist, partial antagonist/agonist, inverse agonist etc.).

In a preferred embodiment, the present invention relates to the use of compounds of the invention of the formula I or of an N-oxide, a stereoisomer or of pharmaceutically acceptable salts thereof for the manufacture of a medicament for the treatment and/or prophylaxis of diseases selected from diabetes, insulin resistance, nocturnal enuresis, incontinence and diseases in which impairments of blood clotting occur, and/or for delaying micturition. The term "diabetes" means all types of diabetes, especially diabetes mellitus (including type I and especially type II), diabetes renalis and in particular diabetes insipidus. The types of diabetes are preferably diabetes mellitus of type II (with insulin resistance) or diabetes insipidus.

In a further preferred embodiment, the present invention relates to the use of compounds of the invention of the formula I or of an N-oxide, a stereoisomer or of pharmaceutically acceptable salts thereof for the manufacture of a medicament for the treatment and/or prophylaxis of diseases selected from hypertension, pulmonary hypertension, heart failure, myocardial infarction, coronary spasm, unstable angina, PTCA (percutaneous transluminal coronary angioplasty), ischemias of the heart, impairments of the renal system, edemas, renal vasospasm, necrosis of the renal cortex, hyponatremia, hypokalemia, Schwartz-Bartter syndrome, impairments of the gastrointestinal tract, gastritic vasospasm, hepatocirrhosis, gastric and intestinal ulcers, emesis, emesis occurring during chemotherapy, and travel sickness.

The compounds of the invention of the formula I or their N-oxides, stereoisomers or pharmaceutically acceptable salts or the pharmaceutical composition of the invention can also be used for the treatment of various vasopressin-related complaints which have central nervous causes or alterations in the HPA axis (hypothalamic pituitary adrenal axis), for example for affective disorders such as depressive disorders and anxiety disorders. Depressive disorders include for example dysthymic disorders, major depression, seasonal depression, treatment-resistant depression disorders, bipolar disorders, or childhood onset mood disorders. Anxiety disorders include for example phobias, post-traumatic stress disorders, general anxiety disorders, panic disorders, drug withdrawal-induced anxiety disorders, and obsessive-compulsive disorders.

Vasopressin-related complaints which have central nervous causes or alterations in the HPA axis are further cognitive disorders such as Alzheimer's disease, MCI (Mild Cognitive Impairment) and CIAS (Cognitive Impairment Associated with Schizophrenia).

The compounds of the invention of the formula I and their N-oxides, a stereoisomers or pharmaceutically acceptable salts or the pharmaceutical composition of the invention can likewise be employed for the treatment of anxiety disorders and stress-dependent anxiety disorders, such as, for example, generalized anxiety disorders, phobias, post-traumatic anxiety disorders, panic anxiety disorders, obsessive-compulsive anxiety disorders, acute stress-dependent anxiety disorders, drug withdrawal-induced anxiety disorders and social phobia.

The compounds of the invention of the formula I and their N-oxides, stereoisomers or pharmaceutically acceptable salts or the pharmaceutical composition of the invention can likewise be employed for the treatment and/or prophylaxis of social impairment, such as autism or social impairment related with schizophrenia.

The compounds of the invention of the formula I and their N-oxides, stereoisomers or pharmaceutically acceptable salts or the pharmaceutical composition of the invention can likewise be employed for the treatment and/or prophylaxis of increased aggression in conditions such as Alzheimer's disease and schizophrenia.

The compounds of the invention can furthermore also be employed for the treatment of memory impairments, Alzheimer's disease, psychoses, psychotic disorders, sleep disorders and/or Cushing's syndrome, and all stress-dependent diseases.

Accordingly, a further preferred embodiment of the present invention relates to the use of compounds of the invention of the formula I or of an N-oxide, a stereoisomer or pharmaceutically acceptable salts thereof for the manufacture of a medicament for the treatment of affective disorders.

In a further preferred embodiment, the present invention relates to the use of compounds of the invention of the formula I or of an N-oxide, a stereoisomer or pharmaceutically acceptable salts thereof for the manufacture of a medicament for the treatment of anxiety disorders and/or stress-dependent anxiety disorders.

In a further preferred embodiment, the present invention relates to the use of compounds of the invention of the formula I or of an N-oxide, a stereoisomer or pharmaceutically acceptable salts thereof for the manufacture of a medicament for the treatment of memory impairments and/or Alzheimer's disease.

In a further preferred embodiment, the present invention relates to the use of compounds of the invention of the formula I or of an N-oxide, a stereoisomer or pharmaceutically acceptable salts thereof for the manufacture of a medicament for the treatment of psychoses and/or psychotic disorders.

In a further preferred embodiment, the present invention relates to the use of compounds of the invention of the formula I or of an N-oxide, a stereoisomer or pharmaceutically acceptable salts thereof for the manufacture of a medicament for the treatment of Cushing's syndrome or other stress-dependent diseases.

In a further preferred embodiment, the present invention relates to the use of compounds of the invention of the formula I or of an N-oxide, a stereoisomer or pharmaceutically acceptable salts thereof for the manufacture of a medicament for the treatment of sleep disorders.

In a further preferred embodiment, the present invention relates to the use of compounds of the invention of the formula I or of an N-oxide, a stereoisomer or pharmaceutically acceptable salts thereof for the manufacture of a medicament for the treatment of depressive disorders. In the case of depressive disorders, specific mention is to be made of childhood onset mood disorders, i.e. depressive moods having their onset in childhood, but also of major depression, seasonal depression, bipolar disorders and dysthymic disorders, and especially of major depression and seasonal depression as well as of the depressive phases of bipolar disorders. The invention also relates to compounds of the formula I or N-oxides, stereoisomers or pharmaceutically acceptable salts thereof for the manufacture of a medicament for the treatment of treatment-resistant depression disorders and for the use in an add-on therapy of depressive disorders.

In a further preferred embodiment, the present invention relates to the use of compounds of the invention of the formula I or of an N-oxide, a stereoisomer or pharmaceutically acceptable salts thereof for the manufacture of a medicament for the treatment of vasomotor symptoms and/or thermoregulatory dysfunctions such as, for example, the hot flush symptom.

In a further preferred embodiment, the present invention relates to the use of compounds of the invention of the formula I or of an N-oxide, a stereoisomer or pharmaceutically acceptable salts thereof for the manufacture of a medicament for the treatment and/or prophylaxis of drug or pharmaceutical dependencies and/or dependencies mediated by other factors, for the treatment of drug-use disorders, for the treatment and/or prophylaxis of stress caused by withdrawal of one or more factors mediating the dependence and/or for the treatment and/or prophylaxis of stress-induced relapses into drug or pharmaceutical dependencies and/or dependencies mediated by other factors.

In a further preferred embodiment, the present invention relates to the use of compounds of the invention of the formula I or of an N-oxide, a stereoisomer or pharmaceutically acceptable salts thereof for the manufacture of a medicament for the treatment and/or prophylaxis of schizophrenia and/or psychosis.

In a further preferred embodiment, the present invention relates to the use of compounds of the invention of the formula I or of an N-oxide, a stereoisomer or pharmaceutically acceptable salts thereof for the manufacture of a medicament for the treatment and/or prophylaxis of pain, e.g. acute or chronic pain, preferably chronic pain, especially neuropathic pain. Chronic pain may be a complex regional pain syndrome, pain arising from peripheral neuropathies, post-operative pain, chronic fatigue syndrome pain, tension-type headache, pain arising from mechanical nerve injury and severe pain associated with diseases such as cancer, metabolic disease, neurotropic viral disease, neurotoxicity, inflammation, multiple sclerosis or any pain arising as a consequence of or associated with stress or depressive illness.

A further aspect of the invention relates to a compound I or pharmaceutically acceptable salts thereof for use as a medicament, and to a compound I or an N-oxide, a stereoisomer or pharmaceutically acceptable salts thereof for the manufacture of a medicament for the treatment and/or prophylaxis of the above-defined diseases.

A further aspect of the invention relates to a method for the treatment and/or prophylaxis of vasopressin-related diseases, in which an effective amount of at least one compound of the invention of the formula I or of an N-oxide, a stereoisomer or of at least one pharmaceutically acceptable salt thereof or of a pharmaceutical composition of the invention is administered to a patient.

Concerning the definition of vasopressin-related diseases, reference is made to the above statements.

In a preferred embodiment of the invention, the method of the invention serves for the treatment and/or prophylaxis of disorders selected from diabetes, insulin resistance, nocturnal enuresis, incontinence and diseases in which impairments of blood clotting occur, and/or for delaying micturition. Concerning the definition of diabetes, reference is made to the above statements.

In a further preferred embodiment, the method of the invention serves for the treatment and/or prophylaxis of disorders selected from hypertension, pulmonary hypertension, heart failure, myocardial infarction, coronary spasm, unstable angina, PTCA (percutaneous transluminal coronary angioplasty), ischemias of the heart, impairments of the renal system, edemas, renal vasospasm, necrosis of the renal cortex, hyponatremia, hypokalemia, Schwartz-Bartter syndrome, impairments of the gastrointestinal tract, gastritic vasospasm, hepatocirrhosis, gastric and intestinal ulcers, emesis, emesis occurring during chemotherapy, and travel sickness.

In a further preferred embodiment, the method of the invention serves for the treatment and/or prophylaxis of affective disorders.

In a further preferred embodiment, the method of the invention serves for the treatment and/or prophylaxis of anxiety disorders and/or stress-dependent anxiety disorders.

In a further preferred embodiment, the method of the invention serves for the treatment and/or prophylaxis of memory impairments and/or Alzheimer's disease.

In a further preferred embodiment, the method of the invention serves for the treatment and/or prophylaxis of psychoses and/or psychotic disorders.

In a further preferred embodiment, the method of the invention serves for the treatment and/or prophylaxis of Cushing's syndrome.

In a further preferred embodiment, the method of the invention serves for the treatment and/or prophylaxis of sleep disorders in a patient.

In a further preferred embodiment, the method of the invention serves for the treatment and/or prophylaxis of depressive disorders. In the case of depressive disorders, specific mention is to be made of major depression, seasonal depression, bipolar disorders, dysthymic disorders and childhood onset mood disorders, i.e. depressive moods having their onset in childhood, and especially of major depression and seasonal depression as well as of the depressive phases of bipolar disorders. The method of the invention also serves for the treatment of treatment-resistant depression disorders and as an add-on therapy of depressive disorders.

In a further preferred embodiment, the method of the invention serves for the treatment and/or prophylaxis of vasomotor symptoms and/or thermoregulatory dysfunctions, such as, for example, the hot flush symptom.

In a further preferred embodiment, the method of the invention serves for the treatment and/or prophylaxis of drug or pharmaceutical dependencies and/or dependencies mediated by other factors, for the treatment of drug-use disorders, for the treatment and/or prophylaxis of stress caused by withdrawal of one or more factors mediating the dependence, and/or for the treatment and/or prophylaxis of stress-induced relapses into drug or pharmaceutical dependencies and/or dependencies mediated by other factors.

In a further preferred embodiment, the method of the invention serves for the treatment and/or prophylaxis of schizophrenia and/or psychosis.

In a further preferred embodiment, the method of the invention serves for the treatment and/or prophylaxis of pain, e.g. acute or chronic pain, preferably chronic pain, especially neuropathic pain.

The patient to be treated prophylactically or therapeutically with the method of the invention is preferably a mammal, for example a human or a nonhuman mammal or a nonhuman transgenic mammal Specifically it is a human.

The compounds of the general formula I and their pharmaceutically acceptable salts as detailed above can be prepared by a skilled worker with knowledge of the technical teaching of the invention in implementing and/or in analogous implementation of process steps known per se.

The compounds I and/or their pharmaceutically acceptable salts, N-oxides and their stereoisomers are distinguished by having a selectivity for the vasopressin V1b receptor subtype vis-à-vis at least one of the closely related vasopressin/oxytocin receptor subtypes (for example vasopressin V1a, vasopressin V2 and/or oxytocin).

Alternatively, or preferably in addition, the compounds I and/or their pharmaceutically acceptable salts, N-oxides and a stereoisomers are distinguished by having an improved metabolic stability.

The metabolic stability of a compound can be measured for example by incubating a solution of this compound with liver microsomes from particular species (for example rat, dog or human) and determining the half-life of the compound under these conditions (R S Obach, Curr Opin Drug Discov Devel. 2001, 4, 36-44). It is possible in this connection to conclude from an observed longer half-life that the metabolic stability of the compound is improved. The stability in the presence of human liver microsomes is of particular interest because it makes it possible to predict the metabolic degradation of the compound in the human liver. Compounds with increased metabolic stability (measured in the liver microsome test) are therefore probably also degraded more slowly in the liver. The slower metabolic degradation in the liver may lead to higher and/or longer-lasting concentrations (active levels) of the compound in the body, so that the elimination half-life of the compounds of the invention is increased. Increased and/or longer-lasting active levels may lead to a better activity of the compound in the treatment or prophylaxis of various vasopressin-related diseases. In addition, an improved metabolic stability may lead to an increased bioavailability after oral administration, because the compound is subject, after absorption in the intestine, to less metabolic degradation in the liver (so-called first pass effect). An increased oral bioavailability may, owing to an increased concentration (active level) of the compound, lead to a better activity of the compound after oral administration.

The compounds of the invention are effective after administration by various routes. Possible examples are intravenous, intramuscular, subcutaneous, topical, intratracheal, intranasal, transdermal, vaginal, rectal, sublingual, buccal or oral administration, and administration is frequently intravenous, intramuscular or, in particular, oral.

The present invention also relates to pharmaceutical compositions which comprise an effective dose of a compound I of the invention and/or an N-oxide, a stereoisomer and/or a pharmaceutically acceptable salt thereof and suitable pharmaceutical carriers (drug carriers).

These drug carriers are chosen according to the pharmaceutical form and the desired mode of administration and are known in principle to the skilled worker.

The compounds of the invention of the formula I, their N-oxides, stereoisomers or optionally suitable salts of these compounds can be used to produce pharmaceutical compositions for oral, sublingual, buccal, subcutaneous, intramuscular, intravenous, topical, intratracheal, intranasal, transdermal, vaginal or rectal administration, and be administered to animals or humans in uniform administration forms, mixed with conventional pharmaceutical carriers, for the prophylaxis or treatment of the above disorders or diseases.

The suitable administration forms (dose units) include forms for oral administration such as tablets, gelatin capsules, powders, granules and solutions or suspensions for oral intake, forms for sublingual, buccal, intratracheal or intranasal administration, aerosols, implants, forms of subcutaneous, intramuscular or intravenous administration and forms of rectal administration.

The compounds of the invention can be used in creams, ointments or lotions for topical administration.

In order to achieve the desired prophylactic or therapeutic effect, the dose of the active ingredient can vary between 0.01 and 50 mg per kg of body weight and per day.

Each unit dose may comprise from 0.05 to 5000 mg, preferably 1 to 1000 mg, of the active ingredient in combination with a pharmaceutical carrier. This unit dose can be administered once to 5 times a day, so that a daily dose of from 0.5 to 25 000 mg, preferably 1 to 5000 mg, is administered.

If a solid composition is prepared in the form of tablets, the active ingredient is mixed with a solid pharmaceutical carrier such as gelatin, starch, lactose, magnesium stearate, talc, silicon dioxide or the like.

The tablets can be coated with sucrose, a cellulose derivative or another suitable substance or be treated otherwise in order to display a sustained or delayed activity and to release a predetermined amount of the active ingredient continuously.

A preparation in the form of gelatin capsules is obtained by mixing the active ingredient with an extender and including the resulting mixture in soft or hard gelatin capsules.

A preparation in the form of a syrup or elixir or for administration in the form of drops may contain active ingredients together with a sweetener, which is preferably calorie-free, methylparaben or propylparaben as antiseptics, a flavoring and a suitable coloring substance.

Water-dispersible powders or granules may comprise the active ingredients mixed with dispersants, wetting agents or suspending agents, such as polyvinylpyrrolidones, and sweeteners or masking flavors.

Rectal or vaginal administration is achieved by using suppositories which are prepared with binders which melt at rectal temperature, for example cocoa butter or polyethylene glycols. Parenteral administration is effected by using aqueous suspensions, isotonic saline solutions or sterile and injectable solutions which comprise pharmacologically acceptable dispersants and/or wetting agents, for example propylene glycol or polyethylene glycol.

The active ingredient may also be formulated as microcapsules or centrosomes, if suitable with one or more carriers or additives.

The compositions of the invention may, in addition to the compounds of the invention, comprise other active ingredients which may be beneficial for the treatment of the disorders or diseases indicated above.

The present invention thus further relates to pharmaceutical compositions in which a plurality of active ingredients are present together, where at least one of these is a compound I of the invention, or salt thereof.

The invention is explained in more detail below by means of examples, but the examples are not to be understood to be restrictive.

The compounds of the invention can be prepared by various synthetic routes. The methods mentioned, as described accordingly in synthesis scheme 1, are explained in greater detail merely by way of example using the given examples without being exclusively restricted to synthesis route 1 or analogous methods.

EXPERIMENTAL SECTION

Abbreviations Used
THF: Tetrahydrofuran
DMSO: Dimethyl sulfoxide
TFA: Trifluoroacetic acid
p: pseudo (for example pt pseudo triplet)
b: broad (for example bs broad singlet)
s: singlet
d: doublet
t: triplet
m: multiplet
dd: doublet of doublets
dt: doublet of triplets
tt: triplet of triplets I. Preparation of the Starting Compounds a.) Synthesis of 1-(1-(oxetan-3-yl)-piperidin-4-yl)-piperazine (trifluoroacetic acid salt)

a.1) Synthesis of tert-butyl 4-(1-(oxetan-3-yl)-piperidin-4-yl)-piperazine-1-carboxylate In a 100 ml round-bottom flask 2 g (7.42 mmol) of 1-boc-4-(piperidin-4-yl)-piperazine and 1.07 g (14.85 mmol) of 3-oxetanone were dissolved in 30 ml of dichloromethane. 3.16 g (22.27 mmol) of sodium sulfate were added and the reaction was stirred for 10 min. Subsequently, 2.203 g (10.39 mmol) of sodium triacetoxyborohydride were added and the reaction was stirred for 5 min. pH was adjusted to 5-6 with acetic acid and the reaction was stirred over night. Then, 50 ml of water were added and the resulting two phases were separated. The organic phase was washed twice with water dried over $MgSO_4$, filtered and evaporated. The resulting solid was digested in methyl-tert-butyl ether, filtered off, washed with 10 ml of methyl-tert-butyl ether and dried. Flash chromatography (silica gel/gradient from 0 to 20% methanol in dichloromethane) yielded 650 mg of the title compound as a yellowish solid.

a.2) Synthesis of 1-(1-(oxetan-3-yl)-piperidin-4-yl)-piperazine (trifluoroacetic acid salt)

In a 100 ml round-bottom flask 1.63 g (5.01 mmol) of tert-butyl 4-(1-(oxetan-3-yl)-piperidin-4-yl)-piperazine-1-carboxylate were dissolved in 5 ml of dichloromethane. 3 ml (38.9 mmol) of trifluoroacetic acid were added and the reaction was stirred for 30 min. The solution was concentrated and digested in 40 ml of methyl-tert-butyl ether. The solid was filtered and washed with 20 ml of methyl-tert-butyl ether to yield 2.79 of the title compound as a white solid.

b.) Synthesis of 1-(oxetan-3-yl)-4-(piperidin-4-yl) piperazine, (trifluoroacetic acid salt)

The compound was synthesized in analogy to a.), using however 1-boc-4-(piperazin-4-yl)-piperidine as starting amine compound and $NaBH_3CN/ZnCl$ as reduction agent.

c) Synthesis of 1-(oxetan-3-yl)-4,4'-bipiperidine c.1) Synthesis of benzyl 1'-(oxetan-3-yl)-[4,4'-bipiperidine]-1-carboxylate The compound was synthesized in analogy to a), using however benzyl[4,4'-bipieridine]-1-carboxylate as starting amine compound.

c.2) Synthesis of 1-(oxetan-3-yl)-4,4'-bipiperidine 520 mg (1.45 mmol) of benzyl 1'-(oxetan-3-yl)-[4,4'-bipiperidine]-1-carboxylate was dissolved in 30 ml methanol and hydrogenated in the H-cube® flow hydrogenator using a 10 mol % Pd (C) cartridge at a flow rate of 1 ml/min. The solvent was removed in vacuo providing 372 mg of the title compound which was used without further purification.

II. Preparation of the Compounds of the Formula I

Enantiomers of the compounds I were prepared by using enantiomerically pure starting compounds.

Example 1

(S)—N-(5-cyano-1-((2,4-dimethoxyphenyl)sulfonyl)-3-(2-ethoxypyridin-3-yl)-2-oxoindolin-3-yl)-4-(1-(oxetan-3-yl)piperidin-4-yl)piperazine-1-carboxamide (S-Enantiomer of the compound of formula I.1, wherein $R^{8a}, R^{8b}, R^{8c}, R^{8d}, R^{9a}, R^{9b}, R^{9c}, R^{9d}, R^{10a}, R^{10b}$ and $R^{10c}$ are as defined in Table 1 and $R^1, R^2, R^3, R^6$ and $R^7$ correspond to row A-61 of Table A)

Route A

In a 100 ml 3-necked flask, 100 mg (0.163 mmol) of (S)-phenyl (5-cyano-1-((2,4-dimethoxyphenyl)-sulfonyl)-3-(2-ethoxypyridin-3-yl)-2-oxoindolin-3-yl)-carbamate was stirred in THF for 5 min. 111 mg (0.195 mmol) of 1-(1-(oxetan-3-yl)piperidin-4-yl)-piperazine (used as trifluoroacetic acid salt) and 82 mg (0.814 mmol) of triethylamine were added and the reaction was stirred over night at room temperature. The solvent was removed, dichloromethane was added and the solution was extracted with water. The organic phase was washed with aqueous $Na_2CO_3$, dried over $MgSO_4$ and the solvent was removed. The resulting crude product was subjected to flash chromatography (silica gel/dichloromethane:methanol=90:10) to yield 98.2 mg (81%) of the title compound.

Route B

B.1) (S)-tert-butyl 4-(4-((5-cyano-1-((2,4-dimethoxyphenyl)sulfonyl)-3-(2-ethoxypyridin-3-yl)-2-oxoindolin-3-yl)carbamoyl)piperazin-1-yl)piperidine-1-carboxylate The compound was synthesized in analogy to Route A) using 4-(1-(tert-butoxycarbonyl)piperidin-4-yl)piperazine as amine compound.

B.2) (S)—N-(5-cyano-1-(2,4-dimethoxyphenyl)sulfonyl)-3-(2-ethoxypyridin-3-yl)-2-oxoindolin-3-yl)-4-(piperidin-4-yl)piperazine-1-carboxamide To a solution of 2.53 g (3.20 mmol) of (S)-tert-butyl 4-(4-((5-cyano-1-((2,4-dimethoxyphenyl)sulfonyl)-3-(2-ethoxypyridin-3-yl)-2-oxoindolin-3-yl)carbamoyl)piperazin-1-yl)piperidine-1-carboxylate in DCM (35 ml) was added 2.5 mL trifluoroacetic acid (32.4 mmol) and the reaction mixture was stirred overnight. The solvent was removed in vacuo and the residue was taken up in water/EtOAc (70 ml/70 ml). After neutralization with sat. aqueous $NaHCO_3^-$ solution (20 ml), the organic phase was separated and the aqueous phase extracted with EtOAc. The combined organic layers werde washed with brine and dried (MgSO4). Purification by flash chromatography (silica, DCM/MeOH gradient 0-100% MeOH) provided 1 g (36%) of the title compound as colorless solid.

B.3) (S)—N-(5-cyano-1-((2,4-dimethoxyphenyl)sulfonyl)-3-(2-ethoxypyridin-3-yl)-2-oxoindolin-3-yl)-4-(1-(oxetan-3-yl)piperidin-4-yl)piperazine-1-carboxamide In a 100 ml 3-necked flask, 100 mg (0.145 mmol) of (S)—N-(5-cyano-1-((2,4-dimethoxyphenyl)sulfonyl)-3-(2-ethoxypyridin-3-yl)-2-oxoindolin-3-yl)-4-(piperidin-4-yl)-piperazine-1-carboxamide were stirred in 4 ml of dichloromethane. 10.45 mg (0.145 mmol) of oxetan-3-one dissolved in 2 ml of dichloromethane were added and the mixture was stirred for 5 min. 30.7 mg of $Na_2SO_4$ were added and the mixture was stirred for another 5 min. 17.41 mg of acetic acid were added and the reaction was stirred for another 30 min. 46.1 mg (0.217 mmol) of sodium triacetoxyhydroborate were added and the reaction was stirred overnight. 1 ml of 2N NaOH and then 7 ml of water were added and the mixture was extracted thrice with ethylacetate and water. The organic phase was died over $MgSO_4$ and the solvent was removed. The resulting crude product was subjected to flash chromatography (silica gel/gradient from 0 to 5% methanol in dichloromethane) to yield 26.4 mg (24.4%) of the title compound.

ESI-MS [M+H$^+$]=746.3

Example 2

(S)—N-(5-cyano-1-((2,4-dimethoxyphenyl)sulfonyl)-3-(2-ethoxypyridin-3-yl)-2-oxoindolin-3-yl)-4-(4-(oxetan-3-yl)piperazin-1-yl)piperidine-1-carboxamide (S-Enantiomer of the compound of formula I.2, wherein $R^{8a}, R^{8b}, R^{8c}, R^{8d}, R^{9a}, R^{9b}, R^{9c}, R^{9d}, R^{10a}, R^{10b}$ and $R^{10c}$ are as defined in Table 1 and $R^1, R^2, R^3, R^6$ and $R^7$ correspond to row A-61 of Table A)

The compound was prepared in analogy to route B of example 1.

ESI-MS [M+H$^+$]=704.3

$^1$H-NMR (400 MHz DMSO), δ [ppm]: 8.14-8.13 (m, 1H), 8.88 (d, 1H), 7.87 (d, 1H), 7.83 (m, 1H), 7.74-7.72 (m, 1H), 7.70 (s, 1H), 7.68 (d, 1H), 7.04-7.02 (m, 1H), 6.69-6.66 (m, 2H), 4.52-4.49 (m, 2H), 4.40-4.38 (m, 2H), 4.21-4.11 (m, 2H), 3.85 (s, 3H), 3.84-8.79 (m, 2H), 3.43 (s, 3H), 2.66-2.56 (m, 2H), 2.47-2.15 (m, 9H), 1.65-1.58 (m, 2H), 1.20-1.10 (m, 2H), 1.08 (t, 3H).

Example 3

N-(5-cyano-3-(2-ethoxypyridin-3-yl)-1-((4-methoxyphenyl)sulfonyl)-2-oxoindolin-3-yl)-4-(1-(oxetan-3-yl)piperidin-4-yl)piperazine-1-carboxamide (Compound of formula I.1, wherein $R^{8a}, R^{8b}, R^{8c}, R^{8d}, R^{9a}, R^{9b}, R^{9c}, R^{9d}, R^{10a}, R^{10b}$ and $R^{10c}$ are as defined in Table 1 and $R^1, R^2, R^3, R^6$ and $R^7$ correspond to row A-13 of Table A)

The compound was prepared in analogy to route A of example 1.

ESI-MS [M+H$^+$]=716.3

Example 4

N-(5-cyano-3-(2-ethoxypyridin-3-yl)-2-oxo-1-(phenylsulfonyl)indolin-3-yl)-4-(1-(oxetan-3-yl)piperidin-4-yl)piperazine-1-carboxamide (Compound of formula I.1, wherein $R^{8a}, R^{8b}, R^{8c}, R^{8d}, R^{9a}, R^{9b}, R^{9c}, R^{9d}, R^{10a}, R^{10b}$ and $R^{10c}$ are as defined in Table 1 and $R^1, R^2, R^3, R^6$ and $R^7$ correspond to row A-1 of Table A)

The compound was prepared in analogy to route A of example 1.

ESI-MS [M+H$^+$]=686.1

Example 5

(S)—N-(5-cyano-1-((4-cyanophenyl)sulfonyl)-3-(2-ethoxypyridin-3-yl)-2-oxoindolin-3-yl)-4-(1-(oxetan-3-yl)piperidin-4-yl)piperazine-1-carboxamide (S-Enantiomer of the compound of formula I.1, wherein $R^{8a}, R^{8b}, R^{8c}, R^{8d}, R^{9a}, R^{9b}, R^{9c}, R^{9d}, R^{10a}, R^{10b}$ and $R^{10c}$ are as defined in Table 1 and $R^1, R^2, R^3, R^6$ and $R^7$ correspond to row A-14 of Table A)

The compound was prepared in analogy to route A of example 1.

ESI-MS [M+H$^+$]=711.3

Example 6

(S)—N-(5-cyano-3-(2-ethoxypyridin-3-yl)-1-((2-fluoro-4-methoxyphenyl)sulfonyl)-2-oxoindolin-3-yl)-4-(1-(oxetan-3-yl)piperidin-4-yl)piperazine-1-carboxamide (S-Enantiomer of the compound of formula I.1, wherein $R^{8a}, R^{8b}, R^{8c}, R^{8d}, R^{9a}, R^{9b}, R^{9c}, R^{9d}, R^{10a}, R^{10b}$ and $R^{10c}$ are as defined in Table 1 and $R^1, R^2, R^3, R^6$ and $R^7$ correspond to row A-29 of Table A)

The compound was prepared in analogy to route A of example 1.

ESI-MS [M+H$^+$]=734.0

Example 7

N-(5-cyano-1-((2,4-dimethoxyphenyl)sulfonyl)-3-(2-ethoxypyridin-3-yl)-6-fluoro-2-oxoindolin-3-yl)-4-(1-(oxetan-3-yl)piperidin-4-yl)piperazine-1-carboxamide (Compound of formula I.1, wherein $R^{8a}, R^{8b}, R^{8c}, R^{8d}, R^{9a}, R^{9b}, R^{9c}, R^{9d}, R^{10a}, R^{10b}$ and $R^{10c}$ are as defined in Table 1 and $R^1, R^2, R^3, R^6$ and $R^7$ correspond to row A-2083 of Table A)

The compound was prepared in analogy to route A of example 1.

ESI-MS [M+H$^+$]=764.3

Example 7A (S)—N-(5-cyano-1-((2,4-dimethoxyphenyl)sulfonyl)-3-(2-ethoxypyridin-3-yl)-6-fluoro-2-oxoindolin-3-yl)-4-(1-(oxetan-3-yl)piperidin-4-yl)piperazine-1-carboxamide (S-Enantiomer of the compound of formula I.1, wherein $R^{8a}, R^{8b}, R^{8c}, R^{8d}, R^{9a}, R^{9b}, R^{9c}, R^{9d}, R^{10a}, R^{10b}$ and $R^{10c}$ are as defined in Table 1 and $R^1, R^2, R^3, R^6$ and $R^7$ correspond to row A-2083 of Table A)

The compound was prepared in analogy to route A of example 1.

ESI-MS [M+H$^+$]=764.3

Example 8

(S)—N-(5-cyano-3-(2-ethoxypyridin-3-yl)-1-((5-fluoro-2,4-dimethoxyphenyl)sulfonyl)-2-oxoindolin-3-yl)-4-(1-(oxetan-3-yl)piperidin-4-yl)piperazine-1-carboxamide (S-Enantiomer of the compound of formula I.1, wherein $R^{8a}, R^{8b}, R^{8c}, R^{8d}, R^{9a}, R^{9b}, R^{9c}, R^{9d}, R^{10a}, R^{10b}$ and $R^{10c}$ are as defined in Table 1 and $R^1, R^2, R^3, R^6$ and $R^7$ correspond to row A-270 of Table A)

The compound was prepared in analogy to route A of example 1.

ESI-MS [M+H$^+$]=764.0

Example 9

(S)—N-(1-((2,4-dimethoxyphenyl)sulfonyl)-3-(2-ethoxypyridin-3-yl)-5,6-difluoro-2-oxoindolin-3-yl)-4-(1-(oxetan-3-yl)piperidin-4-yl)piperazine-1-carboxamide (S-Enantiomer of the compound of formula I.1, wherein $R^{8a}, R^{8b}, R^{8c}, R^{8d}, R^{9a}, R^{9b}, R^{9c}, R^{9d}, R^{10a}, R^{10b}$ and $R^{10c}$ are as defined in Table 1 and $R^1, R^2, R^3, R^6$ and $R^7$ correspond to row A-2757 of Table A)

The compound was prepared in analogy to route A of example 1.

ESI-MS [M+H$^+$]=757.3

Example 10

(S)—N-(5-chloro-1-((2,4-dimethoxyphenyl)sulfonyl)-3-(2-ethoxypyridin-3-yl)-2-oxoindolin-3-yl)-4-(1-(oxetan-3-yl)piperidin-4-yl)piperazine-1-carboxamide (S-Enantiomer of the compound of formula I.1, wherein $R^{8a}, R^{8b}, R^{8c}, R^{8d}, R^{9a}, R^{9b}, R^{9c}, R^{9d}, R^{10a}, R^{10b}$ and $R^{10c}$ are as defined in Table 1 and $R^1, R^2, R^3, R^6$ and $R^7$ correspond to row A-1409 of Table A)

The compound was prepared in analogy to route A of example 1.

ESI-MS [M+H$^+$]=755.5

Example 11

(S)—N-(5-cyano-1-((2,4-dimethoxyphenyl)sulfonyl)-3-(2-ethoxypyridin-3-yl)-2-oxoindolin-3-yl)-1'-(oxetan-3-yl)-[4,4'-bipiperidine]-1-carboxamide (S-Enantiomer of the compound of formula I.3, wherein $R^{8a}, R^{8b}, R^{8c}, R^{8d}, R^{9a}, R^{9b}, R^{9c}, R^{9d}, R^{10a}, R^{10b}$ and $R^{10c}$ are as defined in Table 1 and $R^1, R^2, R^3, R^6$ and $R^7$ correspond to row A-61 of Table A)

The compound was prepared in analogy to route A of example 1.

ESI-MS [M+H$^+$]=745.3

Example 12

(S)—N-(5-cyano-1-((4-cyanophenyl)sulfonyl)-3-(2-ethoxypyridin-3-yl)-2-oxoindolin-3-yl)-4-(4-(oxetan-3-yl)piperazin-1-yl)piperidine-1-carboxamide (S-Enantiomer of the compound of formula I.2, wherein $R^{8a}, R^{8b}, R^{8c}, R^{8d}, R^{9a}, R^{9b}, R^{9c}, R^{9d}, R^{10a}, R^{10b}$ and $R^{10c}$ are as defined in Table 1 and $R^1, R^2, R^3, R^6$ and $R^7$ correspond to row A-14 of Table A)

The compound was prepared in analogy to route A of example 1.

ESI-MS [M+H$^+$]=711.3

Example 13

(S)—N-(5-cyano-3-(2-ethoxypyridin-3-yl)-1-((4-methoxyphenyl)sulfonyl)-2-oxoindolin-3-yl)-4-(4-(oxetan-3-yl)piperazin-1-yl)piperidine-1-carboxamide (S-Enantiomer of the compound of formula I.2, wherein $R^{8a}, R^{8b}, R^{8c}, R^{8d}, R^{9a}, R^{9b}, R^{9c}, R^{9d}, R^{10a}, R^{10b}$ and $R^{10c}$ are as defined in Table 1 and $R^1, R^2, R^3, R^6$ and $R^7$ correspond to row A-13 of Table A)

The compound was prepared in analogy to route A of example 1.

ESI-MS [M+H$^+$]=716.3

Example 14

(S)—N-(5-chloro-1-((2,4-dimethoxyphenyl)sulfonyl)-3-(2-ethoxypyridin-3-yl)-2-oxoindolin-3-yl)-4-(4-(oxetan-3-yl)piperazin-1-yl)piperidine-1-carboxamide (S-Enantiomer of the compound of formula I.2, wherein $R^{8a}, R^{8b}, R^{8c}, R^{8d}, R^{9a}, R^{9b}, R^{9c}, R^{9d}, R^{10a}, R^{10b}$ and $R^{10c}$ are as defined in Table 1 and $R^1, R^2, R^3, R^6$ and $R^7$ correspond to row A-1409 of Table A)

The compound was prepared in analogy to route A of example 1.

ESI-MS [M+H$^+$]=756.3

Example 15

N-(5-cyano-1-((2,4-dimethoxyphenyl)sulfonyl)-3-(2-methoxypyridin-3-yl)-2-oxoindolin-3-yl)-4-(1-(oxetan-3-yl)piperidin-4-yl)piperazine-1-carboxamide (Compound of formula I.4, wherein $R^{8a}, R^{8b}, R^{8c}, R^{8d}, R^{9a}, R^{9b}, R^{9c}, R^{9d}, R^{10a}, R^{10b}$ and $R^{10c}$ are as defined in Table 1 and $R^1, R^2, R^3, R^6$ and $R^7$ correspond to row A-61 of Table A)

The compound was prepared in analogy to route A of example 1.

ESI-MS [M+H$^+$]=732.3

Example 16

N-(5-cyano-1-((2,4-dimethoxyphenyl)sulfonyl)-3-(2-methoxypyridin-3-yl)-2-oxoindolin-3-yl)-4-(4-(oxetan-3-yl)piperazin-1-yl)piperidine-1-carboxamide (Compound of formula I.5, wherein $R^{8a}, R^{8b}, R^{8c}, R^{8d}, R^{9a}, R^{9b}, R^{9c}, R^{9d}, R^{10a}, R^{10b}$ and $R^{10c}$ are as defined in Table 1 and $R^1, R^2, R^3, R^6$ and $R^7$ correspond to row A-61 of Table A)

The compound was prepared in analogy to route A of example 1.

ESI-MS [M+H$^+$]=732.3

Example 17

N—((S)-5-cyano-1-((2,4-dimethoxyphenyl)sulfonyl)-3-(2-ethoxypyridin-3-yl)-2-oxoindolin-3-yl)-4-((1S,4S)-5-(oxetan-3-yl)-2,5-diazabicyclo[2.2.1]heptan-2-yl)piperidine-1-carboxamide (S-Enantiomer of the compound of formula I.2, wherein $R^{8a}, R^{8b}, R^{8c}, R^{8d}, R^{9a}, R^{9b}, R^{9c}, R^{9d}, R^{10a}, R^{10b}$ and $R^{10c}$ are as defined in Table 47 and $R^1, R^2, R^3, R^6$ and $R^7$ correspond to row A-61 of Table A)

The compound was prepared in analogy to route B of example 1.

ESI-MS [M+H$^+$]=758.3

Example 18

(S)—N-(5-cyano-3-(2-ethoxypyridin-3-yl)-1-((4-methoxy-2,3-dimethylphenyl)sulfonyl)-2-oxoindolin-3-yl)-4-(1-(oxetan-3-yl)piperidin-4-yl)piperazine-1-carboxamide (S-Enantiomer of the compound of formula I.1, wherein $R^{8a}, R^{8b}, R^{8c}, R^{8d}, R^{9a}, R^{9b}, R^{9c}, R^{9d}, R^{10a}, R^{10b}$ and $R^{10c}$ are as defined in Table 1 and $R^1, R^2, R^3, R^6$ and $R^7$ correspond to row A-208 of Table A)

The compound was prepared in analogy to route A of example 1.

ESI-MS [M+H$^+$]=744.3

Example 19

(S)—N-(5-cyano-1-((2,4-dimethoxyphenyl)sulfonyl)-3-(2-ethoxypyridin-3-yl)-2-oxoindolin-3-yl)-4-(1-(oxetan-3-ylmethyl)piperidin-4-yl)piperazine-1-carboxamide (S-Enantiomer of the compound of formula I.61, wherein $R^{8a}, R^{8b}, R^{8c}, R^{8d}, R^{9a}, R^{9b}, R^{9c}, R^{9d}, R^{10a}, R^{10b}$ and $R^{10c}$ are as defined in Table 1 and $R^1, R^2, R^3, R^6$ and $R^7$ correspond to row A-61 of Table A)

The compound was prepared in analogy to route B of example 1, using however oxetane-3-carbaldehyde.

ESI-MS [M+H$^+$]=764.3

III. Determination of the Biological Activity

1. Vasopressin V1b Receptor Binding Assay

Substances:

The test substances were dissolved in a concentration of 5 mM in 100% DMSO and further diluted to $5 \times 10^{-4}$ M to $5 \times 10^{-9}$ M. These serial DMSO predilutions were diluted 1:10 with assay buffer. The substance concentration was further diluted 1:5 in the assay mixture resulting in 2% DMSO in the mixture. All dilutions were performed in a Biomek NX automation workstation (Beckman)

Membrane Preparation:

CHO-K1 cells with stably expressed human vasopressin V1b receptor (clone 3H2) were harvested and homogenized in 50 mM Tris-HCl and in the presence of protease inhibitors (Roche complete Mini #1836170) using a Polytron homogenizer at intermediate setting for 2×10 seconds, and subsequently centrifuged at 40 000×g for 1 h. The membrane pellet was again homogenized and centrifuged as described and subsequently taken up in 50 mM Tris-HCl, pH 7.4, homogenized and stored in aliquots frozen in liquid nitrogen at −190° C.

Binding Assay:

The binding assay was carried out by the method based on that of Tahara et al. (Tahara A et al., Brit. J. Pharmacol. 125, 1463-1470 (1998)).

The incubation buffer was: 50 mM Tris, 10 mM $MgCl_2$, 0.1% BSA, pH 7.4. In the assay mixture (200 µl), membranes (26 µg protein in incubation buffer) from CHO-K1 cells with stably expressed human V1b receptors (cell line hV1b_3H2_CHO) were incubated with 1.5 nM $^3$H-AVP (8-Arg-vasopressin, PerkinElmer, NET 800) in incubation buffer (50 mM Tris, 10 mM $MgCl_2$, 0.1% BSA, pH 7.4) (total binding) or additionally with increasing concentrations of test substance (displacement experiment). The nonspecific binding was determined with 1 µM AVP (Fluka 94836). All determinations were carried out as duplicate determinations. After incubation (60 minutes at room temperature), the free radioligand was filtered off by vacuum filtration (Tomtec Mach III) through Wathman GF/B glass fiber filter plates (UniFilter, PerkinElmer 6005177). The liquid scintillation measurement took place in a Microbeta TriLux 12 (Wallac).

Analysis:

The binding parameters were calculated by nonlinear regression in SAS. The algorithms of the program operate in analogy to the LIGAND analysis program (Munson P J and Rodbard D, Analytical Biochem. 107, 220-239 (1980)). The Kd of $^3$H-AVP for the recombinant human V1b receptors is 0.4 nM and was used to determine the Ki.

2. Vasopressin V1a Receptor Binding Assay

Substances:

The test substances were dissolved in a concentration of 5 mM M in DMSO. Further dilution of these DMSO solutions took place as described for V1b.

Membrane Preparation:

CHO-K1 cells with stably expressed human vasopressin V1a receptor (clone 5) were harvested and homogenized in 50 mM Tris-HCl and in the presence of protease inhibitors (Roche complete Mini #1836170) using a Polytron homogenizer at intermediate setting for 2×10 seconds, and subsequently centrifuged at 40 000×g for 1 h. The membrane pellet was again homogenized in a High-Pressure-Homogenizer, Polytec 50K at 1500 PSI (Heinemann, Germany) and subsequently taken up in 50 mM Tris-HCl, pH 7.4, homogenized and stored in aliquots frozen in liquid nitrogen at −190° C.

Binding Assay:

The binding assay was carried out by the method based on that of Tahara et al. (Tahara A et al., Brit. J. Pharmacol. 125, 1463-1470 (1998)).

The incubation buffer was: 50 mM Tris, 10 mM $MgCl_2$, 0.1% BSA, pH 7.4.

In the assay mixture (200 µl), membranes (40 µg protein in incubation buffer) from CHO-K1 cells with stably expressed human V1a receptors (cell line hV1a_5_CHO) were incubated with 0.04 nM $^{125}$I-AVP (8-Arg-vasopressin, PerkinElmer NEX 128) in incubation buffer (50 mM Tris, 10 mM $MgCl_2$, 0.1% BSA, pH 7.4) (total binding) or additionally with increasing concentrations of test substance (displacement experiment). The nonspecific binding was determined with 1 µM AVP (Fluka 94836). Duplicate determinations were carried out.

After incubation (60 minutes at room temperature), the samples were processed as described for V1b.

Analysis:

The binding parameters were calculated by nonlinear regression in SAS. The algorithms of the program operate in analogy to the LIGAND analysis program (Munson P J and Rodbard D, Analytical Biochem. 107, 220-239 (1980)). The Kd of $^{125}$I-AVP for the recombinant hV1a receptors was determined in saturation experiments. A Kd of 1.33 nM was used to determine the Ki.

3. Oxytocin Receptor Binding Assay

Substances:

The substances were dissolved in a concentration of 5 mM in DMSO and diluted further as described for V1b.

Cell Preparation:

Confluent HEK-293 cells with transiently expressing recombinant human oxytocin receptors were centrifuged at 750×g at room temperature for 5 minutes. The residue was taken up in ice-cold lysis buffer (50 mM Tris-HCl, 10% glycerol, pH 7.4 and Roche complete protease inhibitor) and subjected to an osmotic shock at 4° C. for 20 minutes. The lyzed cells were then centrifuged at 750×g at 4° C. for 20 minutes, the residue was taken up in incubation buffer, and aliquots of $10^7$ cells/ml were prepared. The aliquots were frozen at −80° C. until used.

The incubation buffer was: 50 mM Tris, 10 mM $MgCl_2$, 0.1% BSA, pH 7.4.

In the assay mixture (200 µl), ghosts corresponding to $5×10^4$ cells (HEK-293 cells expressing transiently human OT receptors) were incubated with 3H-oxytocin (PerkinElmer NET858) in incubation buffer (50 mM Tris, 10 mM $MgCl_2$, 0.1% BSA, pH 7.4) (total binding) or additionally with increasing concentrations of test substance (displacement experiment). The nonspecific binding was determined with 1 µM A-797879 (AbbVie, Ludwigshafen, Germany). Duplicate determinations were carried out. After incubation (60 minutes at room temperature), the samples were processed as described for V1b.

Binding Assay:

Analysis:

The binding parameters were calculated by nonlinear regression analysis (SAS) in analogy to the LIGAND program of Munson and Rodbard (Analytical Biochem 1980; 107: 220-239). The Kd of $^3$H-oxytocin for the recombinant hOT receptors is 7.6 nM and was used to determine the Ki.

4. Determination of the Microsomal Half-Life

The metabolic stability of the compounds of the invention was determined in the following assay.

The test substances were incubated in a concentration of 0.5 µM as follows: 0.5 µM test substance are preincubated together with liver microsomes from different species (from rat, human or other species) (0.25 mg of microsomal protein/ml) in 0.05 M potassium phosphate buffer of pH 7.4 in microtiter plates at 37° C. for 5 min. The reaction is started by adding NADPH (1 mg/mL). After 0, 5, 10, 15, 20 and 30 min, 50 µl aliquots are removed, and the reaction is immediately stopped and cooled with the same volume of acetonitrile. The samples are frozen until analyzed. The remaining concentration of undegraded test substance is determined by MSMS. The half-life (T½) is determined from the gradient of the signal of test substance/unit time plot, it being possible to calculate the half-life of the test substance, assuming first order kinetics, from the decrease in the concentration of the compound with time. The microsomal clearance (mCl) is calculated from mCl=In2/T½/(content of microsomal protein in mg/ml)×1000 [ml/min/mg] (modified from references: Di, The Society for Biomoleculur Screening, 2003, 453-462; Obach, DMD, 1999 vol 27. N 11, 1350-1359).

5. Methods for In Vitro Determination of the Cytochrome P450 (CYP) Inhibition Luminescent Substrates for 2C9 and 3A4:

0.4 mg/ml human liver microsomes are preincubated with the test substances to be investigated (0-20 μM), the CYP-specific substrates, in 0.05 M potassium phosphate buffer of pH 7.4 at 37° C. for 10 min. The Cyp-specific substrate for CYP 2C9 is luciferin H, and for CYP 3A4 is luciferin BE. The reaction is started by adding NADPH. After incubation at RT for 30 min, the luciferin detection reagent is added, and the resulting luminescence signal is measured (modified from reference: Promega, Technical Bulletin P450-GLO™ Assays).

Midazolam CYP 3A4 Time-Dependent Inhibition

The assay consists of 2 parts. Firstly, the test substance is preincubated with the liver microsomes (with NADPH=preincubation, then addition of the substrate; in the second part the substrate and the test substance are added simultaneously=coincubation.

Preincubation:

0.05 mg/ml microsomal protein (human liver microsomes) are preincubated with 0-10 μM (or 50 μM) test substance in 50 mM potassium phosphate buffer for 5 min. The reaction is started with NADPH. After 30 min 4 μM midazolam (final concentration) are added, and incubation is continued for 10 min. 75 μl of the reaction solution are removed after 10 min, and stopped with 150 μl of acetonitrile solution.

Coincubation:

0.05 mg/ml microsomal protein (human liver microsomes) are preincubated with 4 μm midazolam (final concentration) and 0-10 μM (or 50 μM) test substance in 50 mM potassium phosphate buffer for 5 min. The reaction is started with NADPH. 75 μl of the reaction solution are removed after 10 min and stopped with 150 μl of acetonitrile solution. The samples are frozen until the MSMS analysis (modified from references: Obdach, Journal of Pharmacology & Experimental Therapeutics, Vol 316, 1, 336-348, 2006; Walsky, Drug Metabolism and Disposition Vol 32, 6, 647-660, 2004).

6. Method for Determining the Solubility in Water (in mg/ml)

The solubility in water of the compounds of the invention can be determined for example by the so-called shake flask method (as specified in *ASTM International: E* 1148-02, *Standard test methods for measurement of aqueous solubility, Book of Standards Volume* 11.05.). This entails an excess of the solid compound being put into a buffer solution with a particular pH (for example phosphate buffer of pH 7.4), and the resulting mixture being shaken or stirred until equilibrium has been set up (typically 24 or 48 hours, sometimes even up to 7 days). The undissolved solid is then removed by filtration or centrifugation, and the concentration of the dissolved compound is determined by UV spectroscopy or high pressure liquid chromatography (HPLC) by means of an appropriate calibration plot.

7. Results

The results of the receptor binding investigations are expressed as receptor binding constants [$K_i$(V1b)] or selectivities [$K_i$(V1a)/$K_i$(V1b)]. The results of the investigation of the metabolic stability are indicated as microsomal clearance (mCl).

The compounds of the invention show very high affinities for the V1b receptor in these assays (maximally 100 nM, or maximally 10 nM, frequently <1 nM). The compounds also show high selectivities vis-à-vis the V1a receptor and a good metabolic stability, measured as microsomal clearance.

The results are listed in table C. The numbers of the compounds refer to the synthesis examples.

TABLE C

| Example | $K_i$(h-V1b)* [nM] |
|---|---|
| 1 | +++ |
| 2 | ++ |
| 3 | ++ |
| 4 | + |
| 5 | ++ |
| 6 | ++ |
| 7 | +++ |
| 8 | ++ |
| 9 | ++ |
| 10 | +++ |
| 12 | + |
| 13 | + |
| 14 | ++ |
| 15 | ++ |
| 16 | + |
| 17 | + |
| 18 | + |

*h = human
Key:

| | $K_i$(V1b) |
|---|---|
| + | >10-100 nM |
| ++ | 1-10 nM |
| +++ | <1 nM |

The invention claimed is:

1. A compound of formula I (I)

wherein
  $X^1$ and $X^2$ are N or CH, with the proviso that $X^1$ and $X^2$ are not simultaneously N;
  $X^3$ is a bond, $C_1$-$C_4$-alkylene, $C_1$-$C_4$-haloalkylene or CO;
  $X^4$ is N or CH;
  $X^5$ is C-$R^1$ or N;
  $R^1$, $R^2$ and $R^3$, independently of each other, are selected from hydrogen, halogen, cyano, $C_1$-$C_3$-alkyl, fluorinated $C_1$-$C_3$-alkyl, $C_1$-$C_3$-hydroxyalkyl, $C_1$-$C_3$-alkoxy and fluorinated $C_1$-$C_3$-alkoxy;

$R^4$ is selected from $C_1$-$C_3$-alkoxy;

$R^5$ is selected from hydrogen and $C_1$-$C_3$-alkoxy;

$R^6$ is selected from cyano and halogen;

$R^7$ is selected from hydrogen, halogen and cyano;

$R^8$ and $R^9$, independently of each other and independently of each occurrence, are selected from halogen, $C_1$-$C_4$-alkyl, $C_1$-$C_4$-haloalkyl, $C_1$-$C_4$-alkoxy and $C_1$-$C_4$-haloalkoxy, with the proviso that $R^8$ and $R^9$ are not halogen, $C_1$-$C_4$-alkoxy or $C_1$-$C_4$-haloalkoxy if they are bound to a carbon atom in α-position to a nitrogen ring atom; or two non-geminal radicals $R^8$ form together a group —$(CH_2)_n$—, where n is 1, 2, 3 or 4, where 1 or 2 hydrogen atoms in this group may be replaced a methyl group; or two non-geminal radicals $R^9$ form together a group —$(CH_2)_n$—, where n is 1, 2, 3 or 4, where 1 or 2 hydrogen atoms in this group may be replaced a methyl group;

each $R^{10}$ is independently selected from halogen, $C_1$-$C_4$-alkyl and $C_1$-$C_4$-haloalkyl;

a is 0, 1, 2, 3 or 4;

b is 0, 1, 2, 3 or 4; and c is 0, 1, 2, 3 or 4;

or an N-oxide, stereoisomer or pharmaceutically acceptable salt thereof.

2. The compound of claim 1, where $R^1$, $R^2$ and $R^3$, independently of each other, are selected from hydrogen, fluorine, cyano, methyl, fluoromethyl, difluoromethyl, trifluoromethyl, methoxy, fluoromethoxy, difluoromethoxy and trifluoromethoxy.

3. The compound of claim 2, where $R^1$, $R^2$ and $R^3$, independently of each other, are selected from hydrogen, fluorine, cyano, methyl and methoxy.

4. The compound of claim 3, where $R^1$ is selected from hydrogen, fluorine, methyl and methoxy.

5. The compound of claim 3, where $R^2$ is selected from hydrogen, cyano and methoxy.

6. The compound of claim 3, where $R^3$ is selected from hydrogen, fluorine and methyl.

7. The compound of claim 1, where $R^4$ is selected from methoxy and ethoxy.

8. The compound of claim 1, where $R^5$ is hydrogen or methoxy.

9. The compound of claim 1, where $R^6$ is selected from cyano, fluorine and chlorine.

10. The compound of claim 1, where $R^7$ is selected from hydrogen and fluorine.

11. The compound of claim 1, where each $R^8$ is independently selected from halogen and $C_1$-$C_4$-alkyl, with the proviso that $R^8$ is not halogen if it is bound to a carbon atom in α-position to a nitrogen ring atom, or two non-geminal radicals $R^8$ form together a group —$CH_2$—.

12. The compound of claim 1, where each $R^9$ is independently selected from halogen and $C_1$-$C_4$-alkyl, with the proviso that $R^9$ is not halogen if it is bound to a carbon atom in α-position to a nitrogen ring atom, or two non-geminal radicals $R^9$ form together a group —$CH_2$—.

13. The compound of claim 12, where two non-geminal radicals $R^9$ form together a group —$CH_2$—.

14. The compound of claim 13, where the two non-geminal radicals $R^9$ forming together a group —$CH_2$— are bound in 2- and 5-position, relative to the 1-position of $X^2$.

15. The compound of claim 1, where each $R^{10}$ is independently selected from halogen and $C_1$-$C_4$-alkyl.

16. The compound of claim 1, where $X^3$ is a bond or $CH_2$.

17. The compound of claim 16, where $X^3$ is a bond.

18. The compound of claim 1, where $X^4$ is N.

19. The compound of claim 1, where $X^4$ is CH.

20. The compound of claim 1, where $X^5$ is C—$R^1$.

21. The compound of claim 1, where $X^5$ is N.

22. The compound of claim 1, where a is 0, 1 or 2.

23. The compound of claim 1, where b is 0, 1 or 2.

24. The compound of claim 1, where c is 0, 1 or 2.

25. The compound of claim 1, selected from the group consisting of:

(S)-N-(5-cyano-1-((2,4-dimethoxyphenyl)sulfonyl)-3-(2-ethoxypyridin-3-yl)-2-oxoindolin-3-yl)-4-(1-(oxetan-3-yl)piperidin-4-yl)piperazine-1-carboxamide;

(S)-N-(5-cyano-1-((2,4-dimethoxyphenyl)sulfonyl)-3-(2-ethoxypyridin-3-yl)-2-oxoindolin-3-yl)-4-(4-(oxetan-3-yl)piperazin-1-yl)piperidine-1-carboxamide;

N-(5-cyano-3-(2-ethoxypyridin-3-yl)-1((4-methoxyphenyl)sulfonyl)-2-oxoindolin-3-yl)-4-(1-(oxetan-3-yl)piperidin-4-yl)piperazine-1-carboxamide;

N-(5-cyano-3-(2-ethoxypyridin-3-yl)-2-oxo-1-(phenylsulfonyl)indolin-3-yl)-4-(1-(oxetan-3-yl)piperidin-4-yl)piperazine-1-carboxamide;

(S)-N-(5-cyano-1-((4-cyanophenyl)sulfonyl)-3-(2-ethoxypyridin-3-yl)-2-oxoindolin-3-yl)-4-(1-(oxetan-3-yl)piperidin-4-yl)piperazine-1-carboxamide;

(S)-N-(5-cyano-3-(2-ethoxypyridin-3-yl)-1-((2-fluoro-4-methoxyphenyl)sulfonyl)-2-oxoindolin-3-yl)-4-(1-(oxetan-3-yl)piperidin-4-yl)piperazine-1-carboxamide;

N-(5-cyano-1((2,4-dimethoxyphenyl)sulfonyl)-3-(2-ethoxypyridin-3-yl)-6-fluoro-2-oxoindolin-3-yl)-4-(1-(oxetan-3-yl)piperidin-4-yl)piperazine-1-carboxamide;

(S)-N-(5-cyano-1-((2,4-dimethoxyphenyl)sulfonyl)-3-(2-ethoxypyridin-3-yl)-6-fluoro-2-oxoindolin-3-yl)-4-(1-(oxetan-3-yl)piperidin-4-yl)piperazine-1-carboxamide;

(S)-N-(5-cyano-3-(2-ethoxypyridin-3-yl)-1-((5-fluoro-2,4-dimethoxyphenyl)sulfonyl)-2-oxoindolin-3-yl)-4-(1-(oxetan-3-yl)piperidin-4-yl)piperazine-1-carboxamide;

(S)-N-(1-((2,4-dimethoxyphenyl)sulfonyl)-3-(2-ethoxypyridin-3-yl)-5,6-difluoro-2-oxoindolin-3-yl)-4-(1-(oxetan-3-yl)piperidin-4-yl)piperazine-1-carboxamide;

(S)-N-(5-chloro-1-((2,4-dimethoxyphenyl)sulfonyl)-3-(2-ethoxypyridin-3-yl)-2-oxoindolin-3-yl)-4-(1-(oxetan-3-yl)piperidin-4-yl)piperazine-1-carboxamide;

(S)-N-(5-cyano-1-((2,4-dimethoxyphenyl)sulfonyl)-3-(2-ethoxypyridin-3-yl)-2-oxoindolin-3-yl)-1'-(oxetan-3-yl)-[4,4'-bipiperidine]-1-carboxamide;

(S)-N-(5-cyano-1-((4-cyanophenyl)sulfonyl)-3-(2-ethoxypyridin-3-yl)-2-oxoindolin-3-yl) -4-(4-(oxetan-3-yl)piperazin-1-yl)piperidine-1-carboxamide;

(S)-N-(5-cyano-3-(2-ethoxypyridin-3-yl)-1-((4-methoxyphenyl)sulfonyl)-2-oxoindolin-3-yl )-4-(4-(oxetan-3-yl)piperazin-1-yl)piperidine-1-carboxamide;

(S)-N-(5-chloro-1-((2,4-dimethoxyphenyl)sulfonyl)-3-(2-ethoxypyridin-3-yl)-2-oxoindolin-3-yl)-4-(4-(oxetan-3-yl)piperazin-1-yl)piperidine-1-carboxamide;

N-(5-cyano-14(2,4-dimethoxyphenyl)sulfonyl)-3-(2-methoxypyridin-3-yl)-2-oxoindolin -3-yl)-4-(1-(oxetan-3-yl)piperidin-4-yl)piperazine-1-carboxamide;

N-(5-cyano-1((2,4-dimethoxyphenyl)sulfonyl)-3-(2-methoxypyridin-3-yl)-2-oxoindolin-3-yl)-4-(4-(oxetan-3-yl)piperazin-1-yl)piperidine-1-carboxamide;

N-((S)-5-cyano-1-((2,4-dimethoxyphenyl)sulfonyl)-3-(2-ethoxypyridin-3-yl)-2-oxoindolin-3-yl)-4-((1S,4S)-5-(oxetan-3-yl)-2,5-diazabicyclo[2.2.1]heptan-2-yl)piperidine-1-carboxamide;

(S)-N-(5-cyano-3-(2-ethoxypyridin-3-yl)-1-((4-methoxy-2,3-dimethylphenyl)sulfonyl)-2-oxoindolin-3-yl)-4-(1-(oxetan-3-yl)piperidin-4-yl)piperazine-1-carboxamide; and (S)-N-(5-cyano-1-((2,4-dimethoxyphenyl)sulfonyl)-3-(2-ethoxypyridin-3-yl)-2-oxoindolin-3-yl)-4-(1-(oxetan-3-ylmethyl)piperidin-4-yl)piperazine-1-carboxamide;

or an N-oxide, stereoisomer, or pharmaceutically acceptable salt thereof.

26. A pharmaceutical composition comprising at least one compound of the formula I of claim 1 or an N-oxide, a stereoisomer or pharmaceutically acceptable salt thereof and at least one pharmaceutically acceptable carrier.

27. A method for the treatment of diseases selected from hypertension, pulmonary hypertension, heart failure, myocardial infarction, coronary spasm;

anxiety disorders and stress-dependent anxiety disorders; and depressive disorders selected from major depression, seasonal depression, treatment-resistant depression, dysthymic disorders, and childhood onset mood disorders; the method comprising administering an effective amount of at least one compound of the formula I of claim 1, or an N-oxide, stereoisomer or pharmaceutically acceptable salt thereof to a patient in need thereof.

* * * * *